(12) United States Patent
Sørensen et al.

(10) Patent No.: US 9,181,259 B2
(45) Date of Patent: Nov. 10, 2015

(54) SUBSTITUTED PYRROLO[1,2-A]PIPERAZINES AND PYRROLO[1,2-A][1,4]DIAZEPINES AS NEUROKININ 1 RECEPTOR ANTAGONISTS

(71) Applicant: LEO PHARMA A/S, Ballerup (DK)

(72) Inventors: Morten Dahl Sørensen, Ballerup (DK); Romano Di Fabio, Verona (IT); Alfonso Pozzan, Verona (IT); Maria Pia Catalani, Verona (IT); Haakon Bladh, Ballerup (DK); Jakob Felding, Ballerup (DK)

(73) Assignee: LEO PHARMA A/S, Ballerup (DK)

( * ) Notice: Subject to any disclaimer, the term of this patent is extended or adjusted under 35 U.S.C. 154(b) by 0 days.

(21) Appl. No.: 14/380,078

(22) PCT Filed: Feb. 20, 2013

(86) PCT No.: PCT/EP2013/053319
§ 371 (c)(1),
(2) Date: Aug. 21, 2014

(87) PCT Pub. No.: WO2013/124286
PCT Pub. Date: Aug. 29, 2013

(65) Prior Publication Data
US 2015/0018345 A1    Jan. 15, 2015

Related U.S. Application Data

(60) Provisional application No. 61/601,902, filed on Feb. 22, 2012.

(51) Int. Cl.
| | | |
|---|---|---|
| *A61K 31/4985* | (2006.01) | |
| *A61K 31/551* | (2006.01) | |
| *C07D 241/38* | (2006.01) | |
| *C07D 243/10* | (2006.01) | |
| *C07D 487/04* | (2006.01) | |
| *A61K 31/5377* | (2006.01) | |
| *C07D 471/20* | (2006.01) | |
| *C07D 491/20* | (2006.01) | |

(52) U.S. Cl.
CPC .......... *C07D 487/04* (2013.01); *A61K 31/4985* (2013.01); *A61K 31/5377* (2013.01); *A61K 31/551* (2013.01); *C07D 471/20* (2013.01); *C07D 491/20* (2013.01)

(58) Field of Classification Search
CPC ............. A61K 31/4985; A61K 31/551; C07D 241/38; C07D 243/10
USPC ................... 514/221, 249; 540/580; 544/349
See application file for complete search history.

(56) References Cited

FOREIGN PATENT DOCUMENTS

| WO | WO 01/25219 A2 | 4/2001 |
| WO | WO 02/32867 A1 | 4/2002 |
| WO | WO 02/081457 A1 | 10/2002 |

(Continued)

OTHER PUBLICATIONS

Jordan, V. C. Nature Reviews: Drug Discovery, 2, 2003, 205.*
Vippagunta, et al. Advanced Drug Delivery Reviews, 48, 2001, 18.*
Jordan, V. C. Nature Reviews: Drug Discovery, 2, 2003, 205-213.*
Hackam, et al. JAMA, 296(14), 2006, 1731-1732.*
A. Duval, L. Dubertret: "Aprepitant as an Antipruritic Agent", New England Journal of Medicine, vol. 361, 2009, pp. 1415-1416, XP002698518.

(Continued)

*Primary Examiner* — Douglas M Willis
(74) *Attorney, Agent, or Firm* — Birch Stewart Kolasch & Birch, LLP

(57) ABSTRACT

The present invention relates to a compound according to formula (A) wherein n is 1 or 2; R1 and R2 are independently hydrogen, $C_{1-4}$ alkyl, $C_{1-4}$ haloalkyl, $C_{1-4}$ alkoxy, CD3 or halogen; R3 is hydrogen, C(=O)OR7 or $C_{1-4}$ alkyl optionally substituted with hydroxy or NR8R9; R4 is hydrogen or oxo; R5 and R6 are independently hydrogen, hydroxy, NR8R9, C(=O)R7, C(=O)OR7, C(=O)NR8R9, $C_{1-4}$ alkyl, wherein said $C_{1-4}$ alkyl is optionally substituted with hydroxy, NR8R9 or a 5- or 6-membered heterocyclic ring, wherein said 5- or 6-membered heterocyclic ring is optionally substituted with $C_{1-4}$ alkyl or C(=O)R7; or R5 and R6, together with the carbon atom to which they are attached, form =$CH_2$ or a 5- or 6-membered heterocycloalkyl, wherein said heterocycloalkyl is optionally substituted with $C_{1-4}$ alkyl; R7 is hydrogen or $C_{1-4}$ alkyl; R8 and R9 are independently hydrogen or $C_{1-4}$ alkyl, or R8 and R9, together with the nitrogen atom to which they are attached, form a 5- or 6-membered heterocyclic ring, or a pharmaceutically acceptable salt or solvate thereof. The invention relates further to intermediates for the preparation of said compounds, to said compounds for use in therapy, to pharmaceutical compositions comprising said compounds, to methods of treating or ameliorating pruritic dermal diseases or conditions with said compounds, and to the use of said compounds in the manufacture of medicaments.

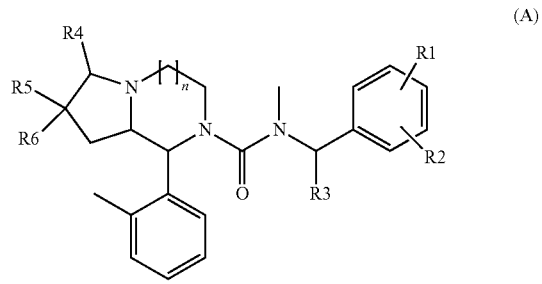

(A)

25 Claims, 6 Drawing Sheets

(56) References Cited

FOREIGN PATENT DOCUMENTS

WO     WO 2009/002770 A1     12/2008
WO     WO 2013/124286     *     8/2013

OTHER PUBLICATIONS

International Search Report, issued in PCT/EP2013/053319, dated Jun. 25, 2013.
Chang et al., "Neuropeptides and Their Receptors in Psoriatic Skin in Relation to Pruritus", Br. J. Dermatol. 156, 2007, pp. 1272-1277.
Greaves, "Pathogenesis and Treatment of Pruritus", Curr Allergy Asthma Rep, 10, 2010, pp. 236-242.
Patel et al., "Therapy of Pruritus", Expert Opinion, Pharmacother, 11(10), 2010, pp. 1673-1682.
Raap et al., Pathophysiology of Itch and New Treatments, Current Opinion in Allergy and Clinical Immunology, 11, 2011, pp. 420-427.
Salomon, "The Role of Selected Neuropeptides in Pathogenesis of Atopic Dermatitis", 22, 2008, pp. 223-228.
Stander et al., "Targeting the Neurokinin Receptor 1 with Aprepitant: A Novel Antipruritic Strategy", Plos One, 2010, p. 5.

* cited by examiner

Figure 1. Time course of scratching after a topical application of Compound 9 and Compound 44 in the NK-1 agonist-induced scratching model in the gerbil.

The figure shows the time course of scratching after an intradermal injection of GR73632 (GR in the figure) and the effect of the topical application of Compound 9 and Compound 44 (1% w/v) in the scratching model.

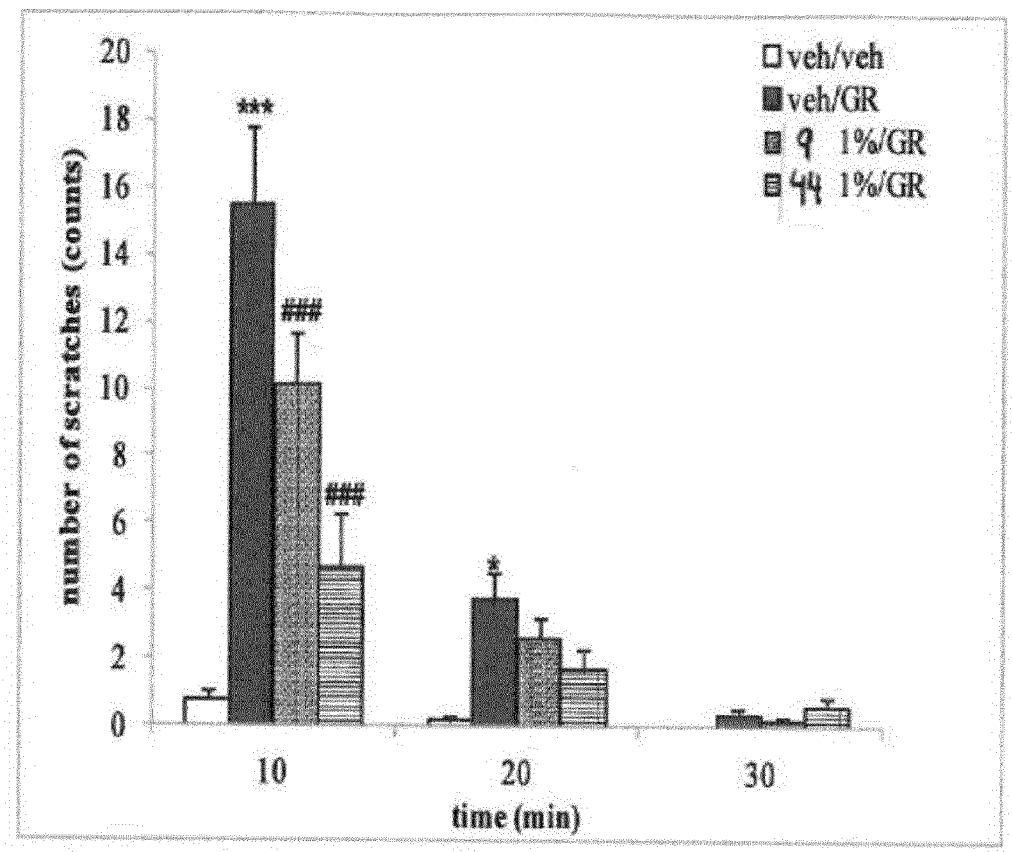

The figure shows the time course of scratching after an intradermal injection of GR73632 (GR in the figure) and the effect of the topical application of Compound 9 and Compound 44 (1% w/v) in the scratching model.

Values are expressed as mean ± SEM.

*p<0.05, ***p<0.01 for GR73632 vs vehicle;

p<0.001 for antagonist compounds vs GR73632

Figure 1a. Effect of a topical application of Compound 9 and Compound 44 in the scratching gerbil model
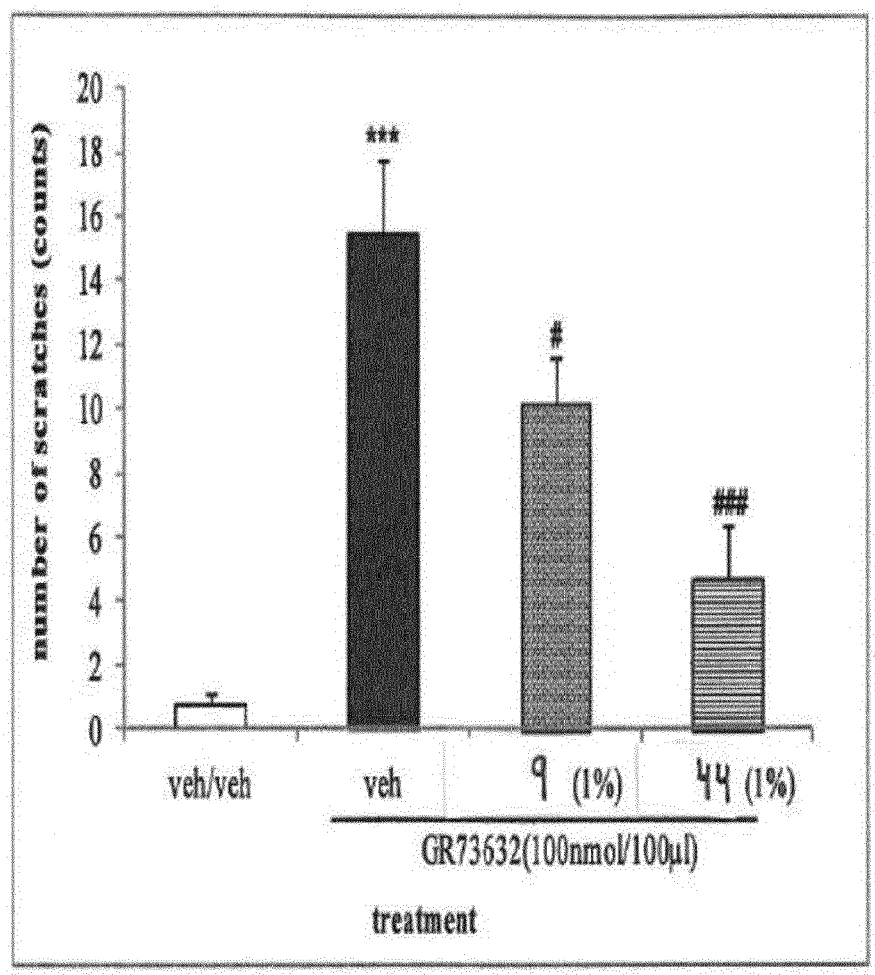
The figure shows the effect of a topical application of Compound 9 and Compound 44 (dose 1%) in the first 10 minutes observation time of scratching model.
Values are expressed as mean ± SEM.
***$p<0.01$ for GR73632 *vs* vehicle;
$p<0.05$, ##$p<0.01$ for test compounds *vs* GR73632

Figure 2. Time course of scratching after a topical application of Compound 54 and Compound 60 in the NK-1 agonist-induced scratching model in the gerbil.

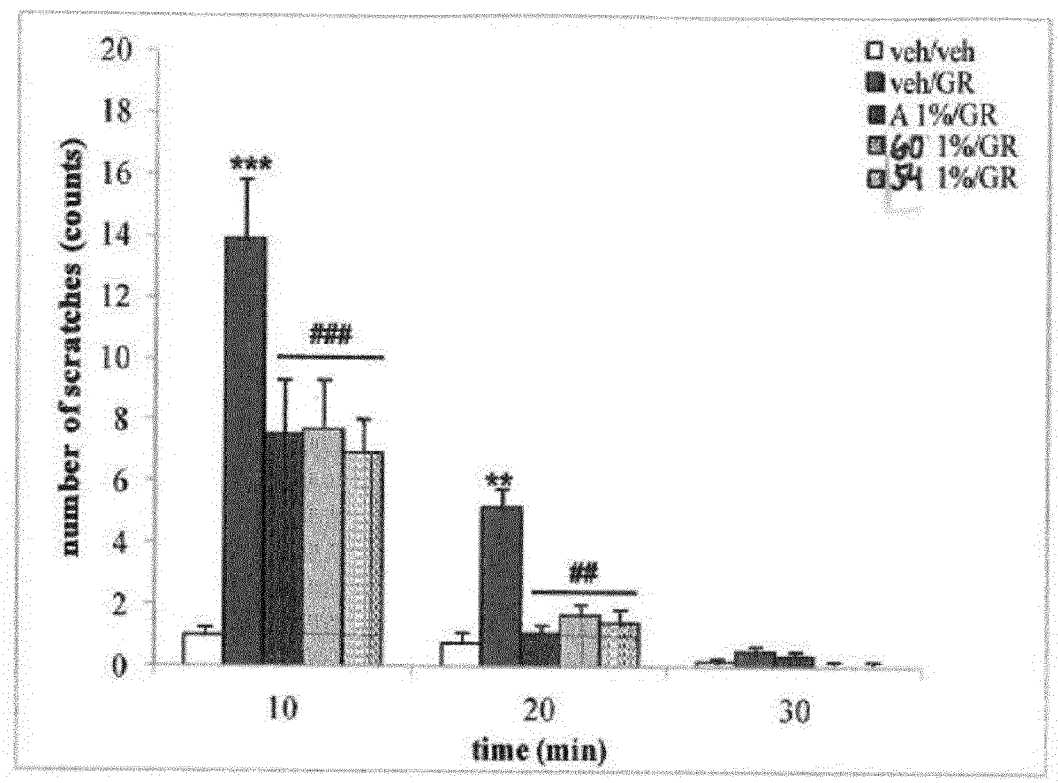

The figure shows the time course of scratching after an intradermal injection of GR73632 (GR in the figure) and the effect of the topical application of Aprepitant (A in the figure), Compound 54 and Compound 60 (all at 1% w/v) in the scratching model.
Values are expressed as mean ± SEM.
*p<0.05, ***p<0.01 for GR73632 vs vehicle;
p<0.001 for antagonists compounds vs GR73632

Figure 2a. Effect of a topical application of Compound 54 and Compound 60 in the scratching gerbil model
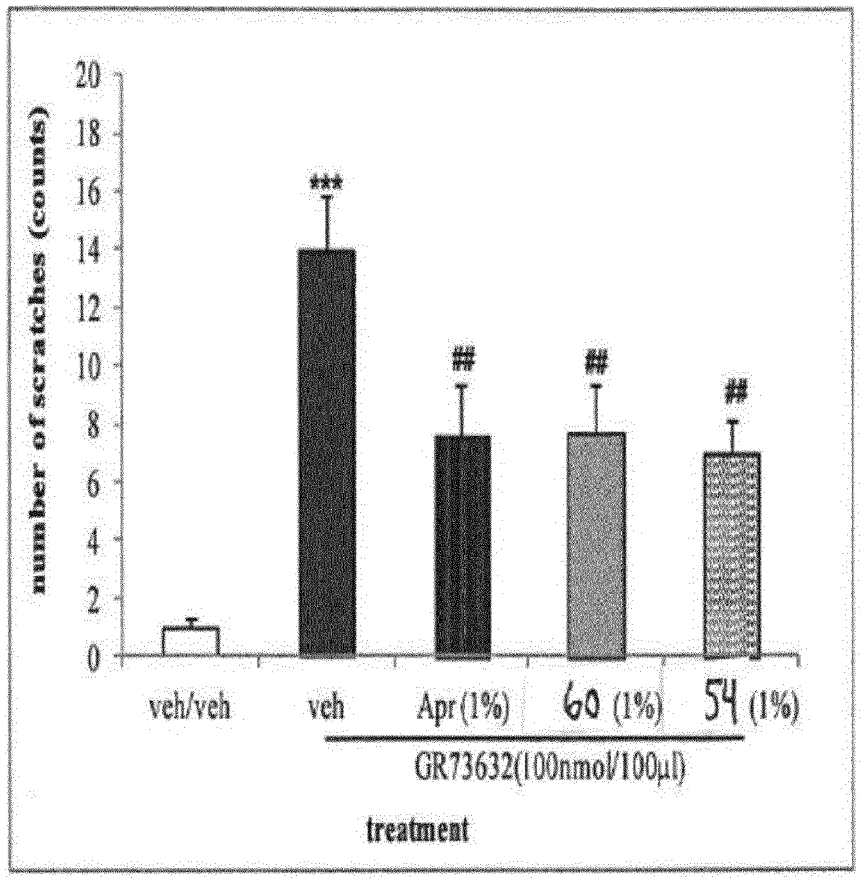
The figure shows the effect of a topical application of Aprepitant (Apr in the figure), Compound 54 and Compound 60 (all at 1% w/v) in the first 10 minutes observation time of scratching model.
Values are expressed as mean ± SEM.
***p<0.01 for GR73632 vs vehicle;
p<0.01 for test compounds vs GR73632

Figure 3. Time course of scratching after a topical application of Compound 38 and Compound 55 in the NK-1 agonist-induced scratching model in the gerbil.

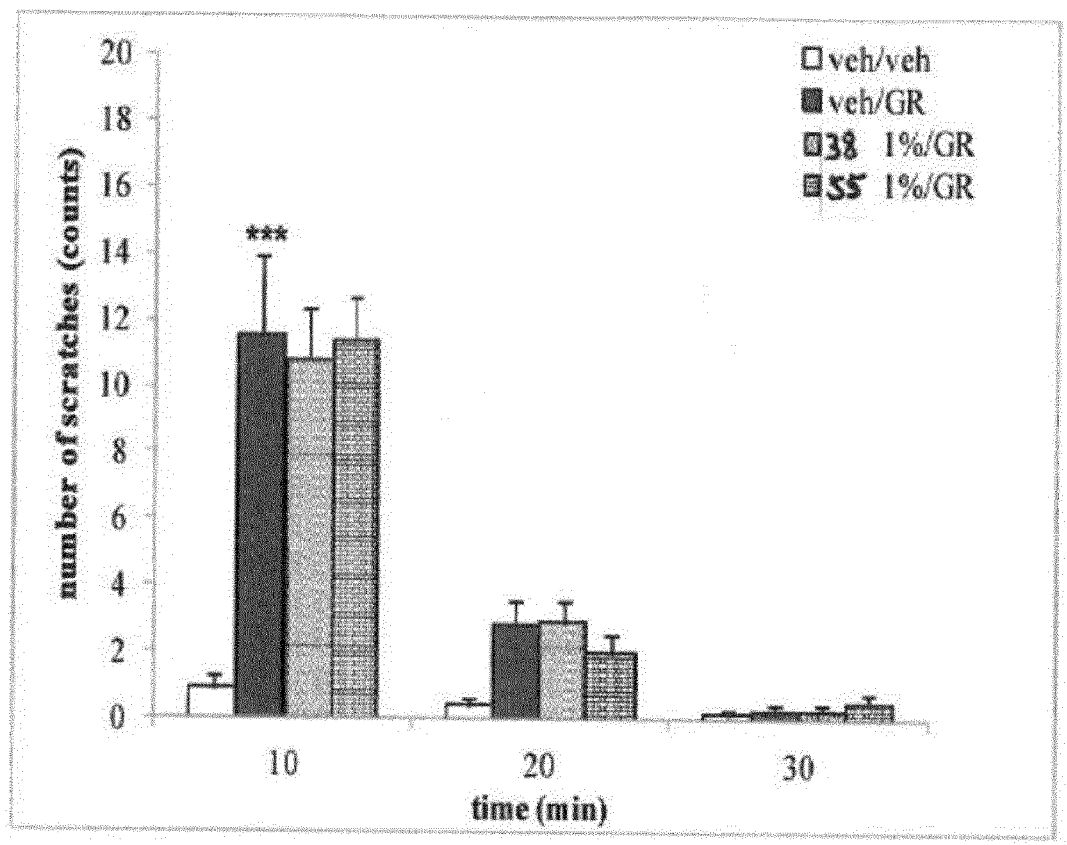

The figure shows the time course of scratching after an intradermal injection of GR73632 (GR in the figure) and the effect of the topical application of Compound 38 and Compound 55 (both 1% w/v) in the scratching model.
Values are expressed as mean ± SEM.
***p<0.01 for GR73632 vs vehicle;

Figure 3a. Effect of a topical application of Compound 38 and Compound 55 in the scratching gerbil model
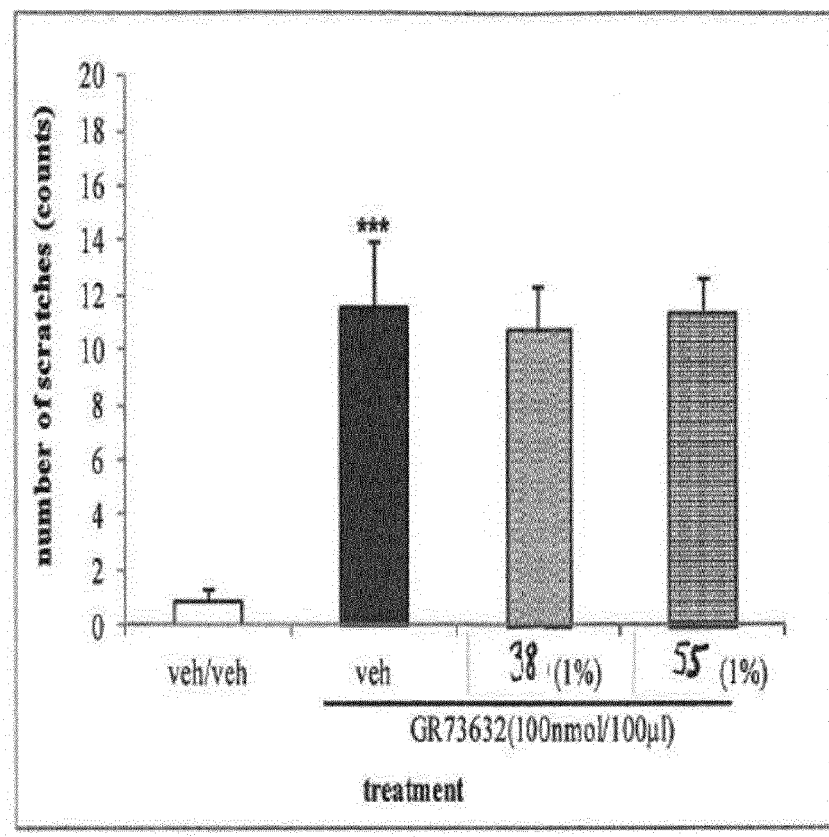
The figure shows the effect of a topical application of Compound 38 and Compound 55 (dose 1%) in the first 10 minutes observation time of scratching model.
Values are expressed as mean ± SEM.
***$p<0.01$ for GR73632 vs vehicle;

SUBSTITUTED PYRROLO[1,2-A]PIPERAZINES AND PYRROLO[1,2-A][1,4]DIAZEPINES AS NEUROKININ 1 RECEPTOR ANTAGONISTS

CROSS REFERENCE TO RELATED APPLICATIONS

This application is the National Phase of PCT International Application No. PCT/EP2013/053319 filed on Feb. 20, 2013, which claims priority under 35 U.S.C. 119(e) to U.S. Provisional Application No. 61/601,902 filed on Feb. 22, 2012, all of which are hereby expressly incorporated by reference into the present application.

FIELD OF INVENTION

The present invention relates to novel heterocyclic compounds which are neurokinin 1 receptor antagonists, to intermediates for the preparation of said compounds, to their use in therapy such as in the prophylaxis or treatment of pruritic dermal diseases or conditions, and to pharmaceutical compositions comprising said compounds.

BACKGROUND OF THE INVENTION

Pruritus is a common symptom of skin diseases as well as a sign of an underlying systemic pathology. Pruritus is an unpleasant sensation in the skin that provokes a desire to scracth and may be acute (of short duration) such as the reaction to an insect bite or chronic (lasting for more than 6 weeks) such as in many inflammatory skin diseases. It is well known that patients with inflammatory skin diseases perceive pruritus as seriously compromising their quality of life.

Pruritus is mediated via free nerve endings of non-myelinated C-type nerve fibres in epidermis. These have been found to express neuropeptides, and the epidermal keratinocytes produce neuropeptides, receptors for neuropeptides, nerve growth factor, vanilloid receptors proteinase-activated receptor type 2 (PAR2) and voltage-gated ATP channels (M W Greaves, Curr. *Allergy Asthma Rep.* 10, 2010, pp. 236-242). Neuropeptides suchs as Substance P have been shown to increase the production and release of nerve growth factor from cultured keratinocytes, suggesting that interactions between the immune system and the nervous system are important in the development of inflammation including pruritus. Inflammatory skin diseases such as atopic dermatitis, contact dermatitis, psoriasis and urticaria are associated with increased production of cytokines, neurotrophins and neuropeptides that may exacerbate the pruritus (U. Raap et al., *Curr. Opin. Allergy Clin. Immunol.* 11, 2011, pp. 420-427). While neuropeptides such as Substance P are not considered crucial for the pathogenesis of inflammatory skin diseases such as atopic dermatitis, they do play an important role in the development and severity of the condition, for instance by provoking the itch-scratch cycle where scratching exacerbates the inflammatory symptoms of atopic dermatitis (J. Salomon and E. Baran, *JEADV* 22, 2008, pp. 223-228). Furthermore, an increase of dermal nerves and upregulation of receptors for neuropeptides, e.g. the neurokinin 1 receptor has been found in skin from psoriasis patients with pruritus as opposed to skin from psoriasis patients without pruritus (S-E. Chang et al., *Br. J. Dermatol.* 156, 2007, pp. 1272-1277).

It has also been found that other cell types resident in skin release mediators of pruritus. Thus, mast cells contain large amounts of histamine that are released on activation of the cells and induce pruritus by targeting histamine H1 receptors on nerve endings. Eosinophils which infiltrate inflamed skin in atopic dermatitis, urticaria and contact dermatitis produce and release neurotrophins such as nerve growth factor.

Current therapeutic treatments of pruritus include both topical and systemic medicaments. Topical treatments include emollients and barrier creams that are believed to act by improving the barrier function of the skin, corticosteroids that do not appear to be antipruritic in themselves but act by relieving the attendant skin inflammation. This may also be the case for calcineurin inhibitors such as tacrolimus which has been shown to reduce pruritus in atopic dermatitis patients. Histamine H1 antagonists have also shown effect against pruritus in atopic dermatitis patients, but exhibits systemic side effects in the form of drowsiness in a significant number of patients. Local anesthetics such as lidocain have been found to exhibit anti-pruritic properties (Patel and Yosipovitch, *Expert. Opin. Pharmacother.* 11(10), 2010, 1673-1682).

Systemic therapy of pruritus include oral antihistamines, antidepressants, neuroleptics and immunosuppressants such as cyclosporin. A neurokinin-1 receptor antagonist, aprepitant, which has been developed as an oral antiemetic drug for use to counteract the nausea and vomiting caused by chemotherapy or post surgery, has been found to relieve pruritus in patients suffering from Sézary syndrome by oral administration (Duval and Dubertret, *New Engl. J. Med.* 361, 2009, pp. 1415-1416) and in patients with atopic diathesis, prurigo nodularis and systemic pruritus (S. Stander et al., *Plos One*, 2010, p. 5).

WO01/25219 discloses piperazine derivatives which are antagonists of tachykinins, including substance P and other neurokinins.

WO02/32867 discloses piperidine derivatives which are antagonists of tachykinins, including substance P and other neurokinins WO02/081457 discloses 1,4-diazepane-1-carboxylic acid derivatives process for their preparation and their use as tachykinin antagonists WO2009002770 discloses 6.5 pyrrolopiperidine tachykinin receptor antagonists.

As many of the antipruritic treatments available at present have side-effects that may limit their use, and as many dermal conditions are preferentially treated with topical medications, especially when the conditions is of mild to moderate severity, there is a continued need to develop neurokinin 1 receptor (NK1R) antagonists which are effective in the treatment of itch on topical application, but which have reduced systemic effects on the central nervous system.

SUMMARY OF THE INVENTION

In one aspect, the present invention relates to compounds of general formula A

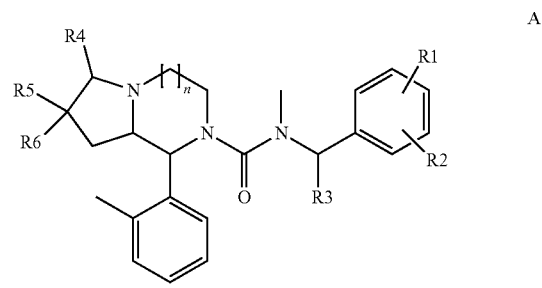

wherein
n is 1 or 2;
R1 and R2 are independently hydrogen, $C_{1-4}$ alkyl, $C_{1-4}$ haloalkyl, $C_{1-4}$ alkoxy, $CD_3$ or halogen;
R3 is hydrogen, C(=O)OR7 or $C_{1-4}$ alkyl optionally substituted with hydroxy or NR8R9;
R4 is hydrogen or oxo;
R5 and R6 are independently hydrogen, hydroxy, NR8R9, C(=O)R7, C(=O)OR7, C(=O)NR8R9, $C_{1-4}$ alkyl, wherein said $C_{1-4}$ alkyl is optionally substituted with hydroxy, NR8R9 or a 5- or 6-membered heterocyclic ring, wherein said 5- or 6-membered heterocyclic ring is optionally substituted with $C_{1-4}$ alkyl or C(=O)R7; or R5 and R6, together with the carbon atom to which they are attached, form =$CH_2$ or a 5- or 6-membered heterocycloalkyl, wherein said heterocycloalkyl is optionally substituted with $C_{1-4}$ alkyl;
R7 is hydrogen or $C_{1-4}$ alkyl;
R8 and R9 are independently hydrogen or $C_{1-4}$ alkyl, or R8 and R9, together with the nitrogen atom to which they are attached, form a 5- or 6-membered heterocyclic ring, or a pharmaceutically acceptable salt or solvate thereof.

In another aspect, the present invention relates to a compound according to general formula A for use in therapy.

In another aspect, the present invention relates to a compound according to general formula A for use in the prevention, treatment or amelioration of pruritic skin conditions, e.g. acute pruritus in any condition; chronic pruritus on diseased skin, such as inflammatory, infectious, or autoimmune cutaneous diseases, genodermatoses, drug reactions, dermatoses of pregnancy and skin lymphomas, prurigo, lichen planus, atopic dermatitis, eczema, contact dermatitis, allergic dermatitis, nummular dermatitis, lichen simplex, psoriasis, Sézary syndrome, cutaneous lymphomas, bullous pemphigoid, alopecia greata, scabies, vitiligo, urticaria and drug-induced pruritus; pruritic diseases on non-diseased skin of systemic, neurological or psychosomatic/psychiatric origin, including endocrine and metabolicdisorders, infections, haematological and lymphoproliferative diseases, solid neoplasms and drug-induced pruritus; mastocytosis; pruritus of unknown cause; pruritus with chronic secondary scratch lesions, such as prurigo nodularis, and all types of prurigo; or any other dermal disease or condition characterized by pruritus.

In another aspect, the present invention relates to a pharmaceutical composition comprising, as a therapeutically active ingredient, a compound according to general formula A and a pharmaceutically acceptable carrier or vehicle.

In another aspect, the present invention relates to intermediates for the preparation of a compound according to general formula A, such as a compound according to general formula B,

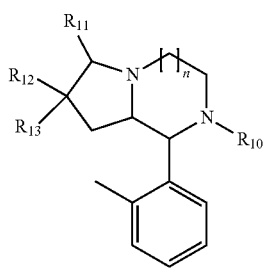

B wherein R10 is selected from the group consisting of hydrogen and —C(O)O$C_1$-$C_4$ alkyl;

R11 is selected from the group consisting of hydrogen and oxo;
R12 and R13 are independently selected from the group consisting of hydrogen, $C_1$-$C_4$ alkyl, allyl and —C(O)O($C_1$-$C_4$ alkyl);
R14 is selected from the group consisting of $C_1$-$C_4$ alkyl;
n is 1 or 2;
or a pharmaceutically acceptable salt thereof.

The compounds of formula A have been found to act as potent antagonists of NK1R and are therefore potentially useful in the treatment of any disease or condition where Substance P is involved in the disease pathology, in particular in the prevention, treatment or amelioration of a pruritic dermal disease or condition.

It has been found that some compounds of general formula A attenuate NK-1 agonist induced scratching in the gerbil upon topical pre-treatment with said compounds.

It has surprisingly been found that some compounds of formula A exhibit a high metabolic clearance, i.e. are quickly degraded upon systemic administration, which makes them uniquely suitable for topical application with a favourable safety profile.

It has surprisingly been found that some compounds of general formula A exhibit a favourable ratio between the in vitro efficacy of the compound and the in vitro efficacy of metabolites of the compound, thus providing a favourable safety profile of the compounds.

It has surprisingly been found that some compounds of general formula A exhibit a mode of action indicating a competitive, non-surmountable antagonism, suggesting a slow dissociating antagonist-receptor complex.

It has surprisingly been found that some compounds of general formula A both exhibit a mode of action indicating a competitive, non-surmountable antagonism as well as exhibiting a favourable ratio between the in vitro efficacy of the compound and the in vitro efficacy of metabolites of the compound.

BRIEF DESCRIPTION OF THE DRAWINGS

FIG. 1 is a graph showing the time course of scratching after a topical application of Compound 9 and Compound 44 in the NK-1 agonist-induced scratching model in the gerbil. The X-axis shows the time (minutes). The Y-axis shows the number of scratches (counts).

FIG. 1a shows the effect of a topical application of Compound 9 and Compound 44 (dose 1%) in the first 10 minutes observation time of scratching model. The X-axis shows the compounds. The Y-axis shows the number of scratches (counts).

FIG. 2 is a graph showing the time course of scratching after a topical application of Compound 60 and Compound 54 in the NK-1 agonist-induced scratching model in the gerbil. The X-axis shows the time (minutes). The Y-axis shows the number of scratches (counts).

FIG. 2a shows the effect of a topical application of Compound 60 and Compound 54 (dose 1%) in the first 10 minutes observation time of scratching model. The X-axis shows the compounds. The Y-axis shows the number of scratches (counts).

FIG. 3 is a graph showing the time course of scratching after a topical application of Compound 38 and Compound 55 in the NK-1 agonist-induced scratching model in the gerbil. The X-axis shows the time (minutes). The Y-axis shows the number of scratches (counts).

FIG. 3a shows the effect of a topical application of Compound 38 and Compound 55 (dose 1%) in the first 10 minutes observation time of scratching model. The X-axis shows the compounds. The Y-axis shows the number of scratches (counts).

DETAILED DESCRIPTION OF THE INVENTION

Definitions

The term "alkyl" is intended to indicate a radical obtained when one hydrogen atom is removed from a hydrocarbon. Said alkyl may be branched or straight and may comprise 1-20, preferably 1-12, such as 1-6, such as 1-4 carbon atoms, such as 1-3 carbon atoms, such as 1-2 carbon atoms, such as 2-3 carbon atoms. The term includes the subclasses normal alkyl (n-alkyl), secondary and tertiary alkyl, such as methyl, ethyl, n-propyl, isopropyl, n-butyl, isobutyl, sec.-butyl, tert.-butyl, pentyl, isopentyl, neopentyl and hexyl.

The term "cycloalkyl" is intended to indicate a saturated cycloalkane hydrocarbon radical, comprising 3-6 carbon atoms, such as 3-5 carbon atoms, such as 5-6 carbon atoms or such as 3-4 carbon atoms, e.g. cyclopropyl, cyclobutyl, cyclopentyl or cyclohexyl.

The term "heterocyclic ring" is intended to indicate radicals of 5- or 6-membered heterocyclic aromatic rings (also termed "heteroaryl") with 1-4 heteroatoms selected from O, S and N, e.g. pyridyl, quinolyl, isoquinolyl, indolyl, dihydroisoindolyl, tetrazolyl, thiazolyl, imidazolyl, pyrazolyl, oxazolyl, isoxazolyl, thienyl, pyrazinyl, pyridazinyl, isothiazolyl, or heterocycloalkyl with 1-4 heteroatoms selected from O, S and N, e.g. piperidinyl, piperazinyl, morpholinyl, pyrrolidinyl, tetrahydropyranyl, tetrahydrothiopyranyl, thiane-1-oxid or thiane-1-dioxid or tetrahydrofuranyl, The term "halogen" is intended to indicate a substituent from the $7^{th}$ main group of the periodic table, such as fluoro, chloro, bromo and iodo.

The term "haloalkyl" is intended to indicate an alkyl radical as defined above substituted with one or more halogen atoms, e.g trifluoromethyl, difluoromethyl or fluoromethyl.

The term "heterocycloalkyl" is intended to indicate a cycloalkyl as described herein, wherein one or more carbon atoms are replaced by heteroatoms, comprising 1-5 carbon atoms, e.g. 2-5 or 2-4 carbon atoms, further comprising 1-4 heteroatoms, preferably 1, 2, or 3 heteroatoms, such as 1 or 2 heteroatoms, selected from O, N, or S.

The term "hydroxyalkyl" is intended to indicate an alkyl group as defined above substituted with one or more hydroxy, e.g. hydroxymethyl, hydroxyethyl, hydroxypropyl.

The term "alkoxy" is intended to indicate a radical of the formula —OR', wherein R' is alkyl as indicated above, e.g. methoxy, ethoxy, n-propoxy, isopropoxy, butoxy, etc.

The term "oxo" is intended to indicate an oxygen atom which is connected to a carbon atom by a double bond, thereby forming a carbonyl group together with the carbon-atom to which it is connected.

The term "pharmaceutically acceptable salt" is intended to indicate salts prepared by reacting a compound of formula A or B with a suitable inorganic or organic acid, such as hydrochloric, hydrobromic, hydroiodic, sulfuric, nitric, phosphoric, formic, acetic, 2,2-dichloroaetic, adipic, ascorbic, L-aspartic, L-glutamic, galactaric, lactic, maleic, L-malic, phthalic, citric, propionic, benzoic, glutaric, gluconic, D-glucuronic, methanesulfonic, salicylic, succinic, malonic, tartaric, benzenesulfonic, ethane-1,2-disulfonic, 2-hydroxy ethanesulfonic acid, toluenesulfonic, sulfamic or fumaric acid.

The term "solvate" is intended to indicate a species formed by interaction between a compound, e.g. a compound of formula A, and a solvent, e.g. alcohol, glycerol or water, wherein said species are in a solid form. When water is the solvent, said species is referred to as a hydrate.

The term 'non-surmountable antagonist' or 'insurmountable antagonist' is intended to indicate an antagonist which produces shifts to the right of agonist concentration-response curves in the presence of increasing antagonist concentrations with depression of the maximal response to the agonist (ref. Kenakin, T. et. al., J. Pharm. Exp. Ther., (2006), 319, p. 710-723).

The term 'surmountable antagonist' is intended to indicate an antagonist which produces shifts to the right of agonist concentration-response curves in the presence of increasing antagonist concentrations with no concomitant diminution of the maximal response to the agonist. (ref. Kenakin, T. et. al., J. Pharm. Exp. Ther., (2006), 319, p. 710-723).

Chronic pruritus on diseased skin is intended to indicate pruritus in skin diseases which are accompanied by itch, such as inflammatory, infectious, or autoimmune cutaneous diseases, genodermatoses, drug reactions, dermatoses of pregnancy and skin lymphomas.

Genodermatoses are intended to include Darier's disease, Hailey-Hailey disease, ichthyoses, Sjögren-Larsson syndrome, EB pruriginosa.

Dermatoses of pregnancy are intended to include polymorphic eruption of pregnancy, pemphigoid gestationis, prurigo gestationis.

Skin lymphomas are intended to include cutaneous T-cell-lymphoma, cutaneous B-cellymphoma.

Pruritic diseases of systemic origin are intended to comprise diseases arising from diseases of organs other than the skin, such as liver, e.g. primary biliary cirrhosis; kidney, e.g. chronic renal failure; blood, e.g. Hodgkin's disease; and certain multifactorial, e.g. metabolic states or drugs.

Pruritic systemic endocrine and metabolic diseases are intended to comprise chronic renal failure, liver diseases with or without cholestasis, hyperthyroidism, malabsorption, perimenopausal pruritus.

Pruritic systemic infectious diseases are intended to comprise HIV-infection, helminthosis, Parasitosis.

Pruritic systemic haematological and lymphoproliferative diseases are intended to comprise iron deficiency, polycythaemia vera, Hodgkin's disease, Non-Hodgkin's lymphoma, plasmocytoma.

Chronic secondary scratch lesions are intended to indicate secondary acquired lesions induced by chronic scratching, such as for example lichen simplex chronicus, lichen Vidal, lichen amyloidosus, macular amyloidosus, and prurigo nodularis.

Embodiments of the Present Invention

In an embodiment the present invention relates to compounds of general formula A,
wherein
n is 1 or 2;
R1 and R2 are independently hydrogen, $C_{1-4}$ alkyl, $C_{1-4}$ haloalkyl, $C_{1-4}$ alkoxy or halogen;
R3 is hydrogen, C(=O)OR7 or $C_{1-4}$ alkyl optionally substituted with hydroxy or NR8R9;
R4 is hydrogen or oxo;
R5 and R6 are independently hydrogen, hydroxy, NR8R9, C(=O)R7, C(=O)OR7, C(=O)NR8R9, $C_{1-4}$ alkyl optionally substituted with hydroxy, NR8R9 or a 5- or 6-membered heterocyclic ring optionally substituted with $C_{1-4}$ alkyl or C(=O)R7, or R5 and R6, together with the carbon atom to which they are attached, form =CH$_2$ or a 5- or 6-membered heterocyclic ring optionally substituted with $C_{1-4}$ alkyl;
R7 is hydrogen or $C_{1-4}$ alkyl;

R8 and R9 are independently hydrogen or $C_{1-4}$ alkyl, or N8 and R9, together with the nitrogen atom to which they are attached, form a 5- or 6-membered heterocyclic ring, or a pharmaceutically acceptable salt or solvate thereof.

In an embodiment, n in general formula A is 1.

In an embodiment, R4 is oxo.

In an embodiment, R4 is hydrogen.

In an embodiment, R3 is hydrogen, $CH_3$, $CH_2OH$, $CH_2CH_2OH$, $COOCH_3$ or $CH_2N(CH_3)_2$.

In an embodiment, R5 and R6 are both hydrogen.

In an embodiment, R5 is hydrogen, $CH_3$, $CH_2OH$ or $CH_2CH_2OH$, and R6 is COOH, $COOCH_3$, $CH_2OH$, $CH_2CH_2OH$, $CON(CH_3)_2$ or $CH_2$-morpholine, $CH_2$-pyrrolidine, $CH_2$-piperazine optionally N-substituted with acetyl, or $CH_2$-piperidine.

In an embodiment R5 is hydrogen, $CH_3$, $CH_2OH$ or $CH_2CH_2OH$, and R6 is COOH, $COOCH_3$, $CH_2OH$, $CH_2CH_2OH$, $CON(CH_3)_2$ or $CH_2$-morpholine, $CH_2$-pyrrolidine, $CH_2$-piperazine optionally N-substituted with acetyl, or $CH_2$-piperidine.

In an embodiment, R5 and R6, together with the carbon atom to which they are attached form a piperidine ring optionally substituted with $C_{1-4}$ alkyl.

In an embodiment, R5 and R6, together with the carbon atom to which they are attached form $=CH_2$, a piperidine ring optionally substituted with $C_{1-4}$ alkyl, or a tetrahydropyran ring.

In an embodiment, the compound is one of general formula A(iii)

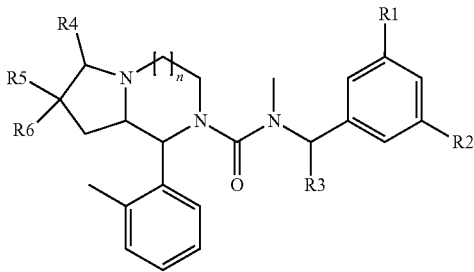

A(iii)

wherein n, R1, R2, R3, R4, R5 and R6 are as indicated above, or a pharmaceutically acceptable salt or solvate thereof.

In an embodiment, R1 is hydrogen, $CH_3$, fluoro or trifluoromethyl.

In an embodiment, R2 is hydrogen, $CH_3$ or trifluoromethyl.

In an embodiment, R2 is hydrogen, chloro, $CH_3$, $CH_2CH_3$, isopropyl, $OCH_3$, difluoromethyl or trifluoromethyl.

In an embodiment, R1 and R2 are both trifluoromethyl.

In an embodiment, R1 is trifluoromethyl and R2 is methyl, ethyl or isopropyl.

Specific examples of compounds of the invention are selected from the group consisting of N-[(3,5-dimethylphenyl)methyl]-N-methyl-1-(2-methylphenyl)-6-oxo-octahydropyrrolo[1,2-a]piperazine-2-carboxamide N-[(3,5-dimethylphenyl)methyl]-N-methyl-1-(2-methylphenyl)-6-oxo-octahydropyrrolo[1,2-a]piperazine-2-carboxamide N-{[3-fluoro-5-(trifluoromethyl)phenyl]methyl}-N-methyl-1-(2-methylphenyl)-6-oxo-octahydropyrrolo[1,2-a]piperazine-2-carboxamide N-{[3-fluoro-5-(trifluoromethyl)phenyl]methyl}-N-methyl-1-(2-methylphenyl)-6-oxo-octahydropyrrolo[1,2-a]piperazine-2-carboxamide N-methyl-1-(2-methylphenyl)-6-oxo-N-{[3-(trifluoromethyl)phenyl]methyl}-octahydropyrrolo[1,2-a]piperazine-2-carboxamide N-methyl-1-(2-methylphenyl)-6-oxo-N-{[3-(trifluoromethyl)phenyl]methyl}-octahydropyrrolo[1,2-a]piperazine-2-carboxamide N-{[3,5-bis(trifluoromethyl)phenyl]methyl}-N-methyl-1-(2-methylphenyl)-7-oxo-octahydro-1H-pyrrolo[1,2-a][1,4]diazepine-2-carboxamide 2-({[3,5-bis(trifluoromethyl)phenyl]methyl}(methyl)carbamoyl)-7-methyl-1-(2-methylphenyl)-6-oxo-octahydropyrrolo[1,2-a]piperazine-7-carboxylic acid N-[(1R)-1-[3,5-bis(trifluoromethyl)phenyl]ethyl]-N-methyl-1-(2-methylphenyl)-6-oxo-octahydropyrrolo[1,2-a]piperazine 2 carboxamide N-[(1R)-1-[3,5-bis(trifluoromethyl)phenyl]ethyl]-N-methyl-1-(2-methylphenyl)-6-oxo-octahydropyrrolo[1,2-a]piperazine 2 carboxamide Methyl 2-({[3,5-bis(trifluoromethyl)phenyl]methyl}(methyl)carbamoyl)-7-methyl-1-(2-methylphenyl)-6-oxo-octahydropyrrolo{1,2-a}piperazine-7-carboxylate Methyl 2-({[3,5-bis(trifluoromethyl)phenyl]methyl}(methyl)carbamoyl)-7-methyl-1-(2-methylphenyl)-6-oxo-octahydropyrrolo{1,2-a}piperazine-7-carboxylate Methyl 2-({[3,5-bis(trifluoromethyl)phenyl]methyl}(methyl)carbamoyl)-7-methyl-1-(2-methylphenyl)-6-oxo-octahydropyrrolo{1,2-a}piperazine-7-carboxylate Methyl 2-({[3,5-bis(trifluoromethyl)phenyl]methyl}(methyl)carbamoyl)-7-methyl-1-(2-methylphenyl)-6-oxo-octahydropyrrolo{1,2-a}piperazine-7-carboxylate Methyl 2-({[3,5-bis(trifluoromethyl)phenyl]methyl}(methyl)carbamoyl)-7-methyl-1-(2-methylphenyl)-6-oxo-octahydropyrrolo{1,2-a}piperazine-7-carboxylate N-{[3,5-bis(trifluoromethyl)phenyl]methyl}-N-methyl-1-(2-methylphenyl)-6-oxo-octahydropyrrolo[1,2-a]piperazine-2-carboxamide N-{[3,5-bis(trifluoromethyl)phenyl]methyl}-N-methyl-1-(2-methylphenyl)-6-oxo-octahydropyrrolo[1,2-a]piperazine-2-carboxamide N-{[3,5-bis(trifluoromethyl)phenyl]methyl}-N-methyl-1-(2-methylphenyl)-6-oxo-octahydropyrrolo[1,2-a]piperazine-2-carboxamide N-{[3,5-bis(trifluoromethyl)phenyl]methyl}-7-(hydroxymethyl)-N-methyl-1-(2-methylphenyl)-6-oxo-octahydropyrrolo[1,2-a]piperazine-2-carboxamide N-{[3,5-bis(trifluoromethyl)phenyl]methyl}-7-(hydroxyethyl)-N-methyl-1-(2-methylphenyl)-6-oxo-octahydropyrrolo[1,2-a]piperazine-2-carboxamide N-{[3,5-bis(trifluoromethyl)phenyl]methyl}-7-(hydroxyethyl)-N-methyl-1-(2-methylphenyl)-6-oxo-octahydropyrrolo[1,2-a]piperazine-2-carboxamide N-{[3,5-bis(trifluoromethyl)phenyl]methyl}-7-(hydroxyethyl)-N-methyl-1-(2-methylphenyl)-6-oxo-octahydropyrrolo[1,2-a]piperazine-2-carboxamide N-{[3,5-bis(trifluoromethyl)phenyl]methyl}-7-(hydroxyethyl)-N-methyl-1-(2-methylphenyl)-6-oxo-octahydropyrrolo[1,2-a]piperazine-2-carboxamide N-{[3,5-bis(trifluoromethyl)phenyl]methyl}-N-methyl-1-(2-methylphenyl)-octahydropyrrolo[1,2-a]piperazine-2-carboxamide 2-N-{[3,5-bis(trifluoromethyl)phenyl]methyl}-2-N,7-N,7-N,7-tetramethyl-1-(2-methylphenyl)-6-oxo-octahydropyrrolo[1,2-a]piperazine-2,7-dicarboxamide 2-N-{[3,5-bis(trifluoromethyl)phenyl]methyl}-2-N,7-N,7-N,7-tetramethyl-1-(2-methylphenyl)-6-oxo-octahydropyrrolo[1,2-a]piperazine-2,7-dicarboxamide N-{[3,5-bis(trifluoromethyl)phenyl]methyl}-7-(hydroxymethyl)-N-methyl-1-(2-methylphenyl)-octahydropyrrolo[1,2-a]piperazine-2-carboxamide methanesulfonic acid salt N-{[3,5-bis(trifluoromethyl)phenyl]methyl}-7-(hydroxymethyl)-N-methyl-1-(2-methylphenyl)-octahydropyrrolo[1,2-a]piperazine-2-carboxamide methanesulfonic acid salt N-{[3,5-bis(trifluoromethyl)phenyl]methyl}-N-methyl-1-(2-methylphenyl)-7-(morpholin-4-ylmethyl)-6-oxo-octahydropyrrolo[1,2-a]piperazine-2-carboxamide N-{[3,5-bis(trifluoromethyl)phenyl]methyl}-N-methyl-1-(2-methylphenyl)-6-oxo-7-(pyrrolidin-1-ylmethyl)-octahydropyrrolo[1,2-a]piperazine-2-carboxamide N-{[3,5-bis(trifluoromethyl)phenyl]methyl}-N-ethyl-1-(2-methylphenyl)-6-oxo-7-(pyrrolidin-1-ylmethyl)-octahydropyrrolo[1,2-a]piperazine-2-carboxamide N-{[3,5-bis(trifluoromethyl)phenyl]methyl}-N-methyl-7-methylidene-1-(2-methylphenyl)-6-oxo-octahydropyrrolo[1,2-a]piperazine-2-carboxamide N-{1-[3,5-bis(trifluoromethyl)phenyl]-3-hydroxypropyl}-7-(2-hydroxyethyl)-N-methyl-1-(2-methylphenyl)-6-oxo-octahydropyrrolo[1,2-a]piperazine-2-carboxamide N-{1-[3,5-bis(trifluoromethyl)phenyl]-3-hydroxypropyl}-7-(2-hydroxyethyl)-N-methyl-1-(2-methylphenyl)-6-oxo-octahydropyrrolo[1,2-a]piperazine-2-carboxamide N-{1-[3,5-bis(trifluoromethyl)phenyl]-3-hydroxypropyl}-7-(2-hydroxyethyl)-N-methyl-1-(2-methylphenyl)-6-oxo-octahydropyrrolo[1,2-a]piperazine-2-carboxamide N-{1-[3,5-bis(trifluoromethyl)phenyl]-3-hydroxypropyl}-7-(2-hydroxyethyl)-N-methyl-1-(2-methylphenyl)-octahydropyrrolo[1,2-a]piperazine-2-carboxamide 7-[(4-acetylpiperazin-1-yl)methyl]-N-{[3,5-bis(trifluoromethyl)phenyl]methyl}-N-methyl-1-(2-methylphenyl)-6-oxo-octahydropyrrolo[1,2-a]piperazine-2-carboxamide N-{[3,4-bis(trifluoromethyl)phenyl]methyl}-N-methyl-1-(2-methylphenyl)-7-(morpholin-4-ylmethyl)-6-oxa-octahydropyrrolo[1,2-a]piperazine-2-carboxamide as methansulfonic acid salt N-{[3,4-bis(trifluoromethyl)phenyl]methyl}-N-methyl-1-(2-methylphenyl)-7-(morpholin-4-ylmethyl)-6-oxa-octahydropyrrolo[1,2-a]piperazine-2-carboxamide methansulfonic acid salt N-{[3,4-bis(trifluoromethyl)phenyl]methyl}-N-methyl-1-(2-methylphenyl)-7-(morpholin-4-ylmethyl)-6-oxa-octahydropyrrolo[1,2-a]piperazine-2-carboxamide methansulfonic acid salt N-{[3,4-bis(trifluoromethyl)phenyl]methyl}-N-methyl-1-(2-methylphenyl)-7-(morpholin-4-ylmethyl)-6-oxa-octahydropyrrolo[1,2-a]piperazine-2-carboxamide methansulfonic acid salt N-{[3,5-bis(trifluoromethyl)phenyl]methyl}-7,7-bis(2-hydroxyethyl)-N-methyl-1-(2-methylphenyl)-6-oxo-octahydropyrrolo[1,2-a]piperazine-2-carboxamide N-{[3,5-bis(trifluoromethyl)phenyl]methyl}-7,7-bis(2-hydroxyethyl)-N-methyl-1-(2-methylphenyl)-6-oxo-octahydropyrrolo[1,2-a]piperazine-2-carboxamide N-{[3,5-bis(trifluoromethyl)phenyl]methyl}-7,7-bis(2-hydroxyethyl)-N-methyl-1-(2-methylphenyl)-6-oxo-octahydropyrrolo[1,2-a]piperazine-2-carboxamide (3'aS,4'S)-N-{[3,5-bis(trifluoromethyl)phenyl]methyl}-N,1-dimethyl-4'-(2-methylphenyl)-1'-oxo-hexahydro-1'H-spiro[piperidine-4,2'-pyrrolo[1,2-a]piperazine]-5'-carboxamide N-{[3,5-bis(trifluoromethyl)phenyl]methyl}-N,1-dimethyl-4'-(2-methylphenyl)-1'-oxo-hexahydro-1'H-spiro[piperidine-4,2'-pyrrolo[1,2-a]piperazine]-5'-carboxamide N-{[3,5-bis(trifluoromethyl)phenyl]methyl}-N,1-dimethyl-4'-(2-methylphenyl)-1'-oxo-hexahydro-1'H-spiro[piperidine-4,2'-pyrrolo[1,2-a]piperazine]-5'-carboxamide N-{[3,5-bis(trifluoromethyl)phenyl]methyl}-7-(hydroxymethyl)-N-methyl-1-(2-methylphenyl)-octahydropyrrolo[1,2-a]piperazine-2-carboxamide N-{[3,5-bis(trifluoromethyl)phenyl]methyl}-7-(hydroxymethyl)-N-methyl-1-(2-methylphenyl)-octahydropyrrolo[1,2-a]piperazine-2-carboxamide In an embodiment specific examples of compounds of the invention are selected from the group consisting of N-[(3,5-dimethylphenyl)methyl]-N-methyl-1-(2-methylphenyl)-6-oxo-octahydropyrrolo[1,2-a]piperazine-2-carboxamide, N-[(3,5-dimethylphenyl)methyl]-N-methyl-1-(2-methylphenyl)-6-oxo-octahydropyrrolo[1,2-a]piperazine-2-carboxamide, N-{[3-fluoro-5-(trifluoromethyl)phenyl]methyl}-N-methyl-1-(2-methylphenyl)-6-oxo-octahydropyrrolo[1,2-a]piperazine-2-carboxamide, N-{[3-fluoro-5-(trifluoromethyl)phenyl]methyl}-N-methyl-1-(2-methylphenyl)-6-oxo-octahydropyrrolo[1,2-a]piperazine-2-carboxamide, N-methyl-1-(2-methylphenyl)-6-oxo-N-{[3-(trifluoromethyl)phenyl]methyl}-octahydropyrrolo[1,2-a]piperazine-2-carboxamide, N-methyl-1-(2-methylphenyl)-6-oxo-N-{[3-(trifluoromethyl)phenyl]methyl}-octahydropyrrolo[1,2-a]piperazine-2-carboxamide, (1S,8aS)-N-[(1R)-1-[3,5-bis(trifluoromethyl)phenyl]ethyl]-N-methyl-1-(2-methylphenyl)-6-oxo-octahydropyrrolo[1,2-a]piperazine-2-carboxamide, (1R,8aR)-N-[(1R)-1-[3,5-bis(trifluoromethyl)phenyl]ethyl]-N-methyl-1-(2-methylphenyl)-6-oxo-octahydropyrrolo[1,2-a]piperazine-2-carboxamide, N-{[3,5-bis(trifluoromethyl)phenyl]methyl}-N-methyl-1-(2-methylphenyl)-7-oxo-octahydro-1H-pyrrolo[1,2-a][1,4]diazepine-2-carboxamide, 2-({[3,5-bis(trifluoromethyl)phenyl]methyl}(methyl)carbamoyl)-7-methyl-1-(2-methylphenyl)-6-oxo-octahydropyrrolo[1,2-a]piperazine-7-carboxylic acid, N-[(1R)-1-[3,5-bis(trifluoromethyl)phenyl]ethyl]-N-methyl-1-(2-methylphenyl)-6-oxo-octahydropyrrolo[1,2-a]piperazine 2 carboxamide, N-[(1R)-1-[3,5-bis(trifluoromethyl)phenyl]ethyl]-N-methyl-1-(2-methylphenyl)-6-oxo-octahydropyrrolo[1,2-a]piperazine 2 carboxamide, Methyl 2-({[3,5-bis(trifluoromethyl)phenyl]methyl}(methyl)carbamoyl)-7-methyl-1-(2-methylphenyl)-6-oxo-octahydropyrrolo{1,2-a}piperazine-7-carboxylate, Methyl 2-({[3,5-bis(trifluoromethyl)phenyl]methyl}(methyl)carbamoyl)-7-methyl-1-(2-methylphenyl)-6-oxo-octahydropyrrolo{1,2-a}piperazine-7-carboxylate, Methyl 2-({[3,5-bis(trifluoromethyl)phenyl]methyl}(methyl)carbamoyl)-7-methyl-1-(2-methylphenyl)-6-oxo-octahydropyrrolo{1,2-a}piperazine-7-carboxylate, Methyl 2-({[3,5-bis(trifluoromethyl)phenyl]methyl}(methyl)carbamoyl)-7-methyl-1-(2-methylphenyl)-6-oxo-octahydropyrrolo{1,2-a}piperazine-7-carboxylate, Methyl 2-({[3,5-bis(trifluoromethyl)phenyl]methyl}(methyl)carbamoyl)-7-methyl-1-(2-methylphenyl)-6-oxo-octahydropyrrolo{1,2-a}piperazine-7-carboxylate, N-{[3,5-bis(trifluoromethyl)phenyl]methyl}-N-methyl-1-(2-methylphenyl)-6-oxo-octahydropyrrolo[1,2-a]piperazine-2-carboxamide, N-{[3,5-bis(trifluoromethyl)phenyl]methyl}-N-methyl-1-(2-methylphenyl)-6-oxo-octahydropyrrolo[1,2-a]piperazine-2-carboxamide, N-{[3,5-bis(trifluoromethyl)phenyl]methyl}-N-methyl-1-(2-methylphenyl)-6-oxo-octahydropyrrolo[1,2-a]piperazine-2-carboxamide, N-{[3,5-bis(trifluoromethyl)phenyl]methyl}-7-(hydroxymethyl)-N-methyl-1-(2-methylphenyl)-6-oxo-octahydropyrrolo[1,2-a]piperazine-2-carboxamide, N-{[3,5-bis(trifluoromethyl)phenyl]methyl}-7-(hydroxymethyl)-N-methyl-1-(2-methylphenyl)-6-oxo-octahydropyrrolo[1,2-a]piperazine-2-carboxamide, N-{[3,5-bis(trifluoromethyl)phenyl]methyl}-7-(hydroxymethyl)-N-methyl-1-(2-methylphenyl)-6-oxo-octahydropyrrolo[1,2-a]piperazine-2-carboxamide, N-{[3,5-bis(trifluoromethyl)phenyl]methyl}-7-(hydroxymethyl)-N-methyl-1-(2-methylphenyl)-6-oxo-octahydropyrrolo[1,2-a]piperazine-2-carboxamide, N-{[3,5-bis(trifluoromethyl)phenyl]methyl}-7-(hydroxymethyl)-N-methyl-1-(2-methylphenyl)-6-oxo-octahydropyrrolo[1,2-a]piperazine-2-carboxamide, N-{[3,5-bis(trifluoromethyl)phenyl]methyl}-N-methyl-1-(2-methylphenyl)-octahydropyrrolo[1,2-a]piperazine-2-carboxamide, 2-N-{[3,5-bis(trifluoromethyl)phenyl]methyl}-2-N,7-N,7-N,7-tetramethyl-1-(2-methylphenyl)-6-oxo-octahydropyrrolo[1,2-a]piperazine-2,7-dicarboxamide, 2-N-{[3,5-bis(trifluoromethyl)phenyl]methyl}-2-N,7-N,7-N,7-tetramethyl-1-(2-methylphenyl)-6-oxo-octahydropyrrolo[1,2-a]piperazine-2,7-dicarboxamide, N-{[3,5-bis(trifluoromethyl)phenyl]methyl}-7-(hydroxymethyl)-N-methyl-1-(2-methylphenyl)-octahydropyrrolo[1,2-a]piperazine-2-carboxamide methanesulfonic acid salt, N-{[3,5-bis(trifluoromethyl)phenyl]methyl}-7-(hydroxymethyl)-N-methyl-1-(2-methylphenyl)-octahydropyrrolo[1,2-a]piperazine-2-carboxamide methanesulfonic acid salt, N-{[3,5-bis(trifluoromethyl)phenyl]methyl}-N-methyl-1-(2-methylphenyl)-7-(morpholin-4-ylmethyl)-6-oxo-octahydropyrrolo[1,2-a]piperazine-2-carboxamide, N-{[3,5-bis(trifluoromethyl)phenyl]methyl}-N-methyl-1-(2-methylphenyl)-6-oxo-7-(pyrrolidin-1-ylmethyl)-octahydropyrrolo[1,2-a]piperazine-2-carboxamide, N-{[3,5-bis(trifluoromethyl)phenyl]methyl}-N-ethyl-1-(2-methylphenyl)-6-oxo-7-(pyrrolidin-1-ylmethyl)-octahydropyrrolo[1,2-a]piperazine-2-carboxamide, N-{[3,5-bis(trifluoromethyl)phenyl]methyl}-N-methyl-7-methylidene-1-(2-methylphenyl)-6-oxo-octahydropyrrolo[1,2-a]piperazine-2-carboxamide, N-{1-[3,5-bis(trifluoromethyl)phenyl]-3-hydroxypropyl}-7-(2-hydroxyethyl)-N-methyl-1-(2-methylphenyl)-6-oxo-octahydropyrrolo[1,2-a]piperazine-2-carboxamide, N-{1-[3,5-bis(trifluoromethyl)phenyl]-3-hydroxypropyl}-7-(2-hydroxyethyl)-N-methyl-1-(2-methylphenyl)-6-oxo-octahydropyrrolo[1,2-a]piperazine-2-carboxamide, N-{1-[3,5-bis(trifluoromethyl)phenyl]-3-hydroxypropyl}-7-(2-hydroxyethyl)-N-methyl-1-(2-methylphenyl)-6-oxo-octahydropyrrolo[1,2-a]piperazine-2-carboxamide, N-{1-[3,5-bis(trifluoromethyl)phenyl]-3-hydroxypropyl}-7-(2-hydroxyethyl)-N-methyl-1-(2-methylphenyl)-octahydropyrrolo[1,2-a]piperazine-2-carboxamide, 7-[(4-acetylpiperazin-1-yl)methyl]-N-{[3,5-bis(trifluoromethyl)phenyl]methyl}-N-methyl-1-(2-methylphenyl)-6-oxo-octahydropyrrolo[1,2-a]piperazine-2-carboxamide, N-{[3,4-bis(trifluoromethyl)phenyl]methyl}-N-methyl-1-(2-methylphenyl)-7-(morpholin-4-ylmethyl)-6-oxa-octahydropyrrolo[1,2-a]piperazine-2-carboxamide as methansulfonic acid salt, N-{[3,4-bis(trifluoromethyl)phenyl]methyl}-N-methyl-1-(2-methylphenyl)-7-(morpholin-4-ylmethyl)-6-oxa-octahydropyrrolo[1,2-a]piperazine-2-carboxamide methansulfonic acid salt, N-{[3,4-bis(trifluoromethyl)phenyl]methyl}-N-methyl-1-(2-methylphenyl)-7-(morpholin-4-ylmethyl)-6-oxa-octahydropyrrolo[1,2-a]piperazine-2-carboxamide methansulfonic acid salt, N-{[3,4-bis(trifluoromethyl)phenyl]methyl}-N-methyl-1-(2-methylphenyl)-7-(morpholin-4-ylmethyl)-6-oxa-octahydropyrrolo[1,2-a]piperazine-2-carboxamide methansulfonic acid salt, N-{[3,5-bis(trifluoromethyl)phenyl]methyl}-7,7-bis(2-hydroxyethyl)-N-methyl-1-(2-methylphenyl)-6-oxo-octahydropyrrolo[1,2-a]piperazine-2-carboxamide, N-{[3,5-bis(trifluoromethyl)phenyl]methyl}-7,7-bis(2-hydroxyethyl)-N-methyl-1-(2-methylphenyl)-6-oxo-octahydropyrrolo[1,2-a]piperazine-2-carboxamide, N-{[3,5-bis(trifluoromethyl)phenyl]methyl}-7,7-bis(2-hydroxyethyl)-N-methyl-1-(2-methylphenyl)-6-oxo-octahydropyrrolo[1,2-a]piperazine-2-carboxamide, (3'aS,4'S)-N-{[3,5-bis(trifluoromethyl)phenyl]methyl}-N,1-dimethyl-4'-(2-methylphenyl)-1'-oxo-hexahydro-1'H-spiro[piperidine-4,2'-pyrrolo[1,2-a]piperazine]-5'-carboxamide, N-{[3,5-bis(trifluoromethyl)phenyl]methyl}-N,1-dimethyl-4'-(2-methylphenyl)-1'-oxo-hexahydro-1'H-spiro[piperidine-4,2'-pyrrolo[1,2-a]piperazine]-5'-carboxamide, N-{[3,5-bis(trifluoromethyl)phenyl]methyl}-N,1-dimethyl-4'-(2-methylphenyl)-1'-oxo-hexahydro-1'H-spiro[piperidine-4,2'-pyrrolo[1,2-a]piperazine]-5'-carboxamide, N-{[3,5-bis(trifluoromethyl)phenyl]methyl}-7-(hydroxymethyl)-N-methyl-1-(2-methylphenyl)-octahydropyrrolo[1,2-a]piperazine-2-carboxamide, N-{[3,5-bis(trifluoromethyl)phenyl]methyl}-7-(hydroxymethyl)-N-methyl-1-(2-methylphenyl)-octahydropyrrolo[1,2-a]piperazine-2-carboxamide, N-[(1R)-1-[3,5-bis(trifluoromethyl)phenyl]ethyl]-7,7-bis(2-hydroxyethyl)-N-methyl-1-(2-methylphenyl)-6-oxo-octahydropyrrolo[1,2-a]piperazine-2-carboxamide, N-[(1R)-1-[3,5-bis(trifluoromethyl)phenyl]ethyl]-7,7-bis(2-hydroxyethyl)-N-methyl-1-2-methylphenyl)-6-oxo-octahydropyrrolo[1,2-a]piperazine-2-carboxamide, N-[(1R)-1-[3,5-bis(trifluoromethyl)phenyl]ethyl]-7-(hydroxymethyl)-N-methyl-1-(2-methylphenyl)-6-oxo-octahydropyrrolo[1,2-a]piperazine-2-carboxamide, N-[(1R)-1-[3,5-bis(trifluoromethyl)phenyl]ethyl]-7-(hydroxymethyl)-N-methyl-1-(2-methylphenyl)-6-oxo-octahydropyrrolo[1,2-a]piperazine-2-carboxamide, N-[(1R)-1-[3,5-bis(trifluoromethyl)phenyl]ethyl]-7-(hydroxymethyl)-N-methyl-1-(2-methylphenyl)-6-oxo-octahydropyrrolo[1,2-a]piperazine-2-carboxamide, N-[(1R)-1-[3,5-bis(trifluoromethyl)phenyl]ethyl]-7-(hydroxymethyl)-N-methyl-1-(2-methylphenyl)-6-oxo-octahydropyrrolo[1,2-a]piperazine-2-carboxamide, N-[(1R)-1-[3,5-bis(trifluoromethyl)phenyl]ethyl]-7,7-bis(2-hydroxyethyl)-N-methyl-1-(2-methylphenyl)-octahydropyrrolo[1,2-a]piperazine-2-carboxamide, N-[(1R)-1-[3,5-bis(trifluoromethyl)phenyl]ethyl]-7,7-bis(2-hydroxyethyl)-N-methyl-1-(2-methylphenyl)-octahydropyrrolo[1,2-a]piperazine-2-carboxamide, N-{[3,5-bis(trifluoromethyl)phenyl]methyl}-N-methyl-1-(2-methylphenyl)-octahydropyrrolo[1,2-a]piperazine-2-carboxamide, N-{[3,5-bis(trifluoromethyl)phenyl]methyl}-N-methyl-1-(2-methylphenyl)-octahydropyrrolo[1,2-a]piperazine-2-carboxamide, N-[(1R)-1-[3,5-bis(trifluoromethyl)phenyl]ethyl]-N-methyl-1-(2-methylphenyl)-octahydropyrrolo[1,2-a]piperazine-2-carboxamide, N-[(1R)-1-[3,5-bis(trifluoromethyl)phenyl]ethyl]-N-methyl-1-(2-methylphenyl)-octahydropyrrolo[1,2-a]piperazine-2-carboxamide, N-{[3,5-bis(trifluoromethyl)phenyl]methyl}-7,7-bis(2-hydroxyethyl)-N-methyl-1-(2-methylphenyl)-octahydropyrrolo[1,2-a]piperazine-2-carboxamide, N-{[3,5-bis(trifluoromethyl)phenyl]methyl}-7,7-bis(2-hydroxyethyl)-N-methyl-1-(2-methylphenyl)-octahydropyrrolo[1,2-a]piperazine-2-carboxamide, N-[(1R)-1-[3,5-bis(trifluoromethyl)phenyl]ethyl]-7-(hydroxymethyl)-N-methyl-1-(2-methylphenyl)-octahydropyrrolo[1,2-a]piperazine-2-carboxamide, N-[(1R)-1-[3,5-bis(trifluoromethyl)phenyl]ethyl]-7-(hydroxymethyl)-N-methyl-1-(2-methylphenyl)-octahydropyrrolo[1,2-a]piperazine-2-carboxamide, N-[(1R)-1-[3,5-bis(trifluoromethyl)phenyl]ethyl]-7-(hydroxymethyl)-N-methyl-1-(2-methylphenyl)-octahydropyrrolo[1,2-a]piperazine-2-carboxamide, N-[(1R)-1-[3,5-bis(trifluoromethyl)phenyl]ethyl]-7-(hydroxymethyl)-N-methyl-1-(2-methylphenyl)-octahydropyrrolo[1,2-a]piperazine-2-carboxamide, N-[(1R)-1-[3,5-bis(trifluoromethyl)phenyl]ethyl]-N-methyl-1-(2-methylphenyl)-7-(morpholin-4-ylmethyl)-6-oxo-octahydropyrrolo[1,2-a]piperazine-2-carboxamide, N-[(1R)-1-[3,5-bis(trifluoromethyl)phenyl]ethyl]-N-methyl-1-(2-methylphenyl)-7-(morpholin-4-ylmethyl)-6-oxo-octahydropyrrolo[1,2-a]piperazine-2-carboxamide, N-[(1R)-1-[3,5-bis(trifluoromethyl)phenyl]ethyl]-N-methyl-1-(2-methylphenyl)-7-(morpholin-4-ylmethyl)-6-oxo-octahydropyrrolo[1,2-a]piperazine-2-carboxamide, N-[(1R)-1-[3,5-bis(trifluoromethyl)phenyl]ethyl]-N-methyl-1-(2-methylphenyl)-7-(morpholin-4-ylmethyl)-6-oxo-octahydropyrrolo[1,2-a]piperazine-2-carboxamide, N-[(1R)-1-[3,5-bis(trifluoromethyl)phenyl]ethyl]-N-methyl-1-(2-methylphenyl)-6-oxo-octahydropyrrolo[1,2-a]piperazine 2 carboxamide, (1S,8aS)-N-(3-fluoro-5-(trifluoromethyl)benzyl)-7,7-bis(2-hydroxyethyl)-N-methyl-6-oxo-1-o-tolylhexahydropyrrolo[1,2-a]pyrazine-2(1H)-carboxamide, (1S,8aS)-7,7-bis(2-hydroxyethyl)-N-methyl-N-(3-methyl-5-(trifluoromethyl)benzyl)-6-oxo-1-o-tolylhexahydropyrrolo[1,2-a]pyrazine-2(1H)-carboxamide, (1S,8aS)-7,7-bis(2-hydroxyethyl)-N-(3-methoxy-5-(trifluoromethyl)benzyl)-N-methyl-6-oxo-1-o-tolylhexahydropyrrolo[1,2-a]pyrazine-2(1H)-carboxamide, (1S,8aS)-N-(3-chloro-5-(trifluoromethyl)benzyl)-7,7-bis(2-hydroxyethyl)-N-methyl-6-oxo-1-o-tolylhexahydropyrrolo[1,2-a]pyrazine-2(1H)-carboxamide, (1S,8aS)-7,7-bis(2-hydroxyethyl)-N-methyl-6-oxo-1-o-tolyl-N-(3-(trifluoromethyl)benzyphexahydropyrrolo[1,2-a]pyrazine-2(1H)-carboxamide, (1S,8aS)-N-(1-(3,5-bis(trifluoromethyl)phenyl)-3-hydroxypropyl)-7,7-bis(2-hydroxyethyl)-N-methyl-6-oxo-1-o-tolylhexahydropyrrolo[1,2-a]pyrazine-2(1H)-carboxamide, (1S,8aS)-N-(1-(3,5-bis(trifluoromethyl)phenyl)propyl)-7,7-bis(2-hydroxyethyl)-N-methyl-6-oxo-1-o-tolylhexahydropyrrolo[1,2-a]pyrazine-2(1H)-carboxamide, (1S,8aS)-7,7-bis(2-hydroxyethyl)-N-methyl-N-((S)-1-(3-methyl-5-(trifluoromethyl)phenyl)ethyl)-6-oxo-1-o-tolyl-hexahydropyrrolo[1,2-a]pyrazine-2(1H)-carboxamide, (1S,8aS)-7,7-bis(2-hydroxyethyl)-N-methyl-N-((R)-1-(3-methyl-5-(trifluoromethyl)phenyl)ethyl)-6-oxo-1-o-tolyl-hexahydropyrrolo[1,2-a]pyrazine-2(1H)-carboxamide, (1S,8aS)-N-((S)-1-(3,5-bis(trifluoromethyl)phenyl)-2-hydroxyethyl)-7,7-bis(2-hydroxyethyl)-N-methyl-6-oxo-1-o-tolylhexahydropyrrolo[1,2-a]pyrazine-2(1H)-carboxamide, (1S,8aS)-N-((R)-1-(3,5-bis(trifluoromethyl)phenyl)-2-hydroxyethyl)-7,7-bis(2-hydroxyethyl)-N-methyl-6-oxo-1-o-tolylhexahydropyrrolo[1,2-a]pyrazine-2(1H)-carboxamide, (1S,8aS)-7,7-bis(2-hydroxyethyl)-N-methyl-6-oxo-1-o-tolyl-N-((R)-1-(3-(trifluoromethyl)phenyl)ethyphexahydropyrrolo[1,2-a]pyrazine-2(1H)-carboxamide, (1S,8aS)-N-((R)-1-(3-chloro-5-(trifluoromethyl)phenyl)ethyl)-7,7-bis(2-hydroxyethyl)-N-methyl-6-oxo-1-o-tolylhexahydropyrrolo[1,2-a]pyrazine-2(1H)-carboxamide, (1S,8aS)-N-((S)-1-(3-chloro-5-(trifluoromethyl)phenyl)ethyl)-7,7-bis(2-hydroxyethyl)-N-methyl-6-oxo-1-o-tolylhexahydropyrrolo[1,2-a]pyrazine-2(1H)-carboxamide, (1S,8aS)-7,7-bis(2-hydroxyethyl)-N-((R)-1-(3-methoxy-5-(trifluoromethyl)phenyl)ethyl)-N-methyl-6-oxo-1-o-tolylhexahydropyrrolo[1,2-a]pyrazine-2(1H)-carboxamide, (1S,8aS)-N-((S)-1-(3-fluoro-5-(trifluoromethyl)phenyl)ethyl)-7,7-bis(2-hydroxyethyl)-N-methyl-6-oxo-1-o-tolylhexahydropyrrolo[1,2-a]pyrazine-2(1H)-carboxamide, (1S,8aS)-N-((R)-1-(3-fluoro-5-(trifluoromethyl)phenyl)ethyl)-7,7-bis(2-hydroxyethyl)-N-methyl-6-oxo-1-o-tolylhexahydropyrrolo[1,2-a]pyrazine-2(1H)-carboxamide, (1S,8aS)-N-((S)-1-(3-fluoro-5-(trifluoromethyl)phenyl)-2-hydroxyethyl)-7,7-bis(2-hydroxyethyl)-N-methyl-6-oxo-1-o-tolylhexahydropyrrolo[1,2-a]pyrazine-2(1H)-carboxamide, (1S,8aS)-N-((S)-2-hydroxy-1-(3-methoxy-5-(trifluoromethyl)phenyl)ethyl)-7,7-bis(2-hydroxyethyl)-N-methyl-6-oxo-1-o-tolylhexahydropyrrolo[1,2-a]pyrazine-2(1H)-carboxamide, (1S,8aS)-N-((S)-2-hydroxy-1-(3-(trifluoromethyl)phenyl)ethyl)-7,7-bis(2-hydroxyethyl)-N-methyl-6-oxo-1-o-tolylhexahydropyrrolo[1,2-a]pyrazine-2(1H)-carboxamide, (1S,8aS)-N-((S)-2-hydroxy-1-(3-methyl-5-(trifluoromethyl)phenyl)ethyl)-7,7-bis(2-hydroxyethyl)-N-methyl-6-oxo-1-o-tolylhexahydropyrrolo[1,2-a]pyrazine-2(1H)-carboxamide, (1S,8aS)-N-((R)-1-(3-(difluoromethyl)-5-(trifluoromethyl)phenyl)ethyl)-7,7-bis(2-hydroxyethyl)-N-methyl-6-oxo-1-o-tolylhexahydropyrrolo[1,2-a]pyrazine-2(1H)-carboxamide, (1S,8aS)-N-((R)-1-(3-(difluoromethyl)-5-(trifluoromethyl)phenyl)ethyl)-7,7-bis(2-hydroxyethyl)-N-methyl-6-oxo-1-o-tolylhexahydropyrrolo[1,2-a]pyrazine-2(1H)-carboxamide, (1S,8aS)-N-((S)-1-(3,5-bis(trifluoromethyl)phenyl)ethyl)-7,7-bis(2-hydroxyethyl)-N-methyl-6-oxo-1-o-tolylhexahydropyrrolo[1,2-a]pyrazine-2(1H)-carboxamide, (1'S,8a'S)-N-((R)-1-(3,5-bis(trifluoromethyl)phenyl)ethyl)-N-methyl-6'-oxo-1'-o-tolyloctahydro-1'H-spiro[pyran-4,7'-pyrrolo[1,2-a]pyrazine]-2'(6'H)-carboxamide, (1'S,8a'S)-N-((R)-1-(3,5-bis(trifluoromethyl)phenyl)ethyl)-N-methyl-6'-oxo-1'-o-tolyloctahydro-1'H-spiro[pyran-4, 7'-pyrrolo[1,2-a]pyrazine]-2'(6'H)-carboxamide, (1S,8aS)-7-(hydroxymethyl)-N-methyl-N-((R)-1-(3-methyl-5-(trifluoromethyl)phenyl)ethyl)-6-oxo-1-o-tolyl-hexahydropyrrolo[1,2-a]pyrazine-2(1H)-carboxamide, (1S,8aS)-7,7-bis(hydroxymethyl)-N-methyl-N-((R)-1-(3-methyl-5-(trifluoromethyl)phenyl)ethyl)-6-oxo-1-o-tolyl-hexahydropyrrolo[1,2-a]pyrazine-2(1H)-carboxamide, (1S,8aS)-N-((R)-1-(3,5-bis(trifluoromethyl)phenyl)ethyl)-7, 7-bis(hydroxymethyl)-N-methyl-6-oxo-1-o-tolylhexahydropyrrolo[1,2-a]pyrazine-2(1H)-carboxamide, (1'S,8a'S)-N-((R)-1-(3,5-bis(trifluoromethyl)phenyl)ethyl)-N,1-dimethyl-6'-oxo-1'-o-tolyltetrahydro-1'H-spiro[piperidine-4,7'-pyrrolo[1,2-a]pyrazine]-2'(6'H)-carboxamide, formic acid salt, (1'S,8a'S)-N-((R)-1-(3,5-bis(trifluoromethyl)phenyl)ethyl)-N-methyl-6'-oxo-1'-o-tolyltetrahydro-1'H-spiro[piperidine-4,7'-pyrrolo[1,2-a]pyrazine]-2'(6'H)-carboxamide, formic acid salt, (1S,8aS)-N-methyl-N-((R)-1-(3-methyl-5-(trifluoromethyl) phenyl)ethyl)-6-oxo-1-o-tolylhexahydropyrrolo[1,2-a] pyrazine-2(1H)-carboxamide, (1S,8aS)-N-((R)-1-(3-chloro-5-(trifluoromethyl)phenyl) ethyl)-7,7-bis(hydroxymethyl)-N-methyl-6-oxo-1-o-tolylhexahydropyrrolo[1,2-a]pyrazine-2(1H)-carboxamide, (1S,8aS)-N-((R)-1-(3-ethyl-5-(trifluoromethyl)phenyl) ethyl)-N-methyl-6-oxo-1-o-tolylhexahydropyrrolo[1,2-a] pyrazine-2(1H)-carboxamide, (1S,8aS)-N-((R)-1-(3-ethyl-5-(trifluoromethyl)phenyl) ethyl)-7,7-bis(2-hydroxyethyl)-N-methyl-6-oxo-1-o-tolylhexahydropyrrolo[1,2-a]pyrazine-2(1H)-carboxamide, (1S,8aS)-N-((R)-1-(3-isopropyl-5-(trifluoromethyl)phenyl) ethyl)-N-methyl-6-oxo-1-o-tolylhexahydropyrrolo[1,2-a] pyrazine-2(1H)-carboxamide, (1S,8aS)-7,7-bis(2-hydroxyethyl)-N-((R)-1-(3-isopropyl-5-(trifluoromethyl)phenyl)ethyl) -N-methyl-6-oxo-1-o-tolylhexahydropyrrolo[1,2-a]pyrazine-2(1H)-carboxamide or a pharmaceutically acceptable salt or solvate thereof.

In an embodiment specific examples of compounds of the invention are selected from the group consisting of N-[(1R)-1-[3,5-bis(trifluoromethyl)phenyl]ethyl]-7,7-bis(2-hydroxyethyl)-N-methyl-1-(2-methylphenyl)-6-oxo-octahydropyrrolo[1,2-a]piperazine-2-carboxamide, N-[(1R)-1-[3,5-bis(trifluoromethyl)phenyl]ethyl]-7,7-bis(2-hydroxyethyl)-N-methyl-1-2-methylphenyl)-6-oxo-octahydropyrrolo[1,2-a]piperazine-2-carboxamide, N-[(1R)-1-[3,5-bis(trifluoromethyl)phenyl]ethyl]-7-(hydroxymethyl)-N-methyl-1-(2-methylphenyl)-6-oxo-octahydropyrrolo[1,2-a]piperazine-2-carboxamide, N-[(1R)-1-[3,5-bis(trifluoromethyl)phenyl]ethyl]-7-(hydroxymethyl)-N-methyl-1-(2-methylphenyl)-6-oxo-octahydropyrrolo[1,2-a]piperazine-2-carboxamide, N-[(1R)-1-[3,5-bis(trifluoromethyl)phenyl]ethyl]-7-(hydroxymethyl)-N-methyl-1-(2-methylphenyl)-6-oxo-octahydropyrrolo[1,2-a]piperazine-2-carboxamide, N-[(1R)-1-[3,5-bis(trifluoromethyl)phenyl]ethyl]-7-(hydroxymethyl)-N-methyl-1-(2-methylphenyl)-6-oxo-octahydropyrrolo[1,2-a]piperazine-2-carboxamide, N-[(1R)-1-[3,5-bis(trifluoromethyl)phenyl]ethyl]-7,7-bis(2-hydroxyethyl)-N-methyl-1-(2-methylphenyl)-octahydropyrrolo[1,2-a]piperazine-2-carboxamide, N-[(1R)-1-[3,5-bis(trifluoromethyl)phenyl]ethyl]-7,7-bis(2-hydroxyethyl)-N-methyl-1-(2-methylphenyl)-octahydropyrrolo[1,2-a]piperazine-2-carboxamide, N-{[3,5-bis(trifluoromethyl)phenyl]methyl}-N-methyl-1-(2-methylphenyl)-octahydropyrrolo[1,2-a]piperazine-2-carboxamide, N-{[3,5-bis(trifluoromethyl)phenyl]methyl}-N-methyl-1-(2-methylphenyl)-octahydropyrrolo[1,2-a]piperazine-2-carboxamide, N-[(1R)-1-[3,5-bis(trifluoromethyl)phenyl]ethyl]-N-methyl-1-(2-methylphenyl)-octahydropyrrolo[1,2-a]piperazine-2-carboxamide, N-[(1R)-1-[3,5-bis(trifluoromethyl)phenyl]ethyl]-N-methyl-1-(2-methylphenyl)-octahydropyrrolo[1,2-a]piperazine-2-carboxamide, N-{[3,5-bis(trifluoromethyl)phenyl]methyl}-7,7-bis(2-hydroxyethyl)-N-methyl-1-(2-methylphenyl)-octahydropyrrolo[1,2-a]piperazine-2-carboxamide, N-{[3,5-bis(trifluoromethyl)phenyl]methyl}-7,7-bis(2-hydroxyethyl)-N-methyl-1-(2-methylphenyl)-octahydropyrrolo[1,2-a]piperazine-2-carboxamide, N-[(1R)-1-[3,5-bis(trifluoromethyl)phenyl]ethyl]-7-(hydroxymethyl)-N-methyl-1-(2-methylphenyl)-octahydropyrrolo[1,2-a]piperazine-2-carboxamide, N-[(1R)-1-[3,5-bis(trifluoromethyl)phenyl]ethyl]-7-(hydroxymethyl)-N-methyl-1-(2-methylphenyl)-octahydropyrrolo[1,2-a]piperazine-2-carboxamide, N-[(1R)-1-[3,5-bis(trifluoromethyl)phenyl]ethyl]-7-(hydroxymethyl)-N-methyl-1-(2-methylphenyl)-octahydropyrrolo[1,2-a]piperazine-2-carboxamide, N-[(1R)-1-[3,5-bis(trifluoromethyl)phenyl]ethyl]-N-methyl-1-(2-methylphenyl)-7-(morpholin-4-ylmethyl)-6-oxo-octahydropyrrolo[1,2-a]piperazine-2-carboxamide, N-[(1R)-1-[3,5-bis(trifluoromethyl)phenyl]ethyl]-N-methyl-1-(2-methylphenyl)-7-(morpholin-4-ylmethyl)-6-oxo-octahydropyrrolo[1,2-a]piperazine-2-carboxamide, N-[(1R)-1-[3,5-bis(trifluoromethyl)phenyl]ethyl]-N-methyl-1-(2-methylphenyl)-7-(morpholin-4-ylmethyl)-6-oxo-octahydropyrrolo[1,2-a]piperazine-2-carboxamide, N-[(1R)-1-[3,5-bis(trifluoromethyl)phenyl]ethyl]-N-methyl-1-(2-methylphenyl)-7-(morpholin-4-ylmethyl)-6-oxo-octahydropyrrolo[1,2-a]piperazine-2-carboxamide, N-[(1R)-1-[3,5-bis(trifluoromethyl)phenyl]ethyl]-N-methyl-1-(2-methylphenyl)-6-oxo-octahydropyrrolo[1,2-a] piperazine 2 carboxamide, (1S,8aS)-N-(3-fluoro-5-(trifluoromethyl)benzyl)-7,7-bis(2-hydroxyethyl)-N-methyl-6-oxo-1-o-tolylhexahydropyrrolo[1,2-a]pyrazine-2(1H)-carboxamide, (1S,8aS)-7,7-bis(2-hydroxyethyl)-N-methyl-N-(3-methyl-5-(trifluoromethyl)benzyl)-6-oxo-1-o-tolylhexahydropyrrolo[1,2-a]pyrazine-2(1H)-carboxamide, (1S,8aS)-7,7-bis(2-hydroxyethyl)-N-(3-methoxy-5-(trifluoromethyl)benzyl)-N-methyl-6-oxo-1-o-tolylhexahydropyrrolo[1,2-a]pyrazine-2(1H)-carboxamide, (1S,8aS)-N-(3-chloro-5-(trifluoromethyl)benzyl)-7,7-bis(2-hydroxyethyl)-N-methyl-6-oxo-1-o-tolylhexahydropyrrolo[1,2-a]pyrazine-2(1H)-carboxamide, (1S,8aS)-7,7-bis(2-hydroxyethyl)-N-methyl-6-oxo-1-o-tolyl-N-(3-(trifluoromethyl)benzyphexahydropyrrolo[1, 2-a]pyrazine-2(1H)-carboxamide, (1S,8aS)-N-(1-(3,5-bis(trifluoromethyl)phenyl)-3-hydroxypropyl)-7,7-bis(2-hydroxyethyl)-N-methyl-6-oxo-1-o-tolylhexahydropyrrolo[1,2-a]pyrazine-2(1H)-carboxamide, (1S,8aS)-N-(1-(3,5-bis(trifluoromethyl)phenyl)propyl)-7,7-bis(2-hydroxyethyl)-N-methyl-6-oxo-1-o-tolylhexahydropyrrolo[1,2-a]pyrazine-2(1H)-carboxamide, (1S,8aS)-7,7-bis(2-hydroxyethyl)-N-methyl-N-((S)-1-(3-methyl-5-(trifluoromethyl)phenyl)ethyl)-6-oxo-1-o-tolyl-hexahydropyrrolo[1,2-a]pyrazine-2(1H)-carboxamide, (1S,8aS)-7,7-bis(2-hydroxyethyl)-N-methyl-N-((R)-1-(3-methyl-5-(trifluoromethyl)phenyl)ethyl)-6-oxo-1-o-tolyl-hexahydropyrrolo[1,2-a]pyrazine-2(1H)-carboxamide, (1S,8aS)-N-((S)-1-(3,5-bis(trifluoromethyl)phenyl)-2-hydroxyethyl)-7,7-bis(2-hydroxyethyl)-N-methyl-6-oxo-1-o-tolylhexahydropyrrolo[1,2-a]pyrazine-2(1H)-carboxamide, (1S,8aS)-N-((R)-1-(3,5-bis(trifluoromethyl)phenyl)-2-hydroxyethyl)-7,7-bis(2-hydroxyethyl)-N-methyl-6-oxo-1-o-tolylhexahydropyrrolo[1,2-a]pyrazine-2(1H)-carboxamide, (1S,8aS)-7,7-bis(2-hydroxyethyl)-N-methyl-6-oxo-1-tolyl-N-((R)-1-(3-(trifluoromethyl)phenyl)ethyphexahydropyrrolo[1,2-a]pyrazine-2(1H)-carboxamide, (1S,8aS)-N-((R)-1-(3-chloro-5-(trifluoromethyl)phenyl)ethyl)-7,7-bis(2-hydroxyethyl)-N-methyl-6-oxo-1-o-tolylhexahydropyrrolo[1,2-a]pyrazine-2(1H)-carboxamide, (1S,8aS)-N-((S)-1-(3-chloro-5-(trifluoromethyl)phenyl)ethyl)-7,7-bis(2-hydroxyethyl)-N-methyl-6-oxo-1-o-tolylhexahydropyrrolo[1,2-a]pyrazine-2(1H)-carboxamide, (1S,8aS)-7,7-bis(2-hydroxyethyl)-N-((R)-1-(3-methoxy-5-(trifluoromethyl)phenyl)ethyl)-N-methyl-6-oxo-1-o-tolylhexahydropyrrolo[1,2-a]pyrazine-2(1H)-carboxamide, (1S,8aS)-N-((S)-1-(3-fluoro-5-(trifluoromethyl)phenyl)ethyl)-7,7-bis(2-hydroxyethyl)-N-methyl-6-oxo-1-o-tolylhexahydropyrrolo[1,2-a]pyrazine-2(1H)-carboxamide, (1S,8aS)-N-((R)-1-(3-fluoro-5-(trifluoromethyl)phenyl)ethyl)-7,7-bis(2-hydroxyethyl)-N-methyl-6-oxo-1-o-tolylhexahydropyrrolo[1,2-a]pyrazine-2(1H)-carboxamide, (1S,8aS)-N-((S)-1-(3-fluoro-5-(trifluoromethyl)phenyl)-2-hydroxyethyl)-7,7-bis(2-hydroxyethyl)-N-methyl-6-oxo-1-o-tolylhexahydropyrrolo[1,2-a]pyrazine-2(1H)-carboxamide, (1S,8aS)-N-((S)-2-hydroxy-1-(3-methoxy-5-(trifluoromethyl)phenyl)ethyl)-7,7-bis(2-hydroxyethyl)-N-methyl-6-oxo-1-o-tolylhexahydropyrrolo[1,2-a]pyrazine-2(1H)-carboxamide, (1S,8aS)-N-((S)-2-hydroxy-1-(3-(trifluoromethyl)phenyl)ethyl)-7,7-bis(2-hydroxyethyl)-N-methyl-6-oxo-1-o-tolylhexahydropyrrolo[1,2-a]pyrazine-2(1H)-carboxamide, (1S,8aS)-N-((S)-2-hydroxy-1-(3-methyl-5-(trifluoromethyl)phenyl)ethyl)-7,7-bis(2-hydroxyethyl)-N-methyl-6-oxo-1-o-tolylhexahydropyrrolo[1,2-a]pyrazine-2(1H)-carboxamide, (1S,8aS)-N-((R)-1-(3-(difluoromethyl)-5-(trifluoromethyl)phenyl)ethyl)-7,7-bis(2-hydroxyethyl)-N-methyl-6-oxo-1-o-tolylhexahydropyrrolo[1,2-a]pyrazine-2(1H)-carboxamide, (1S,8aS)-N-((R)-1-(3-(difluoromethyl)-5-(trifluoromethyl)phenyl)ethyl)-7,7-bis(2-hydroxyethyl)-N-methyl-6-oxo-1-o-tolylhexahydropyrrolo[1,2-a]pyrazine-2(1H)-carboxamide, (1S,8aS)-N-((S)-1-(3,5-bis(trifluoromethyl)phenyl)ethyl)-7,7-bis(2-hydroxyethyl)-N-methyl-6-oxo-1-o-tolylhexahydropyrrolo[1,2-a]pyrazine-2(1H)-carboxamide, (1'S,8a'S)-N-((R)-1-(3,5-bis(trifluoromethyl)phenyl)ethyl)-N-methyl-6'-oxo-1'-o-tolyloctahydro-1'H-spiro[pyran-4,7'-pyrrolo[1,2-a]pyrazine]-2'(6'H)-carboxamide, (1'S,8a'S)-N-((R)-1-(3,5-bis(trifluoromethyl)phenyl)ethyl)-N-methyl-6'-oxo-1'-o-tolyloctahydro-1'H-spiro[pyran-4,7'-pyrrolo[1,2-a]pyrazine]-2'(6'H)-carboxamide, (1S,8aS)-7-(hydroxymethyl)-N-methyl-N-((R)-1-(3-methyl-5-(trifluoromethyl)phenyl)ethyl)-6-oxo-1-o-tolyl-hexahydropyrrolo[1,2-a]pyrazine-2(1H)-carboxamide, (1S,8aS)-7,7-bis(hydroxymethyl)-N-methyl-N-((R)-1-(3-methyl-5-(trifluoromethyl)phenyl)ethyl)-6-oxo-1-o-tolyl-hexahydropyrrolo[1,2-a]pyrazine-2(1H)-carboxamide, (1S,8aS)-N-((R)-1-(3,5-bis(trifluoromethyl)phenyl)ethyl)-7,7-bis(hydroxymethyl)-N-methyl-6-oxo-1-o-tolylhexahydropyrrolo[1,2-a]pyrazine-2(1H)-carboxamide, (1'S,8a'S)-N-((R)-1-(3,5-bis(trifluoromethyl)phenyl)ethyl)-N,1-dimethyl-6'-oxo-1'-o-tolyltetrahydro-1'H-spiro[piperidine-4,7'-pyrrolo[1,2-a]pyrazine]-2'(6'H)-carboxamide, formic acid salt, (1'S,8a'S)-N-((R)-1-(3,5-bis(trifluoromethyl)phenyl)ethyl)-N-methyl-6'-oxo-1'-o-tolyltetrahydro-1'H-spiro[piperidine-4,7'-pyrrolo[1,2-a]pyrazine]-2'(6'H)-carboxamide, formic acid salt, (1S,8aS)-N-methyl-N-((R)-1-(3-methyl-5-(trifluoromethyl)phenyl)ethyl)-6-oxo-1-o-tolylhexahydropyrrolo[1,2-a]pyrazine-2(1H)-carboxamide, (1S,8aS)-N-((R)-1-(3-chloro-5-(trifluoromethyl)phenyl)ethyl)-7,7-bis(hydroxymethyl)-N-methyl-6-oxo-1-o-tolylhexahydropyrrolo[1,2-a]pyrazine-2(1H)-carboxamide, (1S,8aS)-N-((R)-1-(3-ethyl-5-(trifluoromethyl)phenyl)ethyl)-N-methyl-6-oxo-1-o-tolylhexahydropyrrolo[1,2-a]pyrazine-2(1H)-carboxamide, (1S,8aS)-N-(R)-1-(3-ethyl-5-(trifluoromethyl)phenyl)ethyl)-7,7-bis(2-hydroxyethyl)-N-methyl-6-oxo-1-o-tolylhexahydropyrrolo[1,2-a]pyrazine-2(1H)-carboxamide, (1S,8aS)-N-(R)-1-(3-isopropyl-5-(trifluoromethyl)phenyl)ethyl)-N-methyl-6-oxo-1-o-tolylhexahydropyrrolo[1,2-a]pyrazine-2(1H)-carboxamide, (1S,8aS)-7,7-bis(2-hydroxyethyl)-N-((R)-1-(3-isopropyl-5-(trifluoromethyl)phenyl)ethyl)-N-methyl-6-oxo-1-o-tolylhexahydropyrrolo[1,2-a]pyrazine-2(1H)-carboxamide or a pharmaceutically acceptable salt or solvate thereof.

In an embodiment of the invention the compound according to formula A is N-[(1R)-1-[3,5-bis(trifluoromethyl)phenyl]ethyl]-N-methyl-1-(2-methylphenyl)-6-oxo-octahydro-pyrrolo[1,2-a]piperazine-2-carboxamide or a pharmaceutically acceptable salt or solvate thereof.

In an embodiment of the invention the compound according to formula A is (1S,8aS)-N-[(1R)-1-[3,5-bis(trifluoromethyl)phenyl]ethyl]-N-methyl-1-(2-methylphenyl)-6-oxo-octahydropyrrolo[1,2-a]piperazine-2-carboxamide, or a pharmaceutically acceptable salt or solvate thereof.

In an embodiment of the invention the compound according to formula A is (1R,8aR)-N-[(1R)-1-[3,5-bis(trifluoromethyl)phenyl]ethyl]-N-methyl-1-(2-methylphenyl)-6-oxo-octahydropyrrolo[1,2-a]piperazine-2-carboxamide, or a pharmaceutically acceptable salt or solvate thereof.

In an embodiment of the invention the compound according to formula A is N-{[3,5-bis(trifluoromethyl)phenyl]methyl}-7,7-bis(2-hydroxyethyl)-N-methyl-1-(2-methylphenyl)-6-oxo-octahydropyrrolo[1,2-a]piperazine-2-carboxamide or a pharmaceutically acceptable salt or solvate thereof.

In an embodiment of the invention the compound according to formula A is N-[(1R)-1-[3,5-bis(trifluoromethyl)phenyl]ethyl]-7,7-bis(2-hydroxyethyl)-N-methyl-1-2-methylphenyl)-6-oxo-octahydropyrrolo[1,2-a]piperazine-2-carboxamide or a pharmaceutically acceptable salt or solvate thereof.

In an embodiment of the invention the compound according to formula A is N-[(1R)-1-[3,5-bis(trifluoromethyl)phenyl]ethyl]-7,7-bis(2-hydroxyethyl)-N-methyl-1-(2-methylphenyl)-octahydropyrrolo[1,2-a]piperazine-2-carboxamide or a pharmaceutically acceptable salt or solvate thereof.

In an embodiment of the invention the compound according to formula A is (1S,8aS)-7,7-bis(2-hydroxyethyl)-N-methyl-N-((S)-1-(3-methyl-5-(trifluoromethyl)phenyl)ethyl)-6-oxo-1-o-tolylhexahydropyrrolo[1,2-a]pyrazine-2(1H)-carboxamide or a pharmaceutically acceptable salt or solvate thereof.

In an embodiment of the invention the compound according to formula A is (1S,8aS)-7,7-bis(2-hydroxyethyl)-N-methyl-N-((R)-1-(3-methyl-5-(trifluoromethyl)phenyl)ethyl)-6-oxo-1-o-tolylhexahydropyrrolo[1,2-a]pyrazine-2(1H)-carboxamide or a pharmaceutically acceptable salt or solvate thereof.

In an embodiment of the invention the compound according to formula A is (1S,8aS)-N-((R)-1-(3-chloro-5-(trifluoromethyl)phenyl)ethyl)-7,7-bis(2-hydroxyethyl)-N-methyl-6-oxo-1-o-tolylhexahydropyrrolo[1,2-a]pyrazine-2(1H)-carboxamide or a pharmaceutically acceptable salt or solvate thereof.

In an embodiment of the invention the compound according to formula A is (1S,8aS)-N-((R)-1-(3,5-bis(trifluoromethyl)phenyl)ethyl)-7,7-bis(hydroxymethyl)-N-methyl-6-oxo-1-o-tolylhexahydropyrrolo[1,2-a]pyrazine-2(1H)-carboxamide or a pharmaceutically acceptable salt or solvate thereof.

In an embodiment of the invention the compound according to formula A is (1S,8aS)-N-((R)-1-(3-ethyl-5-(trifluoromethyl)phenyl)ethyl)-N-methyl-6-oxo-1-o-tolylhexahydropyrrolo[1,2-a]pyrazine-2(1H)-carboxamide or a pharmaceutically acceptable salt or solvate thereof.

In an embodiment of the invention the compound according to formula A is (1S,8aS)-N-((R)-1-(3-ethyl-5-(trifluoromethyl)phenyl)ethyl)-7,7-bis(2-hydroxyethyl)-N-methyl-6-oxo-1-o-tolylhexahydropyrrolo[1,2-a]pyrazine-2(1H)-carboxamide or a pharmaceutically acceptable salt or solvate thereof.

In an embodiment of the invention the compound according to formula A is (1S,8aS)-N-((R)-1-(3-isopropyl-5-(trifluoromethyl)phenyl)ethyl)-N-methyl-6-oxo-1-o-tolylhexahydropyrrolo[1,2-a]pyrazine-2(1H)-carboxamide or a pharmaceutically acceptable salt or solvate thereof.

In an embodiment of the invention the compound according to formula A is (1S,8aS)-7,7-bis(2-hydroxyethyl)-N-((R)-1-(3-isopropyl-5-(trifluoromethyl)phenyl)ethyl)-N-methyl-6-oxo-1-o-tolylhexahydropyrrolo[1,2-a]pyrazine-2(1H)-carboxamide or a pharmaceutically acceptable salt or solvate thereof.

In an embodiment R1 is $C_{1-4}$ haloalkyl and R2 is $C_{1-4}$ haloalkyl, $C_{1-4}$ alkyl or halogen.

In an embodiment R1 is $C_{1-4}$ haloalkyl and R2 is $C_{1-4}$ alkyl.
In an embodiment R1 and R2 are $C_{1-4}$ haloalkyl.
In an embodiment R1 is trifluoromethyl or difluoromethyl and R2 is $C_{1-4}$ alkyl.
In an embodiment R1 is trifluoromethyl and R2 is methyl, ethyl or isopropyl.
In an embodiment R3 is $C_{1-4}$ alkyl.
In an embodiment R3 is methyl.

In an embodiment R3 is $C_{1-4}$ alkyl optionally substituted with hydroxy.
In an embodiment n is 1 and R4 is oxo.
In an embodiment n is 1 and R4 is hydrogen.
In an embodiment R5 and R6 are hydrogen.
In an embodiment R5 is hydrogen and R6 is $C_{1-4}$ alkyl optionally substituted with hydroxyl.
In an embodiment R5 and R6 are independently $C_{1-4}$ alkyl optionally substituted with hydroxyl.
In an embodiment R5 and R6 are hydroxymethyl or hydroxyethyl.
In an embodiment R5 and R6 are hydroxyethyl.
In an embodiment R5 and R6 together with the carbon atom to which they are attached, form a 5- or 6-membered heterocycloalkyl, wherein said heterocycloalkyl is optionally substituted with $C_{1-4}$ alkyl.
In an embodiment R1 is $C_{1-4}$ haloalkyl, R2 is $C_{1-4}$ alkyl and R3 is $C_{1-4}$ alkyl.
In an embodiment R1 is $C_{1-4}$ haloalkyl, R2 is $C_{1-4}$ alkyl and R3 is $C_{1-4}$ alkyl optionally substituted with hydroxyl.
In an embodiment R1 is $C_{1-4}$ haloalkyl, R2 is $C_{1-4}$ alkyl, R3 is $C_{1-4}$ alkyl optionally substituted with hydroxyl and R5 and R6 are hydroxy-$C_{1-4}$ alkyl.
In an embodiment R1 is $C_{1-4}$ haloalkyl, R2 is $C_{1-4}$ alkyl and R5 and R6 are hydroxy-$C_{1-4}$ alkyl.
In an embodiment R1 is $C_{1-4}$ haloalkyl, R2 is $C_{1-4}$ alkyl and R5 and R6 are hydrogen
In an embodiment R1 is $C_{1-4}$ haloalkyl, R2 is $C_{1-4}$ alkyl and R5 is hydrogen and R6 is $C_{1-4}$ alkyl optionally substituted with hydroxyl.
In an embodiment R1 is $C_{1-4}$ haloalkyl, R2 is $C_{1-4}$ alkyl and R5 and R6 are independently $C_{1-4}$ alkyl optionally substituted with hydroxyl.
In an embodiment R1 is $C_{1-4}$ haloalkyl, R2 is $C_{1-4}$ alkyl and n is 1.
In an embodiment R1 is $C_{1-4}$ haloalkyl, R2 is $C_{1-4}$ alkyl and R4 is oxo.
In an embodiment R1 is $C_{1-4}$ haloalkyl, R2 is $C_{1-4}$ alkyl and R4 is hydrogen.
In an embodiment R1 is $C_{1-4}$ haloalkyl, R2 is $C_{1-4}$ alkyl and R5 and R6 together with the carbon atom to which they are attached, form a 5- or 6-membered heterocycloalkyl, wherein said heterocycloalkyl is optionally substituted with $C_{1-4}$ alkyl.
In an embodiment R1 is $C_{1-4}$ haloalkyl, R2 is $C_{1-4}$ alkyl, R3 is $C_{1-4}$ alkyl and n is 1.
In an embodiment R1 is $C_{1-4}$ haloalkyl, R2 is $C_{1-4}$ alkyl, R3 is $C_{1-4}$ alkyl optionally substituted with hydroxyl and n is 1.
In an embodiment R1 is $C_{1-4}$ haloalkyl, R2 is $C_{1-4}$ alkyl, R3 is $C_{1-4}$ alkyl optionally substituted with hydroxyl, R5 and R6 are hydroxy-$C_{1-4}$ alkyl and n is 1.
In an embodiment R1 is $C_{1-4}$ haloalkyl, R2 is $C_{1-4}$ alkyl, R5 and R6 are hydroxy-$C_{1-4}$ alkyl and n is 1.
In an embodiment R1 is $C_{1-4}$ haloalkyl, R2 is $C_{1-4}$ alkyl, R5 and R6 are hydrogen and n is 1.
In an embodiment R1 is $C_{1-4}$ haloalkyl, R2 is $C_{1-4}$ alkyl, R5 is hydrogen and R6 is $C_{1-4}$ alkyl optionally substituted with hydroxyl and n is 1.
In an embodiment R1 is $C_{1-4}$ haloalkyl, R2 is $C_{1-4}$ alkyl, R5 and R6 are independently $C_{1-4}$ alkyl optionally substituted with hydroxyl and n is 1.
In an embodiment R1 is $C_{1-4}$ haloalkyl, R2 is $C_{1-4}$ alkyl, R5 and R6 together with the carbon atom to which they are attached, form a 5- or 6-membered heterocycloalkyl, wherein said heterocycloalkyl is optionally substituted with $C_{1-4}$ alkyl and n is 1.

In an embodiment R1 is $C_{1-4}$ haloalkyl, R2 is $C_{1-4}$ alkyl, R3 is $C_{1-4}$ alkyl and R4 is oxo.

In an embodiment R1 is $C_{1-4}$ haloalkyl, R2 is $C_{1-4}$ alkyl, R3 is $C_{1-4}$ alkyl optionally substituted with hydroxyl and R4 is oxo.

In an embodiment R1 is $C_{1-4}$ haloalkyl, R2 is $C_{1-4}$ alkyl, R3 is $C_{1-4}$ alkyl optionally substituted with hydroxyl, R4 is oxo and R5 and R6 are hydroxy-$C_{1-4}$ alkyl.

In an embodiment R1 is $C_{1-4}$ haloalkyl, R2 is $C_{1-4}$ alkyl, R4 is oxo and R5 and R6 are hydroxy-$C_{1-4}$ alkyl.

In an embodiment R1 is $C_{1-4}$ haloalkyl, R2 is $C_{1-4}$ alkyl, R4 is oxo and R5 and R6 are hydrogen.

In an embodiment R1 is $C_{1-4}$ haloalkyl, R2 is $C_{1-4}$ alkyl, R4 is oxo and R5 is hydrogen and R6 is $C_{1-4}$ alkyl optionally substituted with hydroxyl.

In an embodiment R1 is $C_{1-4}$ haloalkyl, R2 is $C_{1-4}$ alkyl, R4 is oxo and R5 and R6 are independently $C_{1-4}$ alkyl optionally substituted with hydroxyl.

In an embodiment R1 is $C_{1-4}$ haloalkyl, R2 is $C_{1-4}$ alkyl, R4 is oxo and R5 and R6 together with the carbon atom to which they are attached, form a 5- or 6-membered heterocycloalkyl, wherein said heterocycloalkyl is optionally substituted with $C_{1-4}$ alkyl.

In an embodiment R1 is $C_{1-4}$ haloalkyl, R2 is $C_{1-4}$ alkyl, R3 is $C_{1-4}$ alkyl optionally substituted with hydroxyl, R5 and R6 are hydroxy-$C_{1-4}$ alkyl, n is 1 and R4 is oxo.

In an embodiment R1 is $C_{1-4}$ haloalkyl, R2 is $C_{1-4}$ alkyl, R3 is $C_{1-4}$ alkyl optionally substituted with hydroxyl, R5 and R6 are hydroxy-$C_{1-4}$ alkyl, n is 1 and R4 is hydrogen.

An embodiment of the invention is a compound of general formula A(i) wherein R1 is $C_{1-4}$ haloalkyl, R2 is $C_{1-4}$ alkyl, R3 is $C_{1-4}$ alkyl optionally substituted with hydroxyl, R5 and R6 are hydroxy-$C_{1-4}$ alkyl, n is 1 and R4 is hydrogen, or a pharmaceutically acceptable salt or solvate thereof.

An embodiment of the invention is a compound of general formula A(i) wherein R1 is $C_{1-4}$ haloalkyl, R2 is $C_{1-4}$ alkyl, R3 is $C_{1-4}$ alkyl optionally substituted with hydroxyl, R5 and R6 are hydroxy-$C_{1-4}$ alkyl, n is 1 and R4 is oxo, or a pharmaceutically acceptable salt or solvate thereof.

An embodiment of the invention is a compound of general formula A(ii) wherein R1 is $C_{1-4}$ haloalkyl, R2 is $C_{1-4}$ alkyl, R3 is $C_{1-4}$ alkyl optionally substituted with hydroxyl, R5 and R6 are hydroxy-$C_{1-4}$ alkyl, n is 1 and R4 is hydrogen, or a pharmaceutically acceptable salt or solvate thereof.

An embodiment of the invention is a compound of general formula A(ii) wherein R1 is $C_{1-4}$ haloalkyl, R2 is $C_{1-4}$ alkyl, R3 is $C_{1-4}$ alkyl optionally substituted with hydroxyl, R5 and R6 are hydroxy-$C_{1-4}$ alkyl, n is 1 and R4 is oxo, or a pharmaceutically acceptable salt or solvate thereof.

An embodiment of the invention is a compound of general formula A(iii) wherein R1 is $C_{1-4}$ haloalkyl, R2 is $C_{1-4}$ alkyl, R3 is $C_{1-4}$ alkyl optionally substituted with hydroxyl, R5 and R6 are hydroxy-$C_{1-4}$ alkyl, n is 1 and R4 is hydrogen, or a pharmaceutically acceptable salt or solvate thereof.

An embodiment of the invention is a compound of general formula A(iii) wherein R1 is $C_{1-4}$ haloalkyl, R2 is $C_{1-4}$ alkyl, R3 is $C_{1-4}$ alkyl optionally substituted with hydroxyl, R5 and R6 are hydroxy-$C_{1-4}$ alkyl, n is 1 and R4 is oxo, or a pharmaceutically acceptable salt or solvate thereof.

An embodiment of the invention is a compound of general formula A(iv) wherein R1 is $C_{1-4}$ haloalkyl, R2 is $C_{1-4}$ alkyl, R3 is $C_{1-4}$ alkyl optionally substituted with hydroxyl, R5 and R6 are hydroxy-$C_{1-4}$ alkyl, n is 1 and R4 is hydrogen, or a pharmaceutically acceptable salt or solvate thereof.

An embodiment of the invention is a compound of general formula A(iv) wherein R1 is $C_{1-4}$ haloalkyl, R2 is $C_{1-4}$ alkyl, R3 is $C_{1-4}$ alkyl optionally substituted with hydroxyl, R5 and R6 are hydroxy-$C_{1-4}$ alkyl, n is 1 and R4 is oxo, or a pharmaceutically acceptable salt or solvate thereof.

An embodiment of the invention is a compound of general formula A(v) wherein R1 is $C_{1-4}$ haloalkyl, R2 is $C_{1-4}$ alkyl, R3 is $C_{1-4}$ alkyl optionally substituted with hydroxyl, R5 and R6 are hydroxy-$C_{1-4}$ alkyl, n is 1 and R4 is hydrogen, or a pharmaceutically acceptable salt or solvate thereof.

An embodiment of the invention is a compound of general formula A(v) wherein R1 is $C_{1-4}$ haloalkyl, R2 is $C_{1-4}$ alkyl, R3 is $C_{1-4}$ alkyl optionally substituted with hydroxyl, R5 and R6 are hydroxy-$C_{1-4}$ alkyl, n is 1 and R4 is oxo, or a pharmaceutically acceptable salt or solvate thereof.

In an embodiment R1 is $C_{1-4}$ haloalkyl, R2 is $C_{1-4}$ alkyl or $C_{1-4}$ haloalkyl and R3 is $C_{1-4}$ alkyl.

In an embodiment R1 is $C_{1-4}$ haloalkyl, R2 is $C_{1-4}$ alkyl or $C_{1-4}$ haloalkyl and R3 is $C_{1-4}$ alkyl optionally substituted with hydroxyl.

In an embodiment R1 is $C_{1-4}$ haloalkyl, R2 is $C_{1-4}$ alkyl or $C_{1-4}$ haloalkyl, R3 is $C_{1-4}$ alkyl optionally substituted with hydroxyl and R5 and R6 are hydroxy-$C_{1-4}$ alkyl.

In an embodiment R1 is $C_{1-4}$ haloalkyl, R2 is $C_{1-4}$ alkyl or $C_{1-4}$ haloalkyl and R5 and R6 are hydroxy-$C_{1-4}$ alkyl.

In an embodiment R1 is $C_{1-4}$ haloalkyl, R2 is $C_{1-4}$ alkyl or $C_{1-4}$ haloalkyl and R5 and R6 are hydrogen In an embodiment R1 is $C_{1-4}$ haloalkyl, R2 is $C_{1-4}$ alkyl or $C_{1-4}$ haloalkyl and R5 is hydrogen and R6 is $C_{1-4}$ alkyl optionally substituted with hydroxyl.

In an embodiment R1 is $C_{1-4}$ haloalkyl, R2 is $C_{1-4}$ alkyl or $C_{1-4}$ haloalkyl and R5 and R6 are independently $C_{1-4}$ alkyl optionally substituted with hydroxyl.

In an embodiment R1 is $C_{1-4}$ haloalkyl, R2 is $C_{1-4}$ alkyl or $C_{1-4}$ haloalkyl and n is 1.

In an embodiment R1 is $C_{1-4}$ haloalkyl, R2 is $C_{1-4}$ alkyl or $C_{1-4}$ haloalkyl and R4 is oxo.

In an embodiment R1 is $C_{1-4}$ haloalkyl, R2 is $C_{1-4}$ alkyl or $C_{1-4}$ haloalkyl and R4 is hydrogen.

In an embodiment R1 is $C_{1-4}$ haloalkyl, R2 is $C_{1-4}$ alkyl or $C_{1-4}$ haloalkyl and R5 and R6 together with the carbon atom to which they are attached, form a 5- or 6-membered heterocycloalkyl, wherein said heterocycloalkyl is optionally substituted with $C_{1-4}$ alkyl.

In an embodiment R1 is $C_{1-4}$ haloalkyl, R2 is $C_{1-4}$ alkyl or $C_{1-4}$ haloalkyl, R3 is $C_{1-4}$ alkyl and n is 1.

In an embodiment R1 is $C_{1-4}$ haloalkyl, R2 is $C_{1-4}$ alkyl or $C_{1-4}$ haloalkyl, R3 is $C_{1-4}$ alkyl optionally substituted with hydroxyl and n is 1.

In an embodiment R1 is $C_{1-4}$ haloalkyl, R2 is $C_{1-4}$ alkyl or $C_{1-4}$ haloalkyl, R3 is $C_{1-4}$ alkyl optionally substituted with hydroxyl, R5 and R6 are hydroxy-$C_{1-4}$ alkyl and n is 1.

In an embodiment R1 is $C_{1-4}$ haloalkyl, R2 is $C_{1-4}$ alkyl or $C_{1-4}$ haloalkyl, R5 and R6 are hydroxy-$C_{1-4}$ alkyl and n is 1.

In an embodiment R1 is $C_{1-4}$ haloalkyl, R2 is $C_{1-4}$ alkyl or $C_{1-4}$ haloalkyl, R5 and R6 are hydrogen and n is 1.

In an embodiment R1 is $C_{1-4}$ haloalkyl, R2 is $C_{1-4}$ alkyl or $C_{1-4}$ haloalkyl, R5 is hydrogen and R6 is $C_{1-4}$ alkyl optionally substituted with hydroxyl and n is 1.

In an embodiment R1 is $C_{1-4}$ haloalkyl, R2 is $C_{1-4}$ alkyl or $C_{1-4}$ haloalkyl, R5 and R6 are independently $C_{1-4}$ alkyl optionally substituted with hydroxyl and n is 1.

In an embodiment R1 is $C_{1-4}$ haloalkyl, R2 is $C_{1-4}$ alkyl or $C_{1-4}$ haloalkyl, R5 and R6 together with the carbon atom to which they are attached, form a 5- or 6-membered heterocycloalkyl, wherein said heterocycloalkyl is optionally substituted with $C_{1-4}$ alkyl and n is 1.

In an embodiment R1 is $C_{1-4}$ haloalkyl, R2 is $C_{1-4}$ alkyl or $C_{1-4}$ haloalkyl, R3 is $C_{1-4}$ alkyl and R4 is oxo.

In an embodiment R1 is $C_{1-4}$ haloalkyl, R2 is $C_{1-4}$ alkyl or $C_{1-4}$ haloalkyl, $C_{1-4}$ haloalkyl or halogen, R3 is $C_{1-4}$ alkyl optionally substituted with hydroxyl and R4 is oxo.

In an embodiment R1 is $C_{1-4}$ haloalkyl, R2 is $C_{1-4}$ alkyl or $C_{1-4}$ haloalkyl, R3 is $C_{1-4}$ alkyl optionally substituted with hydroxyl, R4 is oxo and R5 and R6 are hydroxy-$C_{1-4}$ alkyl.

In an embodiment R1 is $C_{1-4}$ haloalkyl, R2 is $C_{1-4}$ alkyl or $C_{1-4}$ haloalkyl, R4 is oxo and R5 and R6 are hydroxy-$C_{1-4}$ alkyl.

In an embodiment R1 is $C_{1-4}$ haloalkyl, R2 is $C_{1-4}$ alkyl or $C_{1-4}$ haloalkyl, R4 is oxo and R5 and R6 are hydrogen.

In an embodiment R1 is $C_{1-4}$ haloalkyl, R2 is $C_{1-4}$ alkyl or $C_{1-4}$ haloalkyl, R4 is oxo and R5 is hydrogen and R6 is $C_{1-4}$ alkyl optionally substituted with hydroxyl.

In an embodiment R1 is $C_{1-4}$ haloalkyl, R2 is $C_{1-4}$ alkyl or $C_{1-4}$ haloalkyl, R4 is oxo and R5 and R6 are independently $C_{1-4}$ alkyl optionally substituted with hydroxyl.

In an embodiment R1 is $C_{1-4}$ haloalkyl, R2 is $C_{1-4}$ alkyl or $C_{1-4}$ haloalkyl, R4 is oxo and R5 and R6 together with the carbon atom to which they are attached, form a 5- or 6-membered heterocycloalkyl, wherein said heterocycloalkyl is optionally substituted with $C_{1-4}$ alkyl.

In an embodiment R1 is $C_{1-4}$ haloalkyl, R2 is $C_{1-4}$ alkyl or $C_{1-4}$ haloalkyl, R3 is $C_{1-4}$ alkyl optionally substituted with hydroxyl, R5 and R6 are hydroxy-$C_{1-4}$ alkyl, n is 1 and R4 is oxo.

In an embodiment R1 is $C_{1-4}$ haloalkyl, R2 is $C_{1-4}$ alkyl or $C_{1-4}$ haloalkyl, R3 is $C_{1-4}$ alkyl optionally substituted with hydroxyl, R5 and R6 are hydroxy-$C_{1-4}$ alkyl, n is 1 and R4 is hydrogen.

In an embodiment R1 is $C_{1-4}$ haloalkyl, R2 is $C_{1-4}$ alkyl or $C_{1-4}$ haloalkyl, R3 is $C_{1-4}$ alkyl optionally substituted with hydroxyl, R5 and R6 are hydrogen, n is 1 and R4 is oxo.

In an embodiment R1 is $C_{1-4}$ haloalkyl, R2 is $C_{1-4}$ alkyl or $C_{1-4}$ haloalkyl, R3 is $C_{1-4}$ alkyl optionally substituted with hydroxyl, R5 and R6 are hydrogen, n is 1 and R4 is hydrogen.

An embodiment of the invention is a compound of general formula A(i) wherein R1 is $C_{1-4}$ haloalkyl, R2 is $C_{1-4}$ alkyl or $C_{1-4}$ haloalkyl, R3 is $C_{1-4}$ alkyl optionally substituted with hydroxyl, R5 and R6 are hydroxy-$C_{1-4}$ alkyl, n is 1 and R4 is hydrogen, or a pharmaceutically acceptable salt or solvate thereof.

An embodiment of the invention is a compound of general formula A(i) wherein R1 is $C_{1-4}$ haloalkyl, R2 is $C_{1-4}$ alkyl or $C_{1-4}$ haloalkyl, R3 is $C_{1-4}$ alkyl optionally substituted with hydroxyl, R5 and R6 are hydroxy-$C_{1-4}$ alkyl, n is 1 and R4 is oxo, or a pharmaceutically acceptable salt or solvate thereof.

An embodiment of the invention is a compound of general formula A(i) wherein R1 is $C_{1-4}$ haloalkyl, R2 is $C_{1-4}$ alkyl or $C_{1-4}$ haloalkyl, R3 is $C_{1-4}$ alkyl optionally substituted with hydroxyl, R5 and R6 are hydrogen, n is 1 and R4 is hydrogen, or a pharmaceutically acceptable salt or solvate thereof.

An embodiment of the invention is a compound of general formula A(i) wherein R1 is $C_{1-4}$ haloalkyl, R2 is $C_{1-4}$ alkyl or $C_{1-4}$ haloalkyl, R3 is $C_{1-4}$ alkyl optionally substituted with hydroxyl, R5 and R6 are hydrogen, n is 1 and R4 is oxo, or a pharmaceutically acceptable salt or solvate thereof.

An embodiment of the invention is a compound of general formula A(ii) wherein R1 is $C_{1-4}$ haloalkyl, R2 is $C_{1-4}$ alkyl or $C_{1-4}$ haloalkyl, R3 is $C_{1-4}$ alkyl optionally substituted with hydroxyl, R5 and R6 are hydroxy-$C_{1-4}$ alkyl, n is 1 and R4 is hydrogen, or a pharmaceutically acceptable salt or solvate thereof.

An embodiment of the invention is a compound of general formula A(ii) wherein R1 is $C_{1-4}$ haloalkyl, R2 is $C_{1-4}$ alkyl or $C_{1-4}$ haloalkyl, R3 is $C_{1-4}$ alkyl optionally substituted with hydroxyl, R5 and R6 are hydroxy-$C_{1-4}$ alkyl, n is 1 and R4 is oxo, or a pharmaceutically acceptable salt or solvate thereof.

An embodiment of the invention is a compound of general formula A(ii) wherein R1 is $C_{1-4}$ haloalkyl, R2 is $C_{1-4}$ alkyl or $C_{1-4}$ haloalkyl, R3 is $C_{1-4}$ alkyl optionally substituted with hydroxyl, R5 and R6 are hydrogen, n is 1 and R4 is hydrogen, or a pharmaceutically acceptable salt or solvate thereof.

An embodiment of the invention is a compound of general formula A(ii) wherein R1 is $C_{1-4}$ haloalkyl, R2 is $C_{1-4}$ alkyl or $C_{1-4}$ haloalkyl, R3 is $C_{1-4}$ alkyl optionally substituted with hydroxyl, R5 and R6 are hydrogen, n is 1 and R4 is oxo, or a pharmaceutically acceptable salt or solvate thereof.

An embodiment of the invention is a compound of general formula A(iii) wherein R1 is $C_{1-4}$ haloalkyl, R2 is $C_{1-4}$ alkyl or $C_{1-4}$ haloalkyl, R3 is $C_{1-4}$ alkyl optionally substituted with hydroxyl, R5 and R6 are hydroxy-$C_{1-4}$ alkyl, n is 1 and R4 is hydrogen, or a pharmaceutically acceptable salt or solvate thereof.

An embodiment of the invention is a compound of general formula A(iii) wherein R1 is $C_{1-4}$ haloalkyl, R2 is $C_{1-4}$ alkyl or $C_{1-4}$ haloalkyl, R3 is $C_{1-4}$ alkyl optionally substituted with hydroxyl, R5 and R6 are hydroxy-$C_{1-4}$ alkyl, n is 1 and R4 is oxo, or a pharmaceutically acceptable salt or solvate thereof.

An embodiment of the invention is a compound of general formula A(iii) wherein R1 is $C_{1-4}$ haloalkyl, R2 is $C_{1-4}$ alkyl or $C_{1-4}$ haloalkyl, R3 is $C_{1-4}$ alkyl optionally substituted with hydroxyl, R5 and R6 are hydrogen, n is 1 and R4 is hydrogen, or a pharmaceutically acceptable salt or solvate thereof.

An embodiment of the invention is a compound of general formula A(iii) wherein R1 is $C_{1-4}$ haloalkyl, R2 is $C_{1-4}$ alkyl or $C_{1-4}$ haloalkyl, R3 is $C_{1-4}$ alkyl optionally substituted with hydroxyl, R5 and R6 are hydrogen, n is 1 and R4 is oxo, or a pharmaceutically acceptable salt or solvate thereof.

An embodiment of the invention is a compound of general formula A(iv) wherein R1 is $C_{1-4}$ haloalkyl, R2 is $C_{1-4}$ alkyl or $C_{1-4}$ haloalkyl, R3 is $C_{1-4}$ alkyl optionally substituted with hydroxyl, R5 and R6 are hydroxy-$C_{1-4}$ alkyl, n is 1 and R4 is hydrogen, or a pharmaceutically acceptable salt or solvate thereof.

An embodiment of the invention is a compound of general formula A(iv) wherein R1 is $C_{1-4}$ haloalkyl, R2 is $C_{1-4}$ alkyl or $C_{1-4}$ haloalkyl, R3 is $C_{1-4}$ alkyl optionally substituted with hydroxyl, R5 and R6 are hydroxy-$C_{1-4}$ alkyl, n is 1 and R4 is oxo, or a pharmaceutically acceptable salt or solvate thereof.

An embodiment of the invention is a compound of general formula A(iv) wherein R1 is $C_{1-4}$ haloalkyl, R2 is $C_{1-4}$ alkyl or $C_{1-4}$ haloalkyl, R3 is $C_{1-4}$ alkyl optionally substituted with hydroxyl, R5 and R6 are hydrogen, n is 1 and R4 is hydrogen, or a pharmaceutically acceptable salt or solvate thereof.

An embodiment of the invention is a compound of general formula A(iv) wherein R1 is $C_{1-4}$ haloalkyl, R2 is $C_{1-4}$ alkyl or $C_{1-4}$ haloalkyl, R3 is $C_{1-4}$ alkyl optionally substituted with hydroxyl, R5 and R6 are hydrogen, n is 1 and R4 is oxo, or a pharmaceutically acceptable salt or solvate thereof.

An embodiment of the invention is a compound of general formula A(v) wherein R1 is $C_{1-4}$ haloalkyl, R2 is $C_{1-4}$ alkyl or $C_{1-4}$ haloalkyl, R3 is $C_{1-4}$ alkyl optionally substituted with hydroxyl, R5 and R6 are hydroxy-$C_{1-4}$ alkyl, n is 1 and R4 is hydrogen, or a pharmaceutically acceptable salt or solvate thereof.

An embodiment of the invention is a compound of general formula A(v) wherein R1 is $C_{1-4}$ haloalkyl, R2 is $C_{1-4}$ alkyl or $C_{1-4}$ haloalkyl, R3 is $C_{1-4}$ alkyl optionally substituted with hydroxyl, R5 and R6 are hydroxy-$C_{1-4}$ alkyl, n is 1 and R4 is oxo, or a pharmaceutically acceptable salt or solvate thereof.

An embodiment of the invention is a compound of general formula A(v) wherein R1 is $C_{1-4}$ haloalkyl, R2 is $C_{1-4}$ alkyl or $C_{1-4}$ haloalkyl, R3 is $C_{1-4}$ alkyl optionally substituted with hydroxyl, R5 and R6 are hydrogen, n is 1 and R4 is hydrogen, or a pharmaceutically acceptable salt or solvate thereof.

An embodiment of the invention is a compound of general formula A(v) wherein R1 is $C_{1-4}$ haloalkyl, R2 is $C_{1-4}$ alkyl or $C_{1-4}$ haloalkyl, R3 is $C_{1-4}$ alkyl optionally substituted with hydroxyl, R5 and R6 are hydrogen, n is 1 and R4 is oxo, or a pharmaceutically acceptable salt or solvate thereof.

An embodiment of the invention is a compound of general formula A(i) wherein R1 is $C_{1-4}$ haloalkyl, R2 is $C_{1-4}$ haloalkyl, R3 is $C_{1-4}$ alkyl optionally substituted with hydroxyl, R5 and R6 are hydroxy-$C_{1-4}$ alkyl, n is 1 and R4 is hydrogen, or a pharmaceutically acceptable salt or solvate thereof.

An embodiment of the invention is a compound of general formula A(i) wherein R1 is $C_{1-4}$ haloalkyl, R2 is $C_{1-4}$ haloalkyl, R3 is $C_{1-4}$ alkyl optionally substituted with hydroxyl, R5 and R6 are hydroxy-$C_{1-4}$ alkyl, n is 1 and R4 is oxo, or a pharmaceutically acceptable salt or solvate thereof.

An embodiment of the invention is a compound of general formula A(ii) wherein R1 is $C_{1-4}$ haloalkyl, R2 is $C_{1-4}$ haloalkyl, R3 is $C_{1-4}$ alkyl optionally substituted with hydroxyl, R5 and R6 are hydroxy-$C_{1-4}$ alkyl, n is 1 and R4 is hydrogen, or a pharmaceutically acceptable salt or solvate thereof.

An embodiment of the invention is a compound of general formula A(ii) wherein R1 is $C_{1-4}$ haloalkyl, R2 is $C_{1-4}$ haloalkyl, R3 is $C_{1-4}$ alkyl optionally substituted with hydroxyl, R5 and R6 are hydroxy-$C_{1-4}$ alkyl, n is 1 and R4 is oxo, or a pharmaceutically acceptable salt or solvate thereof.

An embodiment of the invention is a compound of general formula A(iii) wherein R1 is $C_{1-4}$ haloalkyl, R2 is $C_{1-4}$ haloalkyl, R3 is $C_{1-4}$ alkyl optionally substituted with hydroxyl, R5 and R6 are hydroxy-$C_{1-4}$ alkyl, n is 1 and R4 is hydrogen, or a pharmaceutically acceptable salt or solvate thereof.

An embodiment of the invention is a compound of general formula A(iii) wherein R1 is $C_{1-4}$ haloalkyl, R2 is $C_{1-4}$ haloalkyl, R3 is $C_{1-4}$ alkyl optionally substituted with hydroxyl, R5 and R6 are hydroxy-$C_{1-4}$ alkyl, n is 1 and R4 is oxo, or a pharmaceutically acceptable salt or solvate thereof.

An embodiment of the invention is a compound of general formula A(iv) wherein R1 is $C_{1-4}$ haloalkyl, R2 is $C_{1-4}$ haloalkyl, R3 is $C_{1-4}$ alkyl optionally substituted with hydroxyl, R5 and R6 are hydroxy-$C_{1-4}$ alkyl, n is 1 and R4 is hydrogen, or a pharmaceutically acceptable salt or solvate thereof.

An embodiment of the invention is a compound of general formula A(iv) wherein R1 is $C_{1-4}$ haloalkyl, R2 is $C_{1-4}$ haloalkyl, R3 is $C_{1-4}$ alkyl optionally substituted with hydroxyl, R5 and R6 are hydroxy-$C_{1-4}$ alkyl, n is 1 and R4 is oxo, or a pharmaceutically acceptable salt or solvate thereof.

An embodiment of the invention is a compound of general formula A(v) wherein R1 is $C_{1-4}$ haloalkyl, R2 is $C_{1-4}$ haloalkyl, R3 is $C_{1-4}$ alkyl optionally substituted with hydroxyl, R5 and R6 are hydroxy-$C_{1-4}$ alkyl, n is 1 and R4 is hydrogen, or a pharmaceutically acceptable salt or solvate thereof.

An embodiment of the invention is a compound of general formula A(v) wherein R1 is $C_{1-4}$ haloalkyl, R2 is $C_{1-4}$ haloalkyl, R3 is $C_{1-4}$ alkyl optionally substituted with hydroxyl, R5 and R6 are hydroxy-$C_{1-4}$ alkyl, n is 1 and R4 is oxo, or a pharmaceutically acceptable salt or solvate thereof.

The compounds of formula A may be obtained in crystalline form either directly by concentration from an organic solvent or by crystallisation or recrystallisation from an organic solvent or mixture of said solvent and a cosolvent that may be organic or inorganic, such as water. The crystals may be isolated in essentially solvent-free form or as a solvate, such as a hydrate. The invention covers all crystalline modifications and forms and also mixtures thereof.

Compounds of formula A may comprise asymmetrically substituted (chiral) carbon atoms which give rise to the existence of isomeric forms, e.g. enantiomers and possibly diastereomers. The present invention relates to all such isomers, either in pure form or as mixtures thereof (e.g. racemates). Pure stereoisomeric forms of the compounds and the intermediates of this invention may be obtained by the application of procedures known in the art. The various isomeric forms may be separated by physical separation methods such as selective crystallization and chromatographic techniques, e.g. liquid chromatography using chiral stationary phases. Enantiomers may be separated from each other by the selective crystallization of their diastereomeric salts with optically active acids. Alternatively, enantiomers may be separated by chromatographic techniques using chiral stationary phases. Said pure stereoisomeric forms may also be derived from the corresponding pure stereoisomeric forms of the appropriate starting materials, provided that the reaction occurs stereoselectively or stereospecifically. Preferably, if a specific stereoisomer is desired, said compound will be synthesized by stereoselective or stereospecific methods of preparation. These methods will advantageously employ chiral pure starting materials.

In a particular embodiment, the compound of the invention may be an isomer of general formula A(i)

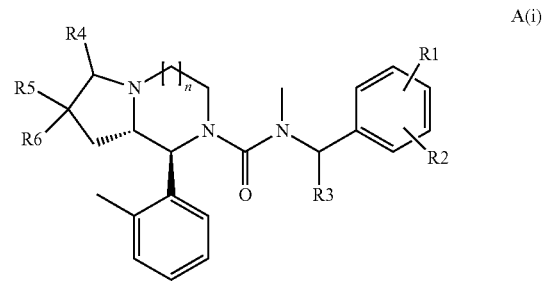

A(i)

wherein n, R1, R2, R3, R4, R5 and R6 are as indicated above, or a pharmaceutically acceptable salt or solvate thereof.

In an alternative embodiment, the compound may be an isomer of general formula A(ii)

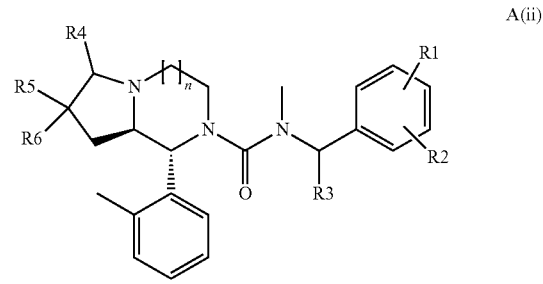

A(ii)

wherein n, R1, R2, R3, R4, R5 and R6 are as indicated above, or a pharmaceutically acceptable salt or solvate thereof.

In a particular embodiment, the compound of the invention may be an isomer of general formula A(iv)

A(iv)

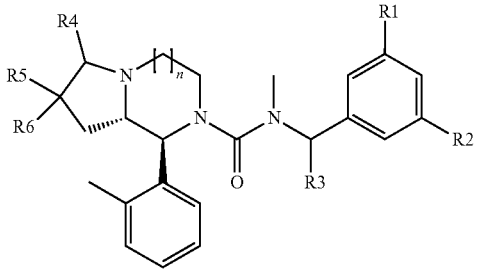

wherein n, R1, R2, R3, R4, R5 and R6 are as indicated above, or a pharmaceutically acceptable salt or solvate thereof.

In an alternative embodiment, the compound may be an isomer of general formula A(v)

A(v)

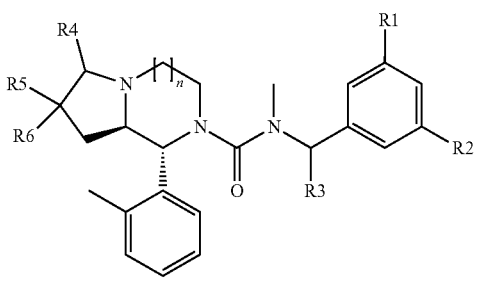

wherein n, R1, R2, R3, R4, R5 and R6 are as indicated above, or a pharmaceutically acceptable salt or solvate thereof.

In an embodiment, a compound of the invention may be an isomer of general formula B(i)

B(i)

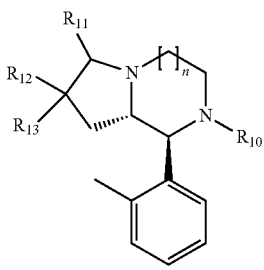

wherein R10, RU, R12, R13 are as indicated above, or a pharmaceutically acceptable salt thereof.

In an embodiment, a compound of the invention may be an isomer of general formula B(ii)

B(ii)

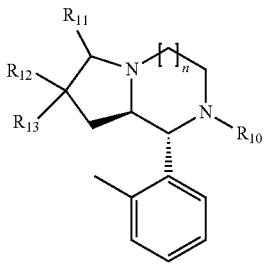

wherein R10, RU, R12, R13 are as indicated above, or a pharmaceutically acceptable salt thereof.

An embodiment of the invention is the compound according to general formula B wherein R10 is hydrogen or —C(O)O(t-butyl);

R11 is selected from the group consisting of hydrogen and oxo;

R12 and R13 are independently selected from the group consisting of hydrogen, allyl and —C(O)O methyl;

n is 1 or 2.

An embodiment of the invention is the compound according to general formula B selected from the group consisting of:

1-(2-methylphenyl)-octahydro-1H-pyrrolo[1,2-a][1,4]diazepin-7-one;
1-(2-methylphenyl)-octahydropyrrolo[1,2-a]piperazin-6-one benzyl N-(2-{2-[(2-methylphenyl)carbonyl]-5-oxopyrrolidin-1-yl}ethyl)carbamate;
tert-butyl 1-(2-methylphenyl)-6-oxo-octahydropyrrolo[1,2-a]piperazine-2-carboxylate;
2-tert-butyl 7-methyl 1-(2-methylphenyl)-6-oxo-octahydropyrrolo[1,2-a]piperazine-2,7 dicarboxylate;
(tert-butyl 1-(2-methylphenyl)-6-oxohexahydropyrrolo[1,2-a]pyrazine-2(1H)-carboxylate);
Methyl 7-methyl-1-(2-methylphenyl)-6-oxo-octahydropyrrolo{1,2-a}piperazine-7-carboxylate;
Methyl 1-(2-methylphenyl)-6-oxo-octahydropyrrolo[1,2-a]piperazine-7-carboxylate;
tert-butyl 1-(2-methylphenyl)-octahydropyrrolo[1,2-a]piperazine-2-carboxylate;
1-(2-methylphenyl)-octahydropyrrolo[1,2-a]piperazine;
1-(2-methylphenyl)-octahydropyrrolo[1,2-a]piperazin-6-one hydrochloride salt; 2-tert-butyl 7,7-dimethyl 1-(2-methylphenyl)-6-oxo-octahydropyrrolo[1,2-a]piperazine-2,7,7-tricarboxylate;
7,7-dimethyl 1-(2-methylphenyl)-6-oxo-octahydropyrrolo[1,2-a]piperazine-7,7-dicarboxylate;
tert-butyl 1-(2-methylphenyl)-6-oxo-7,7-bis(prop-2-en-1-yl)-octahydropyrrolo[1,2-a]piperazine-2-carboxylate and
1-(2-methylphenyl)-7,7-bis(prop-2-en-1-yl)-octahydropyrrolo[1,2-a]piperazin-6-one;

or a pharmaceutically acceptable salt thereof.

Compounds of general formula B, B(i) and B(ii) may be used as intermediates in the preparation of compounds of general formula A, A(i) and A(ii).

Compounds of the invention, optionally in combination with other active compounds, may be useful for the prevention, treatment or amelioration of dermal diseases, e.g. pruritus, prurigo nodularis, chronic pruritus, atopic dermatitis, eczema, contact dermatitis, allergic dermatitis, nummular dermatitis, lichen simplex, urticaria, psoriasis, Sézary syndrome, alopecia greata, scabies or vitiligo, or any other dermal disease or condition characterized by pruritus.

An embodiment of the invention is a compound according to general formula A for use in the prevention, treatment or amelioration of prurigo, lichen planus, atopic dermatitis, eczema, contact dermatitis, allergic dermatitis, nummular dermatitis, lichen simplex, psoriasis, Sézary syndrome, cutaneous lymphomas, urticaria, mastocytosis and pruritus with chronic secondary scratch lesions.

An embodiment of the invention is a pharmaceutical composition comprising, as a therapeutically active ingredient, a compound according to general formula A and a pharmaceutically acceptable carrier or vehicle, together with one or more other therapeutically active compound(s).

An embodiment of the invention is a pharmaceutical composition comprising, as a therapeutically active ingredient, a compound according to general formula A and a pharmaceutically acceptable carrier or vehicle, optionally together with one or more other therapeutically active compound(s), suitable for topical administration.

An embodiment the invention relates to a method of preventing, treating or ameliorating a condition involving pruritus of the skin, wherein the condition is selected from the group consisting of acute pruritus in any condition; chronic pruritus on diseased skin, such as inflammatory, infectious, or autoimmune cutaneous diseases, genodermatoses, drug reactions, dermatoses of pregnancy and skin lymphomas, prurigo, lichen planus, atopic dermatitis, eczema, contact dermatitis, allergic dermatitis, nummular dermatitis, lichen simplex, psoriasis, Sézary syndrome, cutaneous lymphomas, bullous pemphigoid, alopecia greata, scabies, vitiligo, urticaria and drug-induced pruritus; pruritic diseases on non-diseased skin of systemic, neurological or psychosomatic/psychiatric origin, including endocrine and metabolic disorders, infections, haematological and lymphoproliferative diseases, solid neoplasms and drug-induced pruritus; mastocytosis; pruritus of unknown cause; pruritus with chronic secondary scratch lesions, such as prurigo nodularis, and all types of prurigo; or any other dermal disease or condition characterized by pruritus, the method comprising applying, on the skin of a patient in need thereof, a therapeutically effective amount of a compound according to general formula A, optionally together with a pharmaceutically acceptable carrier or one or more excipients, optionally in combination with other therapeutically active compounds.

An embodiment the invention relates to the use of a compound according to general formula A in the manufacture of a medicament for the prevention, treatment or amelioration of pruritic skin conditions, e.g. acute pruritus in any condition; chronic pruritus on diseased skin, such as inflammatory, infectious, or autoimmune cutaneous diseases, genodermatoses, drug reactions, dermatoses of pregnancy and skin lymphomas, prurigo, lichen planus, atopic dermatitis, eczema, contact dermatitis, allergic dermatitis, nummular dermatitis, lichen simplex, psoriasis, Sézary syndrome, cutaneous lymphomas, bullous pemphigoid, alopecia greata, scabies, vitiligo, urticaria and drug-induced pruritus; pruritic diseases on non-diseased skin of systemic, neurological or psychosomatic/psychiatric origin, including endocrine and metabolic disorders, infections, haematological and lymphoproliferative diseases, solid neoplasms and drug-induced pruritus; mastocytosis; pruritus of unknown cause; pruritus with chronic secondary scratch lesions, such as prurigo nodularis, and all types of prurigo; or any other dermal disease or condition characterized by pruritus.

An embodiment of the invention relates to a pharmaceutical composition comprising, as a therapeutically active ingredient, a compound according to general formula A and a pharmaceutically acceptable carrier or vehicle.

An embodiment of the invention relates to a pharmaceutical composition suitable for topical administration comprising, comprising as a therapeutically active ingredient, a compound according to general formula A and a pharmaceutically acceptable carrier or vehicle.

An embodiment of the invention relates to a method of preventing, treating or ameliorating a condition involving pruritus of the skin, the method comprising applying, on the skin of a patient in need thereof, a therapeutically effective amount of a compound according to general formula A.

In an embodiment compounds of general formula A may be useful in the prevention, treatment or amelioration of prurigo.

In an embodiment compounds of general formula A may be useful in the prevention, treatment or amelioration of lichen planus.

In an embodiment compounds of general formula A may be useful in the prevention, treatment or amelioration of atopic dermatitis.

In an embodiment compounds of general formula A may be useful in the prevention, treatment or amelioration of eczema.

In an embodiment compounds of general formula A may be useful in the prevention, treatment or amelioration of contact dermatitis.

In an embodiment compounds of general formula A may be useful in the prevention, treatment or amelioration of allergic dermatitis.

In an embodiment compounds of general formula A may be useful in the prevention, treatment or amelioration of nummular dermatitis.

In an embodiment compounds of the invention may be useful in the prevention, treatment or amelioration of lichen simplex.

In an embodiment compounds of general formula A may be useful in the prevention, treatment or amelioration of psoriasis.

In an embodiment compounds of general formula A may be useful in the prevention, treatment or amelioration of Sézary syndrome.

In an embodiment compounds of general formula A may be useful in the prevention, treatment or amelioration of cutaneous lymphomas.

In an embodiment compounds of general formula A may be useful in the prevention, treatment or amelioration of urticaria.

In an embodiment compounds of general formula A may be useful in the prevention, treatment or amelioration of mastocytosis.

In an embodiment compounds of general formula A may be useful in the prevention, treatment or amelioration of pruritus with chronic secondary scratch lesions.

In an embodiment compounds of general formula A may be useful in the prevention, treatment or amelioration of acute pruritus in any condition.

In an embodiment compounds of general formula A may be useful in the prevention, treatment or amelioration of chronic pruritus on diseased skin.

In an embodiment compounds of general formula A may be useful in the prevention, treatment or amelioration of pruritic diseases on non-diseased skin of systemic origin.

In an embodiment compounds of general formula A may be useful in the prevention, treatment or amelioration of pruritic diseases on non-diseased skin of neurological or psychosomatic/psychiatric origin.

In an embodiment compounds of general formula A may be useful in the prevention, treatment or amelioration of pruritus of unknown cause.

Besides being useful for human treatment, the compounds of the present invention may also be useful for veterinary treatment of animals including mammals such as horses, cattle, sheep, pigs, dogs, and cats.

Pharmaceutical Compositions of the Invention

For use in therapy, compounds of the present invention are typically in the form of a pharmaceutical composition. The invention therefore relates to a pharmaceutical composition comprising a compound of formula A, optionally together with one or more other therapeutically active compound(s), together with a pharmaceutically acceptable excipient or vehicle. The excipient must be "acceptable" in the sense of being compatible with the other ingredients of the composition and not deleterious to the recipient thereof.

Conveniently, the active ingredient comprises from 0.05-99.9% by weight of the formulation.

In the form of a dosage unit, the compound may be administered one or more times a day at appropriate intervals, always depending, however, on the condition of the patient, and in accordance with the prescription made by the medical practitioner. Conveniently, a dosage unit of a formulation contain between 0.1 mg and 1000 mg, preferably between 1 mg and 100 mg, such as 5-50 mg of a compound of formula A.

A suitable dosage of the compound of the invention will depend, inter alia, on the age and condition of the patient, the severity of the disease to be treated and other factors well known to the practising physician. The compound may be administered orally, parenterally or topically according to different dosing schedules, e.g. daily or with weekly intervals. In general a single dose will be in the range from 0.01 to 400 mg/kg body weight. The compound may be administered as a bolus (i.e. the entire daily dosis is administered at once) or in divided doses two or more times a day.

In the context of topical treatment it may be more appropriate to refer to a "usage unit", which denotes a single dose which is capable of being administered to a patient, and which may be readily handled and packed, remaining as a physically and chemically stable unit dose comprising either the active material as such or a mixture of it with solid or liquid pharmaceutical diluents or carriers.

The term "usage unit" in connection with topical use means a unitary, i.e. a single dose capable of being administered topically to a patient in an application per square centimeter of the infected area of from 0.1 mg to 10 mg and preferably from 0.2 mg to 1 mg of the active ingredient in question.

It is also envisaged that in certain treatment regimes, administration with longer intervals, e.g. every other day, every week, or even with longer intervals may be beneficial.

If the treatment involves administration of another therapeutically active compound it is recommended to consult *Goodman & Gilman's The Pharmacological Basis of Therapeutics,* $9^{th}$ Ed., J. G. Hardman and L. E. Limbird (Eds.), McGraw-Hill 1995, for useful dosages of said compounds.

The administration of a compound of the present invention with one or more other active compounds may be either concomitantly or sequentially.

The formulations include e.g. those in a form suitable for oral (including sustained or timed release), rectal, parenteral (including subcutaneous, intraperitoneal, intramuscular, intraarticular and intravenous), transdermal, ophthalmic, topical, dermal, nasal, buccal or intradermal administration. Topical administration of the claimed formulation is particularly suitable.

The formulations may conveniently be presented in dosage unit form and may be prepared by any of the methods well known in the art of pharmacy, e.g. as disclosed in Remington, *The Science and Practice of Pharmacy,* $20^{th}$ ed., 2000. All methods include the step of bringing the active ingredient into association with the carrier, which constitutes one or more accessory ingredients. In general, the formulations are prepared by uniformly and intimately bringing the active ingredient into association with a liquid carrier or a finely divided solid carrier or both, and then, if necessary, shaping the product into the desired formulation.

Formulations of the present invention suitable for oral administration may be in the form of discrete units as capsules, sachets, tablets or lozenges, each containing a predetermined amount of the active ingredient; in the form of a powder or granules; in the form of a solution or a suspension in an aqueous liquid or non-aqueous liquid, such as ethanol or glycerol; or in the form of an oil-in-water emulsion or a water-in-oil emulsion. Such oils may be edible oils, such as e.g. cottonseed oil, sesame oil, coconut oil or peanut oil. Suitable dispersing or suspending agents for aqueous suspensions include synthetic or natural gums such as tragacanth, alginate, acacia, dextran, sodium carboxymethylcellulose, gelatin, methylcellulose, hydroxypropylmethylcellulose, hydroxypropylcellulose, carbomers and polyvinylpyrrolidone. The active ingredients may also be administered in the form of a bolus, electuary or paste.

A tablet may be made by compressing or moulding the active ingredient optionally with one or more accessory ingredients. Compressed tablets may be prepared by compressing, in a suitable machine, the active ingredient(s) in a free-flowing form such as a powder or granules, optionally mixed by a binder, such as e.g. lactose, glucose, starch, gelatine, acacia gum, tragacanth gum, sodium alginate, carboxymethylcellulose, methylcellulose, hydroxypropylmethylcellulose, polyethylene glycol, waxes or the like; a lubricant such as e.g. sodium oleate, sodium stearate, magnesium stearate, sodium benzoate, sodium acetate, sodium chloride or the like; a disintegrating agent such as e.g. starch, methylcellulose, agar, bentonite, croscarmellose sodium, sodium starch glycollate, crospovidone or the like or a dispersing agent, such as polysorbate 80. Moulded tablets may be made by moulding, in a suitable machine, a mixture of the powdered active ingredient and suitable carrier moistened with an inert liquid diluent.

Formulations for rectal administration may be in the form of suppositories in which the compound of the present invention is admixed with low melting water soluble or insoluble solids such as cocoa butter, hydrogenated vegetable oils, polyethylene glycol or fatty acids esters of polyethylene glycols, while elixirs may be prepared using myristyl palmitate.

Formulations suitable for parenteral administration conveniently comprise a sterile oily or aqueous preparation of the active ingredients, which is preferably isotonic with the blood of the recipient, e.g. isotonic saline, isotonic glucose solution or buffer solution. The formulation may be conveniently sterilised by for instance filtration through a bacteria retaining filter, addition of sterilising agent to the formulation, irradiation of the formulation or heating of the formulation. Liposomal formulations as disclosed in e.g. Encyclopedia of Pharmaceutical Technology, vol. 9, 1994, are also suitable for parenteral administration.

Alternatively, the compounds of formula A may be presented as a sterile, solid preparation, e.g. a freeze-dried powder, which is readily dissolved in a sterile solvent immediately prior to use.

Transdermal formulations may be in the form of a plaster, patch, microneedles, liposomal or nanoparticulate delivery systems or other cutaneous formulations applied to the skin.

Formulations suitable for ophthalmic administration may be in the form of a sterile aqueous preparation of the active ingredients, which may be in microcrystalline form, for example, in the form of an aqueous microcrystalline suspension. Liposomal formulations or biodegradable polymer systems e.g. as disclosed in Encyclopedia of Pharmaceutical Technology, vol. 2, 1989, may also be used to present the active ingredient for ophthalmic administration.

Formulations suitable for topical, such as dermal, intradermal or ophthalmic administration include liquid or semi-liquid preparations such as liniments, lotions, gels, sprays, micro or nano-emulsions, oil-in-water or water-in-oil emulsions such as creams, ointments, pastes, applicants, foams, filmforming systems or microneedles; or solutions or suspensions such as drops. Compositions for ophthalmic treatment may preferably additionally contain a cyclodextrin.

For topical administration, the compound of formula A may typically be present in an amount of from 0.01 to 20% by weight of the composition, such as 0.1% to about 10%, but may also be present in an amount of up to about 50% of the composition.

Formulations suitable for nasal or buccal administration include powder, self-propelling and spray formulations, such as aerosols and atomisers. Such formulations are disclosed in greater detail in e.g. Modern Pharmaceutics, $2^{nd}$ ed., G. S. Banker and C. T. Rhodes (Eds.), page 427-432, Marcel Dekker, New York; Modern Pharmaceutics, $3^{th}$ ed., G. S. Banker and C. T. Rhodes (Eds.), page 618-619 and 718-721, Marcel Dekker, New York and Encyclopedia of Pharmaceutical Technology, vol. 10, J. Swarbrick and J. C. Boylan (Eds), page 191-221, Marcel Dekker, New York.

In addition to the aforementioned ingredients, the formulations of a compound of formula A may include one or more additional ingredients such as diluents, buffers, flavouring agents, colourant, surface active agents, thickeners, preservatives, e.g. methyl hydroxybenzoate (including anti-oxidants), emulsifying agents and the like.

When the active ingredient is administered in the form of salts with pharmaceutically acceptable non-toxic acids, preferred salts are for instance easily water-soluble or slightly soluble in water, in order to obtain a particular and appropriate rate of absorption.

The pharmaceutical composition may additionally comprise one or more other active components conventionally used in the treatment of dermal disease or conditions, e.g. selected from the group consisting of glucocorticoids, vitamin D and vitamin D analogues, antihistamines, phosphodiesterase 4 (PDE4) inhibitors, JAK inhibitors, methylxanthines, β-adrenergic agents, COX-2 inhibitors, salicylates, indomethacin, flufenamate, naproxen, timegadine, retinoids, zinc salts, salicylazosulfapyridine and calcineurin inhibitors.

The term "compound of formula A" as used herein is intended to include compounds of formula A(i), formula A(ii), formula A(iii), formula A(iv) or formula A(v).

The invention is further described in the appended examples which are not in any way intended to limit the scope of the invention as claimed.

Methods of Preparation

The compounds of the present invention can be prepared in a number of ways well known to those skilled in the art of synthesis. The compounds of formula A may for example be prepared using the reactions and techniques outlined below together with methods known in the art of synthetic organic chemistry, or variations thereof as appreciated by those skilled in the art. Preferred methods include, but are not limited to, those described below. The reactions are carried out in solvents appropriate to the reagents and materials employed and suitable for the transformations being effected. Also, in the synthetic methods described below, it is to be understood that all proposed reaction conditions, including choice of solvent, reaction atmosphere, reaction temperature, duration of experiment and work-up procedures, are chosen to be conditions of standard for that reaction, which should be readily recognized by one skilled in the art of organic synthesis. Not all compounds falling into a given class may be compatible with some of the reaction conditions required in some of the methods described. Such restrictions to the substituents which are compatible with the reaction conditions will be readily apparent to one skilled in the art and alternative methods can be used.

Starting materials of general formula I are prepared according to standard procedures known to a chemist skilled in the art of organic synthesis. A benzyl halide derivative of formula I is treated with methylamine in a suitable solvent (e.g. methanol) under suitable conditions (e.g. RT to 50° C.) for a suitable period of time (e.g. 3-5 h) to form a compound of general formula II.

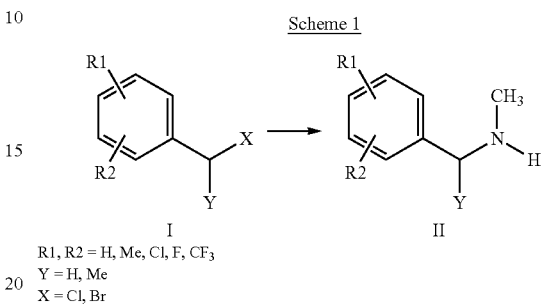

Scheme 1

R1, R2 = H, Me, Cl, F, CF3
Y = H, Me
X = Cl, Br

Starting material of formula IV is prepared according to standard procedures known to a chemist skilled in the art of organic synthesis. An acetophenone derivative of formula III can be converted into the chirally pure compound of formula IV according to a published procedure (PCT Int. Appl., 2008090117). Thus, reacting III with methylamine in a suitable solvent (e.g. methanol) under suitable conditions (e.g. RT to 50° C.) for a suitable period of time (e.g. 3-5 h), followed by addition of a suitable reducing agent (e.g. NaBH$_4$) and treatment, under suitable conditions, with a suitable chiral acid (e.g. L(+)-Malic acid) and subsequent basic treatment (e.g. with NaOH), compound IV is obtained.

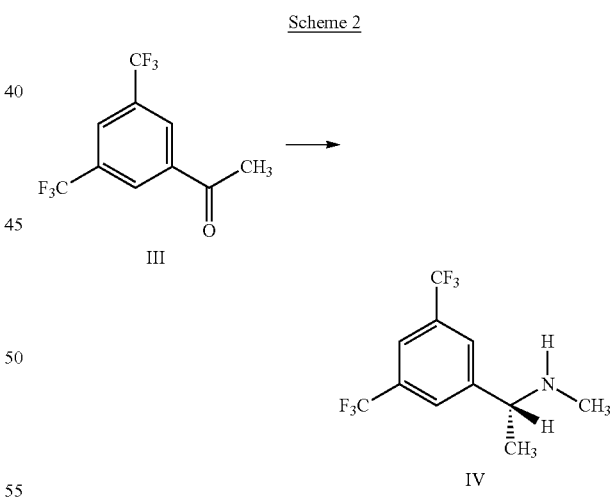

Scheme 2

A compound of general formula VII can be prepared as described in Scheme 3. A diamine derivative of general formula V is treated with a suitable acylating agent (e.g. benzyl chloroformate) in a suitable solvent (e.g. DCM), under suitable conditions (e.g. 0° C. to RT) for a suitable period of time (e.g. 3 h) to form a compound of general formula VI, which in turn is treated with pentynoic acid in the presence of suitable coupling agents (e.g. EDCI, HOBT), in a suitable solvent (e.g. DCM), under suitable conditions (e.g. 0° C. to RT) in the presence of a suitable base (e.g. TEA) for a suitable period of time (e.g. 12 h) to form a compound of general formula VII.

Scheme 3

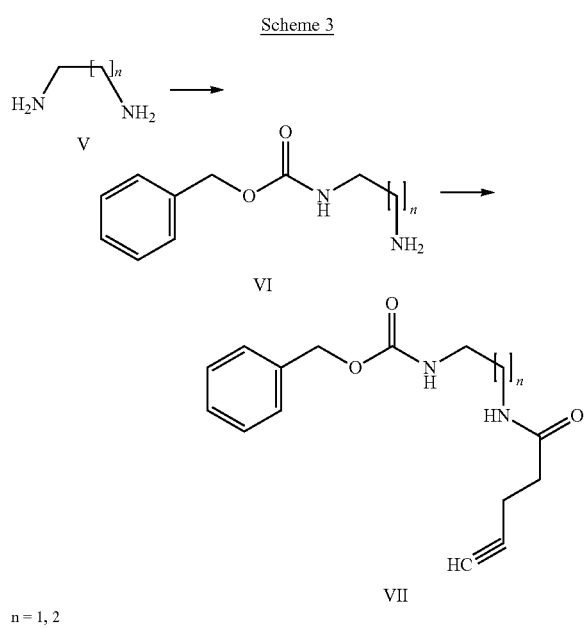

n = 1, 2

A compound of general formula VIII can be prepared as described in Scheme 4. A compound of general formula VII is treated with 2-Iodotoluene in a suitable solvent (e.g. DMF), in the presence of a suitable base (e.g. TEA), under suitable coupling conditions (e.g. catalytic amounts of copper iodide and a palladium catalyst such as PdCl$_2$(PPh$_3$)$_2$), for a suitable period of time (e.g. 3 h) at a suitable temperature (e.g. RT) to form a compound of general formula VIII.

Scheme 4

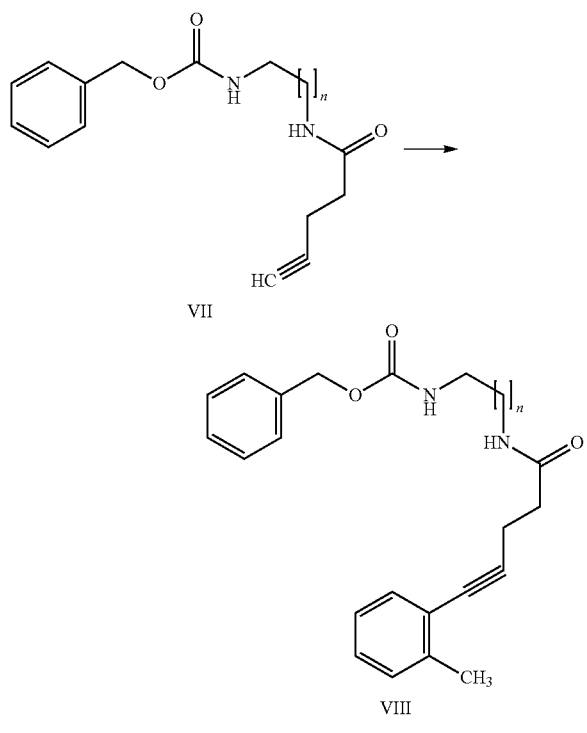

A compound of general formula IX can be prepared as described in Scheme 5. A compound of general formula VIII is treated with a suitable oxidizing agent (e.g. PIFA) in a suitable solvent (e.g. TFEA) for a suitable period of time (e.g. 3 h) at a suitable temperature (e.g. 0° C. to RT) to form a compound of general formula IX.

Scheme 5

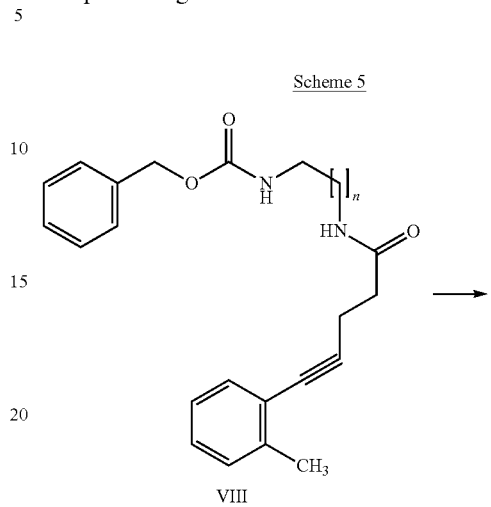

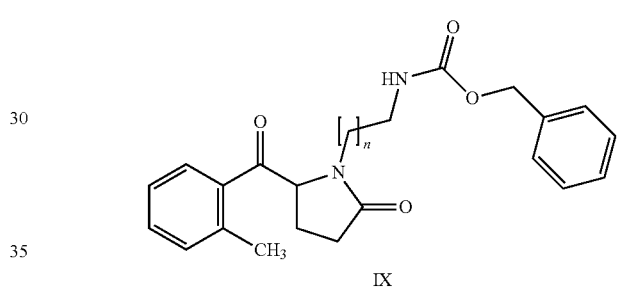

A compound of general formula X can be prepared as described in Scheme 6. A compound of general formula IX is treated with a suitable acid agent (e.g. hydrobromic acid in acetic acid), in the presence of a suitable agent (e.g. titanium isopropoxide) and a suitable agent (e.g. PIFA) in a suitable solvent (e.g. TFEA) for a suitable period of time (e.g. 3 h) at a suitable temperature (e.g. 0° C. to RT) to form a compound of general formula IX. Alternatively, a compound of general formula IX can be treated under suitable hydrogenation conditions (e.g. 5 Atm H$_2$) in a suitable acidic media (e.g. HCl/MeOH) for a suitable period of time (e.g. 24 h) and in the presence of a suitable catalyst (e.g. Pd/C 5%) to afford a compound of general formula X.

Scheme 6

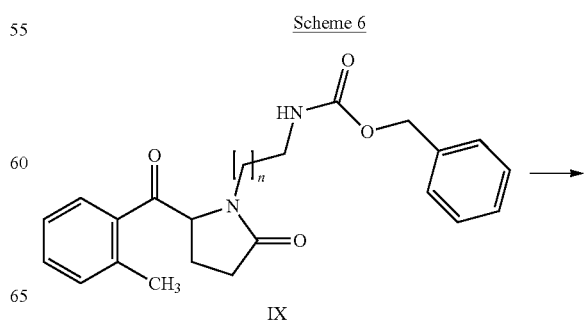

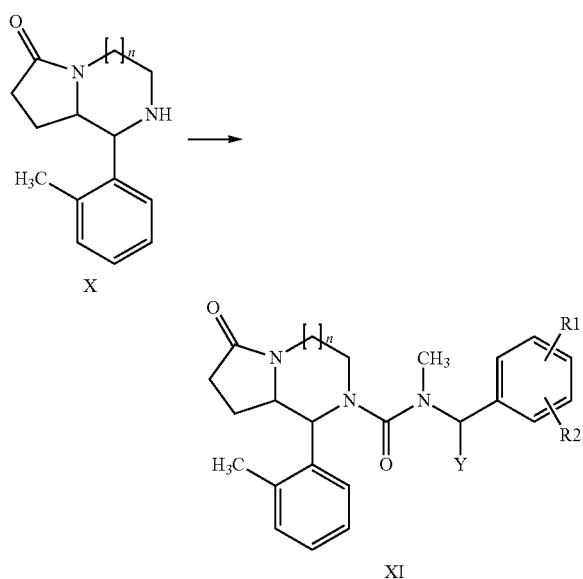

A compound of general formula XI can be prepared as described in Scheme 7. A compound of general formula X is treated with a suitable acylating agent (e.g. triphosgene) in a suitable solvent (e.g. EtOAc) in the presence of a compound of general formula II or IV and of a suitable base (e.g. TEA), at a suitable temperature (e.g. 0° C. to RT) for a suitable period of time (e.g. 3 h) to afford a compound of general formula XI.

Scheme 7

R1, R2 = H, CH$_3$, Cl, F, CF$_3$
Y = H, CH$_3$

A compound of general formula XIII can be prepared as described in Scheme 8. A compound of formula general X is treated with a suitable acylating agent (e.g. Boc anhydride) in the presence of a suitable base (e.g. TEA) in a suitable solvent (e.g. DCM) at a suitable temperature (e.g. RT) for a suitable period of time (e.g. 12 h) to give a compound of formula XII, which in turn can be treated with a suitable acylating or alkylating agent (methyl chloroformate (possibly followed by MeI), allyl bromide) in the presence of a suitable base (e.g. LHMDS) in a suitable solvent (e.g. THF) at a suitable temperature (e.g. −78° C. to 0° C.) for a suitable period of time (e.g. 3 h). The resulting compound (XIII, R$_4$=Boc) can in turn be treated with a suitable acid (e.g. TFA) in a suitable solvent (e.g. DCM) to afford a compound of general formula XIII (R═H).

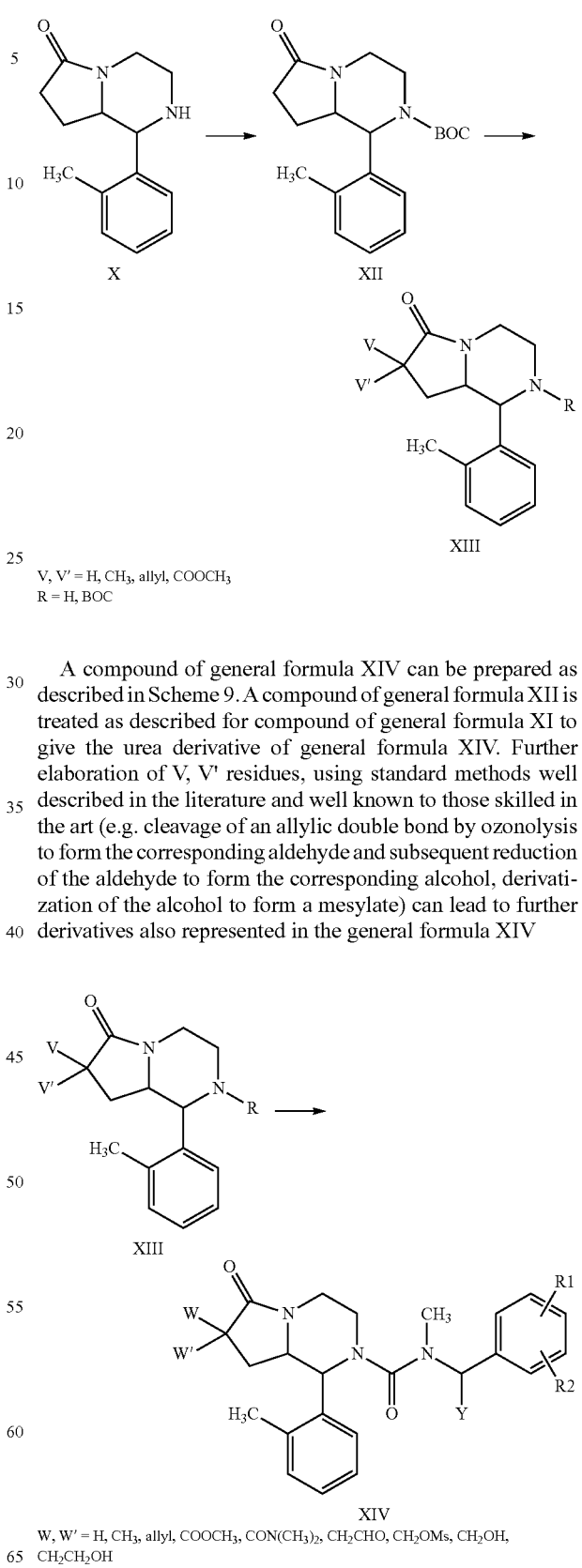

V, V' = H, CH$_3$, allyl, COOCH$_3$
R = H, BOC

A compound of general formula XIV can be prepared as described in Scheme 9. A compound of general formula XII is treated as described for compound of general formula XI to give the urea derivative of general formula XIV. Further elaboration of V, V' residues, using standard methods well described in the literature and well known to those skilled in the art (e.g. cleavage of an allylic double bond by ozonolysis to form the corresponding aldehyde and subsequent reduction of the aldehyde to form the corresponding alcohol, derivatization of the alcohol to form a mesylate) can lead to further derivatives also represented in the general formula XIV W, W' = H, CH$_3$, allyl, COOCH$_3$, CON(CH$_3$)$_2$, CH$_2$CHO, CH$_2$OMs, CH$_2$OH, CH$_2$CH$_2$OH Scheme 9

A compound of general formula XV can be prepared as described in Scheme 10. A compound of general formula XIV (where W=W'=CH₂CHO) is treated with methylamine under suitable reductive amination conditions (e.g. NABH₃(CN) in MeOH at RT for 12 h) to give a compound of general formula XV.

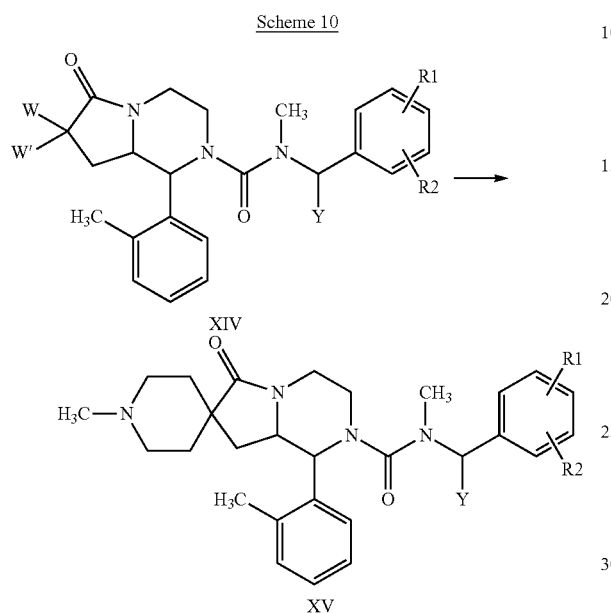

A compound of general formula XVI can be prepared as described in Scheme 11. A compound of general formula XIV (where W=H, W'=CH₂O Ms) is treated with a suitable base (e.g. pyrrolidine) in a suitable solvent (e.g. THF) at a suitable temperature (e.g. 65° C.) and for a suitable period of time (e.g. 20 h) to give a compound of general formula XVI.

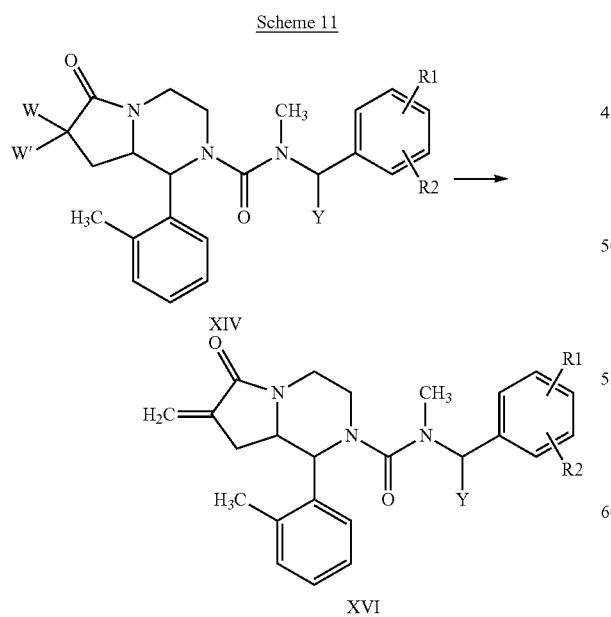

A compound of general formula XVII can be prepared as described in Scheme 12. A compound of general formula XIV (where W=W'=COOMe) is treated with a suitable salt (e.g. calcium chloride) and a suitable reducing agent (e.g. NaBH₄) in a suitable solvent (e.g. MeOH) at a suitable temperature (e.g. 0° C. to RT) for a suitable period of time (e.g. 0.5 h) to give a compound of general formula XVII.

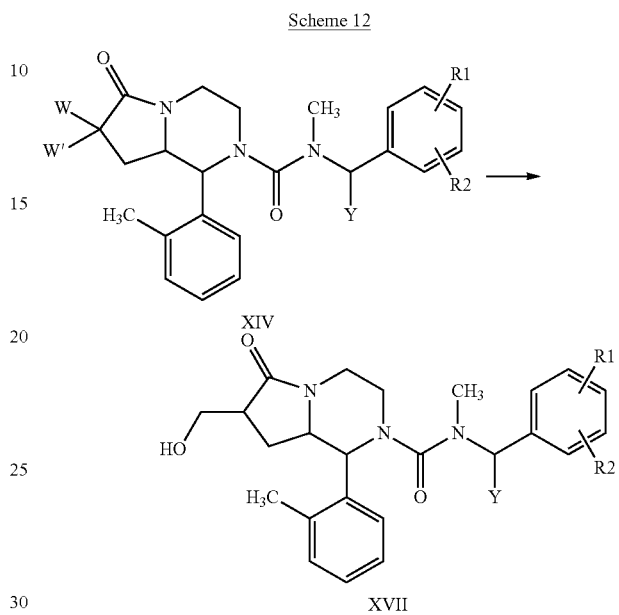

A compound of general formula XVIII can be prepared as described in Scheme 13. A compound of general formula XIV (where W=H, W'=CH₂O Ms) is treated with a suitable amine (e.g. pyrrolidine, morpholine, N-methylpiperazine or N-acetylpiperazine) in a suitable solvent (e.g. THF) at a suitable temperature (e.g. 65° C.) and for a suitable period of time (e.g. 20 h) to give a compound of general formula XVIII.

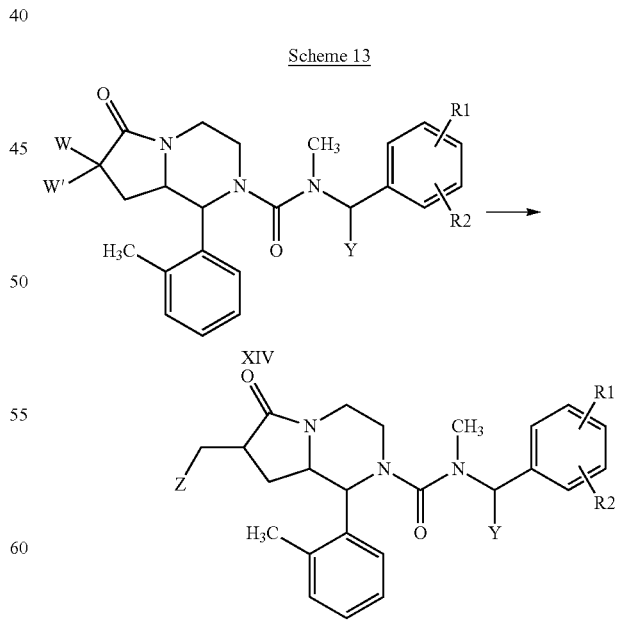

Z = N-linked heterocycyles, e.g. pyrrolidine, morpholine, N-methylpiperazine, N-acetylpiperazine A compound of general formula XIX can be prepared as described in Scheme 14. A compound of general formula XIV is treated with a suitable alkylating agent (e.g. allyl chloride or bromide) in the presence of a suitable base (e.g. LHMDS) in a suitable solvent (e.g. THF) at a suitable temperature (e.g. −78° C. to 0° C.) for a suitable period of time (e.g. 3 h) to give a compound of general formula XIX (where Y'=vinyl). Further elaboration of Y' residue, using standard methods well described in the literature and well known to those skilled in the art (e.g. cleavage of an allylic double bond by ozonolysis to form the corresponding aldehyde and subsequent reduction of the aldehyde to form the corresponding alcohol) can lead to further derivatives also represented in the general formula XIX.

Scheme 14

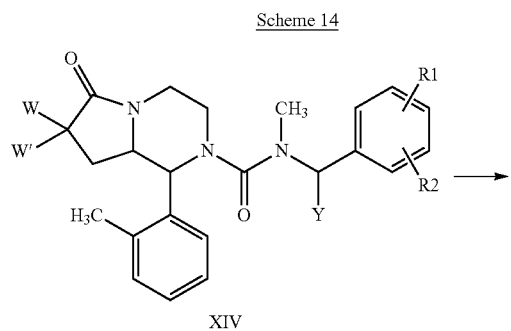

Y' = CH₂OH, vinyl, CHO

A compound of general formula XX can be prepared as described in Scheme 15. A compound of general formula XIV is treated with a suitable reducing agent (e.g. borane dimethylsulfide) at a suitable temperature (e.g. RT) in a suitable solvent (e.g. MeOH) for a suitable period of time (e.g. 12 h) to give a compound of general formula XX.

Scheme 15

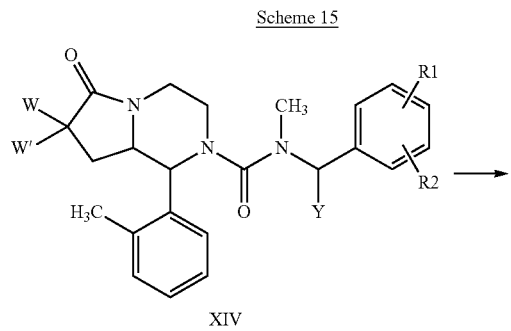

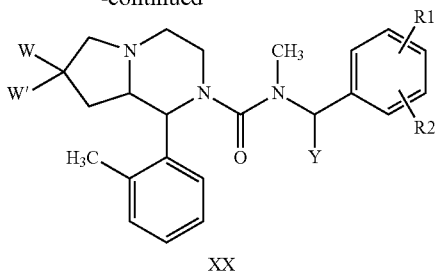

XX

EXAMPLES

Some compounds are named using ACD/Name PRO6.02 chemical naming software (Advanced Chemistry Development Inc., Toronto, Ontario, M5H2L3, Canada).

Proton Magnetic Resonance (NMR) spectra were recorded either on Varian instruments at 400, 500 MHz (Varian Direct-Drive), or 600 MHz (INOVA 600 MHz), or on a Bruker instrument at 400 MHz spectrometers at 25° C. Chemical shifts are reported in ppm (δ) using the residual solvent line as internal standard. Peak multiplicities are expressed as follow: s, singlet; d, doublet; dd doublet of doublets, t, triplet; dt doublet of triplet; q, quartet; quin, quintet; m, multiplet; br s, broad singlet.

Total ion current (TIC) and DAD UV chromatographic traces together with MS and UV spectra associated with the peaks were taken also on a UPLC/PDA/MS Acquity™ system equipped with a Waters SQD™ mass spectrometer operating in positive and/or negative electrospray ionisation mode. [LC/MS/ES (+/−): analyses performed using an Acquity™ UPLC BEH C18 column (50×21 mm, 1.7 μm particle size), column temperature 40° C., mobile phase: A=10 mM ammonium bicarbonate aqueous solution adjusted to pH 10 with ammonia and B=MeCN, Flow rate: 1.0 mL/min, Gradient: t=0 min 3% B, t=1.50 min 99.9% B, t=1.90 min 99.9% B, t=2.0 min 3% B.

Achiral purification were carried out using a mass directed autopurification system (MDAP) Fractionlynx™ (Waters) operated under high pH chromatographic conditions mobile phase: A=10 mM ammonium bicarbonate aqueous solution adjusted to pH 10 with ammonia and B=MeCN, flow rate 17 ml/min and column XBridge Prep. C18 5 μm OBD (100 mm×19.0 mm) @ room T.

Mass spectra (MS) were acquired on an Agilent HP1100 pump coupled with an Agilent MSD Trap XCT mass spectrometer operating in ES(+) and ES(−) ionization mode: analysis performed using a Waters X-Bridge C18 column (50 mm×4.6 mm) at 40° C.: A=10 mM ammonium bicarbonate aqueous solution adjusted to pH 10 with ammonia and B=MeCN, Flow rate: 1.0 mL/min, Gradient: t=0 min 3% B, t=7.0 min 99% B, t=8.0 min 99% B, 8.01 min 3% B, hold for 2 min, post run=3 min.

For the chiral separation and the chiral quality control two different techniques were used: 1) Supercritical Fluid Chromatography (SFC): analytical chromatography was performed on a Berger SFC Analytix, while for the preparative SFC, a Jasco preparative SFC system was used 2) High Performance Liquid Chromatography (HPLC): chiral Preparative HPLC was performed using a Waters 600 HPLC system and Agilent series 1100 instrument, while for analytical chromatography an Agilent series 1100 HPLC was used.

Abbreviations

AcOH: Acetic acid
EtOAc: ethyl acetate
CH: cyclohexane
Cy: cyclohexane
DCM: dichloromethane
DIBAL-H: Diisobutylaluminium hydride
DMSO: dimethylsulfoxide
DMAP: 4-Dimethylaminopyridine
DMF: N,N-dimethylformamide
DMPU: 1,3-Dimethyl-3,4,5,6-tetrahydro-2(1H)-pyrimidinone
EDCI.HCl: N-(3-Dimethylaminopropyl)-N'-ethylcarbodiimide hydrochloride
EtOH: ethanol
HOBT.H$_2$O: hydroxybenzotriazol monohydrate
HPLC: High Pressure Liquid Chromatography
LHMDS: lithium bis(trimethylsilyl)amide
Me: Methyl
MeCN: acetonitrile
MeOH: methanol
MS: Mass Spectrometry
Ms: Mesyl
NMR: Nuclear Magnetic Resonance
Pd(dppf)Cl$_2$: [1,1'-Bis(diphenylphosphino)ferrocene]dichloropalladium(II)
PE: Petroleum Ether
iPr: isopropyl
PIFA ((bis(trifluoroacetoxy)iodo)benzene
RT: room temperature
ee: enantiomeric eccess
Rt: retention time
TEA: triethylamine
TFA: trifluoroacetic acid
TFEA: 2,2,2-trifluoroethanol
THF: tetrahydrofuran
TLC: Thin Layer Chromatography
UPLC: Ultra Performance Liquid Chromatography In the procedures that follow, after each starting material, reference to a Description or Compound by number is typically provided. This is provided merely for assistance to the skilled chemist. Often the terminology enantiomer 1, enantiomer 2, stereoisomer 1, stereoisomer 2, diastereoisomer 1, diastereoisomer 2, isomer 1, isomer 2 is applied: the numbers 1 and 2 refer to the first eluting compound and to the second eluting compound, respectively, in the analytical experiment (generally HPLC, with chiral or achiral column) specified in the experimental part.

Intermediate 1

[(1R)-1-[3,5-bis(trifluoromethyl)phenyl]ethyl](methyl)amine

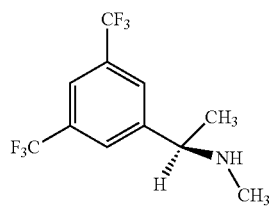

To a solution of 3,5-bistrifluoromethylacetophenone (5.0 g, 19.5 mmol) in MeOH (20 mL), a solution of methylamine 8M in EtOH (6.1 mL, 48.8 mmol) was added dropwise in 15 min at 25° C. under nitrogen atmosphere. The mixture was stirred 24 h. NaBH$_4$ was then added portion wise (0.46 g, 19.92 mmol) at 0° C. A second amount of NaBH$_4$ was added over 30 min. (0.29 g) and the mixture stirred for a further 1.5 h and the solvent evaporated under vacuo. EtOAc (40 mL) was added. L(+)-malic acid was then added portion wise (1.96 g, 14.6 mmol). The suspension was stirred for 2 h at 25° C., then 3 h at 0° C. The suspension was filtered and the cake was washed with EtOAc and the solvent removed under vacuo to give a white solid (6.5 g) which was suspended in EtOAc (30 mL), then heated at reflux till complete dissolution and then cooled to 25° C. The suspension was filtered, washed with EtOAc then dried to give a solid (6.52 g). The solid was stirred in a mixture of NaOH 10% (12 mL) and EtOAc (11 mL). The organic layer was washed with water then concentrated to yield the title compound as a yellow oil (4.78 g). $^1$H NMR (500 MHz, CDCl$_3$) δ ppm 7.81 (s, 2H), 7.77 (s, 1H), 3.80 (q, J=6.6 Hz, 1H), 2.32 (s, 3H), 1.38 (d, J=6.6 Hz, 3H). HPLC: Column Chiralpak IC (25×0.46 cm), 5μ. Mobile phase: n-Hexane/2-Propanol 99/1 v/v; Flow rate: 1 mL/min Detection: DAD t 220 nm, Rt=6.0 min.

Intermediate 2 methyl({[3-(trifluoromethyl)phenyl]methyl})amine

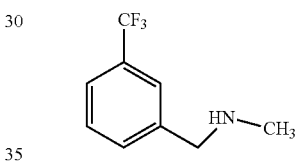

To a solution of methylamine 2M in MeOH (61.5 mL, 123.3 mmol), MeOH (30 mL) was added. The mixture was heated at 50° C. under stirring and 3-(trifluoromethyl)benzyl chloride (1.6 mL, 10.3 mmol) dissolved in MeOH (10 mL) were added. The reaction mixture was stirred at this temperature for 5 h. The solvent was removed under vacuo, then NaOH 1M was added and the aqueous layer was extracted with DCM. The organic layer was filtered through a phase separator and concentrated in vacuo to give 2.19 g of a colourless oil. $^1$H NMR (400 MHz, CDCl$_3$) δ ppm 7.69 (s, 1H), 7.57 (d, 1H), 7.49 (t, 2H), 3.88 (s, 2H), 2.56, (s, 3H). UPLC-MS: Rt=0.39; m/z (ES+): 190 [M+H]$^+$.

Intermediate 3

[(3,5-dimethylphenyl)methyl](methyl)amine

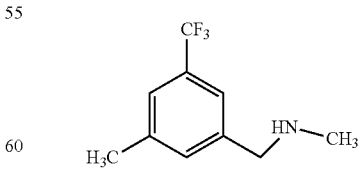

To a solution of methylamine 2M in MeOH (60.2 mL, 120.5 mmol), MeOH (30 mL) was added. The mixture was heated at 50° C. under stirring and 3,5-(dimethyl)benzyl bromide (2 g, 10.05 mmol) was added. The reaction mixture was stirred at this temperature for 5 h. The solvent was removed under vacuo, then NaOH 1M was added and the aqueous layer was extracted with DCM. The organic layer was filtered through a phase separator and concentrated in vacuo to give 1.58 g of a crude that was purified on SP1 (SNAP-NH cartridge, 55 g, CH/EtOAc 9:1 to 7:3 as eluent) to give the title compound as a colourless oil (1 g). $^1$H NMR (400 MHz, CDCl$_3$) δ ppm 7.33 (s, 1H), 7.07 (m, 2H), 6.92 (m, 1H), 3.79 (s, 2H), 2.57, (s, 3H). UPLC-MS: Rt=0.39; m/z (ES+): 150.0 [M+H]$^+$.

Intermediate 4

{[3-fluoro-5-(trifluoromethyl)phenyl]methyl}(methyl)amine

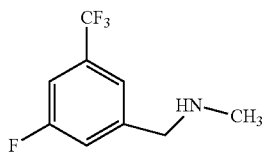

Methylamine 33% in MeOH (1.5 mL, 46.5 mmol) was dissolved in MeOH (15 mL). The mixture was heated at 50° C. under stirring and 1-(bromomethyl)-3-fluoro-5-(trifluoromethyl)benzene (1 g, 3.88 mmol) was added. The reaction mixture was stirred at this temperature for 3 h. The solvent was removed under vacuo, then NaOH 1M (50 mL) was added and the aqueous layer was extracted with DCM (100 mL). The organic layer was dried over Na$_2$SO$_4$, filtered and evaporated under vacuo to give the title compound as a yellow oil (0.5 g). $^1$H NMR (400 MHz, CDCl$_3$) δ ppm 7.50 (s, 1H), 7.30 (m, 2H), 7.25 (m, 1H), 3.88 (s, 2H), 2.54, (s, 3H). UPLC-MS: Rt=0.51; m/z (ES+): 208.1 [M+H]$^+$.

Intermediate 5

Benzyl N-[2-(pent-4-ynamido)propyl]carbamate

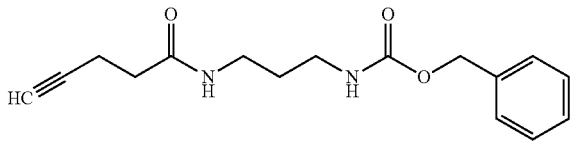 [SMILES: C#CCCC(=O)NCCCNC(=O)OCc1ccccc1]

Pentynoic acid (0.267 g, 2.72 mmol) was added to a suspension of Z-propandiamine hydrochloride (1 g, 4 mmol), EDCI.HCl 767 mg, 4 mmol) and HOBt.H$_2$O (540 mg, 4 mmol) in dry DCM (20 mL). The resulting mixture was cooled at 0° C. and TEA (1.12 mL, 8 mmol) was added dropwise. The reaction mixture was stirred at 25° C. for 16 h. The DCM solution was washed with NH$_4$Cl solution (20 mL×2) and NaHCO$_3$ solution, the organic phase was filtered through a phase separator and evaporated to dryness to obtain the title compound as a white solid (800 mg). The crude product was used in the next step without further purification. $^1$H NMR (400 MHz, CDCl$_3$) δ 7.41-7.31 (m, 5H), 6.20 (br s, 1H), 5.27 (br s, 1H), 5.12 (s, 2H), 3.34 (q, 2H), 3.27 (q, 2H), 2.59-2.52 (m, 2H), 2.42 (t, 2H), 2.02 (br s, 1H). UPLC-MS Rt=0.76; m/z (ES+): 289 [M+H]$^+$.

Intermediate 6

Benzyl N-{2-[5-(2-methylphenyl)pent-4-ynamido]propyl}carbamate

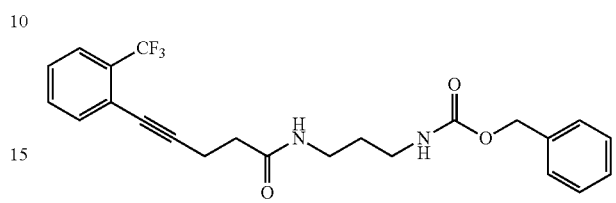

Intermediate 5 (800 mg, 2.77 mmol) and 2-iodotoluene (335 μL, 2.63 mmol) were charged in a two neck bottom flask equipped with vacuum/Argon system. They were dissolved in DMF (8 mL), then TEA (425 μL, 3.04 mmol), CuI (42 mg, 0.22 mmol) and PdCl$_2$(PPh$_3$)$_2$ (78 mg, 0.11 mmol) were added and the resulting mixture was stirred at 25° C. for 12 h. DMF was removed in vacuo, the residue was dissolved in DCM and washed with HCl 1M, NaHCO$_3$ and brine. The layers were separated and the organic one was filtered through a phase separator and evaporated to dryness to obtain a crude material which was purified on SP1 (SNAP-SiO$_2$ cartridge, 50 g, CH/EtOAc 4: 6 to 0:1 as eluent) to give the title compound (726 mg). $^1$H NMR (400 MHz, CDCl$_3$) δ ppm 7.40-7.31 (m, 6H), 7.20-7.16 (m, 2H), 7.13-7.08 (m, 1H), 6.26 (br s, 1H), 5.26 (br s, 1H), 5.10 (s, 2H), 3.35 (q, 2H), 3.23 (q, 2H), 2.81 (t, 2H), 2.51 (t, 2H), 2.40 (s, 3H), 1.66-1.61 (m, 2H). UPLC-MS: Rt=1.05; m/z (ES+): 379 [M+H]$^+$.

Intermediate 7

Benzyl N-(2-{2-[(2-methylphenyl)carbonyl]-5-oxopyrrolidin-1-yl}propyl)carbamate (racemate)

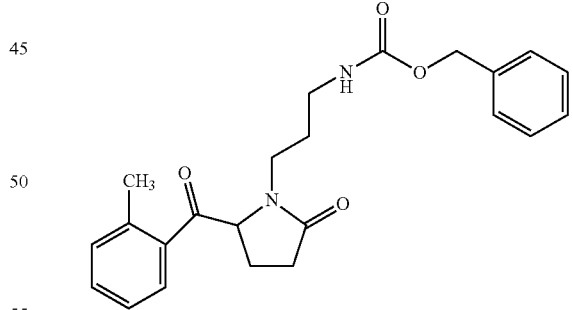

A solution of intermediate 6 (725 mg, 1.515 mmol) in TFEA (25 mL) was cooled and stirred at 0° C., then a solution of PIFA (1.235 g, 2.87 mmol) in TFEA (15 mL) was added dropwise. The reaction was left stirring at 0° C. for 2 h. Na$_2$CO$_3$ 1M solution was added to the reaction and the mixture was extracted several times with DCM. The phases were separated and the organic one was filtered through a phase separator and removed in vacuo. The crude material was purified on SP1 (SNAP-SiO$_2$ cartridge, 50 g, CH/EtOAc 5:5 to 0:1 as eluent) to give the title compound (677 mg). $^1$H NMR (400 MHz, CDCl$_3$) δ ppm 7.66 (d, 1H), 7.48 (t, 1H), 7.40-7.30 (m, 7H), 5.65 (bt, 1H), 5.15-5.07 (m, 3H), 3.75-3.65 (m, 1H), 3.43-3.34 (m, 1H), 3.19-3.09 (m, 2H), 2.53 (s, 3H), 2.51-2.31 (m, 3H), 2.02-1.93 (m, 1H), 1.75-1.69 (m, 2H). UPLC-MS: Rt=0.99; m/z (ES+): 395 [M+H]$^+$.

Intermediate 8

1-(2-methylphenyl)-octahydro-1H-pyrrolo[1,2-a][1,4]diazepin-7-one (diastereomeric mixture)

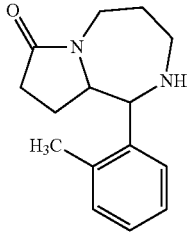

Benzyl N-(2-{2-[(2-methylphenyl)carbonyl]-5-oxopyrrolidin-1-yl}propyl)carbamate (Intermediate 7, 211 mg) was dissolved in hydrobromic acid (33% in acetic acid) (2 mL) and the solution was stirred at room temperature for 1 h. The solvent was evaporated in vacuo and the residue was dissolved in ethanol (2 mL), titanium (IV) isopropoxide (1 mL) and TEA (23 mL) were added to the solution and the reaction mixture was stirred for 6 h. NaBH$_4$ (10 mg) was added to the reaction mixture and the resulting solution was stirred 1 h at room temperature. An aqueous solution of ammonia was added, the precipitate was filtered off and the product was extracted with DCM. The crude was purified on NH-Silica cartridge (EtOAc as eluent) to give the title compound as a yellow oil (23 mg). UPLC-MS: Rt=0.41 and 1.24; m/z (ES+): 245.18 [M+H]$^{+1}$H NMR (500 MHz, CDCl$_3$)) δ ppm 7.53 (d, J=7.6 Hz, 1H), 7.26 (m, 3H), 4.04 (m, 2H), 3.76 (ddd, J=17.4, 11.2, 6.1 Hz, 1H), 3.49 (br s, 1H), 3.29 (m, 1H), 2.65 (m, 1H), 2.37 (m, 4H), 2.01 (m, 2H).

Intermediate 9

Benzyl N-(2-aminoethyl)carbamate

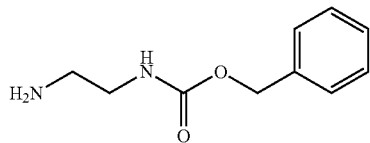 [SMILES: NCCNC(=O)OCc1ccccc1]

A solution of benzylchloroformate (1.3 mL, 9 mmol) in DCM (25 mL) was added over 1.5 h to a solution of 1,2-diaminoethane (6 mL, 90 mmol) in DCM (95 mL) cooled at 0° C. The solution was stirred for 2 h at 0° C., then the solution was washed with brine (40 mL).

The organic phase was filtered through a phase separator and evaporated to dryness to obtain the title compound as a white solid (1.85 g) which was used in the next step without further purification. $^1$H NMR (400 MHz, CDCl$_3$) δ ppm 7.42-7.31 (m, 5H), 5.13 (br s, 3H), 3.27 (dd, 2H), 2.85 (t, 2H). UPLC-MS: Rt=0.46; m/z (ES+): 195 [M+H]$^+$.

Intermediate 10

Benzyl N-[2-(pent-4-ynamido)ethyl]carbamate

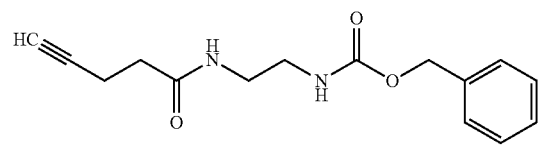 [SMILES: C#CCCC(=O)NCCNC(=O)OCc1ccccc1]

Pentynoic acid (0.590 g, 6 mmol) was added to a suspension of Intermediate 9 (1.8 g, 9 mmol), EDCI.HCl (1.72 g, 9 mmol) and HOBt.H$_2$O (1.21 g, 9 mmol) in dry DCM (30 mL). The resulting mixture was cooled to 0° C. and TEA (1.25 mL, 9 mmol) was added dropwise. The reaction mixture was stirred at 25° C. for 12 h. The DCM solution was washed with NH$_4$Cl solution (15 mL) and NaHCO$_3$ solution (15 mL), the organic phase was filtered through a phase separator and evaporated to dryness to give the title compound as a white solid (1.97 g). The crude product was used in the next step without further purification. $^1$H NMR (400 MHz, CDCl$_3$) δ ppm 7.40-7.34 (m, 5H), 6.15 (br s, 1H), 5.17 (br s, 1H), 5.12 (s, 2H), 3.46-3.34 (m, 4H), 2.52 (dt 2H), 2.38 (t, 2H), 2.0 (br s, 1H). UPLC-MS: Rt=0.75; m/z (ES+): 275 [M+H]$^+$.

Intermediate 11

Benzyl N-{2-[5-(2-methylphenyl)pent-4-ynamido]ethyl}carbamate

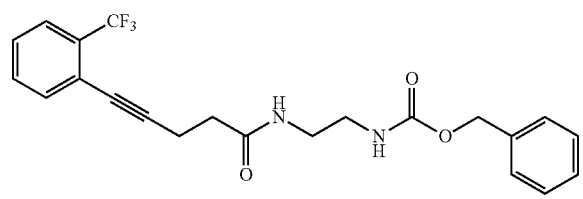 [SMILES: O=C(CCC#Cc1ccccc1C(F)(F)F)NCCNC(=O)OCc1ccccc1]

Intermediate 10 (500 mg, 1.52 mmol) and 2-iodotoluene (186 μL, 1.45 mmol) were charged in a two necks round bottom flask equipped with vacuo/Argon system. They were solubilized in DMF (5 mL), then TEA (235 μL, 1.67 mmol), CuI (22 mg, 0.12 mmol) and PdCl$_2$(PPh$_3$)$_2$ (41 mg, 0.06 mmol) were added and the resulting mixture was stirred at 25° C. for 3 h. DMF was removed in vacuo, the residue was dissolved in DCM and washed with NH$_4$Cl solution (15 mL) and NaHCO$_3$ solution (15 mL). The organic phase was filtered through a phase separator and evaporated to dryness to obtain a yellow crude material which was purified on SP1 (SNAP-SiO$_2$ cartridge, 25 g, CH/EtOAc 9.5:0.5 to 4:6 as eluent) to give the title compound as a white off solid (370 mg). $^1$H NMR (400 MHz, CDCl$_3$) δ ppm 7.40-7.31 (m, 6H), 7.20-7.17 (m, 2H), 7.13-7.09 (m, 1H), 6.22 (br s, 1H), 5.16 (m, 1H), 5.09 (s, 2H), 3.48-3.40 (m, 2H), 3.40-3.33 (m, 2H), 2.79 (t, 2H), 2.49 (t, 2H), 2.41 (s, 3H). UPLC-MS: Rt=1.07; m/z (ES+): 365 [M+H]$^+$.

Intermediate 12

Benzyl N-(2-{2-[(2-methylphenyl)carbonyl]-5-oxopyrrolidin-1-yl}ethyl)carbamate (racemate)

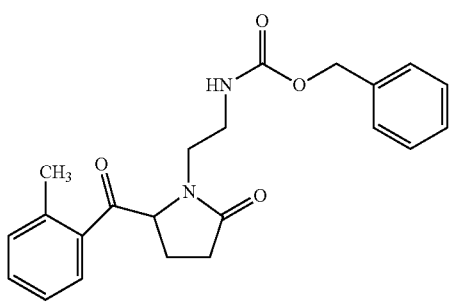 [SMILES: Cc1ccccc1C(=O)C1CCC(=O)N1CCNC(=O)OCc1ccccc1]

A solution of intermediate 11 (370 mg, 1.016 mmol) in TFEA (13 mL) was cooled and stirred at 0° C., then a solution of PIFA (656 mg, 1.52 mmol) in TFEA (7 mL) was added dropwise. The reaction was left stirring at 0° C. for 3 h. $Na_2CO_3$ 1M solution was added to the reaction and the mixture was extracted several times with DCM. The phases were separated and the organic one was filtered through a phase separator and removed in vacuo. The crude material was purified on SP1 (SNAP-SiO$_2$ cartridge, 25 g, CH/EtOAc 7:3 to 3:7 as eluent) to give the title compound as a white foam (300 mg). $^1$H NMR (400 MHz, CDCl$_3$) δ ppm 7.67 (d, 1H), 7.47 (t, 1H), 7.38-7.29 (m, 7H), 5.28 (br s, 1H), 5.20 (bd, 1H), 5.10 (q, 2H), 3.85-3.78 (m, 1H), 3.61-3.51 (m, 1H), 3.28-3.14 (m, 2H), 2.52 (s, 3H), 2.45-2.35 (m, 1H), 2.32-2.19 (m, 2H), 1.94-1.86 (m, 1H). UPLC-MS: Rt=0.99; m/z (ES+): 381 [M+H]$^+$

Intermediate 13

1-(2-methylphenyl)-octahydropyrrolo[1,2-a]piperazin-6-one benzyl N-(2-{2-[(2-methylphenyl)carbonyl]-5-oxopyrrolidin-1-yl}ethyl)carbamate (Racemic Mixture, ANTI Configuration at C1-C8a)

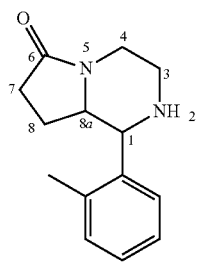 [SMILES: Cc1ccccc1C1NCCN2C(=O)CCC12]

HCl 1M (5 mL) and Pd/C 5% (100 mg) were added to a solution of Intermediate 12 (790 mg, 2.076 mmol) in MeOH (80 mL). The reaction was left stirring under H$_2$ (5 atm) for 12 h. Then further HCl 1M (1 mL) and Pd/C 5% (100 mg) were added and the reaction was left stirring under H$_2$ (5 atm), after 6 h Pd/C 5% (50 mg) was added and the reaction was left stirring under H$_2$ (5 atm) for 12 h. The catalyst was removed by filtration through a celite pad and the solvent was removed in vacuo. NaHCO$_3$ saturated solution and DCM were added to the residue, the two layers were separated and the organic phase was filtered through a phase separator and removed in vacuo. The crude material was purified on SP1 (SNAP-NH cartridge, CH/EtOAc 5:5 to 3:7 as eluent) to give the title compound as a colourless oil (240 mg). $^1$H NMR (400 MHz, CDCl$_3$) δ ppm 7.48 (dd, 1H), 7.27-7.19 (m, 3H), 4.12 (dd, 1H), 3.74-3.66 (m, 1H), 3.62 (d, 1H), 3.15 (dd, 1H), 2.98 (dt, 1H), 2.85 (dt, 1H), 2.43 (s, 3H), 2.40-2.34 (m, 2H), 1.95-1.85 (m, 1H), 1.61-1.52 (m, 1H). UPLC-MS: Rt=0.36; m/z (ES+): 231 [M+H]$^+$.

Intermediate 14 tert-butyl 1-(2-methylphenyl)-6-oxo-octahydropyrrolo[1,2-a]piperazine-2-carboxylate (Racemic Mixture, ANTI Configuration at C1-C8a)

Intermediate 13, (306 mg, 1.33 mmol), was dissolved in 15 mL of DCM. To this solution, TEA (445 mL, 6 mmol) and Boc$_2$O (378 mg, 1.7 mmol) were added and the reaction mixture was stirred at room temperature overnight. Water was added to the reaction and the two layers were separated, the organic layer was again washed with water, filtered through a phase separator and evaporated. The crude was purified by flash chromatography (28 g SNAP NH cartridge, eluting from CH/EtOAc 9:1 to 6:4). The fractions were collected and the solvent removed to give 356 mg of title compound. UPLC-MS: m/z (ES+): 331.23 [M+H]$^+$ Rt=0.98 min. $^1$H NMR (400 MHz, CDCl$_3$) δ ppm 7.23-7.17 (m, 4H), 4.78-4.81 (d, 1H), 4.48-4.44 (m, 1H), 4.08-4.04 (m, 1H), 3.77-3.66 (m, 2H), 3.66-3.56 (m, 1H), 2.50-2.35 (m, 1H), 2.44 (s, 3H), 2.02-1.92 (m, 1H), 2.02-1.92 (m, 1H), 1.83-1.74 (m, 1H), 1.18 (s, 9H).

Intermediate 15

2-tert-butyl 7-methyl 1-(2-methylphenyl)-6-oxo-octahydropyrrolo[1,2-a]piperazine-2,7 dicarboxylate (Diastereomeric Mixture with ANTI Configuration at C1-C8a)

Intermediate 14 (355 mg, 1.074 mmol) was dissolved in THF (15 mL) under N₂ and the solution was cooled to −78° C.; LHMDS 1M in THF (2.68 mL, 2.68 mmol) was added and the reaction was left stirring at this temperature for 10 min and at −30° C. for 15 min, then methylchloroformate (91.5 μL, 1.18 mmol) was added and the reaction was left stirring for 20 min at 25° C. HCl 1N aq was added, followed by EtOAc. The layers were separated, the aqueous one extracted several times with EtOAc. The organic phase was dried over Na₂SO₄, filtered and concentrated. The crude material was purified on SP1 (SNAP-NH cartridge, 28 g, CH/EtOAc 9:1 to 1:1 as eluent) to give the title compound as a white solid (295 mg). UPLC-MS, m/z (ES+): 389.26 [M+H]⁺ Rt=1.03. ¹H NMR (400 MHz, CDCl₃) δ ppm 7.26-7.15 (m), 4.95-4.93 (d), 4.77-4.74 (m), 4.49-4.43 (m), 4.25-4.19 (m), 4.06-4.00 (m), 3.80 (s), 3.75 (s), 3.73-3.62 (m), 3.60-3.45 (m), 2.49 (s), 2.43 (s), 2.36-2.28 (m), 2.25-2.17 (m), 2.04-1.97 (m), 1.18 (s), 1.17 (s).

Intermediate 16 tert-butyl 1-(2-methylphenyl)-6-oxohexahydropyrrolo[1,2-a]pyrazine-2(1H)-carboxylate (Diastereomeric Mixture with ANTI Configuration at C1-C8a)

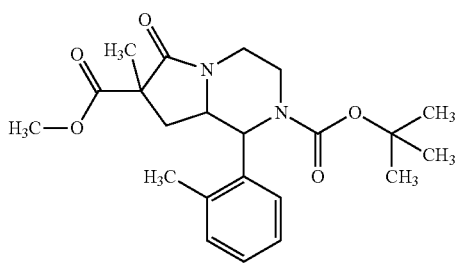 [SMILES: COC(=O)C1(C)CC2C(c3ccccc3C)N(C(=O)OC(C)(C)C)CCN2C1=O]

Intermediate 15 (237 mg, 0.610 mmol) was dissolved in THF (10 mL). The solution was cooled down to −78° C. and LHMDS was added, the reaction was left stirring 20 min at this temperature and 20 min at 0° C. Methyl iodide (57 μL) was added and the reaction was left at 25° C. for 1 h. HCl 1M, followed by EtOAc were added. The phases were separated and the aqueous one was extracted with more EtOAc. The organics were combined, dried over Na₂SO₄, filtered and concentrated. The crude was purified by Flash Chromatography (SNAP column) eluting from CH/EtOAc 9:1 to EtOAc 100%. The fractions were collected and the solvent removed in vacuo obtaining 85 mg of the title compound as a white foam. UPLC-MS: m/z (ES+): 403.32 [M+H]⁺; Rt=1.08 min ¹H NMR (400 MHz, CDCl₃) δ ppm 7.26-7.14 (m), 4.97-4.94 (m), 4.48-4.45 (m), 4.05-4.02 (m), 3.81 (s), 3.77-3.64 (m), 3.58-3.49 (m), 2.45 (s), 2.43-2.37 (m), 1.88-1.82 (m), 1.42 (s), 1.18 (s), 1.17 (s).

Intermediate 17

Methyl 7-methyl-1-(2-methylphenyl)-6-oxo-octahydropyrrolo{1,2-a}piperazine-7-carboxylate (Diastereomeric Mixture with ANTI Configuration at C1-C8a)

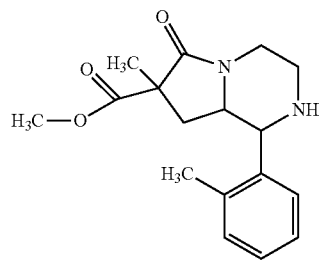 [SMILES: COC(=O)C1(C)CC2C(c3ccccc3C)NCCN2C1=O]

Intermediate 16 (80 mg, 0.206 mmol) was dissolved in DCM (8 mL) and TFA (1 mL) was added dropwise. The reaction was left stirring at 25° C. for 2 h, then the solvent was removed in vacuo and the residue was dissolved in MeOH and filtered through an SCX cartridge eluting with NH₃ in MeOH 2M solution. The solvent was removed in vacuo to give 56 mg of the title compound. UPLC-MS: m/z (ES+): 303.22 [M+H]⁺; Rt=0.51.

Intermediate 18

{[3,5-bis(trifluoromethyl)phenyl]methyl}(methyl)amine

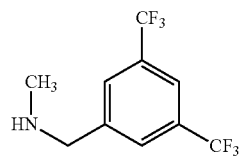 [SMILES: CNCc1cc(C(F)(F)F)cc(C(F)(F)F)c1]

Methylamine (3 g, 40% aqueous solution) was dissolved in 30 mL of MeOH. The reaction mixture was heated at 50° C. under stirring. 3,5-Bis(trifluoromethyl)-benzyl chloride (2 g, 7.6 mmol) dissolved in 10 mL of MeOH, was added. The solution was left stirring at this temperature for 5 h. The solution was concentrated carefully to remove MeOH as much as possible, then an aqueous solution of NaOH 1M was added and the aqueous layer was extracted with DCM. The two phases were separated; the organic phase was filtered through a phase separator and removed carefully in vacuo obtaining the title compound (0.8 g) as a yellow oil. UPLC-MS: m/z (ES+): 258.01 [M+H]⁺ Rt=0.60. ¹H NMR (400 MHz, CDCl₃) δ ppm 7.83 (s, 2H), 7.79 (s, 1H), 3.91 (s, 2H), 3.30 (m, 1H), 2.50 (s, 3H); UPLC-MS: Rt=1.30; m/z (ES+): 586 [M+H]⁺.

Intermediate 19

Methyl 2-({[3,5-bis(trifluoromethyl)phenyl]methyl}(methyl)carbamoyl)-7-methyl-1-(2-methylphenyl)-6-oxo-octahydropyrrolo{1,2-a}piperazine-7-carboxylate (Diastereomeric Mixture with ANTI Configuration at C1-C8a)

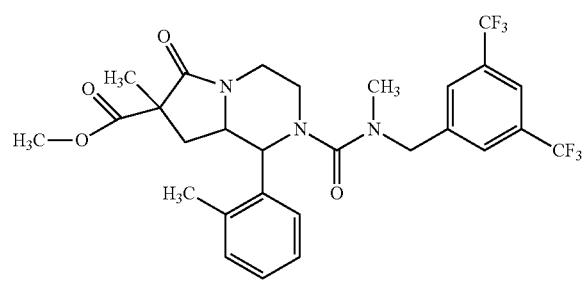 [SMILES: COC(=O)C1(C)CC2C(c3ccccc3C)N(C(=O)N(C)Cc3cc(C(F)(F)F)cc(C(F)(F)F)c3)CCN2C1=O]

Triphosgene (22.44 mg, 0.07 mmol) was dissolved in EtOAc (1 mL), this solution was cooled at 0° C. and a solution of Intermediate 17 (52 mg, 0.172 mmol) and TEA (40 µL, 0.46 mmol) in EtOAC (2 mL) was added. The resulting mixture was left stirring at this temperature for 2 h, then TEA (40 µL, 0.46 mmol) and Intermediate 18 (61.91 mg, 0.240 mmol) in EtOAC (2 mL) were added and the mixture was left stirring for 3 h. NaOH 1M was added to the mixture, the phases were separated and the organic layer was washed with HCl 1M and brine, dried over $Na_2SO_4$ and concentrated in vacuo. The crude material was purified on SP1 (snap-NH cartridge, 11 g, CH/EtOAc 9:1 to 0:1 as eluent) to give the title compound as a white foam (70 mg). $^1$H NMR (500 MHz, $CDCl_3$) δ ppm 7.67 (s, 1H), 7.29 (s, 2H), 7.19 (s, 2H), 7.10 (s, 2H), 4.62 (d, 1H), 4.28 (d, 1H), 4.17 (d, 1H), 4.13 (dt, 1H), 3.73 (s, 3H), 3.68 (m, 1H), 3.30 (m, 1H), 3.12 (m, 1H), 2.96 (m, 1H), 2.89 (s, 3H), 2.17 (m, 1H), 1.69 (m, 1H), 1.31 (s, 2H). UPLC-MS: Rt=1.30; m/z (ES+): 586 [M+H]$^+$.

Intermediate 20 methyl 1-(2-methylphenyl)-6-oxo-octahydropyrrolo[1,2-a]piperazine-7-carboxylate (Diastereomeric Mixture with ANTI Configuration at C1-C8a)

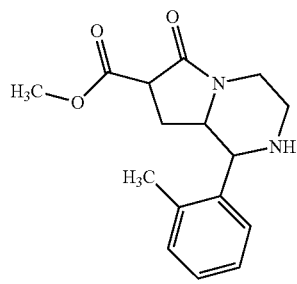 [SMILES: COC(=O)C1CC2C(c3ccccc3C)NCCN2C1=O]

To a 0° C. cooled solution of intermediate 15 (86 mg, 0.22 mmol) in DCM (8 mL) was added TFA (2 mL). The reaction mixture was stirred at 25° C. for 2 h. The solvent was removed in vacuo to give a crude that was purified on SCX cartridge (solution of ammonia 2M in MeOH as eluent) to give the title compound (63 mg). $^1$H NMR (400 MHz, $CDCl_3$) δ ppm 7.51-7.46 (m), 7.26-7.18 (m), 4.14-4.08 (m), 3.93-3.87 (m) 3.83-3.80 (m), 3.76-3.69 (m), 3.60-3.57 (m), 3.46-3.41 (m), 3.16-3.02 (m), 2.91-2.79 (m), 2.48 (s), 2.44-2.41 (m), 2.29-2.22 (m), 2.17-2.09 (m), 2.03-1.95 (m), 1.85-1.72 9m). UPLC-MS: Rt=0.46; m/z (ES+): 289.18 [M+H]$^+$.

Intermediate 21

Methyl 2-({[3,5-bis(trifluoromethyl)phenyl]methyl}(methyl)carbamoyl)-1-(2-methylphenyl)-6-oxo-octahydropyrrolo[1,2-a]piperazine-7-carboxylate (Diastereomeric Mixture with ANTI Configuration at C1-C8a)

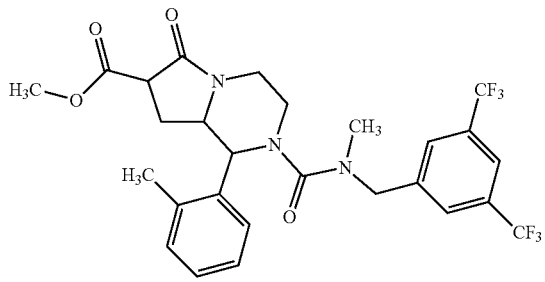 [SMILES: COC(=O)C1CC2C(c3ccccc3C)N(C(=O)N(C)Cc3cc(C(F)(F)F)cc(C(F)(F)F)c3)CCN2C1=O]

To a 0° C. cooled solution of triphosgene (30 mg, 0.087 mmol) in EtOAc (1 mL) under stirring were added intermediate 20 (63 mg, 0.22 mmol) dissolved in EtOAc (2 mL) and TEA (50 µL, 0.59 mmol). The reaction mixture was stirred at this temperature for 2 h, then TEA (50 µL) and Intermediate 18 (79 mg, 0.3 mmol) dissolved in EtOAc (2 mL) were added. The reaction was stirred at 25° C. for 3 h, then NaOH 1M, HCl 1N and brine were added. The organic layer was dried over sodium sulphate, filtered and concentrated in vacuo to give a crude that was purified on SP1 (snap-NH cartridge, 11 g, CH/EtOAc 8:2 to EtOAc as eluent) to give the title compound (60 mg). $^1$H NMR (400 MHz, $CDCl_3$) δ ppm 7.74 (br s), 7.37 (br s), 7.19-7.11 (m), 4.72-4.67 (m), 4.36-4.32 (m), 4.24-4.20 (m), 4.18-4.16 (m), 4.06-4.04 (d), 3.96-3.90 (m), 3.82 (s), 3.77-3.71 (m), 3.52-3.46 (m), 3.45-3.43 (m), 3.41-3.36 (m), 3.27-3.14 (m), 3.05-2.92 (m), 2.58 (s), 2.52 (s), 2.24-2.17 (m), 2.13-2.09 (m), 1.95-1.87 (m), UPLC-MS: Rt=1.27; m/z (ES+): 572.28 [M+H]$^+$.

Intermediate 22

Tert-butyl 1-(2-methylphenyl)-octahydropyrrolo[1,2-a]piperazine-2-carboxylate (Racemic Mixture with ANTI Configuration at C1-C8a)

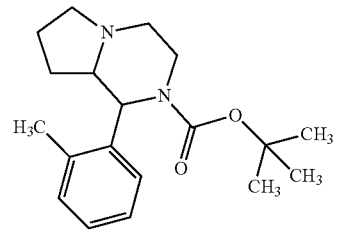 [SMILES: Cc1ccccc1C1C2CCCN2CCN1C(=O)OC(C)(C)C]

To a 0° C. cooled solution of a compound prepared as described for intermediate 14 (67 mg, 0.2 mmol) in THF (5 mL), a solution of borane dimethylsulfide complex 2M in THF (0.404 mL, 0.8 mmol) was added dropwise. The reaction mixture was stirred overnight at 25° C., then a solution of borane dimethylsulfide complex 2M in THF (0.101 mL) was added and the mixture was stirred at 25° C. for 8 h. A solution of borane dimethylsulfide complex 2M in THF (0.101 mL) was added and the mixture was stirred overnight at 25° C. MeOH (6 mL) was carefully added and the reaction mixture was stirred at 25° C. for 2 h. HCl 1M was added and the mixture was stirred overnight. Saturated solution of NaHCO$_3$ was added, followed by EtOAc. The organic layer was dried over sodium sulphate, filtered and concentrated in vacuo, to give the title compound (60 mg) which was used in the next step without further purifications. UPLC-MS: Rt=0.74; m/z (ES+): 317.27 [M+H]$^+$.

Intermediate 23

1-(2-methylphenyl)-octahydropyrrolo[1,2-a]piperazine (Racemic Mixture with ANTI Configuration at C1-C8a)

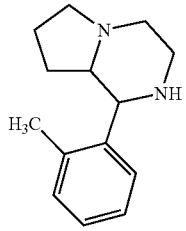

Intermediate 22 (60 mg, 0.19 mmol) was dissolved in a solution of HCl 1.25 M in MeOH (8 mL) and the reaction mixture was stirred over weekend at 25° C. The mixture was concentrated in vacuo, then NaOH 1M was slowly added, followed by addition of DCM. The aqueous layer was extracted several times with DCM. The combined organic layers were filtered through a phase separator and concentrated in vacuo to give 50 mg of the title compound. $^1$H NMR (400 MHz, CDCl$_3$) δ ppm 7.46 (d, 1H), 7.21-7.14 (m, 3H), 3.83 (d, 1H), 3.19-3.06 (m, 4H), 2.41 (s, 3H), 2.37-2.31 (m, 1H), 2.24 (q, 1H), 2.16-2.10 (m, 1H), 1.83-1.34 (m, 5H). UPLC-MS: Rt=0.34; m/z (ES+): 217.15 [M+H]$^+$.

Intermediate 24

1-(2-methylphenyl)-octahydropyrrolo[1,2-a]piperazin-6-one hydrochloride salt (Racemic Mixture with ANTI Configuration at C1-C8a)

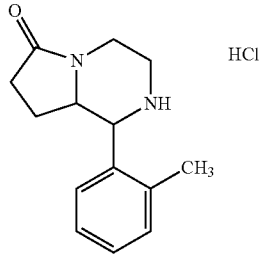 [SMILES: Cc1ccccc1C1NCCN2C(=O)CCC12 ; Cl]

To a stirred solution of Intermediate 13 (1.9 g, 8.26 mmol) in Et$_2$O (25 mL), was added Et$_2$O.HCl (5.0 mL) dropwise at room temperature for 5 min and later stirred at that temperature for 30 min. Solvent was evaporated under reduced pressure and the salt formed was washed with EtOAc and dried to obtain 1.9 g of the title compound. $^1$H NMR (500 MHz, DMSO-d6) δ ppm 9.74 (m, 2H), 7.79 (m, 1H), 7.33 (m, 3H), 4.32 (dd, J=11.2, 9.5 Hz, 1H), 4.05 (m, 2H), 3.18 (m, 1H), 2.42 (s, 3H), 2.27 (dd, J=8.8, 6.4 Hz, 1H), 1.79 (dtd, J=13.4, 7.8, 7.8, 6.6 Hz, 1H), 1.42 (dtd, J=13.0, 9.0, 9.0, 6.6 Hz, 1H).

Intermediate 25

N-{[3,5-bis(trifluoromethyl)phenyl]methyl}-7-(hydroxymethyl)-N-methyl-1-(2-methylphenyl)-6-oxo-octahydropyrrolo[1,2-a]piperazine-2-carboxamide (First Eluting Enantiomeric Pair with ANTI Configuration at C1-C8a)

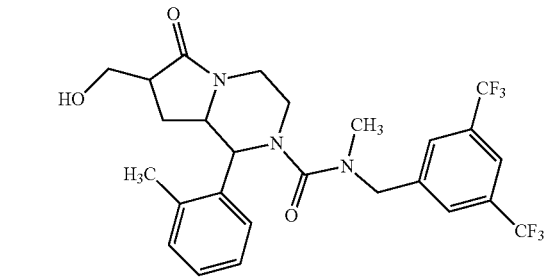 [SMILES: Cc1ccccc1C1C2CC(CO)C(=O)N2CCN1C(=O)N(C)Cc1cc(C(F)(F)F)cc(C(F)(F)F)c1]

To a stirred solution of Intermediate 21 (950 mg, 1.66 mmol) in MeOH (40 mL) was added calcium chloride (276 mg, 2.49 mmol). The resulting suspension was cooled to 0° C. and sodium borohydride (188 mg, 4.98 mmol) was added portionwise. The reaction mixture was stirred at 25° C. for 2 h, then water (20 mL) was added. MeOH was evaporated under vacuo and the aqueous layer was extracted with DCM (3×50 mL). The organic layer was separated, dried over sodium sulphate, filtered and evaporated to give 950 mg of a beige foam which was subjected to semipreparative HPLC. Two fractions were obtained: Intermediate 25 (100 mg, first eluting pair of enantiomers) and Intermediate 26 (280 mg, second eluting pair of enantiomers, described below).

Intermediate 25: semipreparative HPLC, Rt=11' 08". Columns: XTerra PREP MS C18 OBD 10 μm 30×150 mm, room temperature; Injection volume: 300 μl (multiple injections); m/z (ES+): 543.00 [M+H]$^+$.

Intermediate 26

N-{[3,5-bis(trifluoromethyl)phenyl]methyl}-7-(hydroxymethyl)-N-methyl-1-(2-methylphenyl)-6-oxo-octahydropyrrolo[1,2-a]piperazine-2-carboxamide (Second Eluting Enantiomeric Pair with ANTI Configuration at C1-C8a)

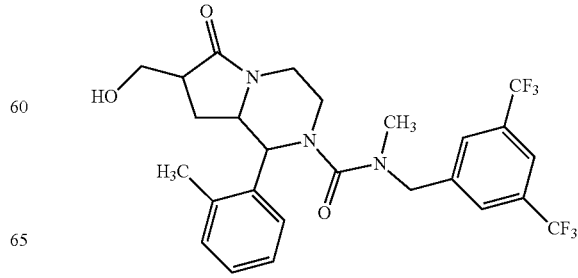

Intermediate 26: semipreparative HPLC: Rt=11' 66". Columns: XTerra PREP MS C18 OBD 10 μm 30×150 mm, room temperature; Injection volume: 300 μl (multiple injections); Solvents: A=10 mM ammonium bicarbonate aqueous solution adjusted to pH 10 with ammonia; B=Acetonitrile. UV Conditions: UV detection range: 210 nm to 350 nm; Acquisition rate: 1.0 spectra/s; m/z (ES+): 543.00 [M+H]$^+$.

Intermediate 27

2-tert-butyl 7,7-dimethyl 1-(2-methylphenyl)-6-oxo-octahydropyrrolo[1,2-a]piperazine-2,7,7-tricarboxylate (Racemic Mixture with ANTI Configuration at C1-C8a)

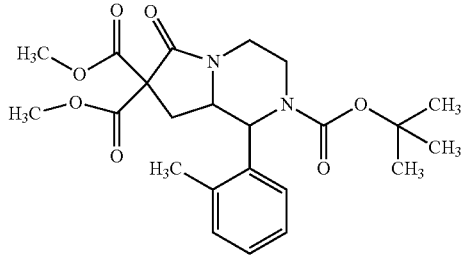 [SMILES: COC(=O)C1(C(=O)OC)CC2C(c3ccccc3C)N(C(=O)OC(C)(C)C)CCN2C1=O]

Intermediate 14 (400 mg, 1.21 mmol) was dissolved in THF (15 mL) and the solution was cooled to −78° C.; LHMDS 1M in THF (2.66 mL, 2.66 mmol) was added and the reaction was left stirring at this temperature for 10' and at −50° C. for 15 min, then methylchloroformate (103 μL, 1.33 mmol) was added and the reaction was left stirring for 45 min while temperature gradually increased to 0° C. HCl 1N aq (2 mL) was added and the mixture was diluted with water (15 mL), then extracted three times with EtOAc. The combined organic phases were dried over Na$_2$SO$_4$, filtered and concentrated in vacuo. The crude material was purified on SP1 (SNAP cartridge, 50 g, CH/EtOAc 4:6 to 1:9 as eluent) to give the title compound as a pale yellow foam (430 mg). UPLC-MS, m/z (ES+): 447.00 [M+H]$^+$ Rt=1.06. $^1$H NMR (400 MHz, CDCl$_3$) δ ppm 7.25-7.13 (m, 4H), 4.85-4.81 (d, 1H), 4.48-4.43 (m, 1H), 4.07-4.00 (m, 1H), 3.86 (s, 3H), 3.78 (s, 3H), 2.59-2.48 (m, 2H), 2.45 (s, 3H), 3.72-3.60 (m, 3H), 1.16 (s, 9H).

Intermediate 28

7,7-dimethyl 1-(2-methylphenyl)-6-oxo-octahydropyrrolo[1,2-a]piperazine-7,7-dicarboxylate (Racemic Mixture with ANTI Configuration at C1-C8a)

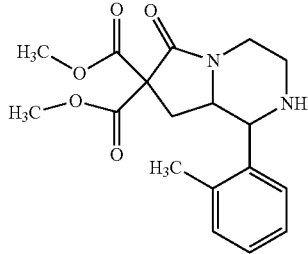 [SMILES: COC(=O)C1(C(=O)OC)CC2C(c3ccccc3C)NCCN2C1=O]

To a 0° C. cooled solution of Intermediate 27 (380 mg, 0.85 mmol) in DCM (20 mL) was added TFA (3 mL). The reaction mixture was stirred at 25° C. for 2 h. The solvent was removed under vacuo to give a crude that was purified on SCX cartridge (solution of ammonia 2M in MeOH as eluent) to give the title compound (256 mg). $^1$H NMR (400 MHz, CDCl$_3$) δ ppm 7.48-7.42 (m, 1H), 7.25-7.18 (m, 3H), 4.14 (dd, 1H), 3.84 (s, 3H), 3.79 (s, 3H), 3.72-3.65 (m, 2H), 3.16 (dd, 1H), 3.06 (td, 1H), 2.88 (td, 1H), 2.55-2.48 (m, 1H), 2.44 (s, 3H), 2.32-2.25 (m, 1H). UPLC-MS: Rt=0.53; m/z (ES+): 347.23 [M+H]$^+$ Intermediate 29

7,7-dimethyl 2-({[3,5-bis(trifluoromethyl)phenyl]methyl}(methyl)carbamoyl)-1-(2-methylphenyl)-6-oxo-octahydropyrrolo[1,2-a]piperazine-7,7-dicarboxylate (Racemic Mixture with ANTI Configuration at C1-C8a)

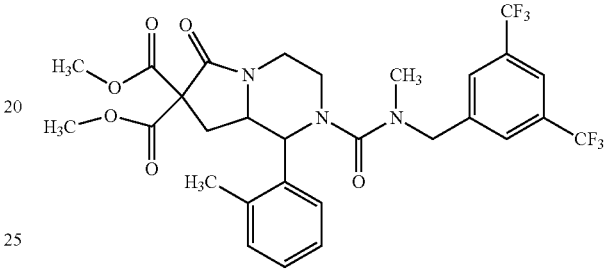

To a 0° C. cooled solution of triphosgene (88 mg, 0.30 mmol) in EtOAc (3 mL) under stirring were added Intermediate 28 (256 mg, 0.74 mmol) and TEA (150 μL, 1.08 mmol) dissolved in EtOAc (4 mL). The reaction mixture was stirred at 0° C. for 2 h, then Intermediate 18 (266 mg, 1.04 mmol) dissolved in EtOAc (4 mL) and TEA (150 μL, 1.08 mmol) were added. The reaction was stirred at 25° C. for 3 hrs, then washed with NaOH 0.5N (10 mL), HCl 1N (10 mL) and brine (10 mL). The organic layer was dried over Na$_2$SO$_4$, filtered and concentrated in vacuo to give 482 mg of the title compound which was used in the next step without further purifications. $^1$H NMR (400 MHz, CDCl$_3$) δ ppm 7.75 (br s, 1H), 7.36 (br s, 2H), 7.27-7.23 (m, 1H), 7.21-7.12 (m, 3H), 4.69 (d, 1H), 4.34 (d, 1H), 4.22 (d, 1H), 4.13 (d, 1H), 3.86 (s, 3H), 3.84-3.75 (m, 4H), 3.38 (d, 1H), 3.25 (td, 1H), 3.04-2.94 (m, 4H), 2.55-2.46 (m, 4H), 2.43-2.35 (m, 1H). UPLC-MS: Rt=1.28; m/z (ES+): 630.32 [M+H]$^+$.

Alternative Procedure for Preparation of Intermediate 29

7,7-dimethyl 2-({[3,5-bis(trifluoromethyl)phenyl]methyl}(methyl)carbamoyl)-1-(2-methylphenyl)-6-oxo-octahydropyrrolo[1,2-a]piperazine-7,7-dicarboxylate (Enantiomeric Pair with ANTI Configuration at C1-C8a)

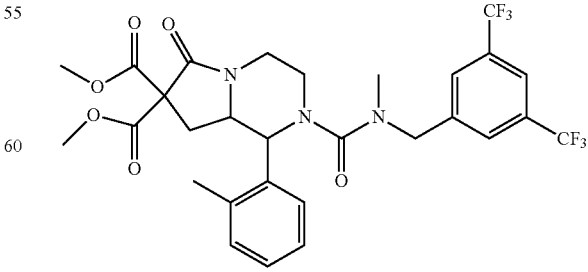

Compound 16 (50 mg, 0.097 mmol) was dissolved in THF (3 mL) under Ar and the solution was cooled to −78° C.;

LHMDS 1M in THF (0.2 mL, 0.194 mmol) was added and the reaction was left stirring at this temperature for 15 min and at −30° C. for 20 min, then DMPU (1,3-Dimethyl-3,4,5,6-tetrahydro-2(1H)-pyrimidinone) (28 μL, 0.232 mmol) and methylchloroformate (10 μL, 0.116 mmol) were added and the reaction was left stirring for 1 h at −30° C. Then the solution was cooled to −78° C. and further LHMDS 1M in THF (0.200 mL, 0.194 mmol) and methylchloroformate (20 μL, 0.232 mmol) were added. After 1 h the reaction was allowed to reach −10° C., further LHMDS 1M in THF (0.400 mL, 0.388 mmol) and methylchloroformate (100 μL, 1.16 mmol) were added. After 30 min HCl 1N aq was added, followed by EtOAc. The layers were separated, the aqueous one extracted several times with EtOAc. The organic phase was filtered through a phase separator and concentrated. The crude material was purified by flash chromatography (SNAP SiO$_2$, cartridge, 10 g, CH/EtOAc 2:8 to EtOAc 100% as eluent) to give the title compound as a light yellow oil (36 mg). $^1$H NMR (400 MHz, CDCl$_3$) δ ppm 7.76 (s, 1H), 7.38 (s, 2H), 7.28-7.12 (m, 4H), 4.70 (d, 1H), 4.35 (d, 1H), 4.27-4.20 (m, 1H), 4.14 (d, 1H), 3.88 (s, 3H), 3.86-3.75 (m, 4H), 3.43-3.37 (m, 1H), 3.30-3.31 (m, 1H), 3.07-2.95 (m, 4H), 2.57-3.48 (m, 4H), 2.44-2.35 (m, 1H). UPLC-MS, Rt=1.26, m/z (ES+): 629.9 [M+H]$^+$.

Intermediate 30

N-{[3,5-bis(trifluoromethyl)phenyl]methyl}-7-(hydroxymethyl)-N-methyl-1-(2-methylphenyl)-6-oxo-octahydropyrrolo[1,2-a]piperazine-2-carboxamide (Diastereoisomeic Mixture with ANTI Configuration at C1-C8a)

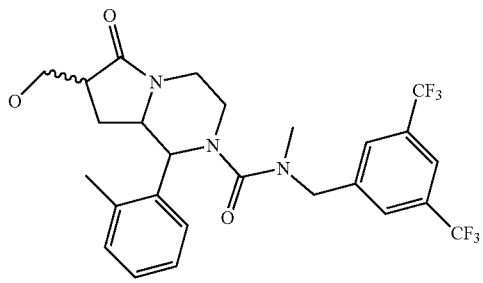 [SMILES: Cc1ccccc1C1C2CC(CO)C(=O)N2CCN1C(=O)N(C)Cc1cc(C(F)(F)F)cc(C(F)(F)F)c1]

To a stirred solution of Intermediate 29 (36 mg, 0.057 mmol) in MeOH (5 mL) was added calcium chloride (20 mg, 0.17 mmol). The resulting suspension was cooled to 0° C. and sodium borohydride (13 mg, 0.34 mmol) was added. The reaction mixture was stirred at 25° C. for 30 min, then H$_2$O was added and MeOH was removed in vacuo. The aqueous layer was extracted several times with EtOAc and the combined organic layers were filtered through a phase separator and concentrated in vacuo to give a crude which was purified by flash chromatography (SNAP NH cartridge, 10 g, CH/EtOAc 8:2 to EtOAc/MeOH 9:1 as eluent) to give the title compound as a white foam (30 mg). $^1$H NMR (400 MHz, CDCl$_3$) δ ppm 7.77 (s, 1H), 7.39 (s, 2H), 7.22 (m, 4H), 4.69 (d, 1H), 4.36 (d, 1H), 4.26-4.07 (m, 2H), 3.96-3.85 (m, 1H), 3.82-3.66 (m, 2H), 3.46-3.34 (m, 1H), 3.19 (td, 1H), 3.06-2.91 (m, 4H), 2.73-2.60 (m, 1H), 2.55 (s, 3H), 2.02-1.93 (m, 1H), 1.55 (m, 1H). UPLC-MS: Rt=1.15; m/z (ES+): 544.28 [M+H]$^+$.

Intermediate 31

N-{1-[3,5-bis(trifluoromethyl)phenyl]but-3-en-1-yl}-N-methyl-1-(2-methylphenyl)-6-oxo-7-(prop-2-en-1-yl)-octahydropyrrolo[1,2-a]piperazine-2-carboxamide (Mixture of Stereoisomers with ANTI Configuration at C1-C8a)

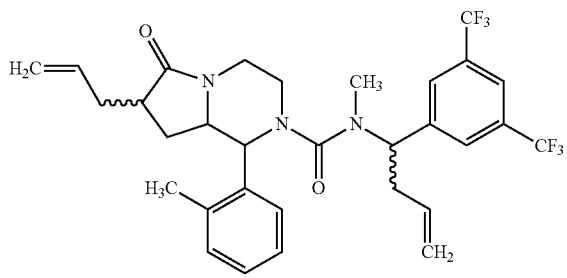 [SMILES: C=CCC1CC2C(c3ccccc3C)N(C(=O)N(C)C(CC=C)c3cc(C(F)(F)F)cc(C(F)(F)F)c3)CCN2C1=O]

To a solution of Intermediate 13 (270 mg, 0.526 mmol) in dry THF (10 mL) stirred at −78° C. under nitrogen was added a 1M solution of LHMDS in THF (1.051 mL, 1.051 mmol), followed after 15 min by the addition of DMPU (317 μL, 2.63 mmol) and allylbromide (91.05 μL, 1.05 mmol). After stirring for 30 min at −78° C., the temperature was slowly raised to −30° C. and the mixture was stirred at this temperature for 40 min. The reaction was cooled again to −78° C. and 1 mL more of LHMDS 1M THF solution was added followed by 50 μL of allylbromide. The reaction was left stirring at this temperature for 15 min and then raised to −30° C. and stirred for 30 min more, then the reaction was quenched by adding NH$_4$Cl sat. sol. and extracted with EtOAc several times. The organic layer was dried over Na$_2$SO$_4$, the solid was filtered out and the solvent removed in vacuo. The crude was purified by FC (SNAP 25 g, eluting from Cy 9/EtOAc 1 to Cy 6/EtOAc 4). The fractions were collected and the solvent removed in vacuo obtaining 182.7 mg of the title compound. UPLC-MS, m/z (ES+): 594.06 [M+H]$^+$ Rt=1.43. $^1$H NMR (400 MHz, CDCl$_3$) δ ppm 7.72 (br s, 1H), 7.35 (br s, 2H), 7.21-7.07 (m, 4H), 5.79-5.65 (m, 2H), 5.62-5.56 (m, 1H), 5.21 (d, 1H), 5.15 (d, 1H), 5.05-5.02 (m, 1H), 5.00 (br s, 1H), 4.21-4.16 (m, 1H), 4.03 (d, 1H), 3.67-3.60 (m, 1H), 3.30-3.24 (m, 1H), 3.16-3.08 (m, 1H), 2.85-2.75 (m, 5H), 2.66-2.56 (m, 2H), 2.54-2.46 (m, 4H), 2.20-2.12 (m, 1H), 1.84-1.77 (m, 1H), 1.65-1.58 (m, 1H).

Intermediate 32

N-{1-[3,5-bis(trifluoromethyl)phenyl]-3-oxopropyl}-N-methyl-1-(2-methylphenyl)-6-oxo-7-(2-oxoethyl)-octahydropyrrolo[1,2-a]piperazine-2-carboxamide (Mixture of Stereoisomers with ANTI Configuration at C1-C8a)

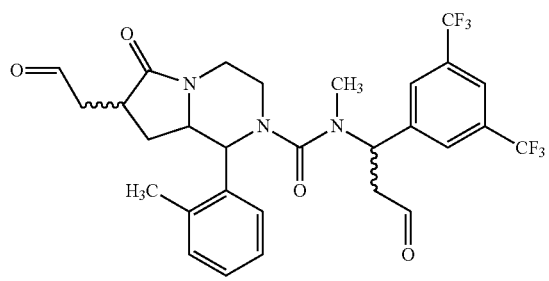 [SMILES: Cc1ccccc1C1C2CC(CC=O)C(=O)N2CCN1C(=O)N(C)C(CC=O)c1cc(C(F)(F)F)cc(C(F)(F)F)c1]

A slow stream of O₃ in O₂ was passed through a −78° C. cooled solution of Intermediate 31 (180 mg, 0.3 mmol) in DCM (30 mL) until a pale blue colour persisted. Excess of O₃ was purged by N₂ bubbling, then a solution of PPh₃ (120 mg, 0.45 mmol) in DCM (3 mL) was added. The solution was allowed to reach 25° C. and it was stirred for 12 h. The solvent was removed in vacuo and the crude material was purified by flash chromatography (SNAP-SiO₂ cartridge, 25 g, eluting from CH/EtOAc 8:2 to EtOAc 100%). The fractions were collected and the solvent removed in vacuo to give the title compound as white solid (130 mg). ¹H NMR (400 MHz, CDCl₃) δ ppm 9.84 (s), 9.78 (s), 9.73 (d), 7.77 (s), 7.35 (s), 7.22-7.08 (m), 6.04-5.98 (m), 4.23-4.05 (m), 3.76-3.69 (m), 3.24-3.08 (m), 3.03-2.93 (m), 2.90-2.79 (m), 2.65-2.58 (m), 2.56 (s), 2.50 (s), 2.05-1.96 (m), 1.57-1.48 (m).

Intermediate 33

[2-{[3,5-bis(trifluoromethyl)phenyl]methyl}-(methyl)carbamoyl)-1-(2-methylphenyl)-6-oxo-octahydropyrrolo[1,2-a]piperazin-7-yl]methyl methanesulfonate (Diastereoisomeic Mixture with ANTI Configuration at C1-C8a)

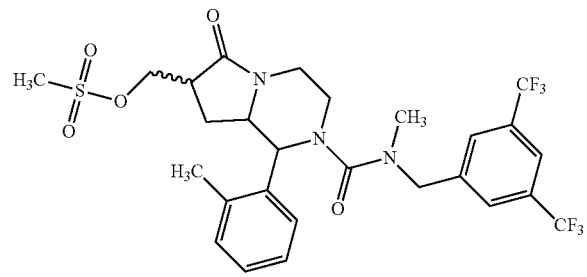 [SMILES: Cc1ccccc1C1C2CC(COS(C)(=O)=O)C(=O)N2CCN1C(=O)N(C)Cc1cc(C(F)(F)F)cc(C(F)(F)F)c1]

To a −5° C. cooled solution of Intermediate 30 (30 mg, 0.055 mmol) in DCM (2 mL), TEA (15 μL, 0.11 mmol) was added followed by mesyl chloride (5 μL, 0.06 mmol). The mixture was stirred for 30 min, then the organic phase was washed with HCl 0.5 N (2 mL), filtered through a phase separator and evaporated in vacuo to obtain the title compound ad pale yellow foam (34 mg) which was used without further purification. UPLC-MS: Rt=1.20; m/z (ES+): 621.7 [M+H]⁺.

Intermediate 34

Tert-butyl 1-(2-methylphenyl)-6-oxo-7,7-bis(prop-2-en-1-yl)-octahydropyrrolo[1,2-a]piperazine-2-carboxylate (Racemic Mixture, ANTI Configuration at C1-C8a)

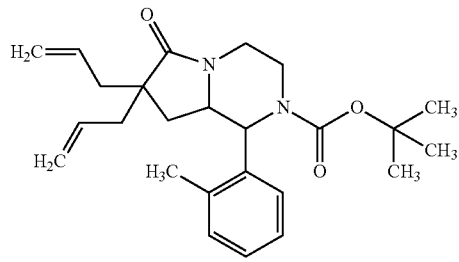 [SMILES: C=CCC1(CC=C)CC2C(c3ccccc3C)N(C(=O)OC(C)(C)C)CCN2C1=O]

To a solution of Intermediate 14, (1 g, 3.027 mmol) in 100 mL of THF dry stirred at −78° C. under N₂ atmosphere, a solution of LHMDS 1M in THF (6.054 mL) was added, followed after 15 min by DMPU (1.823 ml, 15.13 mmol) and allylbromide (524 μL, 6.054 mmol). After stirring at −78° C. for 30 min the temperature was slowly raised to −30° C. and the mixture was stirred at this temperature for 40 min more. The mixture was cooled again to −78° C. and more LHMDS was added (6.054 mL) and left reacting for 30 min; another equivalent of LHMDS. water and EtOAc were added to the reaction and the two layers were separated, the organic layer was again dried over Na₂SO₄, the solid was filtered out and the solvent removed in vacuo. The crude was purified by flash chromatography (50 g SNAP cartridge, eluting from Cy/EtOAc 9:1 to 6:4). The fractions were collected and the solvent removed to give 1.021 g of title compound. UPLC-MS: m/z (ES+): 410.96 [M+H]⁺ Rt=1.27 min. ¹H NMR (400 MHz, CDCl₃) δ ppm 7.24-7.12 (m, 4H), 5.83-5.61 (m, 2H), 5.24-5 (m, 4H), 4.65 (d, 1H), 4.46-4.36 (m, 1H), 3.97-3.87 (m, 1H), 3.79-3.51 (m, 3H), 2.52-2.43 (m, 1H), 2.42 (s, 3H), 2.35-2.26 (m, 1H), 2.23-2.07 (m, 2H), 1.82-1.69 (m, 2H), 1.16 (s, 9H).

Intermediate 35

1-(2-methylphenyl)-7,7-bis(prop-2-en-1-yl)-octahydropyrrolo[1,2-a]piperazin-6-one (Racemic Mixture, ANTI Configuration at C1-C8a)

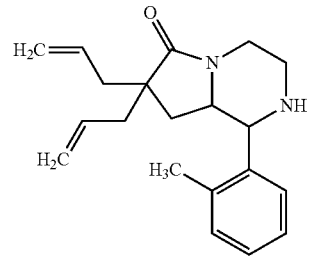 [SMILES: C=CCC1(CC=C)CC2C(c3ccccc3C)NCCN2C1=O]

Intermediate 34 (1.02 g, 2.487 mmol) was dissolved in DCM (60 mL) and TFA (5 mL) was added. The reaction was left stirring at room temperature for 3 h, then the solvent was removed in vacuo and the residue was taken up with DCM and NaOH 1M. The phases were separated and the aqueous one extracted with more DCM. The organics were filtered through a phase separator and concentrated under vacuum obtaining 780 mg of the title compound. UPLC-MS: m/z (ES+): 312.10 [M+H]⁺ Rt=0.66 min. ¹H NMR (400 MHz, CDCl₃) δ ppm 7.46-7.40 (m, 1H), 7.27-7.17 (m, 3H), 5.81-5.65 (m, 2H), 5.18-5.05 (m, 4H), 4.12 (dd, 1H), 3.62-3.47 (m, 2H), 3.14 (dd, 1H), 3.02-2.92 (m, 1H), 2.02-1.92 (m, 1H), 2.87-2.77 (m, 1H), 2.48 (dd, 1H), 2.42 (s, 3H), 2.33 (dd, 1H), 2.20-2.08 (m, 2H), 1.77-1.66 (m, 2H), 1.06-1.52 (m, 1H).

Intermediate 36

N-{[3,5-bis(trifluoromethyl)phenyl]methyl}-N-methyl-1-(2-methyl phenyl)-6-oxo-7,7-bis(prop-2-en-1-yl)-octahydropyrrolo[1,2-a]piperazine-2-carboxamide (Racemic Mixture, ANTI Configuration at C1-C8a)

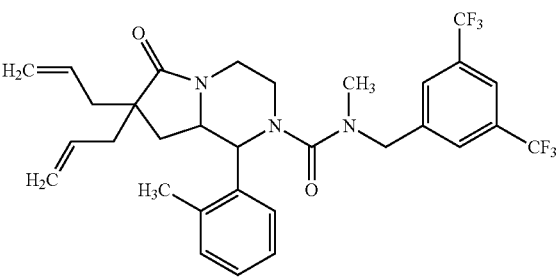 [SMILES: C=CCC1(CC=C)CC2C(c3ccccc3C)N(C(=O)N(C)Cc3cc(C(F)(F)F)cc(C(F)(F)F)c3)CCN2C1=O]

Triphosgene (372.6 mg, 1.256 mmol) was dissolved in 20 mL of EtOAc, a solution of Intermediate 35 (780 mg, 2.51 mmol) and TEA (1 mL) in 50 mL of EtOAc was added at 0° C. The mixture was left stirring for 1.5 h, then intermediate 18 (968.24 mL, 3.765 mmol) in 50 mL of EtOAc and TEA (1 mL) were added and the reaction was left stirring at room temperature for 3 h. Water was added to the mixture, the phases were separated, the aqueous one was extracted several times with more EtOAc and the combined organics were washed with HCl 1M aqueous solution. The organic layer was dried over $Na_2SO_4$, the solid was filtered out and the solvent removed in vacuo obtaining 1.5 g of the titled compound. The product was used in the next step without further purification. MS: m/z (ES+): 594.07 [M+H]$^+$ Rt=1.44 min. $^1$H NMR (400 MHz, CDCl$_3$) δ ppm 7.75 (s, 1H), 7.37 (s, 2H), 7.27-7.11 (m, 4H), 5.81-5.6 (m, 2H), 5.25-5.01 (m, 4H), 4.68 (d, 1H), 4.38 (d, 1H), 4.23-4.15 (m, 1H), 3.96 (d, 1H), 3.65-3.56 (m, 1H), 3.41-3.33 (m, 1H), 3.19-3.09 (m, 1H), 3.00-2.87 (m, 4H), 2.59-2.46 (m, 4H), 2.36-2.27 (m, 1H), 2.21-2.05 (m, 2H), 1.76-1.66 (m, 2H).

Intermediate 37

N-{[3,5-bis(trifluoromethyl)phenyl]methyl}-N-methyl-1-(2-methylphenyl)-6-oxo-7,7-bis(2-oxoethyl)-octahydropyrrolo[1,2-a]piperazine-2-carboxamide (Racemic Mixture, ANTI Configuration at C1-C8a)

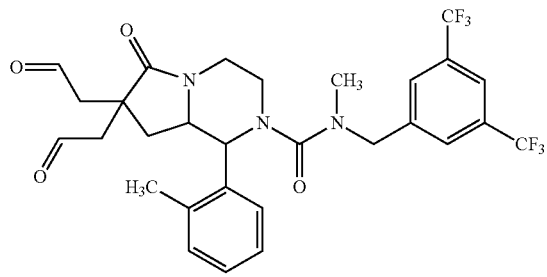 [SMILES: Cc1ccccc1C1C2CC(CC=O)(CC=O)C(=O)N2CCN1C(=O)N(C)Cc1cc(C(F)(F)F)cc(C(F)(F)F)c1]

A slow stream of $O_3$ in $O_2$ was passed through a −78° C. cooled solution of intermediate 36 (1.5 g, 2.53 mmol) in DCM (300 mL) until a pale blue colour persisted. Excess of $O_3$ was purged by $N_2$ bubbling, then a solution of PPh$_3$ (995 mg, 3.79 mmol) in DCM (10 mL) was added. The solution was allowed to reach 25° C. and it was stirred for 12 h. The solvent was removed in vacuo and the crude material was purified by flash chromatography (SNAP-SiO$_2$ cartridge, 50 g, eluting from CH/EtOAc 8:2 to EtOAc 100%). The fractions were collected and the solvent removed in vacuo to give the title compound as white solid (620 mg). $^1$H NMR (400 MHz, CDCl$_3$) δ ppm 9.78 (s, 1H), 9.67 (s, 1H), 7.75 (s, 1H), 7.38 (s, 2H), 7.22-7.08 (m, 3H), 4.70 (d, 2H), 4.41-4.30 (m, 1H), 4.27-4.01 (m, 3H), 3.94-3.84 (m, 1H), 3.47-3.37 (m, 1H), 3.29-3.17 (m, 1H), 3.15-3.03 (m, 1H), 2.98 (s, 3H), 2.91 (q, 1H), 2.72 (q, 1H), 2.57-2.47 (m, 4H), 1.96-1.85 (m, 1H), 1.82-1.74 (m, 1H).

Intermediate 38

N-{[3,5-bis(trifluoromethyl)phenyl]methyl}-7-(hydroxymethyl)-N-methyl-1-(2-methylphenyl)-octahydropyrrolo[1,2-a]piperazine-2-carboxamide (Diastereomeric Mixture with ANTI Configuration at C1-C8a)

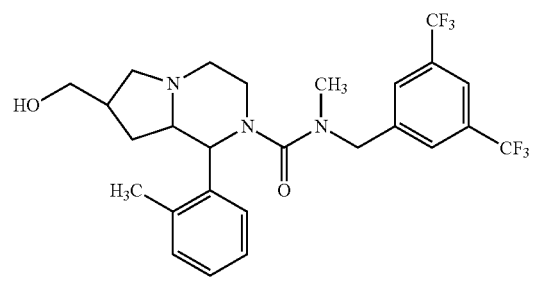 [SMILES: Cc1ccccc1C1C2CC(CO)CN2CCN1C(=O)N(C)Cc1cc(C(F)(F)F)cc(C(F)(F)F)c1]

Intermediate 30 (17 mg, 0.032 mmol) was dissolved in 2 mL of THF and cooled at 0° C. BH$_3$-Me$_2$S (63 µL) was added and the reaction was left stirring at 25° C. for 8 h, then HCl 1 M aq and MeOH were added and the reaction was left stirring over night, further MeOH was added and the reaction was left stirring 6 h. The mixture was concentrated in vacuo and taken up with DCM and NaHCO$_3$ ss. The organic phase was filtered through a phase separator and removed in vacuo obtaining 15 mg of the title compound as diastereoisomeic mixture. UPLC-MS: Rt=1.18 min and 1.24 min; m/z (ES+): 530.03 [M+H]$^+$.

Intermediate 39

N-[(1R)-1-[3,5-bis(trifluoromethyl)phenyl]ethyl]-N-methyl-1-(2-methylphenyl)-6-oxo-7,7-bis(prop-2-en-1-yl)-octahydropyrrolo[1,2-a]piperazine-2-carboxamide (Diastereomeric Mixture with ANTI Configuration at C1-C8a)

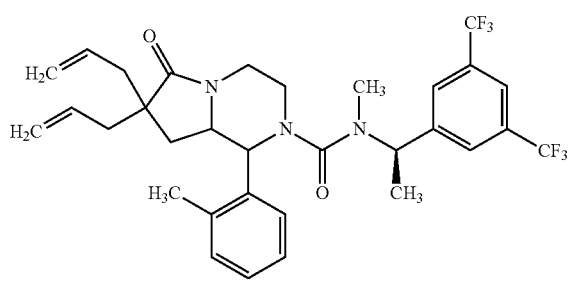 [SMILES: C=CCC1(CC=C)CC2C(c3ccccc3C)N(C(=O)N(C)[C@H](C)c3cc(C(F)(F)F)cc(C(F)(F)F)c3)CCN2C1=O]

Triphosgene (407 mg, 1.37 mmol) was dissolved in 40 mL of EtOAc, a solution of Intermediate 35 (850 mg, 2.74 mmol) and TEA (1.15 mL) in 85 mL of EtOAc was added at 0° C. The mixture was left stirring for 2 h, then intermediate 1 (1.12 vg, 4.11 mmol) in 40 mL of EtOAc and TEA (1.15 mL) were added and the reaction was left stirring at room temperature for 12 h, then heated to 45° C. for 48 h. NaOH 1N was added to the mixture, the phases were separated, the aqueous phase was extracted several times with EtOAc and the combined organics were washed with HCl 1M aqueous solution. The organic layer was dried over Na$_2$SO$_4$, the solid was filtered out and the solvent removed in vacuo obtaining 1.5 g of the title compound. The crude was purified by flash chromatography (SNAP 50 g, eluting from CH/EtOAc 9:1 to CH/EtOAc 1:1). The fractions were collected and the solvent removed in vacuo to give the title compound (1.35 g). UPLC-MS: m/z (ES+): 608.04 [M+H]$^+$ Rt=1.45, 1.48 min. $^1$H NMR (400 MHz, CDCl$_3$) δ ppm 7.80 (s), 7.74 (s), 7.56 (s), 7.36 (s), 7.29-7.11 (m), 5.83-5.53 (m), 5.27-5.01 (m), 4.24-4.16 (m), 4.08-3.97 (m), 3.82-3.54 (m), 3.36-3.23 (m), 3.20-3.07 (m), 2.83 (s), 2.71 (s), 2.59-2.45 (m), 2.37-2.27 (m), 2.22-2.06 (m), 1.77-1.64 (m), 1.53 (d), 1.40 (d).

Intermediate 40

N-[(1R)-1-[3,5-bis(trifluoromethyl)phenyl]ethyl]-N-methyl-1-(2-methylphenyl)-6-oxo-7,7-bis(2-oxoethyl)-octahydropyrrolo[1,2-a]piperazine-2-carboxamide (Diastereomeric Mixture with ANTI Configuration at C1-C8a)

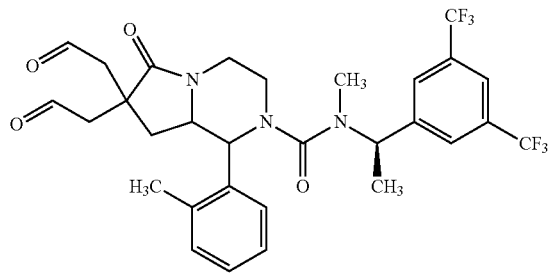 [SMILES: Cc1ccccc1C1C2CC(CC=O)(CC=O)C(=O)N2CCN1C(=O)N(C)[C@H](C)c1cc(C(F)(F)F)cc(C(F)(F)F)c1]

A slow stream of O$_3$ in O$_2$ was passed through a −78° C. cooled solution of Intermediate 39 (1.35 g, 2.22 mmol) in DCM (200 mL) until a pale blue color persisted. Excess of O$_3$ was purged by N$_2$ bubbling, then a solution of PPh$_3$ (875 mg, 3.33 mmol) in DCM (3 mL) was added. The solution was allowed to reach 25° C. and then it was stirred for 12 h. The solvent was removed in vacuo and the crude material was purified by flash chromatography (SNAP-SiO$_2$ cartridge, 50 g, eluting from CH/EtOAc 9:1 to EtOAc 100%). The fractions were collected and the solvent removed in vacuo to give the title compound as a white solid (1.1 g). UPLC-MS: m/z (ES+): 611.99 [M+H]$^+$ Rt=1.10, 1.14 min.

Intermediate 41

N-[(1R)-1-[3,5-bis(trifluoromethyl)phenyl]ethyl]-7,7-bis(2-hydroxyethyl)-N-methyl-1-(2-methylphenyl)-6-oxo-octahydropyrrolo[1,2-a]piperazine-2-carboxamide (Diastereomeric Mixture with ANTI Configuration at C1-C8a)

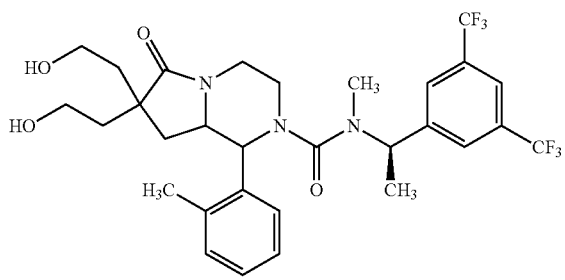 [SMILES: Cc1ccccc1C1C2CC(CCO)(CCO)C(=O)N2CCN1C(=O)N(C)[C@H](C)c1cc(C(F)(F)F)cc(C(F)(F)F)c1]

Intermediate 40 (1.1 g) was dissolved in MeOH (40 mL) and NaBH$_4$ (270 mg) was added at 0° C. The reaction was left stirring at this temperature for 30 min, then NH$_4$Cl aq. Sat. sol. was added, the MeOH was removed in vacuo and the aqueous phase was extracted several times with DCM. The organic layer was filtered through a phase separator and concentrated in vacuo. The crude was purified by flash chromatography (25 g SNAP cartridge, eluting from DCM 100% to DCM/MeOH 95:5). The fractions were collected and the solvent removed to give 900 mg of title compound as a white foam. UPLC/MS: m/z (ES+): 616.03 [M+H]$^+$, Rt=1.08, 1.10 min. $^1$H NMR (400 MHz, CDCl$_3$) δ ppm 7.80 (s), 7.75 (s), 7.56 (s), 7.37 (s), 7.29-7.11 (m), 5.65-5.52 (m), 4.23-4.06 (m), 3.93-3.71 (m), 3.71-3.60 (m), 3.41-3.29 (m), 3.24-3.12 (m), 3.09-2.92 (m), 2.83 (s), 2.71 (s), 2.56 (s), 2.17-1.68 (m), 1.54 (d), 1.43 (d).

Intermediate 42

N-[(1R)-1-[3,5-bis(trifluoromethyl)phenyl]ethyl]-7,7-bis(2-hydroxyethyl)-N-methyl-1-2-methylphenyl)-octahydropyrrolo[1,2-a]piperazine-2-carboxamide (Diastereomeric Mixture with ANTI Configuration at C1-C8a)

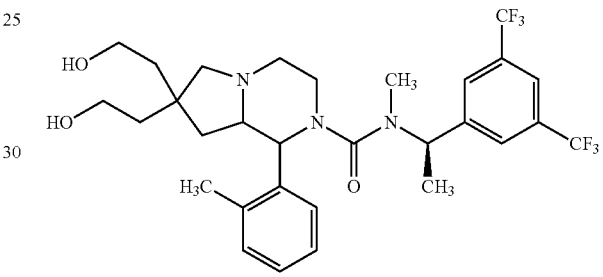

To a 0° C. cooled solution of Intermediate 41 (600 mg, 0.975 mmol) in THF (40 mL), a solution of borane dimethylsulfide complex 2M in THF (1.95 mL, 3.9 mmol) was added dropwise. The reaction mixture was stirred 24 h at 25° C., then heated to 50° C. for 8 h, then stirred for further 12 h at 25° C. MeOH (4 mL) was carefully added and the reaction mixture was stirred at 25° C. for 48 h. The solution was evaporated and the crude material was dissolved in DCM and washed with NaHCO$_3$. The organic phase was filtered through a phase separator. The solvent was removed in vacuo to give the title compound as a white foam (620 mg). UPLC/MS: m/z (ES+): 602.14 [M+H]$^+$, Rt=0.88, 0.90 min.

Intermediate 43

N-[(1R)-1-[3,5-bis(trifluoromethyl)phenyl]ethyl]-N-methyl-1-(2-methylphenyl)-octahydropyrrolo[1,2-a]piperazine-2-carboxamide (Diastereomeric Mixture with ANTI Configuration at C1-C8a)

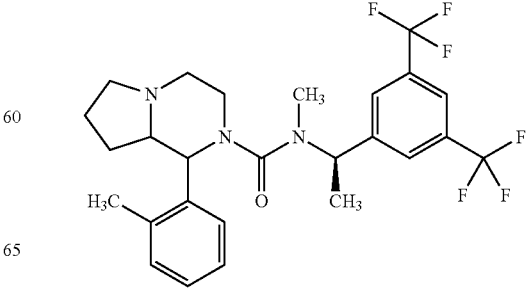

Triphosgene (142 mg, 0.48 mmol) was dissolved in 25 mL of EtOAc, a solution of Intermediate 23 (260 mg, 1.2 mmol) and TEA (0.6 mL) in 20 mL of EtOAc was added at 0° C. The mixture was left stirring for 2 h, then Intermediate 1 (455 mg, 1.68 mmol) in 20 mL of EtOAc and TEA (0.6 mL) were added and the reaction was left stirring at room temperature for 3 days. Water was added to the mixture, the phases were separated, the aqueous phase was extracted several times with EtOAc and the combined organics dried over $Na_2SO_4$, the solid was filtered out and the solvent removed in vacuo. The crude was purified by Flash Chromatography (SNAP NH eluting from Cy/EtOAC 9/1 to 0/1) The fractions were collected and the solvent removed in vacuo obtaining 337 mg of the titled compound. Column: Chiralcel OD-H (25×0.46 cm), 5 um; Mobile phase: n-Hexane/2-Propanol 95/5% v/v; Diast. 1: 50% a/a by UV (3.9 min); Diast. 2:50% a/a by UV (5.3 min).

Intermediate 44

Methyl 2-{[(1R)-1-1-[3,5-bis(trifluoromethyl)phenyl]ethyl](methyl)carbamoyl}-1-(2-methylphenyl)-6-oxo-octahydropyrrolo[1,2-a]piperazine-7-carboxylate (Diastereomeric Mixture with ANTI Configuration at C1-C8a)

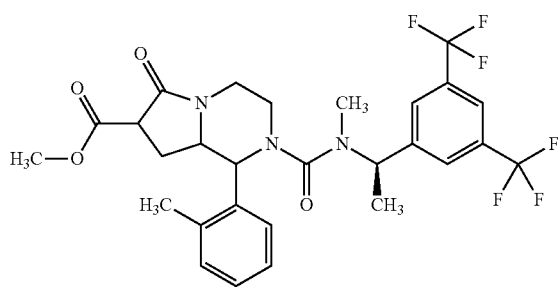 [SMILES: COC(=O)C1CC2C(c3ccccc3C)N(C(=O)N(C)[C@H](C)c3cc(C(F)(F)F)cc(C(F)(F)F)c3)CCN2C1=O]

Triphosgene (330.8 mg, 1.11 mmol) was dissolved in 30 mL of EtOAc, a solution of Intermediate 20 (804 mg, 2.787 mmol) and TEA (1.2 mL) in 40 mL of EtOAc was added at 0° C. The mixture was left stirring for 2 h, then Intermediate 1 (1.058 gr, 3.9 mmol) in 30 mL of EtOAc and TEA (1.2 mL) were added and the reaction was left stirring at room temperature for 3 days. Then 1 eq more of Intermediate 1 in 3 mL of EtOAc was added and the reaction was left stirring at RT 4 days more and heated at 40° C. for 5 h. The mixture was cooled and water was added, the layers were separated. The organic one was washed twice with HCl 1 m aq.sol. The phases were separated and the organics were dried over $Na_2SO_4$. The solid was filtered out and the solvent removed in vacuo. The crude was purified by Flash Chromatography (50 g SNAP Cy/EtOAc from 9/1 to 0/1). The fractions were collected and concentrated in vacuo obtaining 1.075 g of the title compound. UPLC/MS: m/z (ES+): 586.06 [M+H]$^+$ Rt=1.26 min (isomer 1) and RT=1.28 (isomer 2). $^1$H NMR (400 MHz, CDCl$_3$) δ ppm 7.80 (s), 7.73 (s), 7.56 (s), 7.36 (s), 7.28-7.18 (m), 5.66-5.52 (m), 4.27-4.11 (m), 4.08-4.01 (m), 4.01-3.87 (m), 3.84-3.81 (m), 3.8-3.76 (m), 3.74 (s), 3.54-3.39 (m), 3.38-3.12 (m), 3.09-2.88 (m), 2.83 (s), 2.73-2.70 (m), 2.6 (bs), 2.56-2.52 (m), 2.27-2.16 (m), 2.16-2.08 (m), 1.99-1.85 (m), 1.55-1.49 (d), 1.45-1.38 (m).

Intermediate 45 methyl 2-{[(1R)-1-[3,5-bis(trifluoromethyl)phenyl]ethyl](methyl)carbamoyl}-1-(2-methylphenyl)-6-oxo-octahydropyrrolo[1,2-a]piperazine-7-carboxylate (Mixture 1, ANTI Configuration at C1-C8a)

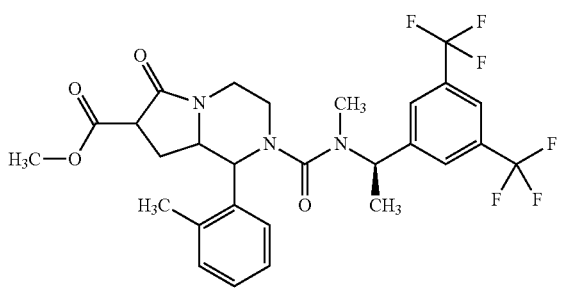 [SMILES: COC(=O)C1CC2C(c3ccccc3C)N(C(=O)N(C)[C@H](C)c3cc(C(F)(F)F)cc(C(F)(F)F)c3)CCN2C1=O]

1.075 g of Intermediate 44 were purified by chiral preparative HPLC obtaining two fractions. After evaporation were obtained: 400 mg of Intermediate 45 (mixture 1, described here) and 395 of Intermediate 46 (mixture 2, described in the next experimental part). Intermediate 45: UPLC/MS: m/z (ES+): 586.06 [M+H]$^+$ Rt=1.26 min. $^1$H NMR (400 MHz, CHLOROFORM-d) δ ppm 7.80 (s), 7.56 (s), 7.28-7.11 (m), 5.61-5.51 (m), 4.71-4.52 (m), 4.28-4.14 (m), 4.09-3.9 (m), 3.83 (s), 3.80-3.71 (m), 3.55-3.38 (m), 3.34-3.11 (m), 3.10-2.93 (m), 2.71 (bs), 2.60 (s), 2.54 (s), 2.26-2.18 (m), 2.15-2.07 (m), 1.96-1.85 (m), 1.67 (bs), 1.45-1.39 (m).

Intermediate 46 methyl 2-{[(1R)-1-[3,5-bis(trifluoromethyl)phenyl]ethyl](methyl)carbamoyl}-1-(2-methylphenyl)-6-oxo-octahydropyrrolo[1,2-a]piperazine-7-carboxylate (Mixture 2, ANTI Configuration at C1-C8a)

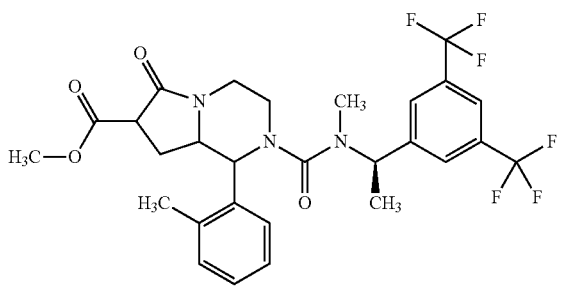 [SMILES: COC(=O)C1CC2C(c3ccccc3C)N(C(=O)N(C)[C@H](C)c3cc(C(F)(F)F)cc(C(F)(F)F)c3)CCN2C1=O]

UPLC/MS: m/z (ES+): 586.06 [M+H]$^+$ Rt=1.28 min. $^1$H NMR (400 MHz, CHLOROFORM-d) δ ppm 7.73 (s), 7.37 (s), 7.28-7.10 (m), 5.66-5.56 (m), 4.27-4.14 (m), 4.08-4.01 (m), 3.96-3.86 (m), 3.83 (s), 3.74 (s), 3.73-3.66 (m), 3.54-3.39 (m), 3.40-3.30 (m), 3.29-3.10 (m), 3.06-2.89 (m), 2.83 (s), 2.60 (s), 2.54 (s), 2.26-2.06 (m), 1.99-1.89 (m), 1.56-1.50 (d).

Intermediate 47

N-[(1R)-1-[3,5-bis(trifluoromethyl)phenyl]ethyl]-7-(hydroxymethyl)-N-methyl-1-(2-methylphenyl)-6-oxo-octahydropyrrolo[1,2-a]piperazine-2-carboxamide (Diasteriomeric Mixture 1, ANTI Configuration at C1-C8a)

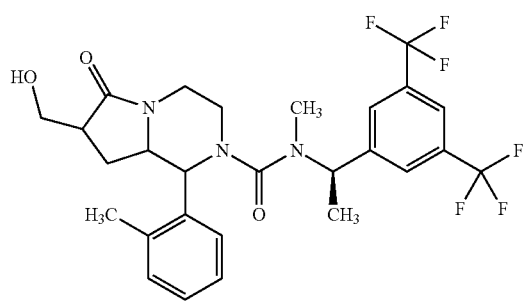 [SMILES: Cc1ccccc1C1C2CC(CO)C(=O)N2CCN1C(=O)N(C)[C@H](C)c1cc(C(F)(F)F)cc(C(F)(F)F)c1]

Intermediate 45 (400 mg) was dissolved in MeOH (20 mL). To this solution, CaCl$_2$ (113.2 mg, 1.02 mmol) was added, the suspension was cooled to 0° C. and NaBH$_4$ (77.52 mg) was added. The reaction was left stirring at room temperature for 2 h. Then the mixture was concentrated under vacuum and the residue taken up with DCM and HCl 1M. The layers were separated and the organic layer was filtered through a phase separator and concentrated in vacuo obtaining 300 mg of the title compound. UPLC/MS: m/z (ES+): 558.02 [M+H]$^+$ Rt=1.14 min and 1.15 min. CHLOROFORM-d) δ ppm 7.80 (s), 7.56 (s), 7.28-7.11 (m), 5.61-5.51 (m), 4.25-4.04 (m), 3.96-3.65 (m), 3.36-3.11 (m), 3.07-2.95 (m), 2.72 (s), 2.55 (s), 2.02-1.91 (s), 1.88-1.68 (m), 1.57-1.39 (m).

Intermediate 48

N-[(1R)-1-[3,5-bis(trifluoromethyl)phenyl]ethyl]-7-(hydroxymethyl)-N-methyl-1-(2-methylphenyl)-6-oxo-octahydropyrrolo[1,2-a]piperazine-2-carboxamide (Diasteriomeric Mixture 2, ANTI Configuration at C1-C8a)

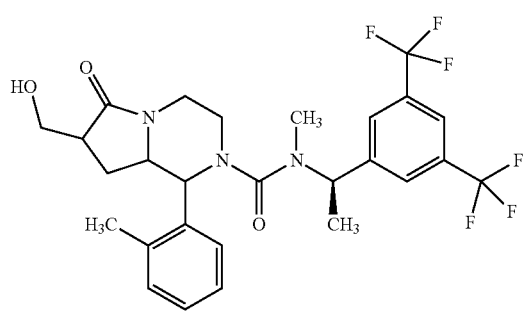 [SMILES: Cc1ccccc1C1C2CC(CO)C(=O)N2CCN1C(=O)N(C)[C@H](C)c1cc(C(F)(F)F)cc(C(F)(F)F)c1]

Intermediate 47 (395 mg) was dissolved in MeOH (20 mL). To the solution CaCl$_2$ (112.2 mg, 1.011 mmol) was added, the suspension was cooled down to 0° C. and NaBH$_4$ (76.55 mg,) was added. The reaction was left stirring at room temperature for 2 h. Then the mixture was concentrated under vacuum and the residue taken up with DCM and HCl 1M. The layers were separated and the organic was filtered through a phase separator and concentrated in vacuo obtaining 350 mg of the title compound. UPLC/MS: m/z (ES+): 558.02 [M+H]$^+$ Rt=1.15 min and 1.17 min. $^1$H NMR (400 MHz, CHLOROFORM-d) δ ppm 7.73 (s), 7.37 (s), 7.32-7.08 (m), 5.66-5.51 (m), 4.28-4.00 (m), 3.99-3.81 (m), 3.80-3.61 (m), 3.43-3.25 (m), 3.25-3.10 (m), 3.07-2.87 (m), 2.84 (s), 2.81-2.59 (m), 2.55 (s), 2.01-1.91 (m), 1.89-1.80 (m), 1.78-1.66 (m), 1.56-1.49 (m).

Intermediate 49

N-{[3,5-bis(trifluoromethyl)phenyl]methyl}-7,7-bis(2-hydroxyethyl)-N-methyl-1-(2-methylphenyl)-6-oxo-octahydropyrrolo[1,2-a]piperazine-2-carboxamide (Diasteriomeric Mixture 2, ANTI Configuration at C1-C8a)

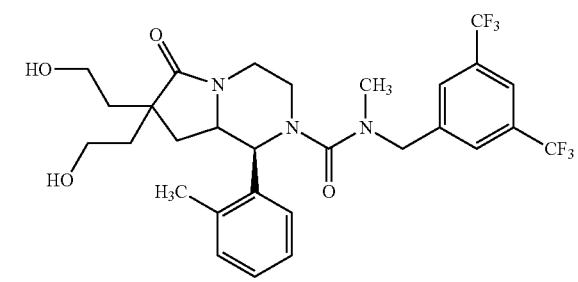 [SMILES: Cc1ccccc1[C@H]1C2CC(CCO)(CCO)C(=O)N2CCN1C(=O)N(C)Cc1cc(C(F)(F)F)cc(C(F)(F)F)c1]

NaBH$_4$ (28 mg, 0.74 mmol), was added to an ice-cooled solution of Intermediate 37 (110 mg, 0.84 mmol) in MeOH (8 mL). The reaction mixture was stirred at 0° C. for 40 min then NH$_4$Cl aq. Sat. sol. (5 mL) was added, MeOH was evaporated and the aqueous solution was extracted several times with DCM. DCM was filtered through a phase separator and evaporated to give a crude that was purified on SP1-SiO$_2$ 10 g cartridge, DCM to DCM/MeOH 85:15 as eluent) to give the title compound as a white solid (20 mg). UPLC-MS, Rt=1.05, m/z (ES+): 602.1 [M+H]$^+$.

Intermediate 50

(2-{[(1R)-1-[3,5-bis(trifluoromethyl)phenyl]ethyl](methyl)carbamoyl}-1-(2-methylphenyl)-6-oxo-octahydropyrrolo[1,2-a]piperazin-7-yl)methyl methanesulfonate (Diasteriomeric Mixture, ANTI Configuration at C1-C8a)

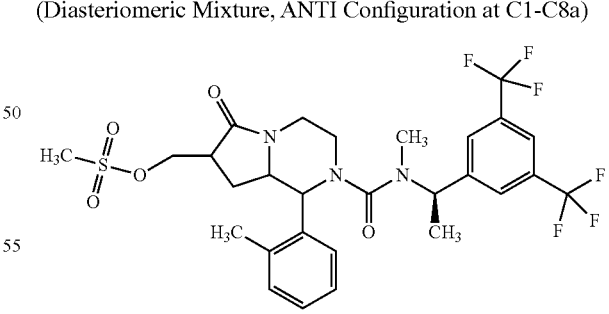

To a −5° C. cooled solution of Intermediate 47 (2.07 g, 3.71 mmol) and TEA (1.034 mL, 7.42 mmol) in dry DCM (45 mL) a solution of mesyl chloride (0.32 mL, 4.08 mmol) in dry DCM (5 mL) was added dropwise. The reaction mixture was stirred at −5° C. for 30 min, then washed with HCl 0.5 N aq. Sol. (3×35 mL). The organic layer was dried on Na$_2$SO$_4$, filtered and concentrated to give the title compound as a pale yellow foam (2.3 g). UPLC-MS, Rt=1.23 and 1.25, m/z (ES+): 636.0 [M+H]$^+$.

Intermediate 51

(1S,8aS)-1-o-tolylhexahydropyrrolo[1,2-a]pyrazin-6(7H)-one

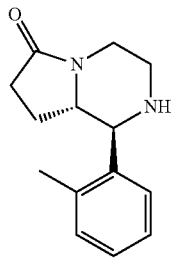 [SMILES: Cc1ccccc1[C@@H]1NCCN2C(=O)CC[C@@H]12]

Intermediate 51 was obtained (white solid, 16.6 g) by SFC separation of Intermediate 24. Rt=5.89 min (Chiral HPLC, Chiralpak AS-H column (15×0.46 cm), 3μ, mobile phase: Ethanol/Diethylamine 100/0.1 v/v, Flow rate: 0.6 mL/min. Detection: DAD at 220 nm).

Intermediate 52

(1S,8aS)-tert-butyl 6-oxo-1-o-tolylhexahydropyrrolo[1,2-a]pyrazine-2(1H)-carboxylate

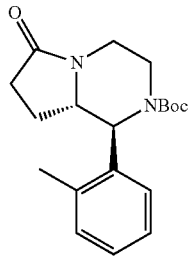 [SMILES: Cc1ccccc1[C@H]1[C@@H]2CCC(=O)N2CCN1C(=O)OC(C)(C)C]

To a solution of Intermediate 51 (6 g, 26 mmol) in DCM (50 mL) was added TEA (5.3 g, 52 mmol), DMAP (317 mg, 2.6 mmol) and Boc$_2$O (8.6 g, 39 mmol). The reaction mixture was stirred at 40° C. overnight and quenched with water. The resulting mixture was washed with water (2×50 mL) and the combined organic layers were dried over anhydrous Na$_2$SO$_4$ and then concentrated. The residue was purified by silica gel chromatography (DCM/MeOH=20/1 to 10/1) to give the title compound (7 g, yield: 81%); m/z (ES+): 331 [M+H]$^+$.

Intermediate 53

(1S,8aS)-tert-butyl 7,7-diallyl-6-oxo-1-o-tolyl-hexahydropyrrolo[1,2-a]pyrazine-2(1H)-carboxylate

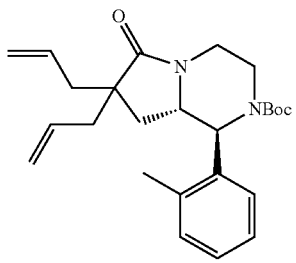 [SMILES: C=CCC1(CC=C)C[C@H]2[C@H](c3ccccc3C)N(C(=O)OC(C)(C)C)CCN2C1=O]

To a solution of Intermediate 52 (2.2 g, 6.7 mmol) in anhydrous THF (100 mL) under N$_2$ atmosphere, was added LiHMDS (1 M in THF, 21 mL) at −78° C. The reaction was stirred for 15 min, followed by addition of DMPU (2.7 g, 21 mmol) and allylbromide (1.8 g, 15 mmol). The reaction mixture was stirred at −78° C. for 30 min and allowed to warm to −30° C., and then stirred at this temperature for another 2 h. After quenched with water at −78° C. and the mixture was then extracted with EtOAc (2×50 mL). The organic layers were dried over anhydrous Na$_2$SO$_4$ and then concentrated in high vacuum. The residue was purified by silica gel chromatography (PE/EtOAc=2/1 to 1/1) to give the title compound (2.3 g, yield: 84%); m/z (ES+): 411 [M+H]$^+$.

Intermediate 54

(1S,8aS)-7,7-diallyl-1-o-tolylhexahydropyrrolo[1,2-a]pyrazin-6(7H)-one

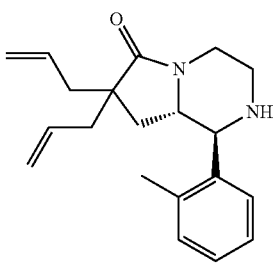 [SMILES: C=CCC1(CC=C)C[C@H]2[C@H](c3ccccc3C)NCCN2C1=O]

To a solution of Intermediate 53 (2.3 g, 5.6 mmol) in DCM (60 mL) was added TFA (5 mL). The reaction was stirred at room temperature for 3 h and then neutralized with 1 M aqueous NaOH solution to pH=8. The resulting mixture was extracted with DCM (2×30 mL). The organic layers were dried over anhydrous Na$_2$SO$_4$, and then concentrated in high vacuum. The residue was purified by silica gel chromatography (DCM/MeOH=20/1 to 10/1) to give the title compound (1.4 g, yield: 83%); m/z (ES+): 311 [M+H]$^+$.

Intermediate 55

1-(3-fluoro-5-(trifluoromethyl)phenyl)-N-methyl-methanamine

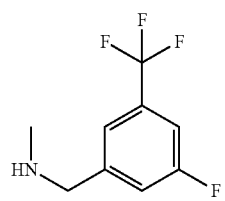

To a solution of 1-(bromomethyl)-3-fluoro-5-(trifluoromethyl)benzene (257 mg, 1 mmol) in MeOH (5 mL) was added methanamine in MeOH (5 mL). The reaction was stirred at 50° C. for 16 h and then concentrated in high vacuum. The residue was purified by silica gel chromatography (DCM/MeOH=20/1 to 10/1) to give the title compound (200 mg, yield: 90%); m/z (ES+): 222 [M+H]$^+$.

Intermediate 56

(1S,8aS)-7,7-diallyl-N-(3-fluoro-5-(trifluoromethyl) benzyl)-N-methyl-6-oxo-1-o-tolylhexahydropyrrolo [1,2-a]pyrazine-2(1H)-carboxamide

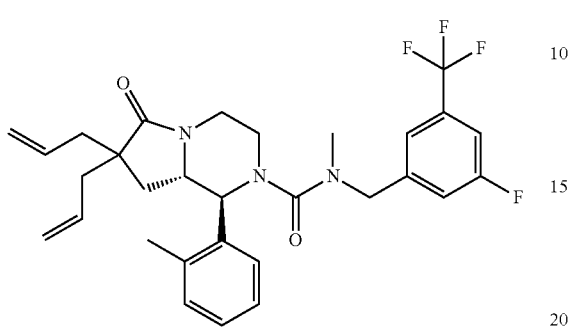

To a solution of triphosgene (24 mg, 0.08 mmol) in EtOAc (2 mL) at 0° C. was added solution of Intermediate 54 (50 mg, 0.16 mmol), DMAP (4 mg, 0.032 mmol) and TEA (49 mg, 0.48 mmol) in EtOAc (2 mL). The mixture was stirred for 1.5 h, followed by addition of 1-(3,5-bis(trifluoromethyl)phenyl)-N-methylmethanamine (50 mg, 0.24 mmol) in EtOAc (2 mL) and TEA (49 mg, 0.48 mmol). The reaction was stirred at 50° C. for 48 h and quenched with water. The resulting mixture was extracted with EtOAc and the organic layer was washed with 1 M aqueous HCl solution, dried over anhydrous $Na_2SO_4$ and then concentrated in high vacuum. The residue was purified by Prep-HPLC to give the title compound (20 mg, yield: 23%); m/z (ES+): 544 [M+H]+.

Intermediate 57

(1S,8aS)-7,7-diallyl-N-methyl-N-(3-methyl-5-(trifluoromethyl)benzyl)-6-oxo-1-o-tolylhexahydropyrrolo[1,2-a]pyrazine-2(1H)-carboxamide

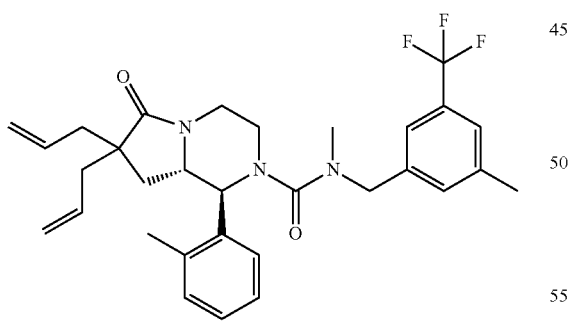

To a solution of triphosgene (47 mg, 0.16 mmol) in EtOAc (2 mL) at 0° C. was added solution of Intermediate 54 (100 mg, 0.32 mmol), DMAP (4 mg, 0.032 mmol) and TEA 49 mg, 0.48 mmol) in EtOAc (2 mL). The mixture was stirred for 1.5 h, followed by addition of N-methyl-1-(3-methyl-5-(trifluoromethyl)phenyl)methanamine (97 mg, 0.48 mmol) in EtOAc (2 mL) and TEA (49 mg, 0.48 mmol). The reaction was stirred at 50° C. for 48 h and quenched with water. The resulting mixture was extracted with EtOAc and the organic layer was washed with 1 M aqueous HCl solution, dried over anhydrous $Na_2SO_4$ and then concentrated in high vacuum. The residue was purified by silica gel chromatography (DCM/MeOH=20/1 to 10/1) to give the title compound (130 mg, yield: 74.3%) as yellow solid; m/z (ES+): 540 [M+H]+.

Intermediate 58

(1S,8aS)-7,7-diallyl-N-(3-methoxy-5-(trifluoromethyl)benzyl)-N-methyl-6-oxo-1-o-tolylhexahydropyrrolo[1,2-a]pyrazine-2(1H)-carboxamide

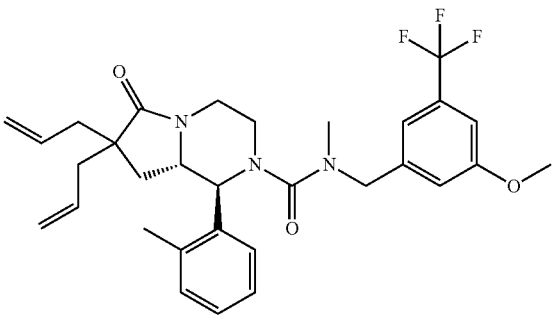 [SMILES: C=CCC1(CC=C)C[C@H]2[C@H](c3ccccc3C)N(C(=O)N(C)Cc3cc(OC)cc(C(F)(F)F)c3)CCN2C1=O]

To a solution of triphosgene (47 mg, 0.16 mmol) in EtOAc (2 mL) at 0° C. was added solution of Intermediate 54 (100 mg, 0.32 mmol), DMAP (4 mg, 0.032 mmol) and TEA (49 mg, 0.48 mmol) in EtOAc (2 mL). The mixture was stirred for 1.5 h, followed by addition of 1-(3-methoxy-5-(trifluoromethyl)phenyl)-N-methylmethanamine (105 mg, 0.48 mmol) in EtOAc (2 mL) and TEA (49 mg, 0.48 mmol). The reaction was stirred at 50° C. for 48 h and quenched with water. The resulting mixture was extracted with EtOAc and the organic layer was washed with 1 M aqueous HCl solution, dried over anhydrous $Na_2SO_4$ and then concentrated in high vacuum. The residue was purified by silica gel chromatography (DCM/MeOH=20/1 to 10/1) to give the title compound (130 mg, yield: 73%) as yellow solid; m/z (ES+): 556 [M+H]+.

Intermediate 59

(1S,8aS)-7,7-diallyl-N-(3-chloro-5-(trifluoromethyl) benzyl)-N-methyl-6-oxo-1-o-tolylhexahydropyrrolo [1,2-a]pyrazine-2(1H)-carboxamide

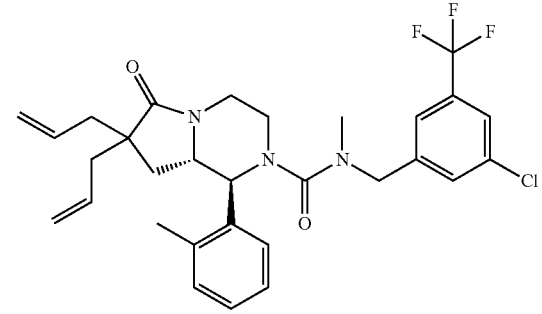 [SMILES: C=CCC1(CC=C)C[C@H]2[C@H](c3ccccc3C)N(C(=O)N(C)Cc3cc(Cl)cc(C(F)(F)F)c3)CCN2C1=O]

To a solution of triphosgene (47 mg, 0.16 mmol) in EtOAc (2 mL) at 0° C. was added solution of Intermediate 54 (100 mg, 0.32 mmol), DMAP (4 mg, 0.032 mmol) and TEA (49 mg, 0.48 mmol) in EtOAc (2 mL). The mixture was stirred for 1.5 h, followed by addition of 1-(3-chloro-5-(trifluoromethyl)phenyl)-N-methylmethanamine (107 mg, 0.48 mmol) in EtOAc (2 mL) and TEA (49 mg, 0.48 mmol). The reaction was stirred at 50° C. for 48 h and quenched with water. The resulting mixture was extracted with EtOAc and the organic layer was washed with 1 M aqueous HCl solution, dried over anhydrous Na₂SO₄ and then concentrated in high vacuum. The residue was purified by silica gel chromatography (DCM/MeOH=20/1 to 10/1) to give the title compound (123 mg, yield: 68%) as yellow solid; m/z (ES+): 560 [M+H]⁺.

Intermediate 60

(1S,8aS)-7,7-diallyl-N-methyl-6-oxo-1-o-tolyl-N-(3-(trifluoromethyl)benzyl)hexahydropyrrolo[1,2-a]pyrazine-2(1H)-carboxamide

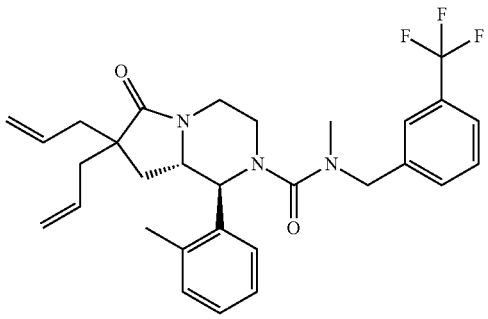 [SMILES: C=CCC1(CC=C)C[C@H]2[C@H](c3ccccc3C)N(C(=O)N(C)Cc3cccc(C(F)(F)F)c3)CCN2C1=O]

To a solution of triphosgene (47 mg, 0.16 mmol) in EtOAc (2 mL) at 0° C. was added solution of Intermediate 54 (100 mg, 0.32 mmol), DMAP (4 mg, 0.032 mmol) and TEA (49 mg, 0.48 mmol) in EtOAc (2 mL). The mixture was stirred for 1.5 h, followed by addition of N-methyl-1-(3-(trifluoromethyl)phenyl)methanamine (91 mg, 0.48 mmol) in EtOAc (2 mL) and TEA (49 mg, 0.48 mmol). The reaction was stirred at 50° C. for 48 h and quenched with water. The resulting mixture was extracted with EtOAc and the organic layer was washed with 1 M aqueous HCl solution, dried over anhydrous Na₂SO₄ and then concentrated in high vacuum. The residue was purified by silica gel chromatography (DCM/MeOH=20/1 to 10/1) to give the title compound (100 mg, yield: 59%) as yellow solid; m/z (ES+): 526 [M+H]⁺.

Intermediate 61

1-(3,5-bis(trifluoromethyl)phenyl)but-3-en-1-ol

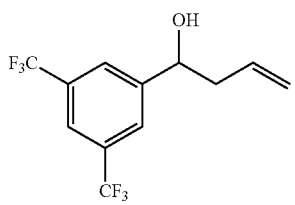

To a solution of 3,5-bis(trifluoromethyl)benzaldehyde (10 g, 41 mmol) in THF (100 mL) was drop wise added allylmagnesium bromide (50 mL, 1 M in THF, 50 mmol) at −40° C. The reaction mixture was stirred at room temperature for 5 h and then poured into saturated aqueous NH₄Cl solution and extracted with EtOAc (2×100 mL). The organic layers were dried over anhydrous Na₂SO₄ and then concentrated in high vacuum. The residue was purified by silica gel chromatography (PE/EtOAc=5/1 to 2/1) to give the title compound (800 mg, yield: 7%).

Intermediate 62

1-(3,5-bis(trifluoromethyl)phenyl)but-3-enyl methanesulfonate

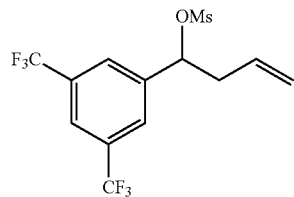 [SMILES: C=CCC(OS(C)(=O)=O)c1cc(C(F)(F)F)cc(C(F)(F)F)c1]

To a solution of Intermediate 61 (0.8 g, 2.8 mmol) and TEA (0.75 g, 7.4 mmol) in DCM (10 mL) was added MsCl (0.32 g, 2.8 mmol) at 0° C. The reaction mixture was stirred at room temperature for 3 h and poured into water and then extracted with EtOAc. The organic layer was dried over anhydrous Na₂SO₄ and then concentrated in high vacuum. The residue was purified by silica gel chromatography (PE/EA=10/1 to 3/1) to give the title compound (691 mg, yield: 68%).

Intermediate 63

1-(3,5-bis(trifluoromethyl)phenyl)-N-methylbut-3-en-1-amine

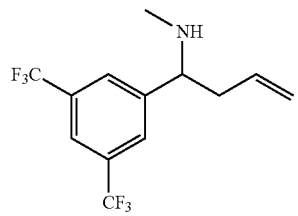 [SMILES: C=CCC(NC)c1cc(C(F)(F)F)cc(C(F)(F)F)c1]

To a solution of Intermediate 62 (691 mg, 1.9 mmol) in THF (10 mL) was added MeNH₂ (3 mL, 1 M in THF, 3 mmol) at 0° C. The reaction mixture was stirred at room temperature for 16 h and poured into water, and then extracted with EtOAc. The organic layer was dried over anhydrous Na₂SO₄ and then concentrated in high vacuum. The residue was purified by silica gel chromatography (DCM/MeOH=10/1) to give the title compound (575 mg, yield: 100%); m/z (ES+): 298 [M+H]⁺.

Intermediate 64 & 65

(1S,8aS)-7,7-diallyl-N-(1-(3,5-bis(trifluoromethyl)phenyl)but-3-enyl)-N-methyl-6-oxo-1-o-tolyl-hexahydropyrrolo[1,2-a]pyrazine-2(1H)-carboxamide

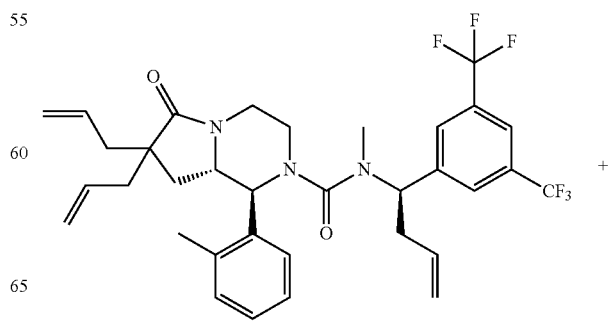

-continued

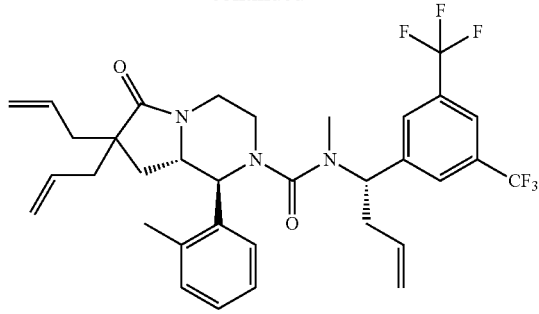

To a solution of triphosgene (47 mg, 0.16 mmol) in EtOAc (2 mL) at 0° C. was added solution of Intermediate 54 (100 mg, 0.32 mmol), DMAP (4 mg, 0.032 mmol) and TEA (49 mg, 0.48 mmol) in EtOAc (2 mL). The mixture was stirred for 1.5 h, followed by addition of Intermediate 63 (144 mg, 0.48 mmol) in EtOAc (2 mL) and TEA (49 mg, 0.48 mmol). The reaction was stirred at 50° C. for 48 h and quenched with water. The resulting mixture was extracted with EtOAc and the organic layer was washed with 1 M aqueous HCl solution, dried over anhydrous $Na_2SO_4$ and then concentrated in high vacuum. The residue was purified by Prep-TLC to give Intermediate 64 (30 mg, yield: 15%) and Intermediate 65 (30 mg, yield: 15%) as yellow solid; m/z (ES+): 634 $[M+H]^+$.

Intermediate 66

(1S,8aS)-7,7-diallyl-N-(1-(3,5-bis(trifluoromethyl)phenyl)but-3-enyl)-N-methyl-6-oxo-1-o-tolyl-hexahydropyrrolo[1,2-a]pyrazine-2(1H)-carboxamide

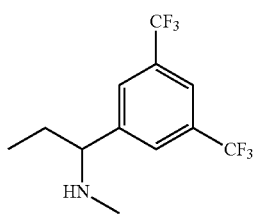 [SMILES: CCC(NC)c1cc(C(F)(F)F)cc(C(F)(F)F)c1]

A solution of 1-(3,5-bis(trifluoromethyl)phenyl)propan-1-one (2 g, 7.4 mmol) in $MeNH_2/MeOH$ (10 mL) under $N_2$ atmosphere was stirred for 16 h. The resulting mixture was concentrated in high vacuum. The residue was dissolved in EtOAc (20 mL), washed with brine (10 mL). The organic layer was dried over anhydrous $Na_2SO_4$ and concentrated. The residue was dissolved in THF (15 mL) followed by addition of $NaBH_4$ (400 mg, 10.6 mmol) at 0° C. The reaction mixture was allowed to warm to room temperature and stirred for 2 h. EtOAc (20 mL) was added and the organic layer was washed with brine, dried over anhydrous $Na_2SO_4$ and then concentrated in high vacuum. The residue was purified by silica gel chromatography (DCM/MeOH=20/1 to 10/1) to give Intermediate 66 (750 mg, yield: 49%) as yellow solid; m/z (ES+): 286 $[M+H]^+$.

Intermediate 67 & 68

(1S,8aS)-7,7-diallyl-N-(1-(3,5-bis(trifluoromethyl)phenyl)propyl)-N-methyl-6-oxo-1-o-tolylhexahydro-pyrrolo[1,2-a]pyrazine-2(1H)-carboxamide

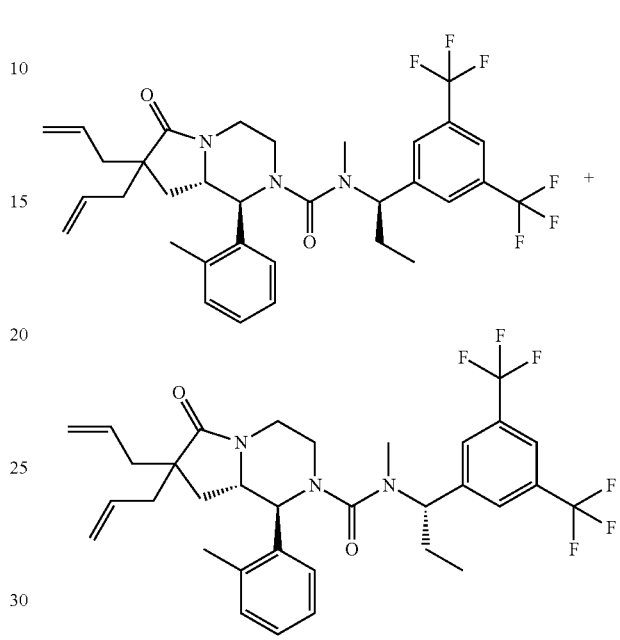

To a solution of triphosgene (47 mg, 0.16 mmol) in EtOAc (2 mL) at 0° C. was added solution of Intermediate 54 (100 mg, 0.32 mmol), DMAP (4 mg, 0.032 mmol) and TEA (49 mg, 0.48 mmol) in EtOAc (2 mL). The mixture was stirred for 1.5 h, followed by addition of Intermediate 66 (144 mg, 0.48 mmol) in EtOAc (2 mL) and TEA (49 mg, 0.48 mmol). The reaction was stirred at 50° C. for 48 h and quenched with water. The resulting mixture was extracted with EtOAc and the organic layer was washed with 1 M aqueous HCl solution, dried over anhydrous $Na_2SO_4$ and then concentrated in high vacuum. The residue was purified by Prep-TLC to give Intermediate 67 (50 mg, yield: 25%) and Intermediate 68 (50 mg, yield: 25%) as yellow solid; m/z (ES+): 622 $[M+H]^+$.

Intermediate 69

3-bromo-N-methoxy-N-methyl-5-(trifluoromethyl)benzamide

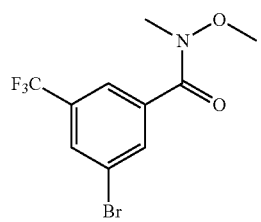 [SMILES: CON(C)C(=O)c1cc(Br)cc(C(F)(F)F)c1]

To a solution of 3-bromo-5-(trifluoromethyl)benzoic acid (50 g, 186 mmol) in DCM (500 mL) at 0° C., was added Oxalyl chloride (30.7 g, 242 mmol) with catalytical amount of DMF (0.5 mL). After stirring for 30 min the reaction mixture was concentrated. To a suspension of N,O-dimethylhydroxylamine hydrochloride (23.5 g, 242 mmol) in DCM (300 mL) at 0° C. was added TEA (51 g, 500 mol). Then a solution of acid chloride in DCM (300 mL) was added slowly. After stirring for 1 h, the reaction mixture was poured into water (200 mL) with vigorous stirring, extracted with DCM (2×200 mL). The organic layers were washed with brine (50 mL), dried over anhydrous MgSO$_4$ and then concentrated. The residue was purified by silica gel chromatography (PE/EtOAc=20/1 to 5/1) to give the title compound (47 g, yield: 81%); m/z (ES+): 312 [M+H]$^+$.

Intermediate 70

3-bromo-5-(trifluoromethyl)benzaldehyde

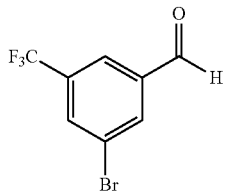

To a solution of Intermediate 69 (47 g, 150 mmol) in THF (400 mL), was added DIBAL-H (120 mL, 1.5 M in toluene, 180 mmol) at −40° C. The reaction was allowed to warm to room temperature slowly and stirred for 20 min. The reaction mixture was poured into water (200 mL) with vigorous stirring. The precipitate was filtered off and the filtrate was extracted with EtOAc (2×300 mL). The combined organic layers were washed with brine (50 mL), dried over anhydrous MgSO$_4$ and then concentrated. The crude was used directly without further purification.

Intermediate 71

(S)-N-(3-bromo-5-(trifluoromethyl)benzylidene)-2-methylpropane-2-sulfinamide

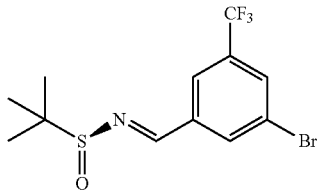 [SMILES: CC(C)(C)[S@](=O)/N=C/c1cc(Br)cc(C(F)(F)F)c1]

To a solution of Intermediate 70 (43 g, 169 mmol) in THF (400 mL) was added (S)-2-methylpropane-2-sulfinamide (22 g, 180 mmol) and Ti(O-iPr)$_4$ (62 g, 220 mmol) at 0° C. After stirring for 6 h at room temperature, the reaction mixture was poured into a suspension of kieselguhr in water (200 mL) with vigorous stirring. The precipitate was filtered off and the filtrate was extracted with EtOAc (2×300 mL). The combined organic layers were washed with brine (50 mL), dried by anhydrous MgSO$_4$ and then concentrated. The residue was purified by silica gel chromatography (PE/EtOAc=10/1 to 1/1) to give the title compound (40 g, yield: 66%); m/z (ES+): 356 [M+H]$^+$.

Intermediate 72 & 63

(S)-N-((R)-1-(3-bromo-5-(trifluoromethyl)phenyl)ethyl)-2-methylpropane-2-sulfinamide, (S)-N-((S)-1-(3-bromo-5-(trifluoromethyl)phenylmethyl)-2-methylpropane-2-sulfinamide

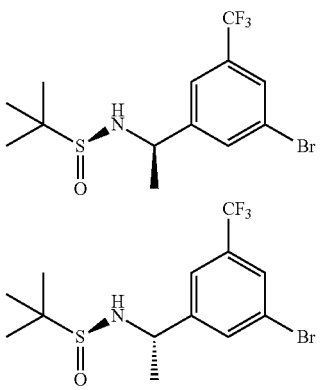

To a solution of Intermediate 70 (8 g, 22.5 mmol) in DCM (100 mL), was dropwise added methyl magnesium bromide (45 mL, 1M in THF, 45 mmol) at −40° C. After stirring for 2 h at room temperature, the reaction mixture was poured into saturated aqueous NH$_4$Cl solution and extracted with DCM (2×100 mL). The combined organic layers were washed with brine (2×100 mL), dried by anhydrous MgSO$_4$ and then concentrated. The residue was purified by silica gel chromatography (PE/EtOAc=10/1 to 1/1) to give the Intermediate 72 (R$_f$=0.30, PE/EtOAc=2/1) with (R)-Me (6.1 g, yield: 73%) and the Intermediate 73 (R$_f$=0.35, PE/EtOAc=2/1) with (S)-Me (1.2 g, yield: 14%). m/z (ES+); 372 [M+H]$^+$.

Intermediate 74

(S)-N-((R)-1-(3-bromo-5-(trifluoromethyl)phenyl)methyl)-N,2-dimethylpropane-2-sulfinamide

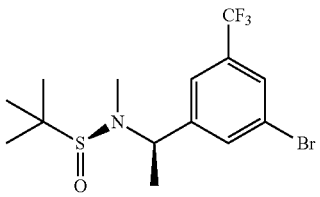 [SMILES: C[C@H](c1cc(Br)cc(C(F)(F)F)c1)N(C)[S@@](=O)C(C)(C)C]

To a solution of Intermediate 72 (6.1 g, 16.4 mmol) in THF (60 mL) under N$_2$ atmosphere was added LHMDS (32 mL, 1 M in THF, 32 mmol) at −60° C. The reaction was stirred for 15 min followed by addition of MeI (4.5 g, 32 mmol). The reaction mixture was then stirred at room temperature for another 1 h and quenched with water at 0° C. The resulting mixture was then extracted with EtOAc (2×100 mL). The combined organic layers were dried over anhydrous Na$_2$SO$_4$ and then concentrated in high vacuum. The residue was purified by silica gel chromatography (PE/EtOAc=10/1 to 1/1) to give the title compound (5.1 g, yield: 80%); m/z (ES+): 386 [M+H]$^+$.

Intermediate 75

(S)-N,2-dimethyl-N-((R)-1-(3-methyl-5-(trifluoromethyl)phenyl)ethyl)propane-2-sulfinamide

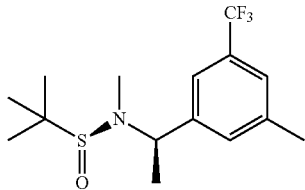 [SMILES: Cc1cc([C@@H](C)N(C)[S@@](=O)C(C)(C)C)cc(C(F)(F)F)c1]

A mixture of Intermediate 74 (1 g, 2.6 mmol), trimethylboroxine (328 mg, 2.6 mmol), Pd(PPh$_3$)$_4$ (300 mg, 0.26 mmol) and Cs$_2$CO$_3$ (1.7 g, 5.2 mmol) in DMF (12 mL) under N$_2$ atmosphere was microwaved at 110° C. for 75 min. The reaction was poured into water (15 mL) and then extracted with EtOAc (2×30 mL). The organic layers were dried over anhydrous Na$_2$SO$_4$ and then concentrated. The residue was purified by silica gel chromatography (PE/EtOAc=10/1 to 1/1) to give the title compound (591 mg, yield: 71%); m/z (ES+): 322 [M+H]$^+$.

Intermediate 76

(R)-N-methyl-1-(3-methyl-5-(trifluoromethyl)phenyl)ethanamine

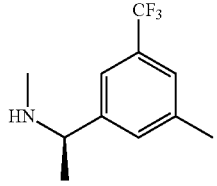

A solution of Intermediate 74 (500 mg, 1.6 mmol) in HCl/MeOH (10 mL) was stirred for 15 min under N$_2$ atmosphere. The reaction was neutralized with 1 M NaOH to pH=10-11 and then extracted with EtOAc (2×20 mL). The combined organic layers were dried over anhydrous Na$_2$SO$_4$ and then concentrated to give the title compound (300 mg, yield: 86%). m/z (ES+): 218 [M+H]$^+$.

Intermediate 77

(1S,8aS)-7,7-diallyl-N-methyl-N-((R)-1-(3-methyl-5-(trifluoromethyl)phenyl)ethyl)-6-oxo-1-o-tolyl-hexahydropyrrolo[1,2-a]pyrazine-2(1H)-carboxamide

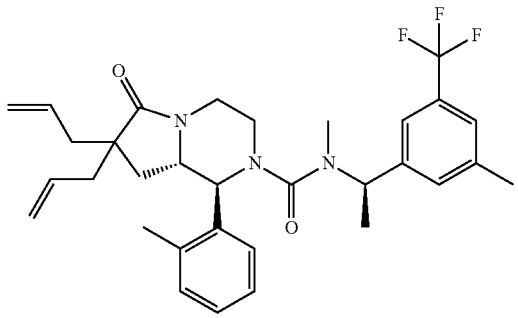 [SMILES: C=CCC1(CC=C)C[C@H]2[C@H](c3ccccc3C)N(C(=O)N(C)[C@H](C)c3cc(C)cc(C(F)(F)F)c3)CCN2C1=O]

To a solution of triphosgene (129 mg, 0.4 mmol) in EtOAc (5 mL) at 0° C. was added a solution of Intermediate 54 (300 mg, 1 mmol), DMAP (11 mg, 0.01 mmol) and TEA (293 mg, 2.9 mmol) in EtOAc (15 mL). The mixture was stirred for 1.5 h, followed by addition of (R)-N-methyl-1-(3-methyl-5-(trifluoromethyl)phenyl)ethanamine (273 mg, 1.26 mmol) in EtOAc (10 mL) and TEA (293 mg, 2.9 mmol). The reaction was stirred at 50° C. for 48 h and quenched with water. The resulting mixture was extracted with EtOAc (2×30 mL). The combined organic layers were washed with 1 M aqueous HCl solution and then dried over anhydrous Na$_2$SO$_4$ and then concentrated in high vacuum. The residue was purified by silica gel chromatography (DCM/MeOH=20/1 to 10/1) to give the title compound (209 mg, yield: 39%) as yellow solid; m/z (ES+): 554 [M+H]$^+$.

Intermediate 78

(S)-N-((S)-1-(3-bromo-5-(trifluoromethyl)phenyl)ethyl)-N,2-dimethylpropane-2-sulfinamide

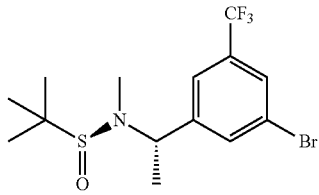 [SMILES: C[C@@H](c1cc(Br)cc(C(F)(F)F)c1)N(C)[S@@](=O)C(C)(C)C]

To a solution of Intermediate 73 (1.2 g, 3.2 mmol) in THF (60 mL) under N$_2$ atmosphere was added LHMDS (6.4 mL, 1 M in THF, 6.4 mmol) at −60° C. The reaction was stirred for 15 min and followed by addition of MeI (0.69 g, 4.8 mmol) then stirred at room temperature for another 1 h. The reaction was quenched with water at 0° C. and then extracted with EtOAc (2×100 mL). The combined organic layers were dried over anhydrous Na$_2$SO$_4$ and then concentrated in high vacuum. The residue was purified by silica gel chromatography (PE/EtOAc=10/1 to 1/1) to give the title compound (1.1 g, yield: 89%); m/z (ES+): 386 [M+H]$^+$.

Intermediate 79

(S)-N,2-dimethyl-N-((s)-1-(3-methyl-5-(trifluoromethyl)phenyl)ethyl)propane-2-sulfinamide

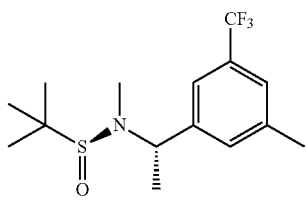 [SMILES: Cc1cc([C@H](C)N(C)[S@@](=O)C(C)(C)C)cc(C(F)(F)F)c1]

A mixture of Intermediate 78 (500 mg, 1.29 mmol), trimethyboroxine (328 mg, 2.6 mmol), Pd(PPh$_3$)$_4$ (142 mg, 0.129 mmol) and Cs$_2$CO$_3$ (844 mg, 2.59 mmol) in DMF (12 mL) under N$_2$ atmosphere was microwaved at 110° C. for 75 min. The reaction was poured into water (15 mL) and then extracted with EtOAc (2×30 mL). The combined organic layers were dried over anhydrous Na$_2$SO$_4$ and then concentrated. The residue was purified by silica gel chromatography (PE/EtOAc=10/1 to 1/1) to give the title compound (380 mg, yield: 91%); m/z (ES+): 322 [M+H]⁺.

Intermediate 80

(R)-N-methyl-1-(3-methyl-5-(trifluoromethyl)phenyl)ethanamine

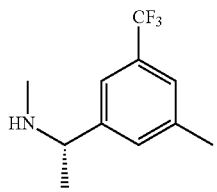

A solution of Intermediate 79 (380 mg, 1.18 mmol) in HCl/MeOH (10 mL) was stirred for 15 min under N₂ atmosphere. The reaction was neutralized with 1 M NaOH solution (15 mL) to pH=10-11 and then extracted with EtOAc (2×20 mL). The combined organic layers were dried by anhydrous Na₂SO₄ and concentrated to give the title compound (180 mg, yield: 70.3%); m/z (ES+): 218 [M+H]⁺.

Intermediate 81

(1S,8aS)-7,7-diallyl-N-methyl-N-((S)-1-(3-methyl-5-(trifluoromethyl)phenyl)ethyl)-6-oxo-1-o-tolyl-hexahydropyrrolo[1,2-a]pyrazine-2(1H)-carboxamide

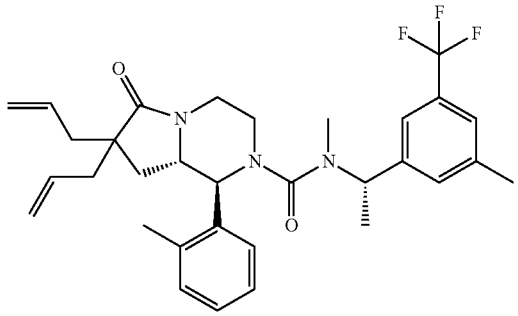 [SMILES: C=CCC1(CC=C)C[C@H]2[C@H](c3ccccc3C)N(C(=O)N(C)[C@@H](C)c3cc(C)cc(C(F)(F)F)c3)CCN2C1=O]

To a solution of triphosgene (47 mg, 0.16 mmol) in EtOAc (2 mL) at 0° C. was added a solution of Intermediate 54 (100 mg, 0.32 mmol), DMAP (4 mg, 0.032 mmol) and TEA (49 mg, 0.48 mmol) in EtOAc (2 mL). The mixture was stirred for 1.5 h, followed by addition of (R)-N-methyl-1-(3-methyl-5-(trifluoromethyl)phenyl)ethanamine (105 mg, 0.48 mmol) and TEA (97 mg, 0.963 mmol) in EtOAc (2 mL). The reaction was stirred for 48 h at 50° C. and quenched with water. The resulting mixture was extracted with EtOAc. The organic layer was washed with 1 M aqueous HCl solution, dried over anhydrous Na₂SO₄ and then concentrated in high vacuum. The residue was purified by silica gel chromatography (DCM/MeOH=20/1 to 10/1) to give the title compound (100 mg, yield: 56.3%) as yellow solid; m/z (ES+): 554 [M+H]⁺.

Intermediate 82

(S)-N-(3,5-bis(trifluoromethyl)benzylidene)-2-methylpropane-2-sulfinamide

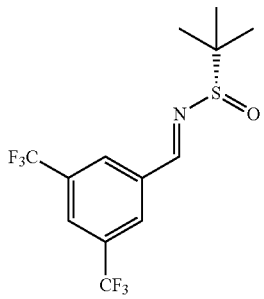 [SMILES: CC(C)(C)[S@](=O)/N=C/c1cc(C(F)(F)F)cc(C(F)(F)F)c1]

To a mixture of 3,5-bis(trifluoromethyl)benzaldehyde (5 g, 20.7 mmol) and (S)-2-methylpropane-2-sulfinamide (3 g, 24.8 mmol) in DCM (50 ml) at 0° C., was drop wise added Ti(O-iPr)₄ (5.9 g, 24.8 mmol) under N₂ atmosphere. After stirring for 20 h at room temperature, the reaction mixture was poured into water (100 mL) with vigorous stirring. The precipitate was filtered and the filtrate was extracted with DCM (2×150 mL). The combined organic layers were washed with brine (80 mL), dried over anhydrous MgSO₄, and then concentrated. The residue was purified by silica gel chromatography (PE/EtOAc=5/1 to 2/1) to give the title compound (6 g, yield: 84%); m/z (ES+): 346 [M+H]⁺.

Intermediate 83 & 84

(S)-N-((R)-1-(3,5-bis(trifluoromethyl)phenyl)allyl)-2-methylpropane-2-sulfinamide (S)-N-((S)-1-(3,5-bis(trifluoromethyl)phenyl)allyl)-2-methylpropane-2-sulfinamide

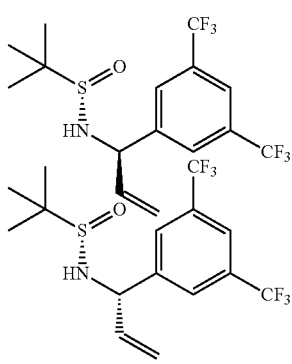

To a solution of Intermediate 82 (6 g, 17.4 mmol) in DCM (100 mL) was drop wise added vinylmagnesium bromide (21 mL, 1 M in THF, 21 mmol) at −60° C. The reaction mixture was stirred for 5 h at room temperature and poured into saturated aqueous NH₄Cl solution. The resulting mixture was extracted with DCM (2×100 mL). The combined organic layers were washed with brine (50 mL), dried over anhydrous MgSO₄, and then concentrated. The residue was purified by silica gel chromatography (PE/EtOAc=5/1 to 2/1) to give the (R)-Allyl-Intermediate 83 (2.6 g, yield: 40%) and (S)-Allyl-Intermediate 84 (1.4 g, yield: 21%); m/z (ES+): 374 [M+H]⁺.

Intermediate 85

(S)-N-((R)-1-(3,5-bis(trifluoromethyl)phenyl)allyl)-N,2-dimethylpropane-2-sulfinamide

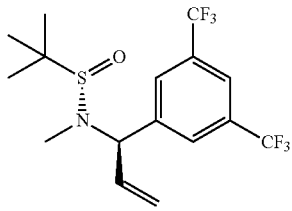 [SMILES: C=C[C@H](c1cc(C(F)(F)F)cc(C(F)(F)F)c1)N(C)[S@@](=O)C(C)(C)C]

To a solution of Intermediate 83 (2.6 g, 7 mmol) in THF (60 mL) under N₂ atmosphere was dropwise added LiHMDS (10.5 mL, 1 M in THF, 10.5 mmol) at −60° C. The reaction was stirred for 30 min at −60° C. followed by addition of MeI (1.5 g, 10.5 mmol). The reaction was then stirred for another 3 h at room temperature and quenched with water at 0° C. The resulting mixture was extracted with EtOAc (2×100 mL). The combined organic layers were dried over anhydrous Na₂SO₄ and then concentrated. The residue was purified by silica gel chromatography (PE/EtOAc=5/1 to 2/1) to give the title compound (900 mg, yield: 30%); m/z (ES+): 388 [M+H]⁺.

Intermediate 86

(R)-1-(3,5-bis(trifluoromethyl)phenyl)-N-methyl-prop-2-en-1-amine

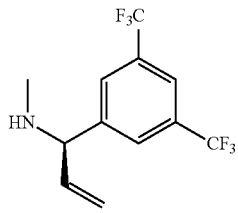 [SMILES: C=C[C@@H](NC)c1cc(C(F)(F)F)cc(C(F)(F)F)c1]

A solution of Intermediate 85 (900 mg, 2.3 mmol) in HCl/MeOH (10 mL) under N₂ atmosphere was stirred for 15 min. The reaction was neutralized with 1 M NaOH solution (15 mL) to pH=10-11 and then extracted with EtOAc (2×20 mL). The organic layer was dried over anhydrous Na₂SO₄ and concentrated to give the title compound (500 mg, yield: 76%); m/z (ES+): 284 [M+H]⁺.

Intermediate 87

(1S,8aS)-7,7-diallyl-N-((R)-1-(3,5-bis(trifluoromethyl)phenyl)allyl)-N-methyl-6-oxo-1-o-tolyl-hexahydropyrrolo[1,2-a]pyrazine-2(1H)-carboxamide

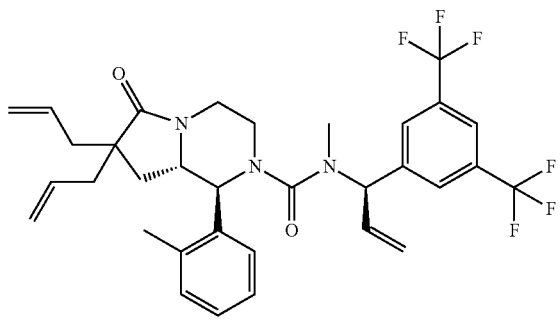 [SMILES: C=CCC1(CC=C)C[C@H]2[C@H](c3ccccc3C)N(C(=O)N(C)[C@H](C=C)c3cc(C(F)(F)F)cc(C(F)(F)F)c3)CCN2C1=O]

To a solution of triphosgene (95 mg, 0.33 mmol) in EtOAc (2 mL) at 0° C. was added solution of Intermediate 54 (200 mg, 0.65 mmol), DMAP (8 mg, 0.065 mmol) and TEA (200 mg, 1.95 mmol) in EtOAc (5 mL). The mixture was stirred for 1.5 h, followed by addition of (R)-1-(3,5-bis(trifluoromethyl)phenyl)-N-methylprop-2-en-1-amine (220 mg, 0.78 mmol) in EtOAc (5 mL) and TEA (200 mg, 1.95 mmol). The reaction was stirred at 50° C. for 48 h and quenched with water. The resulting mixture was extracted with EtOAc. The organic layer was washed with 1 M aqueous HCl solution, dried over anhydrous Na₂SO₄ and then concentrated in high vacuum. The residue was purified by silica gel chromatography (DCM/MeOH=20/1 to 10/1) to give the title compound (100 mg, yield: 25%) as yellow solid; m/z (ES+): 620 [M+H]⁺.

Intermediate 88

(S)-N-((S)-1-(3,5-bis(trifluoromethyl)phenyl)allyl)-N,2-dimethylpropane-2-sulfinamide

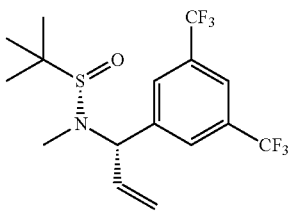 [SMILES: C=C[C@@H](c1cc(C(F)(F)F)cc(C(F)(F)F)c1)N(C)[S@@](=O)C(C)(C)C]

To a solution of Intermediate 84 (1.4 g, 3.8 mmol) in THF (20 mL) under N₂ atmosphere was dropwise added LiHMDS (4.5 mL, 1 M in THF, 4.5 mmol) at −60° C. The reaction was stirred for 30 min at −60° C. followed by addition of MeI (0.5 g, 7.5 mmol). The mixture was stirred at room temperature for another 3 h and quenched with water at 0° C. The resulting mixture was extracted with EtOAc (2×100 mL). The combined organic layers were dried over anhydrous Na₂SO₄ and then concentrated under reduced pressure. The residue was purified by silica gel chromatography (PE/EtOAc=5/1 to 2/1) to give the title compound (726 mg, yield: 50%); m/z (ES+): 388 [M+H]⁺.

Intermediate 89

(S)-1-(3,5-bis(trifluoromethyl)phenyl)-N-methyl-prop-2-en-1-amine

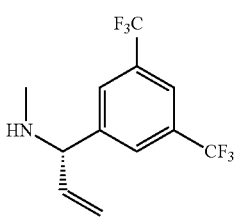 [SMILES: C=C[C@H](NC)c1cc(C(F)(F)F)cc(C(F)(F)F)c1]

A solution of Intermediate 88 (726 mg, 1.9 mmol) in HCl/MeOH (10 mL) was stirred for 15 min under N₂ atmosphere. The reaction was neutralized with 1 M NaOH solution (15 mL) to pH=10-11 and then extracted with EtOAc (2×20 mL). The combined organic phase was washed with brine (10 mL), dried by Na₂SO₄, and then concentrated to give the title compound (400 mg, yield: 74%); m/z (ES+): 284 [M+H]⁺.

Intermediate 90

(1S,8aS)-7,7-diallyl-N-((S)-1-(3,5-bis(trifluoromethyl)phenyl)allyl)-N-methyl-6-oxo-1-o-tolyl-hexahydropyrrolo[1,2-a]pyrazine-2(1H)-carboxamide

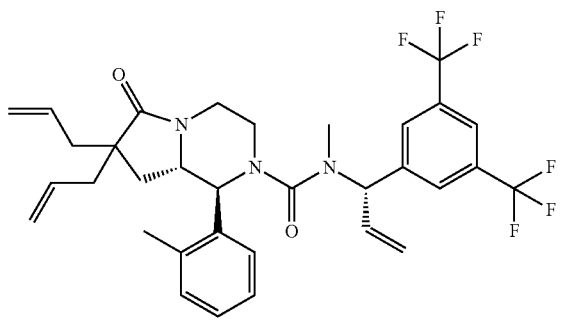 [SMILES: C=CCC1(CC=C)C[C@H]2[C@H](c3ccccc3C)N(C(=O)N(C)[C@@H](C=C)c3cc(C(F)(F)F)cc(C(F)(F)F)c3)CCN2C1=O]

To a solution of triphosgene (47 mg, 0.16 mmol) in EtOAc (2 mL) at 0° C. was added solution of Intermediate 54 (100 mg, 0.32 mmol), DMAP (4 mg, 0.032 mmol) and TEA (49 mg, 0.48 mmol) in EtOAc (2 mL). The mixture was stirred for 1.5 h, followed by addition of (S)-1-(3,5-bis(trifluoromethyl)phenyl)-N-methylprop-2-en-1-amine (136 mg, 0.48 mmol) in EtOAc (2 mL) and TEA (97 mg, 0.963 mmol). The reaction was stirred at 50° C. for 48 h and quenched with water. The resulting mixture was extracted with EtOAc and the organic layer was washed with 1 M aqueous HCl solution, dried over anhydrous Na$_2$SO$_4$ and then concentrated in high vacuum. The residue was purified by Prep-TLC to give the title compound (70 mg, yield: 34%) as yellow solid; m/z (ES+): 620 [M+H]$^+$.

Intermediate 81

(1S,8aS)-7,7-diallyl-N-methyl-6-oxo-1-o-tolyl-N-((R)-1-(3-(trifluoromethyl)phenyl)ethyl)hexahydropyrrolo[1,2-a]pyrazine-2(1H)-carboxamide

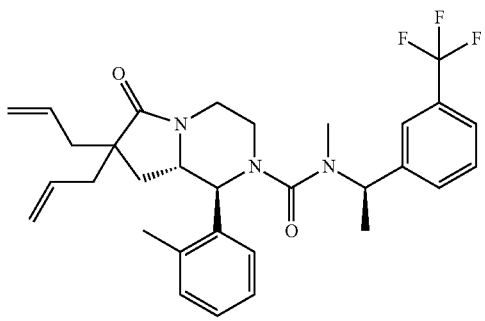 [SMILES: C=CCC1(CC=C)C[C@H]2[C@H](c3ccccc3C)N(C(=O)N(C)[C@H](C)c3cccc(C(F)(F)F)c3)CCN2C1=O]

To a solution of triphosgene (47 mg, 0.16 mmol) in EtOAc (2 mL) at 0° C. was added solution of Intermediate 54 (100 mg, 0.32 mmol), DMAP (4 mg, 0.032 mmol) and TEA (49 mg, 0.48 mmol) in EtOAc (2 mL). The mixture was stirred for 1.5 h, followed by addition of Methyl-[1-(3-trifluoromethyl-phenyl)-ethyl]-amine (100 mg, 0.49 mmol) in EtOAc (2 mL) and TEA (97 mg, 0.963 mmol). The reaction was stirred at 50° C. for 48 h and quenched with water. The resulting mixture was extracted with EtOAc and the organic layer was washed with 1 M aqueous HCl solution, dried over anhydrous Na$_2$SO$_4$ and then concentrated in high vacuum. The residue was purified by Prep-TLC to give the title compound (82 mg, yield: 41%) as yellow solid; m/z (ES+): 540 [M+H]$^+$.

Intermediate 92

(S)-N-((R)-1-(3-chloro-5-(trifluoromethyl)phenyl)ethyl)-N,2-dimethylpropane-2-sulfinamide

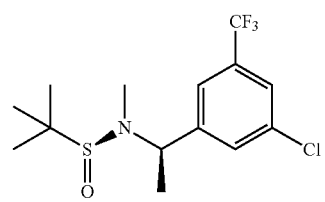 [SMILES: C[C@H](c1cc(Cl)cc(C(F)(F)F)c1)N(C)[S@@](=O)C(C)(C)C]

To a solution of (S)-N-((R)-1-(3-chloro-5-(trifluoromethyl)phenyl)ethyl)-2-methylpropane-2-sulfinamide (1.5 g, 4.6 mmol) in anhydrous THF (20 mL) under N$_2$ atmosphere was dropwise added LHMDS (9.2 mL, 1 M in THF, 9.2 mmol) at −60° C. The reaction was stirred for 30 min at −60° C., followed by addition of MeI (1.04 g, 6.9 mmol). The reaction was stirred at room temperature for another 3 h and quenched with water at 0° C. The resulting mixture was extracted with EtOAc (2×100 mL). The combined organic layers were dried over anhydrous Na$_2$SO$_4$ and then concentrated under reduced pressure. The residue was purified by silica gel chromatography (PE/EtOAc=5/1 to 2/1) to give the title compound (1.2 g, yield: 76.5%); m/z (ES+): 342 [M+H]$^+$.

Intermediate 93

(R)-1-(3-chloro-5-(trifluoromethyl)phenyl)-N-methylethanamine

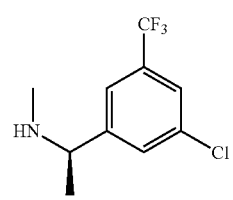

A solution of Intermediate 92 (1.2 g, 3.5 mmol) in HCl/MeOH (10 mL) under N$_2$ atmosphere was stirred for 15 min. The reaction was neutralized with 1 M NaOH solution (15 mL) to pH=10-11 and then extracted with EtOAc (2×50 mL). The combined organic phase was washed with brine (10 mL), dried by Na$_2$SO$_4$, and then concentrated to give the title compound (750 mg, yield: 90%); m/z (ES+): 238 [M+H]$^+$.

Intermediate 94

(1S,8aS)-7,7-diallyl-N-((S)-1-(3-chloro-5-(trifluoromethyl)phenyl)ethyl)-N-methyl-6-oxo-1-o-tolyl-hexahydropyrrolo[1,2-a]pyrazine-2(1H)-carboxamide

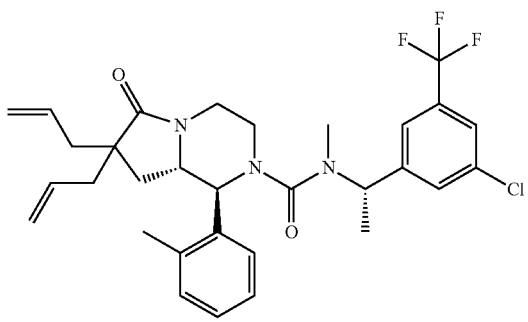 [SMILES: C=CCC1(CC=C)C[C@H]2[C@H](c3ccccc3C)N(C(=O)N(C)[C@@H](C)c3cc(Cl)cc(C(F)(F)F)c3)CCN2C1=O]

To a solution of triphosgene (47 mg, 0.16 mmol) in EtOAc (2 mL) at 0° C. was added solution of Intermediate 54 (100 mg, 0.32 mmol), DMAP (4 mg, 0.032 mmol) and TEA (49 mg, 0.48 mmol) in EtOAc (2 mL). The mixture was stirred for 1.5 h, followed by addition of (S)-1-(3-chloro-5-(trifluoromethyl)phenyl)-N-methylethanamine (114 mg, 0.48 mmol) in EtOAc (2 mL) and TEA (97 mg, 0.963 mmol). The reaction was stirred at 50° C. for 48 h and quenched with water. The resulting mixture was extracted with EtOAc and the organic layer was washed with 1 M aqueous HCl solution, dried over anhydrous Na$_2$SO$_4$ and then concentrated in high vacuum. The residue was purified by Prep-TLC to give the title compound (50 mg, yield: 27%) as yellow solid; m/z (ES+): 574 [M+H]$^+$.

Intermediate 95

(1S,8aS)-7,7-diallyl-N-((R)-1-(3-chloro-5-(trifluoromethyl)phenyl)ethyl)-N-methyl-6-oxo-1-o-tolyl-hexahydropyrrolo[1,2-a]pyrazine-2(1H)-carboxamide

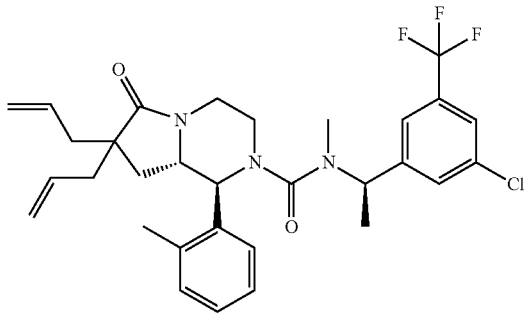 [SMILES: C=CCC1(CC=C)C[C@H]2[C@H](c3ccccc3C)N(C(=O)N(C)[C@H](C)c3cc(Cl)cc(C(F)(F)F)c3)CCN2C1=O]

To a solution of triphosgene (47 mg, 0.16 mmol) in EtOAc (2 mL) at 0° C. was added solution of Intermediate 54 (100 mg, 0.32 mmol), DMAP (4 mg, 0.032 mmol) and TEA (49 mg, 0.48 mmol) in EtOAc (2 mL). The mixture was stirred for 1.5 h, followed by addition of (R)-1-(3-chloro-5-(trifluoromethyl)phenyl)-N-methylethanamine (100 mg, 0.42 mmol) in EtOAc (2 mL) and TEA (97 mg, 0.963 mmol). The reaction was stirred at 50° C. for 48 h and quenched with water. The resulting mixture was extracted with EtOAc and the organic layer was washed with 1 M aqueous HCl solution, dried over anhydrous Na$_2$SO$_4$ and then concentrated in high vacuum. The residue was purified by Prep-TLC to give the title compound (65 mg, yield: 35%) as yellow solid; m/z (ES+): 574 [M+H]$^+$.

Intermediate 96

(S)-N,2-dimethyl-N-((R)-1-(3-(4,4,5,5-tetramethyl-1,3,2-dioxaborolan-2-yl)-5-(trifluoromethyl)phenyl)ethyl)propane-2-sulfinamide

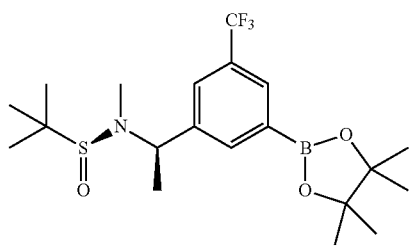 [SMILES: C[C@H](c1cc(B2OC(C)(C)C(C)(C)O2)cc(C(F)(F)F)c1)N(C)[S@@](=O)C(C)(C)C]

To a solution of Intermediate 74 (2.1 g, 5.4 mmol), Bis(pinacolato)diboron (1.5 g, 6 mmol), K$_2$CO$_3$ (1.38 g, 10 mmol) in 30 mL of THF/H$_2$O (5:1) under N$_2$ atmosphere was added Pd(dppf)Cl$_2$ (0.4 g, 0.5 mmol). The reaction was stirred for 5 h at 80° C. and quenched with water. The resulting was extracted with EtOAc (2×100 mL). The organic layers were dried over anhydrous Na$_2$SO$_4$ and then concentrated under reduced pressure. The residue was purified by silica gel chromatography (PE/EtOAc=5/1 to 2/1) to give the title compound (2 g, yield: 85%); m/z (ES+): 434 [M+H]$^+$.

Intermediate 97

(S)-N-((R)-1-(3-hydroxy-5-(trifluoromethyl)phenyl)ethyl)-N,2-dimethylpropane-2-sulfinamide

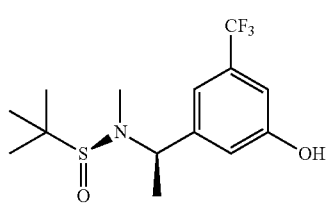 [SMILES: C[C@H](c1cc(O)cc(C(F)(F)F)c1)N(C)[S@@](=O)C(C)(C)C]

To a solution of Intermediate 96 (500 mg, 1.2 mmol) and NaOH (144 mg, 3.6 mmol) in THF (10 mL), was added H$_2$O$_2$ (122 mg, 3.6 mmol) at 0° C. The reaction mixture was allowed to warm to room temperature and stirred for 2 h. The reaction was quenched with water and the resulting mixture was extracted with EtOAc. The organic layer was washed with brine, dried over anhydrous Na$_2$SO$_4$ and then concentrated to give the title compound (500 mg, yield: 134%); m/z (ES+): 324 [M+H]$^+$.

Intermediate 98

(S)-N-((R)-1-(3-methoxy-5-(trifluoromethyl)phenyl)ethyl)-N,2-dimethylpropane-2-sulfinamide

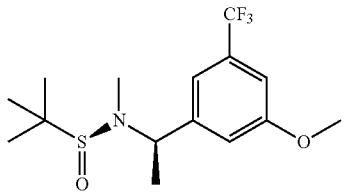 [SMILES: COc1cc([C@@H](C)N(C)[S@@](=O)C(C)(C)C)cc(C(F)(F)F)c1]

To a solution of Intermediate 97 (500 mg, 1.54 mmol) in anhydrous THF (10 mL) under $N_2$ atmosphere was added $K_2CO_3$ (414 mg, 2.98 mmol) and MeI (317 mg, 2.23 mmol). The reaction mixture was stirred for 2 h and quenched with water. The resulting mixture was extracted with EtOAc (2×20 mL). The combined organic layers were washed with brine, dried over anhydrous $Na_2SO_4$ and then concentrated to give the title compound (500 mg, yield: 96%); m/z (ES+): 338 $[M+H]^+$.

Intermediate 99

(R)-1-(3-methoxy-5-(trifluoromethyl)phenyl)-N-methylethanamine

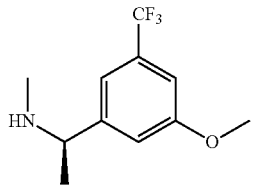 [SMILES: CN[C@H](C)c1cc(OC)cc(C(F)(F)F)c1]

A solution of Intermediate 98 (500 mg, 1.48 mmol) in HCl/MeOH (10 mL) under $N_2$ atmosphere was stirred for 15 min. The reaction was neutralized with 1 M NaOH solution to pH=10-11 and then extracted with EtOAc (2×50 mL). The combined organic layers were washed with brine (10 mL), dried by anhydrous $Na_2SO_4$, and then concentrated. The residue was purified by silica gel chromatography (DCM/MeOH=20/1 to 10/1) to give the title compound (300 mg, yield: 87%); m/z (ES+): 234 $[M+H]^+$.

Intermediate 100

(1S,8aS)-7,7-diallyl-N-((R)-1-(3-methoxy-5-(trifluoromethyl)phenyl)ethyl)-N-methyl-6-oxo-1-o-tolyl-hexahydropyrrolo[1,2-a]pyrazine-2(1H)-carboxamide

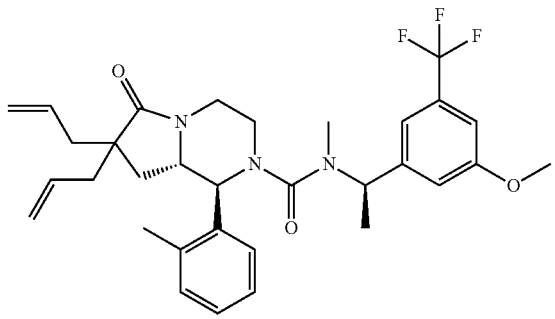

To a solution of triphosgene (129 mg, 0.4 mmol) in EtOAc (5 mL) at 0° C. was added solution of Intermediate 54 (300 mg, 1 mmol), DMAP (11 mg, 0.01 mmol) and TEA (293 mg, 2.9 mmol) in EtOAc (15 mL). The mixture was stirred for 1.5 h, followed by addition of (R)-1-(3-methoxy-5-(trifluoromethyl)phenyl)-N-methylethanamine (300 mg, 1.2 mmol) in EtOAc (10 mL) and TEA (293 mg, 2.9 mmol). The reaction was stirred at 50° C. for 48 h and quenched with water. The resulting mixture was extracted with EtOAc and the organic layer was washed with 1 M aqueous HCl solution, dried over anhydrous $Na_2SO_4$ and then concentrated in high vacuum. The residue was purified by silica gel chromatography (DCM/MeOH=20/1 to 10/1) to give the title compound (450 mg, yield: 66%) as yellow solid; m/z (ES+): 570 $[M+H]^+$.

Intermediate 101

(S)-N-((S)-1-(3-fluoro-5-(trifluoromethyl)phenyl)ethyl)-N,2-dimethylpropane-2-sulfinamide

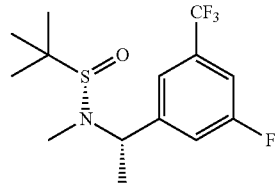 [SMILES: C[C@@H](c1cc(F)cc(C(F)(F)F)c1)N(C)[S@@](=O)C(C)(C)C]

To a solution of (S)-N-((S)-1-(3-fluoro-5-(trifluoromethyl)phenyl)ethyl)-2-methyl propane-2-sulfinamide (350 mg, 1.12 mmol) in THF (10 mL) under $N_2$ atmosphere, was dropwise added LHMDS (2.24 mL, 1 M in THF, 2.24 mmol) at −60° C. The reaction was stirred for 30 min at −60° C. followed by addition of MeI (240 mg, 1.69 mmol). The mixture was stirred at rt for another 3 h and quenched with water at 0° C. The resulting mixture was extracted with EtOAc (2×40 mL). The organic layers were dried over anhydrous $Na_2SO_4$ and then concentrated under reduced pressure. The residue was purified by silica gel chromatography (PE/EtOAc=5/1 to 2/1) to give the title compound (270 mg, yield: 74%); m/z (ES+): 326 $[M+H]^+$.

Intermediate 102

(S)-1-(3-fluoro-5-(trifluoromethyl)phenyl)-N-methylethanamine

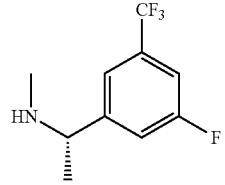

A solution of Intermediate 101 (270 mg, 0.83 mmol) in HCl/MeOH (10 mL) under $N_2$ atmosphere was stirred for 15 min. The reaction was neutralized with 1 M NaOH solution to pH=10-11 and then extracted with EtOAc (2×50 mL). The combined organic layers were washed with brine (10 mL), dried by anhydrous Na$_2$SO$_4$, and then concentrated to give the title compound (100 mg, yield: 54.5%); m/z (ES+): 222 [M+H]$^+$.

Intermediate 103

(1S,8aS)-7,7-diallyl-N-((S)-1-(3-fluoro-5-(trifluoromethyl)phenyl)ethyl)-N-methyl-6-oxo-1-o-tolyl-hexahydropyrrolo[1,2-a]pyrazine-2(1H)-carboxamide

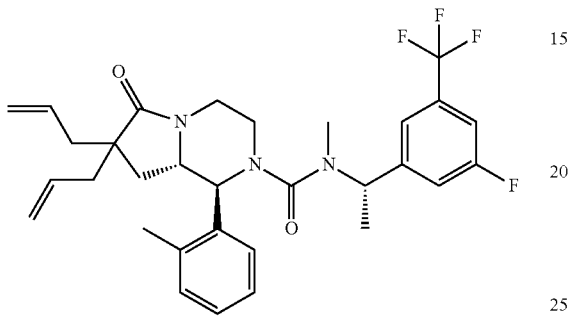

To a solution of triphosgene (47 mg, 0.16 mmol) in EtOAc (2 mL) at 0° C. was added solution of Intermediate 54 (100 mg, 0.32 mmol), DMAP (4 mg, 0.032 mmol) and TEA (49 mg, 0.48 mmol) in EtOAc (2 mL). The mixture was stirred for 1.5 h, followed by addition of (S)-1-(3-fluoro-5-(trifluoromethyl)phenyl)-N-methylethanamine (100 mg, 0.45 mmol) in EtOAc (2 mL) and TEA (97 mg, 0.963 mmol). The reaction was stirred at 50° C. for 48 h and quenched with water. The resulting mixture was extracted with EtOAc and the organic layer was washed with 1 M aqueous HCl solution, dried over anhydrous Na$_2$SO$_4$ and then concentrated in high vacuum. The residue was purified by Prep-TLC to give the title compound (70 mg, yield: 28%) as yellow solid; m/z (ES+): 558 [M+H]$^+$.

Intermediate 104

(1S,8aS)-7,7-diallyl-N-((R)-1-(3-fluoro-5-(trifluoromethyl)phenyl)ethyl)-N-methyl-6-oxo-1-o-tolyl-hexahydropyrrolo[1,2-a]pyrazine-2(1H)-carboxamide

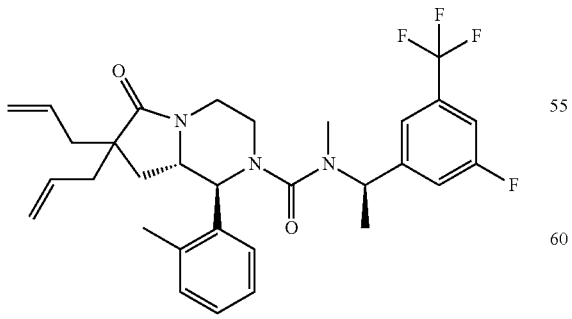

To a solution of triphosgene (47 mg, 0.16 mmol) in EtOAc (2 mL) at 0° C. was added solution of Intermediate 54 (100 mg, 0.32 mmol), DMAP (4 mg, 0.032 mmol) and TEA (49 mg, 0.48 mmol) in EtOAc (2 mL). The mixture was stirred for 1.5 h, followed by addition of (R)-1-(3-fluoro-5-(trifluoromethyl)phenyl)-N-methylethanamine (100 mg, 0.45 mmol) in EtOAc (2 mL) and TEA (97 mg, 0.963 mmol). The reaction was stirred at 50° C. for 48 h and quenched with water. The resulting mixture was extracted with EtOAc and the organic layer was washed with 1 M aqueous HCl solution, dried over anhydrous Na$_2$SO$_4$ and then concentrated in high vacuum. The residue was purified by Prep-TLC to give the title compound (71 mg, yield: 29%) as yellow solid; m/z (ES+): 558 [M+H]$^+$.

Intermediate 105

(1S,8aS)-7,7-diallyl-N-((R)-1-(3-fluoro-5-(trifluoromethyl)phenyl)allyl)-N-methyl-6-oxo-1-o-tolyl-hexahydropyrrolo[1,2-a]pyrazine-2(1H)-carboxamide

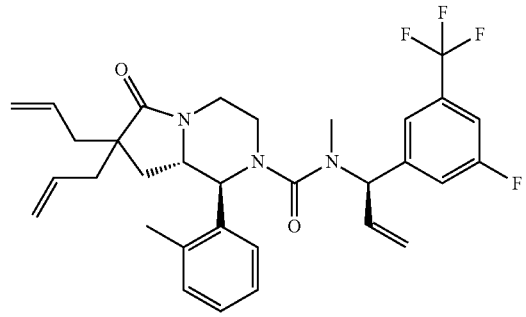 [SMILES: C=CCC1(CC=C)C[C@H]2[C@H](c3ccccc3C)N(C(=O)N(C)[C@H](C=C)c3cc(F)cc(C(F)(F)F)c3)CCN2C1=O]

To a solution of triphosgene (47 mg, 0.16 mmol) in EtOAc (2 mL) at 0° C. was added solution of Intermediate 54 (100 mg, 0.32 mmol), DMAP (4 mg, 0.032 mmol) and TEA (49 mg, 0.48 mmol) in EtOAc (2 mL). The mixture was stirred for 1.5 h, followed by addition of (R)-1-(3-fluoro-5-(trifluoromethyl)phenyl)-N-methylprop-2-en-1-amine (100 mg, 0.43 mmol) in EtOAc (2 mL) and TEA (97 mg, 0.96 mmol). The reaction was stirred at 50° C. for 48 h and quenched with water. The resulting mixture was extracted with EtOAc and the organic layer was washed with 1 M aqueous HCl solution, dried over anhydrous Na$_2$SO$_4$ and then concentrated in high vacuum. The residue was purified by Prep-TLC to give the title compound (84 mg, yield: 42%) as yellow solid; m/z (ES+): 570 [M+H]$^+$.

Intermediate 106

(S)-N-((R)-1-(3-hydroxy-5-(trifluoromethyl)phenyl)allyl)-N,2-dimethylpropane-2-sulfinamide

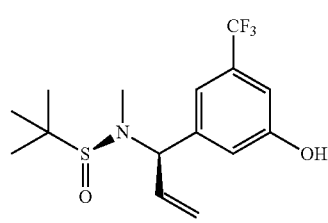 [SMILES: C=C[C@H](c1cc(O)cc(C(F)(F)F)c1)N(C)[S@@](=O)C(C)(C)C]

To a solution of (S)-N,2-dimethyl-N-((R)-1-(3-(4,4,5,5-tetramethyl-1,3,2-dioxaborolan-2-yl)-5-(trifluoromethyl)phenyl)allyl)propane-2-sulfinamide (800 mg, 1.8 mmol) and NaOH (144 mg, 3.6 mmol) in THF (10 mL), was added H$_2$O$_2$ (122 mg, 3.6 mmol) at 0° C. The reaction mixture was allowed to warm to room temperature and stirred for 2 h. After quenched with water, the resulting mixture was extracted with EtOAc. The organic layer was washed with brine, dried over anhydrous Na$_2$SO$_4$. and then concentrated to give the title compound (500 mg, yield: 83%); m/z (ES+): 336 [M+H]$^+$.

Intermediate 107

(S)-N-((R)-1-(3-methoxy-5-(trifluoromethyl)phenyl)allyl)-N,2-dimethylpropane-2-sulfinamide

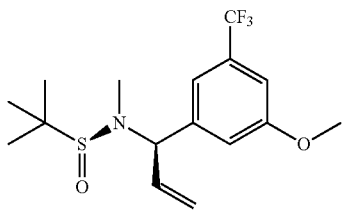 [SMILES: C=C[C@H](c1cc(OC)cc(C(F)(F)F)c1)N(C)[S@@](=O)C(C)(C)C]

To a solution of Intermediate 106 (500 mg, 1.49 mmol) in anhydrous THF (10 mL) under N$_2$ atmosphere was added K$_2$CO$_3$ (414 mg, 2.98 mmol) and MeI (317 mg, 2.23 mmol). The reaction mixture was stirred for 2 h and then quenched with water. The resulting mixture was extracted with EtOAc. The organic layer was washed with brine, dried over anhydrous Na$_2$SO$_4$ and concentrated to give the title compound (400 mg, yield: 76.9%); m/z (ES+): 350 [M+H]$^+$.

Intermediate 108

(R)-1-(3-methoxy-5-(trifluoromethyl)phenyl)-N-methylprop-2-en-1-amine

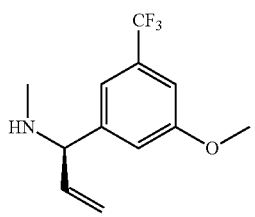 [SMILES: C=C[C@@H](NC)c1cc(OC)cc(C(F)(F)F)c1]

A solution of Intermediate 107 (400 mg, 1.15 mmol) in HCl/MeOH (10 mL) under N$_2$ atmosphere was stirred for 15 min. The reaction was neutralized with 1 M NaOH solution to pH=10-11 and then extracted with EtOAc (2×50 mL). The combined organic layers were washed with brine (10 mL), dried by Na$_2$SO$_4$, and then concentrated. The residue was purified by silica gel chromatography (DCM/MeOH=20/1 to 10/1) to give the title compound (200 mg, yield: 71%); m/z (ES+): 246 [M+H]$^+$.

Intermediate 109

(1S,8aS)-7,7-diallyl-N-((R)-1-(3-methoxy-5-(trifluoromethyl)phenyl)allyl)-N-methyl-6-oxo-1-o-tolyl-hexahydropyrrolo[1,2-a]pyrazine-2(1H)-carboxamide

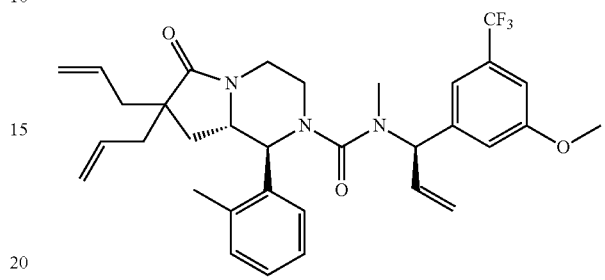

To a solution of triphosgene (47 mg, 0.16 mmol) in EtOAc (2 mL) at 0° C. was added solution of Intermediate 54 (100 mg, 0.32 mmol), DMAP (4 mg, 0.032 mmol) and TEA (49 mg, 0.48 mmol) in EtOAc (2 mL). The mixture was stirred for 1.5 h, followed by addition of (R)-1-(3-methoxy-5-(trifluoromethyl)phenyl)-N-methylprop-2-en-1-amine (104 mg, 0.48 mmol) in EtOAc (2 mL) and TEA (97 mg, 0.963 mmol). The reaction was stirred at 50° C. for 48 h and quenched with water. The resulting mixture was extracted with EtOAc and the organic layer was washed with 1 M aqueous HCl solution, dried over anhydrous Na$_2$SO$_4$ and then concentrated in high vacuum. The residue was purified by Prep-TLC to give the title compound (60 mg, yield: 32.1%) as yellow solid; m/z (ES+): 582 [M+H]$^+$.

Intermediate 110

(S)-2-methyl-N-(3-(trifluoromethyl)benzylidene)propane-2-sulfinamide

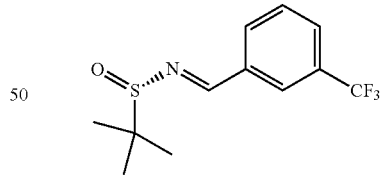

To a mixture of 3-(trifluoromethyl)benzaldehyde (5 g, 28.7 mmol) and (S)-2-methylpropane-2-sulfinamide (4.17 g, 34.4 mmol) in DCM (50 ml) at 0° C., was drop wise added Ti(O-iPr)$_4$ (12 g, 43 mmol) under N$_2$ atmosphere. After stirring for 20 h at room temperature, the reaction mixture was poured into water (100 mL) with vigorous stirring. The precipitate was filtered off and the filtrate was extracted with DCM (2×150 mL). The combined organic layers were washed with brine (100 mL), dried over anhydrous MgSO$_4$, and then concentrated. The residue was purified by silica gel chromatography (PE/EtOAc=5/1 to 2/1) to give the title compound (7 g, yield: 88%); m/z (ES+): 278 [M+H]$^+$.

Intermediate 111

(S)-2-methyl-N-((R)-1-(3-(trifluoromethyl)phenyl)allyl)propane-2-sulfinamide

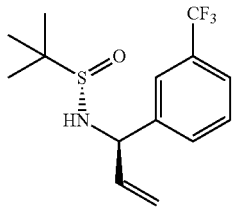 [SMILES: C=C[C@@H](N[S@@](=O)C(C)(C)C)c1cccc(C(F)(F)F)c1]

To a solution of Intermediate 110 (7 g, 25.2 mmol) in DCM (70 mL) was drop wise added vinylmagnesium bromide (50.4 mL, 1M in THF, 50.4 mmol) at −60° C. The reaction mixture was stirred at room temperature for 5 h and then poured into saturated aqueous NH$_4$Cl solution. The resulting mixture was extracted with DCM (2×100 mL). The combined organic layers were washed with brine (50 mL), dried over anhydrous MgSO$_4$, and then concentrated. The residue was purified by silica gel chromatography (PE/EtOAc=5/1 to 2/1) to give the title compound (1.7 g, yield: 22%); m/z (ES+): 306 [M+H]$^+$.

Intermediate 112

(S)-N,2-dimethyl-N-((R)-1-(3-(trifluoromethyl)phenyl)allyl)propane-2-sulfinamide

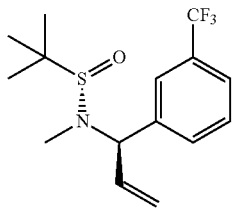 [SMILES: C=C[C@H](c1cccc(C(F)(F)F)c1)N(C)[S@@](=O)C(C)(C)C]

To a solution of Intermediate 111 (1.7 g, 5.6 mmol) in THF (20 mL) under N$_2$ atmosphere was added LiHMDS (11.2 mL, 1 M in THF, 11.2 mmol) dropwisely at −60° C. The reaction was stirred for 30 min at −60° C. followed by addition of MeI (1.5 g, 10.5 mmol). After stirring for another 3 h at room temperature, the reaction was quenched with water at 0° C. and then extracted with EtOAc (2×100 mL). The organic layers were dried over anhydrous Na$_2$SO$_4$ and then concentrated under reduced pressure. The residue was purified by silica gel chromatography (PE/EtOAc=5/1 to 2/1) to give the title compound (1.5 g, yield: 84%); m/z (ES+): 320 [M+H]$^+$.

Intermediate 113

(R)-1-(3,5-bis(trifluoromethyl)phenyl)-N-methyl-prop-2-en-1-amine

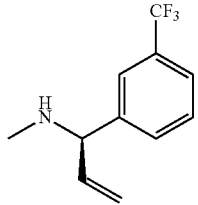

A solution of Intermediate 112 (1.5 g, 4.7 mmol) in HCl/MeOH (10 mL) under N$_2$ atmosphere was stirred for 15 min. The reaction was neutralized with 1 M NaOH solution to pH=10-11 and then extracted with EtOAc (2×50 mL). The combined organic layers were washed with brine (10 mL), dried by Na$_2$SO$_4$, and then concentrated to give the title compound (500 mg, yield: 49%); m/z (ES+): 216 [M+H]$^+$.

Intermediate 114

(1S,8aS)-7,7-diallyl-N-methyl-6-oxo-1-o-tolyl-N-((R)-1-(3-(trifluoromethyl)phenyl)allyl)hexahydro-pyrrolo[1,2-a]pyrazine-2(1H)-carboxamide

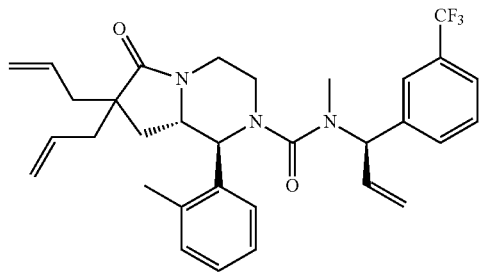 [SMILES: C=CCC1(CC=C)C[C@H]2[C@H](c3ccccc3C)N(C(=O)N(C)[C@H](C=C)c3cccc(C(F)(F)F)c3)CCN2C1=O]

To a solution of triphosgene (47 mg, 0.16 mmol) in EtOAc (2 mL) at 0° C. was added solution of Intermediate 54 (100 mg, 0.32 mmol), DMAP (4 mg, 0.032 mmol) and TEA (49 mg, 0.48 mmol) in EtOAc (2 mL). The mixture was stirred for 1.5 h, followed by addition of (R)-1-(3,5-bis(trifluoromethyl)phenyl)-N-methylprop-2-en-1-amine (104 mg, 0.48 mmol) in EtOAc (2 mL) and TEA (97 mg, 0.963 mmol). The reaction was stirred at 50° C. for 48 h and quenched with water. The resulting mixture was extracted with EtOAc. The organic layer was washed with 1 M aqueous HCl solution, dried over anhydrous Na$_2$SO$_4$ and then concentrated in high vacuum. The residue was purified by Prep-TLC to give the title compound (50 mg, yield: 28%) as yellow solid; m/z (ES+): 552 [M+H]$^+$.

Intermediate 115

(S)-N,2-dimethyl-N-((R)-1-(3-methyl-5-(trifluoromethyl)phenyl)allyl)propane-2-sulfinamide

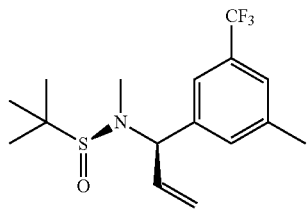 [SMILES: C=C[C@H](c1cc(C)cc(C(F)(F)F)c1)N(C)[S@@](=O)C(C)(C)C]

To a solution of (S)-2-methyl-N-((R)-1-(3-methyl-5-(trifluoromethyl)phenyl)allyl) propane-2-sulfinamide (400 mg, 1.25 mmol) in THF (10 mL) under N$_2$ atmosphere was dropwise added LiHMDS (1.9 ml, 1 M in THF, 1.9 mmol) at −60° C. The reaction was stirred for 30 min at −60° C. followed by addition of MeI (712 mg, 32 mmol). After stirring for another 3 h at room temperature, the reaction was quenched with water at 0° C. and then extracted with EtOAc (2×100 mL). The combined organic layers were dried over anhydrous Na$_2$SO$_4$ and then concentrated under reduced pressure. The residue was purified by silica gel chromatography (PE/

EtOAc=5/1 to 2/1) to give the title compound (300 mg, yield: 75%); m/z (ES+): 334 [M+H]+.

Intermediate 116

(R)-N-methyl-1-(3-methyl-5-(trifluoromethyl)phenyl)prop-2-en-1-amine

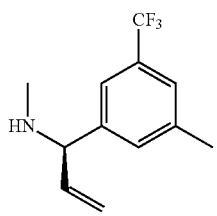 [SMILES: C=C[C@@H](NC)c1cc(C)cc(C(F)(F)F)c1]

A solution of Intermediate 115 (300 mg, 0.9 mmol) in HCl/MeOH (10 mL) under $N_2$ atmosphere was stirred for 15 min. The reaction was neutralized with 1 M NaOH solution to pH=10-11 and then extracted with EtOAc (2×30 mL). The combined organic layers were washed with brine (10 mL), dried by $Na_2SO_4$ and then concentrated to give the title compound (176 mg, yield: 85%); m/z (ES+): 230 [M+H]+.

Intermediate 117

(1S,8aS)-7,7-diallyl-N-methyl-N-((R)-1-(3-methyl-5-(trifluoromethyl)phenyl)allyl)-6-oxo-1-o-tolyl-hexahydropyrrolo[1,2-a]pyrazine-2(1H)-carboxamide

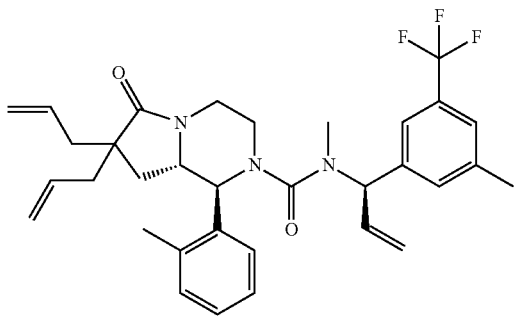 [SMILES: C=CCC1(CC=C)C[C@H]2[C@H](c3ccccc3C)N(C(=O)N(C)[C@H](C=C)c3cc(C)cc(C(F)(F)F)c3)CCN2C1=O]

To a solution of triphosgene (47 mg, 0.16 mmol) in EtOAc (2 mL) at 0° C. was added solution of Intermediate 54 (100 mg, 0.32 mmol), DMAP (4 mg, 0.032 mmol) and TEA (49 mg, 0.48 mmol) in EtOAc (2 mL). The mixture was stirred for 1.5 h, followed by addition of (R)-N-methyl-1-(3-methyl-5-(trifluoromethyl)phenyl)prop-2-en-1-amine (100 mg, 0.44 mmol) in EtOAc (2 mL) and TEA (97 mg, 0.963 mmol). The reaction was stirred at 50° C. for 48 h and quenched with water. The resulting mixture was extracted with EtOAc. The organic layer was washed with 1M aqueous HCl solution, dried over anhydrous $Na_2SO_4$ and then concentrated in high vacuum. The residue was purified by silica gel chromatography (DCM/MeOH=20/1 to 10/1) to give the title compound (74 mg, yield: 37%) as yellow solid; m/z (ES+): 566 [M+H]+.

Intermediate 118

1-bromo-3-(difluoromethyl)-5-(trifluoromethyl)benzene

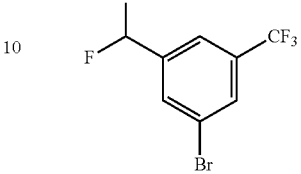

To a solution of 3-bromo-5-(trifluoromethyl)benzaldehyde (5.4 g, 21 mmol) in DCM (50 mL) at 0° C. was added DAST (4.8 g, 30 mmol). The mixture was stirred for 1.5 h and quenched with saturated aq. $NaHCO_3$ solution. The resulting mixture was extracted with DCM (2×50 mL) and dried over anhydrous $Na_2SO_4$ and then concentrated in high vacuum. The residue was purified by silica gel chromatography (PE/EtOAc=20/1 to 5/1) to give the title compound (1.3 g, yield: 22%).

Intermediate 119

1-(difluoromethyl)-3-(trifluoromethyl)-5-vinylbenzene

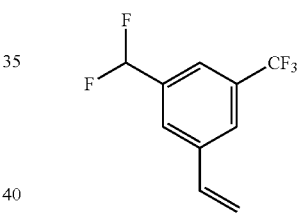

A mixture of Intermediate 118 (1.3 g, 4.7 mmol), tributyl(vinyl)tin (1.9 mg, 5.2 mmol) and Pd(dppf)Cl$_2$ (342 mg, 0.47 mmol) in dioxane (15 mL) was stirred under $N_2$ atmosphere at 110° C. for 75 min. The reaction was concentrated in high vacuum. The residue was purified by silica gel chromatography (PE/EtOAc=20/1 to 5/1) to give the title compound (800 mg, yield: 80%).

Intermediate 120

3-(difluoromethyl)-5-(trifluoromethyl)benzaldehyde

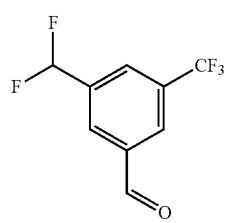

A slow stream of $O_3$ in $O_2$ was passed through a cooled solution of Intermediate 119 (800 mg, 3.6 mmol) in DCM (30 mL) at −78° C. until a pale blue colour persisted. The reaction was purged with N₂ to remove the excess of O₃ followed by addition of PPh₃ (1 g, 3.8 mmol). The reaction mixture was allowed to warm to room temperature and stirred for 20 h. After quenched with water, the mixture was extracted with DCM (2×30 mL). The organic layer was washed with brine (2×10 mL), dried over anhydrous Na₂SO₄ and then concentrated in vacuum. The residue was purified by silica gel chromatography (PE/EtOAc=20/1 to 5/1) to give the title compound (800 mg, yield: 98%).

Intermediate 121

3-(difluoromethyl)-5-(trifluoromethyl)benzaldehyde

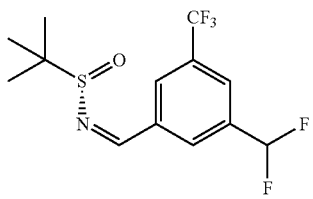 [SMILES: CC(C)(C)[S@](=O)/N=C\c1cc(C(F)F)cc(C(F)(F)F)c1]

To a mixture of Intermediate 120 (800 mg, 3.6 mmol) and (S)-2-methylpropane-2-sulfinamide (480 mg, 4 mmol) in DCM (20 ml) at 0° C., was drop wise added Ti(O-iPr)₄ (1.7 g, 6 mmol) under N₂ atmosphere. After stirring for 20 h at room temperature, the reaction mixture was poured into water (100 mL) with vigorous stirring. The precipitate was filtered off and the filtrate was extracted with DCM (2×50 mL). The combined organic layers were washed with brine (30 mL), dried over anhydrous MgSO₄, and then concentrated. The residue was purified by silica gel chromatography (PE/EtOAc=5/1 to 2/1) to give the title compound (800 mg, yield: 66%); m/z (ES+): 328 [M+H]⁺.

Intermediate 122

(S)-N-((R)-1-(3-(difluoromethyl)-5-(trifluoromethyl)phenyl)ethyl)-2-methylpropane-2-sulfinamide

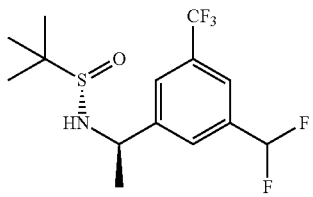 [SMILES: C[C@@H](N[S@@](=O)C(C)(C)C)c1cc(C(F)F)cc(C(F)(F)F)c1]

To a solution of Intermediate 121 (800 mg, 2.4 mmol) in DCM (20 mL) was drop wise added methyl magnesium bromide (3.5 mL, 1 M in THF, 3.5 mmol) at −60° C. The reaction mixture was stirred at room temperature for 5 h and then poured into saturated aqueous NH₄Cl solution. The resulting mixture was extracted with DCM (2×100 mL). The combined organic layers were washed with brine (50 mL), dried over anhydrous MgSO₄, and then concentrated. The residue was purified by silica gel chromatography (PE/EtOAc=5/1 to 2/1) to give the title compound (600 mg, yield: 71%); m/z (ES+): 344 [M+H]⁺.

Intermediate 123

(S)-N-((R)-1-(3-(difluoromethyl)-5-(trifluoromethyl)phenyl)ethyl)-N,2-dimethylpropane-2-sulfinamide

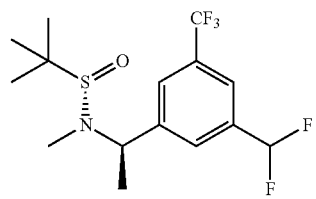 [SMILES: C[C@H](c1cc(C(F)F)cc(C(F)(F)F)c1)N(C)[S@@](=O)C(C)(C)C]

To a solution of Intermediate 122 (850 mg, 2.5 mmol) in THF (20 mL) under N₂ atmosphere was dropwise added LHMDS (5 mL, 1 M in THF, 5 mmol) at −60° C. The reaction was stirred for 30 min at −60° C. followed by addition of MeI (0.62 ml, 9.9 mmol). After stirring for another 3 h at room temperature, the reaction was quenched with water at 0° C. and then extracted with EtOAc (2×50 mL). The combined organic layers were dried over anhydrous Na₂SO₄ and then concentrated under reduced pressure. The residue was purified by silica gel chromatography (PE/EtOAc=5/1 to 2/1) to give the title compound (620 mg, yield: 73%); m/z (ES+): 358 [M+H]⁺.

Intermediate 124

(R)-1-(3-(difluoromethyl)-5-(trifluoromethyl)phenyl)-N-methylethanamine

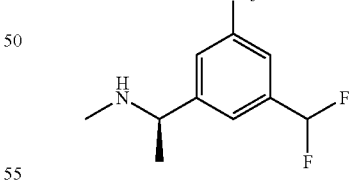

A solution of Intermediate 123 (620 mg, 1.7 mmol) in HCl/MeOH (10 mL) under N₂ atmosphere was stirred for 15 min. The reaction was neutralized with 1 M NaOH solution to pH=10-11 and then extracted with EtOAc (2×50 mL). The combined organic layers were washed with brine (10 mL), dried over anhydrous Na₂SO₄, and then concentrated to give the title compound (340 mg, yield: 76° A)); m/z (ES+): 254 [M+H]⁺.

Intermediate 125

(1S,8aS)-7,7-diallyl-N-((R)-1-(3-(difluoromethyl)-5-(trifluoromethyl)phenyl)ethyl)-N-methyl-6-oxo-1-o-tolylhexahydropyrrolo[1,2-a]pyrazine-2(1H)-carboxamide

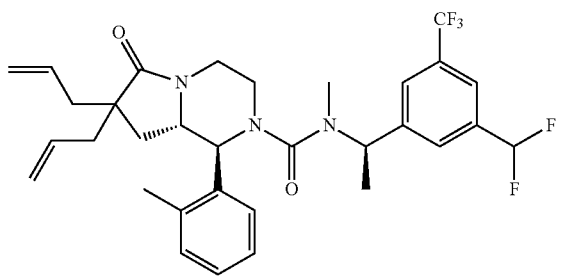 [SMILES: C=CCC1(CC=C)C[C@H]2[C@H](c3ccccc3C)N(C(=O)N(C)[C@H](C)c3cc(C(F)F)cc(C(F)(F)F)c3)CCN2C1=O]

To a solution of triphosgene (47 mg, 0.16 mmol) in EtOAc (2 mL) at 0° C. was added solution of Intermediate 54 (100 mg, 0.32 mmol), DMAP (4 mg, 0.032 mmol) and TEA (49 mg, 0.48 mmol) in EtOAc (2 mL). The mixture was stirred for 1.5 h, followed by addition of (R)-1-(3-(difluoromethyl)-5-(trifluoromethyl)phenyl)-N-methylethanamine (113 mg, 0.42 mmol) in EtOAc (2 mL) and TEA (97 mg, 0.963 mmol). The reaction was stirred at 50° C. for 48 h and quenched with water. The resulting mixture was extracted with EtOAc and the organic layer was washed with 1 M aqueous HCl solution, dried over anhydrous Na$_2$SO$_4$ and then concentrated in high vacuum. The residue was purified by silica gel chromatography (DCM/MeOH=20/1 to 10/1) to give the title compound (70 mg, yield: 32%) as yellow solid; m/z (ES+): 590 [M+H]$^+$.

Intermediate 126

(S)-N-((R)-1-(3-bromo-5-(trifluoromethyl)phenyl)allyl)-2-methylpropane-2-sulfinamide

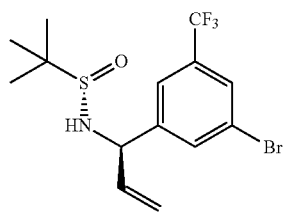 [SMILES: C=C[C@@H](N[S@@](=O)C(C)(C)C)c1cc(Br)cc(C(F)(F)F)c1]

To a solution of (S)-N-(3-bromo-5-(trifluoromethyl)benzylidene)-2-methylpropane-2-sulfinamide (20 g, 56.1 mmol) in DCM (300 mL) was drop wise added vinylmagnesium bromide (84 mL, 1 M in THF, 84 mmol) at −60° C. The reaction mixture was stirred at room temperature for 5 h and poured into aqueous NH$_4$Cl solution. The resulting mixture was extracted with DCM (2×100 mL). The combined organic layers were washed with brine (50 mL), dried over anhydrous MgSO$_4$, and then concentrated. The residue was purified by silica gel chromatography (PE/EtOAc=5/1 to 2/1) to give the title compound (12 g, yield: 56%); m/z (ES+): 384 [M+H]$^+$.

Intermediate 127

(S)-N-((R)-1-(3-bromo-5-(trifluoromethyl)phenyl)allyl)-N,2-dimethylpropane-2-sulfinamide

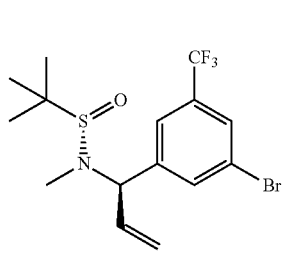 [SMILES: C=C[C@H](c1cc(Br)cc(C(F)(F)F)c1)N(C)[S@@](=O)C(C)(C)C]

To a solution of Intermediate 126 (12 g, 31.2 mmol) in THF (100 mL) under N$_2$ atmosphere was dropwise added LHMDS (5 mL, 1 M in THF, 50 mmol) at −60° C. The reaction was stirred for 30 min at −60° C. followed by addition of MeI (670 mg, 46.8 mmol). After stirring for another 3 h at room temperature, the reaction was quenched with water at 0° C. and then extracted with EtOAc (2×100 mL). The organic layers were dried over anhydrous Na$_2$SO$_4$ and then concentrated under reduced pressure. The residue was purified by silica gel chromatography (PE/EtOAc=5/1 to 2/1) to give the title compound (7 g, yield: 60%); m/z (ES+): 398 [M+H]$^+$.

Intermediate 128

(S)-N,2-dimethyl-N-((R)-1-(3-(4,4,5,5-tetramethyl-1,3,2-dioxaborolan-2-yl)-5-(trifluoromethyl)phenyl)allyl)propane-2-sulfinamide

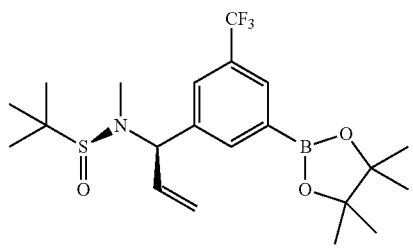 [SMILES: C=C[C@H](c1cc(B2OC(C)(C)C(C)(C)O2)cc(C(F)(F)F)c1)N(C)[S@@](=O)C(C)(C)C]

To a solution of Intermediate 127 (5 g, 12.5 mmol), Bis(pinacolato)diboron (3.8 g, 15 mmol), K$_2$CO$_3$ (3.5 g, 25 mmol) in 60 mL of THF/H$_2$O (5:1) under N$_2$ atmosphere was added Pd(dppf)Cl$_2$ (1 g, 1.25 mmol). The reaction was stirred for 5 h at 80° C. After cooled down to room temperature, the reaction was quenched with water and then extracted with EtOAc (2×50 mL). The combined organic layers were dried over anhydrous Na$_2$SO$_4$ and then concentrated under reduced pressure. The residue was purified by silica gel chromatography (PE/EtOAc=5/1 to 2/1) to give the title compound (900 mg, yield: 45%); m/z (ES+): 446 [M+H]$^+$.

Intermediate 129

(R)-1-(3-chloro-5-(trifluoromethyl)phenyl)-N-methylprop-2-en-1-amine

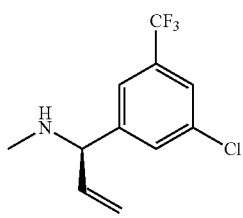 [SMILES: C=C[C@@H](NC)c1cc(Cl)cc(C(F)(F)F)c1]

To a solution of Intermediate 128 (800 mg, 1.8 mmol) in 30 mL of MeOH/H$_2$O (10:1), was added CuCl$_2$ (1.2 g, 9 mmol). The reaction was stirred at 80° C. for 10 h and then quenched with water. The resulting mixture was extracted with EtOAc (2×50 mL). The combined organic layers were dried over anhydrous Na$_2$SO$_4$ and then concentrated under reduced pressure. The residue was purified by silica gel chromatography (PE/EtOAc=5/1 to 2/1) to give the title compound (200 mg, yield: 45%); m/z (ES+): 250 [M+H]$^+$.

Intermediate 130

(1S,8aS)-7,7-diallyl-N-((R)-1-(3-chloro-5-(trifluoromethyl)phenyl)allyl)-N-methyl-6-oxo-1-o-tolyl-hexahydropyrrolo[1,2-a]pyrazine-2(1H)-carboxamide

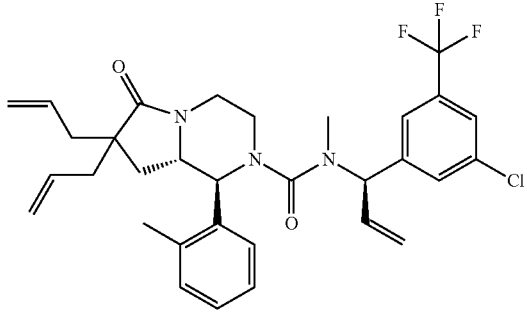 [SMILES: C=CCC1(CC=C)C[C@H]2[C@H](c3ccccc3C)N(C(=O)N(C)[C@H](C=C)c3cc(Cl)cc(C(F)(F)F)c3)CCN2C1=O]

To a solution of triphosgene (47 mg, 0.16 mmol) in EtOAc (2 mL) at 0° C. was added solution of Intermediate 54 (100 mg, 0.32 mmol), DMAP (4 mg, 0.032 mmol) and TEA (49 mg, 0.48 mmol) in EtOAc (2 mL). The mixture was stirred for 1.5 h, followed by addition of (R)-1-(3-chloro-5-(trifluoromethyl)phenyl)-N-methylprop-2-en-1-amine (100 mg, 0.40 mmol) in EtOAc (2 mL) and TEA (97 mg, 0.963 mmol). The reaction was stirred at 50° C. for 48 h and quenched with water. The resulting mixture was extracted with EtOAc. The organic layer was washed with 1 M aqueous HCl solution, dried over anhydrous Na$_2$SO$_4$ and then concentrated in high vacuum. The residue was purified by silica gel chromatography (DCM/MeOH=20/1 to 10/1) to give the title compound (80 mg, yield: 40%) as yellow solid; m/z (ES+): 586 [M+H]$^+$.

Intermediate 131

(R)-N-(3,5-bis(trifluoromethyl)benzylidene)-2-methylpropane-2-sulfinamide

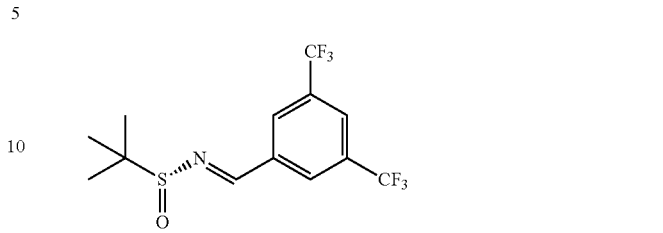

To a mixture of 3,5-bis(trifluoromethyl)benzaldehyde (5 g, 20.7 mmol) and (R)-2-methylpropane-2-sulfinamide (3.3 g, 26.9 mmol) in DCM (50 ml) at 0° C., was drop wise added Ti(O-iPr)$_4$ (5.9 g, 24.8 mmol) under N$_2$ atmosphere. After stirring for 20 h at room temperature, the reaction mixture was poured into water (100 mL) with vigorous stirring. The precipitate was filtered off and the filtrate was extracted with DCM (2×100 mL). The combined organic layers were washed with brine (100 mL), dried over anhydrous MgSO$_4$, and then concentrated. The residue was purified by silica gel chromatography (PE/EtOAc=5/1 to 2/1) to give the title compound (5.5 g, yield: 78%); m/z (ES+): 346 [M+H]$^+$.

Intermediate 132

(R)-N-((S)-1-(3,5-bis(trifluoromethyl)phenyl)ethyl)-2-methylpropane-2-sulfinamide

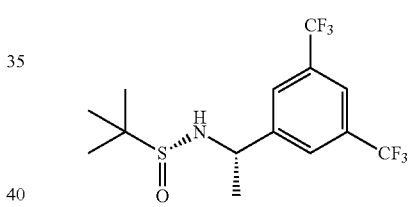

To a solution of Intermediate 131 (5.0 g, 14.5 mmol) in DCM (50 mL) was drop wise added methyl magnesium bromide (6.3 mL, 3 M in THF, 19 mmol) at −60° C. After stirring for 5 h at room temperature, the reaction was poured into saturated aqueous NH$_4$Cl solution and extracted with DCM (2×100 mL). The organic combined layers were washed with brine (50 mL), dried over anhydrous MgSO$_4$, and then concentrated. The residue was purified by silica gel chromatography (PE/EtOAc=5/1 to 2/1) to give the title compound (3.5 g, yield: 67%); m/z (ES+): 362 [M+H]$^+$.

Intermediate 133

(R)-N-((S)-1-(3,5-bis(trifluoromethyl)phenyl)ethyl)-N,2-dimethylpropane-2-sulfinamide

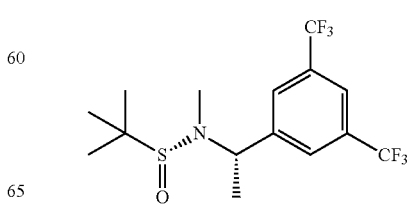

To a solution of Intermediate 132 (2.0 g, 5.5 mmol) in THF (30 mL) under N₂ atmosphere was dropwise added LiHMDS (7.2 mL, 1 M in THF, 7.2 mmol) at −60° C. The reaction was stirred for 30 min at −60° C. followed by addition of MeI (1.6 g, 11 mmol). After stirring for another 3 h at room temperature, the reaction was quenched with water at 0° C. and then extracted with EtOAc (2×60 mL). The combined organic layers were dried over anhydrous Na₂SO₄ and then concentrated under reduced pressure. The residue was purified by silica gel chromatography (PE/EtOAc=5/1 to 2/1) to give the title compound (1.3 g, yield: 65%); m/z (ES+): 376 [M+H]⁺.

Intermediate 134

(S)-1-(3,5-bis(trifluoromethyl)phenyl)-N-methylethanamine

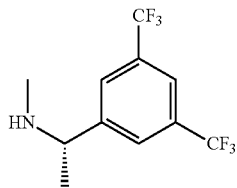 [SMILES: CN[C@@H](C)c1cc(C(F)(F)F)cc(C(F)(F)F)c1]

A solution of Intermediate 133 (1.3 g, 3.47 mmol) in HCl/MeOH (10 mL) under N₂ atmosphere was stirred for 15 min. The reaction was neutralized with 1 M NaOH solution to pH=10-11 and then extracted with EtOAc (2×50 mL). The combined organic layers were washed with brine (10 mL), dried over anhydrous Na₂SO₄, and then concentrated to give the title compound (0.7 g, yield: 75%); m/z (ES+): 272 [M+H]⁺.

Intermediate 135

(1S,8aS)-7,7-diallyl-N-((S)-1-(3,5-bis(trifluoromethyl)phenyl)ethyl)-N-methyl-6-oxo-1-o-tolyl-hexahydropyrrolo[1,2-a]pyrazine-2(1H)-carboxamide

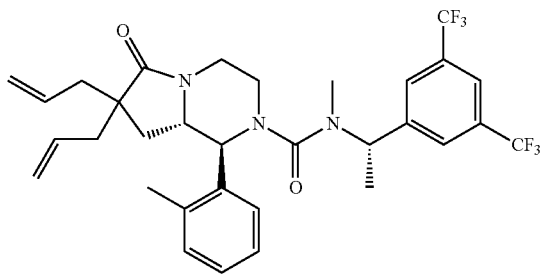 [SMILES: C=CCC1(CC=C)C[C@H]2[C@H](c3ccccc3C)N(C(=O)N(C)[C@@H](C)c3cc(C(F)(F)F)cc(C(F)(F)F)c3)CCN2C1=O]

To a solution of triphosgene (47 mg, 0.16 mmol) in EtOAc (2 mL) at 0° C. was added solution of Intermediate 54 (100 mg, 0.32 mmol), DMAP (4 mg, 0.032 mmol) and TEA (49 mg, 0.48 mmol) in EtOAc (2 mL). The mixture was stirred for 1.5 h, followed by addition of (S)-1-(3,5-bis(trifluoromethyl)phenyl)-N-methylethanamine (147 mg, 0.54 mmol) in EtOAc (2 mL) and TEA (97 mg, 0.963 mmol). The reaction was stirred at 50° C. for 48 h and quenched with water. The resulting mixture was extracted with EtOAc and the organic layer was washed with 1 M aqueous HCl solution, dried over anhydrous Na₂SO₄ and then concentrated in high vacuum. The residue was purified by silica gel chromatography (DCM/MeOH=20/1 to 10/1) to give the title compound (40 mg, yield: 17%) as yellow solid; m/z (ES+): 608 [M+H]⁺.

Intermediate 136

(1S,8aS)-dimethyl 2-(methyl((R)-1-(3-methyl-5-(trifluoromethyl)phenyl)ethyl)carbamoyl)-6-oxo-1-o-tolylhexahydropyrrolo[1,2-a]pyrazine-7,7(6H)-dicarboxylate

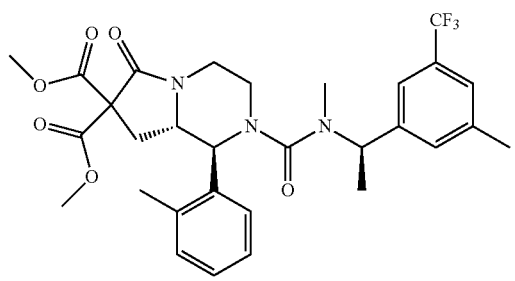

To a solution of (1S,8aS)-N-methyl-N-((R)-1-(3-methyl-5-(trifluoromethyl)phenyl)ethyl)-6-oxo-1-o-tolylhexahydropyrrolo[1,2-a]pyrazine-2(1H)-carboxamide (350 mg, 0.74 mmol) in anhydrous THF (20 mL) under N₂ atmosphere was added LHMDS (4.43 mL, 1 M in THF, 4.43 mmol) at −60° C. The reaction was stirred for 30 min followed by addition of methyl carbonochloridate (174 mg, 1.85 mmol). After stirring for another 3 h at room temperature. The reaction was quenched with water at 0° C. and then extracted with EtOAc (2×30 mL). The combined organic layers were dried over anhydrous Na₂SO₄ and then concentrated in high vacuum. The residue was purified by silica gel chromatography (DCM/MeOH=20/1 to 10/1) to give the title compound (200 mg, yield: 46%); m/z (ES+): 590 [M+H]⁺.

Intermediate 137

(1S,8aS)-dimethyl 2-(((R)-1-(3,5-bis(trifluoromethyl)phenyl)ethyl)(methyl)carbamoyl)-6-oxo-1-o-tolylhexahydropyrrolo[1,2-a]pyrazine-7,7(6H)-dicarboxylate

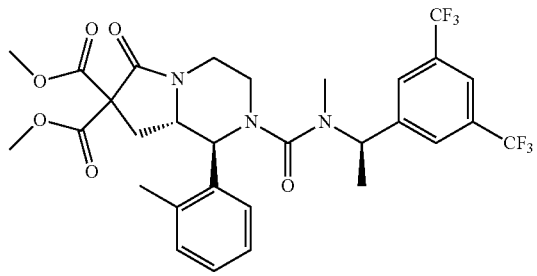 [SMILES: COC(=O)C1(C(=O)OC)C[C@H]2[C@H](c3ccccc3C)N(C(=O)N(C)[C@H](C)c3cc(C(F)(F)F)cc(C(F)(F)F)c3)CCN2C1=O]

To a solution of (1S,8aS)-N-((R)-1-(3,5-bis(trifluoromethyl)phenyl)ethyl)-N-methyl-6-oxo-1-o-tolylhexahydropyrrolo[1,2-a]pyrazine-2(1H)-carboxamide (300 mg, 0.57 mmol) in anhydrous THF (20 mL) under N₂ atmosphere was added LiHMDS (2.3 mL, 1 M in THF, 2.3 mmol) at −60° C. The reaction was stirred for 30 min followed by addition of methyl carbonochloridate (134 mg, 1.43 mmol). After stirring for another 3 h at room temperature. The reaction was quenched with water at 0° C. and then extracted with EA (2×50 mL). The combined organic layers were dried over anhydrous Na$_2$SO$_4$ and then concentrated in high vacuum. The residue was purified by silica gel chromatography (DCM/MeOH=20/1 to 10/1) to give the title compound (166 mg, yield: 45.3%); m/z (ES+): 644 [M+H]$^+$.

Intermediate 138

(1S,8aS)-dimethyl 2-(((R)-1-(3,5-bis(trifluoromethyl)phenyl)ethyl)(methyl)carbamoyl)-6-oxo-1-o-tolylhexahydropyrrolo[1,2-a]pyrazine-7,7(6H)-dicarboxylate

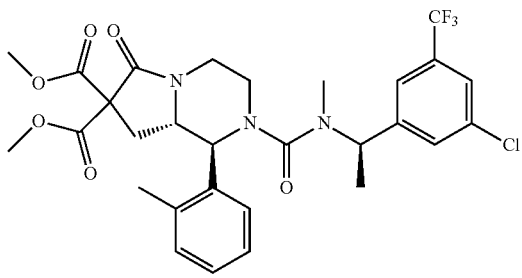 [SMILES: COC(=O)C1(C(=O)OC)C[C@H]2[C@H](c3ccccc3C)N(C(=O)N(C)[C@H](C)c3cc(Cl)cc(C(F)(F)F)c3)CCN2C1=O]

To a solution of (1S,8aS)-N-((R)-1-(3-chloro-5-(trifluoromethyl)phenyl)ethyl)-N-methyl-6-oxo-1-o-tolylhexahydropyrrolo[1,2-a]pyrazine-2(1H)-carboxamide (300 mg, 0.61 mmol) in anhydrous THF (20 mL) under N$_2$ atmosphere was added LiHMDS (2.3 mL, 1 M in THF, 2.3 mmol) at −60° C. The reaction was stirred for 30 min followed by addition of methyl carbonochloridate (134 mg, 1.43 mmol). After stirring for another 3 h at room temperature, the reaction was quenched with water at 0° C. and then extracted with EtOAc (2×30 mL). The combined organic layers were dried over anhydrous Na$_2$SO$_4$ and then concentrated in high vacuum. The residue was purified by silica gel chromatography (DCM/MeOH=20/1 to 10/1) to give the title compound (220 mg, yield: 59%); m/z (ES+): 610 [M+H]$^+$.

Intermediate 139

(S)-N-((R)-1-(3-ethyl-5-(trifluoromethyl)phenyl)ethyl)-N,2-dimethylpropane-2-sulfinamide

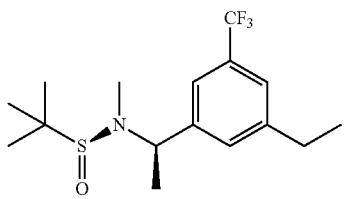 [SMILES: CCc1cc([C@@H](C)N(C)[S@@](=O)C(C)(C)C)cc(C(F)(F)F)c1]

A mixture of (S)-N-((R)-1-(3-bromo-5-(trifluoromethyl)phenyl)ethyl)-N,2-dimethyl propane-2-sulfinamide (1 g, 2.6 mmol), Pd(PPh$_3$)$_2$Cl$_2$ (182 mg, 0.26 mmol) and Et$_2$Zn (640 mg, 5.2 mmol) in THF (10 mL) under N$_2$ atmosphere was stirred at 6° C. for 16 h. The reaction was poured into water (15 mL) and then extracted with EtOAc (2×30 mL). The combined organic layers were dried over anhydrous Na$_2$SO$_4$ and then concentrated. The residue was purified by silica gel chromatography (PE/EtOAc=10/1 to 1/1) to give the title compound (700 mg, yield: 80.3%); m/z (ES+): 336 [M+H]$^+$.

Intermediate 140

(R)-1-(3-ethyl-5-(trifluoromethyl)phenyl)-N-methylethanamine

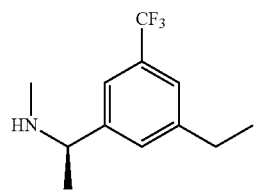 [SMILES: CCc1cc([C@@H](C)NC)cc(C(F)(F)F)c1]

A solution of Intermediate 139 (700 mg, 2.09 mmol) in HCl/MeOH (10 mL) under N$_2$ atmosphere was stirred for 15 min. The reaction was neutralized with 1 M NaOH solution to pH=10-11 and then extracted with EtOAc (2×50 mL). The combined organic layers were washed with brine (20 mL), dried over anhydrous Na$_2$SO$_4$, and then concentrated to give the title compound (300 mg, yield: 62%); m/z (ES+): 232 [M+H]$^+$.

Intermediate 141

(1S,8aS)-7,7-diallyl-N-methyl-N-((S)-1-(3-methyl-5-(trifluoromethyl)phenyl)ethyl)-6-oxo-1-o-tolyl-hexahydropyrrolo[1,2-a]pyrazine-2(1H)-carboxamide

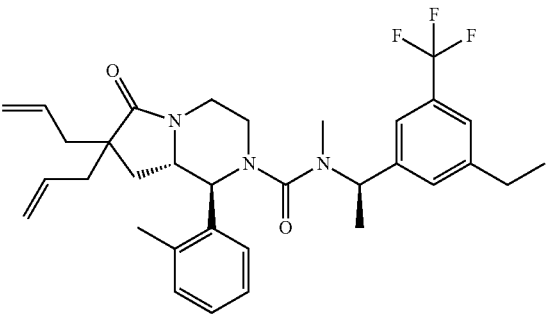 [SMILES: C=CCC1(CC=C)C[C@H]2[C@H](c3ccccc3C)N(C(=O)N(C)[C@H](C)c3cc(CC)cc(C(F)(F)F)c3)CCN2C1=O]

To a solution of triphosgene (47 mg, 0.16 mmol) in EtOAc (2 mL) at 0° C. was added solution of Intermediate 54 (100 mg, 0.32 mmol), DMAP (4 mg, 0.032 mmol) and TEA (49 mg, 0.48 mmol) in EtOAc (2 mL). The mixture was stirred for 1.5 h, followed by addition of (R)-1-(3-ethyl-5-(trifluoromethyl)phenyl)-N-methylethanamine (111 mg, 0.48 mmol) in EtOAc (2 mL) and TEA (97 mg, 0.963 mmol). The reaction was stirred at 50° C. for 48 h and quenched with water. The resulting mixture was extracted with EtOAc and the organic layer was washed with 1 M aqueous HCl solution, dried over anhydrous Na$_2$SO$_4$ and then concentrated in high vacuum. The residue was purified by silica gel chromatography (DCM/MeOH=20/1 to 10/1) to give the title compound (78 mg, yield: 43%) as yellow solid; m/z (ES+): 568 [M+H]$^+$.

Intermediate 142

(S)-N,2-dimethyl-N-((R)-1-(3-(prop-1-en-2-yl)-5-(trifluoromethyl)phenyl)ethyl)propane-2-sulfinamide

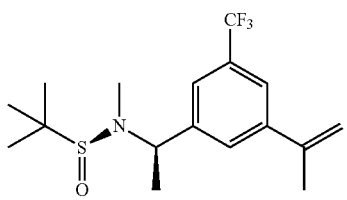 [SMILES: C=C(C)c1cc([C@@H](C)N(C)[S@@](=O)C(C)(C)C)cc(C(F)(F)F)c1]

To a solution of Intermediate 74 (1.8 g, 4.66 mmol) in THF (20 mL) under N₂ atmosphere was added Pd(PPh₃)₄ (100 mg, 0.1 mmol), 4,4,5,5-tetramethyl-2-(prop-1-en-2-yl)-1,3,2-dioxaborolane (1 g, 6 mmol). The reaction was refluxed for 4 h and then quenched with water. The resulting mixture was extracted with EtOAc (2×100 mL). The organic layers were dried over anhydrous Na₂SO₄ and then concentrated in high vacuum. The residue was purified by silica gel chromatography (PE/EtOAc=10/1 to 1/1) to give the title compound (1.4 g, yield: 86%); m/z (ES+): 348 [M+H]⁺.

Intermediate 143

(S)-N-((R)-1-(3-isopropyl-5-(trifluoromethyl)phenyl)ethyl)-N,2-dimethylpropane-2-sulfinamide

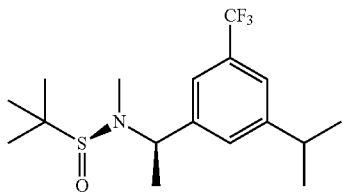 [SMILES: CC(C)c1cc([C@@H](C)N(C)[S@@](=O)C(C)(C)C)cc(C(F)(F)F)c1]

To a solution of Intermediate 142 (1.4 g, 4 mmol) in MeOH (20 mL) under N₂ atmosphere was added Pd/C (0.2 g). The resulting mixture was purged with N2 twices and then stirred under hydrogen atmosphere (50 psi) for 24 h at room temperature. The mixture was filtered and the filtrate was concentrated in high vacuum. The residue was purified by silica gel chromatography (PE/EtOAc=5/1 to 1/1) to give the title compound (1.2 g, yield: 85%); m/z (ES+): 350[M+H]⁺.

Intermediate 144

(R)-1-(3-isopropyl-5-(trifluoromethyl)phenyl)-N-methylethanamine

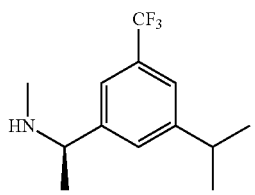 [SMILES: CN[C@H](C)c1cc(C(C)C)cc(C(F)(F)F)c1]

A solution of Intermediate 143 (1.2 g, 3.44 mmol) in HCl/MeOH (2 N, 10 mL) was stirred for 1 h under N₂ atmosphere. The reaction was neutralized with 1 N NaOH to pH=10-11 and then extracted with EtOAc (2×20 mL). The organic layers were dried over anhydrous Na₂SO₄ and then concentrated in high vacuum to give the title compound (0.8 g, yield: 95%) which used directly in the next step; m/z (ES+): 246 [M+H]⁺.

Intermediate 145

(1S,8aS)-7,7-diallyl-N-((R)-1-(3-isopropyl-5-(trifluoromethyl)phenyl)ethyl)-N-methyl-6-oxo-1-o-tolylhexahydropyrrolo[1,2-a]pyrazine-2(1H)-carboxamide

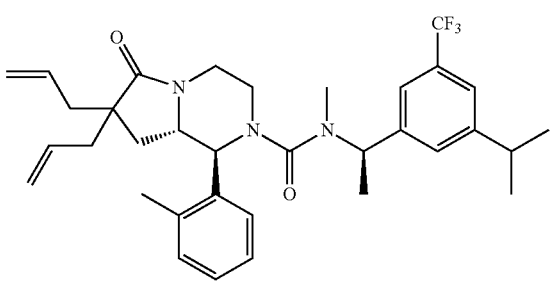 [SMILES: C=CCC1(CC=C)C[C@H]2[C@H](c3ccccc3C)N(C(=O)N(C)[C@H](C)c3cc(C(C)C)cc(C(F)(F)F)c3)CCN2C1=O]

To a solution of triphosgene (72 mg, 0.242 mmol) in EtOAc (2 mL) at 0° C. was added solution of (1S,8aS)-7,7-diallyl-1-o-tolylhexahydropyrrolo[1,2-a]pyrazin-6(7H)-one (150 mg, 0.484 mmol), DMAP (6.2 mg, 0.05 mmol) and TEA (151 mg, 1.5 mmol) in EtOAc (15 mL). The mixture was stirred for 1.5 h, followed by addition of (R)-1-(3-isopropyl-5-(trifluoromethyl)phenyl)-N-methylethanamine (142 mg, 0.58 mmol) in EtOAc (10 mL) and TEA (151 mg, 1.5 mmol). The reaction was stirred at 50° C. for 48 h and quenched with water. The resulting mixture was extracted with EtOAc. The organic layer was washed with 1 M aqueous HCl solution, dried over anhydrous Na₂SO₄ and then concentrated in high vacuum. The residue was purified by silica gel chromatography (DCM/MeOH=20/1 to 10/1) to give the title compound (100 mg, yield: 36%) as yellow solid; m/z (ES+): 582 [M+H]⁺.

Compounds described in the examples below were obtained as amorphous compounds.

EXAMPLE 1

Compound 1

N-[(3,5-dimethylphenyl)methyl]-N-methyl-1-(2-methylphenyl)-6-oxo-octahydropyrrolo[1,2-a]piperazine-2-carboxamide (Enantiomer 1, ANTI Stereochemistry at C1-C8a, Single Unknown Stereoisomer)

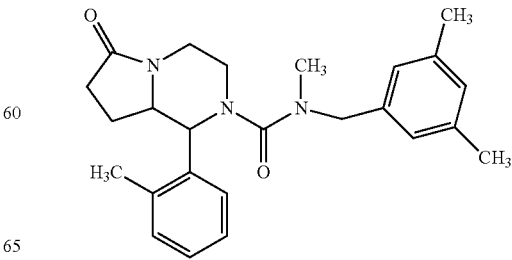

EXAMPLE 1 (continued)

Triphosgene (27.3 mg, 0.09 mmol) was dissolved in EtOAc (1 mL) at 0° C. A solution of 1-(2-methylphenyl)-octahydropyrrolo[1,2-a]piperazin-6-one hydrochloride salt (Intermediate 24, 60 mg, 0.23 mmol) and TEA (110 mL, 0.8 mmol) in EtOAc (2 mL), was added. The reaction mixture was stirred at 0° C. for 1.5 h, then a solution of Intermediate 3 (43.5 mg, 0.32 mmol) and TEA (30 mL) in EtOAc (2 mL), was added. The reaction mixture was stirred 2 h at room temperature. Water (20 mL) was added followed by EtOAc (20 mL). The organic layer was dried over $Na_2SO_4$, filtered and evaporated under vacuo to give a yellow oil (110 mg) which was subjected to chiral preparative HPLC. Two fractions were obtained. After evaporation two products were obtained: enantiomer 1 (Compound 1) and enantiomer 2 (Compound 2, see experimental below). Enantiomer 1 (white solid, 19.4 mg). Chiral HPLC: column Chiralpak AD-H (25× 0.46 cm), 5μ, Mobile phase: n-Hexane/2-Propanol 85/15 v/v, Flow rate: 1 mL/min, Detection: DAD at 220 nm. Rt=10.6 min. $^1$H NMR (500 MHz, $CDCl_3$) δ ppm 7.32 (d, J=6.8 Hz, 1H), 7.18 (m, 3H), 6.86 (s, 1H), 6.52 (s, 2H), 4.39 (m, 2H), 4.15 (m, 1H), 4.08 (d, J=9.8 Hz, 1H), 3.70 (m, J=9.5 Hz, 1H), 3.35 (m, 1H), 3.12 (td, J=12.4, 3.1 Hz, 1H), 2.93 (td, J=12.0, 3.3 Hz, 1H), 2.83 (s, 3H), 2.55 (s, 3H), 2.41 (m, 1H), 2.34 (m, 1H), 2.22 (s, 6H), 1.84 (m, 1H), 1.70 (d, J=7.6 Hz, 1H).

EXAMPLE 2

Compound 2

N-[(3,5-dimethylphenyl)methyl]-N-methyl-1-(2-methylphenyl)-6-oxo-octahydropyrrolo[1,2-a]piperazine-2-carboxamide (Enantiomer 2, ANTI Stereochemistry at C1-C8a, Single Unknown Stereoisomer)

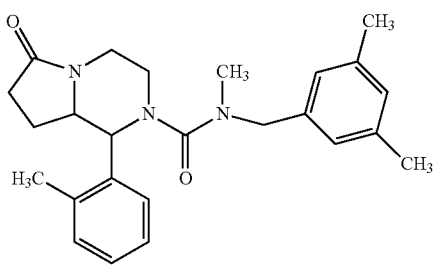 [SMILES: Cc1cc(C)cc(CN(C)C(=O)N2CCN3C(=O)CCC3C2c2ccccc2C)c1]

After evaporation of fraction collected from chiral preparative HPLC of the above described experimental, Compound 2 was obtained (white solid, 14.8 mg). Chiral HPLC, Chiralpak AD-H column (25×0.46 cm), 5μ mobile phase: n-Hexane/2-Propanol 85/15 v/v, Flow rate: 1 mL/min. Detection: DAD at 220 nm. Rt=21.5 min. $^1$H NMR (500 MHz, $CDCl_3$) δ ppm 7.32 (d, J=6.8 Hz, 1H), 7.18 (m, 3H), 6.86 (s, 1H), 6.52 (s, 2H), 4.39 (m, 2H), 4.15 (m, 1H), 4.08 (d, J=9.8 Hz, 1H), 3.70 (m, J=9.5 Hz, 1H), 3.35 (m, 1H), 3.12 (td, J=12.4, 3.1 Hz, 1H), 2.93 (td, J=12.0, 3.3 Hz, 1H), 2.83 (s, 3H), 2.55 (s, 3H), 2.41 (m, 1H), 2.34 (m, 1H), 2.22 (s, 6H), 1.84 (m, 1H), 1.70 (d, J=7.6 Hz, 1H).

EXAMPLE 3

Compound 3

N-{[3-fluoro-5-(trifluoromethyl)phenyl]methyl}-N-methyl-1-(2-methylphenyl)-6-oxo-octahydropyrrolo[1,2-a]piperazine-2-carboxamide (Enantiomer 1, ANTI Stereochemistry at C1-C8a, Single Unknown Stereoisomer)

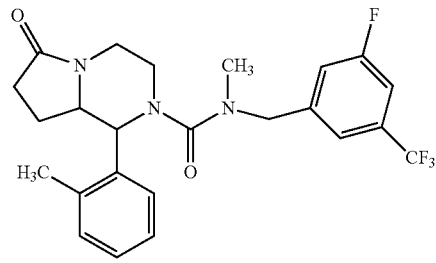 [SMILES: Cc1ccccc1C1C2CCC(=O)N2CCN1C(=O)N(C)Cc1cc(F)cc(C(F)(F)F)c1]

Triphosgene (27.3 mg, 0.09 mmol) was dissolved in ETOAc (1 mL) at 0° C. A solution of 1-(2-methylphenyl)-octahydropyrrolo[1,2-a]piperazin-6-one hydrochloride salt (Intermediate 24, 60 mg, 0.23 mmol) and TEA (110 mL, 0.8 mmol) in EtOAc (2 mL), was added. The reaction mixture was stirred at 0° C. for 1.5 h, then a solution of {[3-fluoro-5-(trifluoromethyl)phenyl]methyl}(methyl)amine (intermediate 4, 66.3 mg, 0.32 mmol) and TEA (30 mL) in EtOAc (2 mL), was added. The reaction mixture was stirred 2 h at room temperature. Water (20 mL) was added followed by EtOAc (20 mL). The organic layer was dried over $Na_2SO_4$, filtered and evaporated in vacuo to give a yellow oil (130 mg) which was subjected to chiral preparative HPLC. Two fractions were obtained. After evaporation two products were obtained: enantiomer 1 (Compound 3) and enantiomer 2 (Compound 4, see experimental below). Compound 3: white foam, 33.8 mg. Chiral HPLC, Chiralpak AD-H column (25× 0.46 cm), 5μ, Mobile phase: n-Hexane/2-Propanol 85/15 v/v, Flow rate: 0.8 mL/min; Detection: DAD at 220 nm. Rt=12.8 min. m/z (ES+): 464.2 $[M+H]^+$. $^1$H NMR (500 MHz, $CDCl_3$) δ ppm 7.28 (m, 1H), 7.19 (m, 4H), 7.03 (s, 1H), 6.57 (d, J=8.8 Hz, 1H), 4.66 (d, J=15.4 Hz, 1H), 4.23 (d, J=15.7 Hz, 1H), 4.18 (dt, J=13.0, 2.7 Hz, 1H), 4.08 (d, J=10.0 Hz, 1H), 3.73 (dt, 7.4 Hz, 1H), 3.35 (dt, J=12.2, 2.8 Hz, 1H), 3.14 (td, J=12.5, 2.7 Hz, 1H), 2.95 (m, 4H), 2.53 (s, 3H), 2.44 (m, 1H), 2.36 (m, 1H), 1.87 (m, 1H), 1.70 (m, 1H).

EXAMPLE 4

Compound 4

N-{[3-fluoro-5-(trifluoromethyl)phenyl]methyl}-N-methyl-1-(2-methylphenyl)-6-oxo-octahydropyrrolo[1,2-a]piperazine-2-carboxamide (Enantiomer 2, ANTI Stereochemistry at C1-C8a, Single Unknown Stereoisomer)

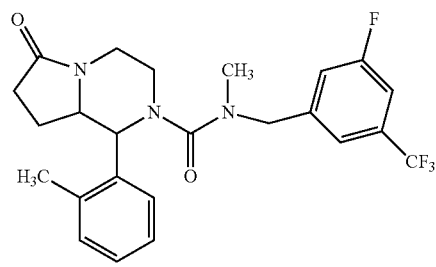 [SMILES: Cc1ccccc1C1C2CCC(=O)N2CCN1C(=O)N(C)Cc1cc(F)cc(C(F)(F)F)c1]

After evaporation of fraction collected from chiral preparative HPLC of the above described experimental, compound 4 was obtained (white foam, 34.8 mg). Chiral HPLC: Chiralpak AD-H column (25×0.46 cm), 5µ Mobile phase: n-Hexane/2-Propanol 85/15 v/v, Flow rate: 0.8 mL/min. Detection: DAD at 220 nm. Rt=15.8 min. m/z (ES+): 464.2 [M+H]⁺. ¹H NMR (500 MHz, CDCl₃) δ ppm 7.28 (m, 1H), 7.19 (m, 4H), 7.03 (s, 1H), 6.57 (d, J=8.8 Hz, 1H), 4.66 (d, J=15.4 Hz, 1H), 4.23 (d, J=15.7 Hz, 1H), 4.18 (dt, J=13.0, 2.7 Hz, 1H), 4.08 (d, 1=10.0 Hz, 1H), 3.73 (dt, J=9.7, 7.4 Hz, 1H), 3.35 (dt, J=12.2, 2.8 Hz, 1H), 3.14 (td, J=12.5, 2.7 Hz, 1H), 2.95 (m, 4H), 2.53 (s, 3H), 2.44 (m, 1H), 2.36 (m, 1H), 1.87 (m, 1H), 1.70 (m, 1H).

EXAMPLE 5

Compound 5

N-methyl-1-(2-methylphenyl)-6-oxo-N-{[3-(trifluoromethyl)phenyl]methyl}-octahydropyrrolo[1,2-a]piperazine-2-carboxamide (Enantiomer 1, ANTI Stereochemistry at C1-C8a, Single Unknown Stereoisomer)

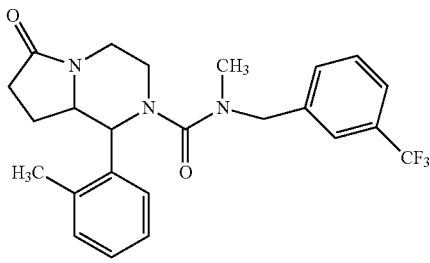 [SMILES: Cc1ccccc1C1C2CCC(=O)N2CCN1C(=O)N(C)Cc1cccc(C(F)(F)F)c1]

Triphosgene (27.3 mg, 0.09 mmol) was dissolved in ETOAc (1 mL) at 0° C. A solution of 1-(2-methylphenyl)-octahydropyrrolo[1,2-a]piperazin-6-one hydrochloride salt (Intermediate 24, 60 mg, 0.23 mmol) and TEA (110 mL, 0.8 mmol) in EtOAc (2 mL), was added. The reaction mixture was stirred at 0° C. for 1.5 h, then a solution of methyl({[3-(trifluoromethyl)phenyl]methyl})amine (Intermediate 2, 60 mg, 0.32 mmol) and TEA (30 mL) in EtOAc (2 mL), was added. The reaction mixture was stirred 2 h at room temperature. Water (20 mL) was added followed by EtOAc (20 mL). The organic layer was dried over Na₂SO₄, filtered and evaporated under vacuo to give a yellow oil (130 mg) which was subjected to chiral preparative HPLC. Two fractions were obtained. After evaporation two products were obtained: enantiomer 1 (Compound 5) and enantiomer 2 (Compound 6, see experimental below). Compound 5 (white solid, 26 mg): chiral HPLC, Chiralpak AD-H column (25×0.46 cm), 5µ, Mobile phase: n-Hexane/2-Propanol 85/15 v/v, Flow rate: 0.8 mL/min; Detection: DAD at 220 nm. Rt=17.9 min. m/z (ES+): 446.2 [M+H]⁺¹H NMR (500 MHz, CDCl₃) δ ppm 7.47 (d, J=7.6 Hz, 1H), 7.21 (m, 6H), 6.88 (d, J=7.8 Hz, 1H), 4.60 (d, J=15.4 Hz, 1H), 4.34 (d, J=15.2 Hz, 1H), 4.17 (d, J=13.0 Hz, 1H), 4.08 (d, J=10.0 Hz, 1H), 3.73 (m, 1H), 3.34 (d, J=12.0 Hz, 1H), 3.13 (m, 1H), 2.95 (m, 4H), 2.54 (s, 3H), 2.40 (m, 2H), 1.87 (m, 1H), 1.69 (m, 1H).

EXAMPLE 6

Compound 6

N-methyl-1-(2-methylphenyl)-6-oxo-N-{[3-(trifluoromethyl)phenyl]methyl}-Octahydropyrrolo[1,2-a]piperazine-2-carboxamide (Enantiomer 2, ANTI Stereochemistry at C1-C8a, Single Unknown Stereoisomer)

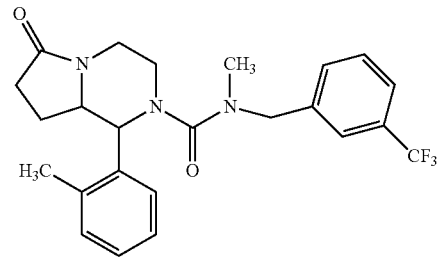 [SMILES: Cc1ccccc1C1C2CCC(=O)N2CCN1C(=O)N(C)Cc1cccc(C(F)(F)F)c1]

After evaporation of fraction collected from chiral preparative HPLC of the above described experimental, Compound 6 was obtained (white solid, 33 mg). Chiral HPLC: Chiralpak AD-H column (25×0.46 cm), 5µ Mobile phase: n-Hexane/2-Propanol 85/15 v/v, Flow rate: 0.8 mL/min. Detection: DAD at 220 nm. Rt=23.6 min. m/z (ES+): 446.2 [M+H]⁺¹H NMR (500 MHz, CDCL₃) δ ppm 7.47 (d, J=7.6 Hz, 1H), 7.21 (m, 6H), 6.88 (d, J=7.8 Hz, 1H), 4.60 (d, J=15.4 Hz, 1H), 4.34 (d, J=15.2 Hz, 1H), 4.17 (d, J=13.0 Hz, 1H), 4.08 (d, J=10.0 Hz, 1H), 3.73 (m, 1H), 3.34 (d, J=12.0 Hz, 1H), 3.13 (m, 1H), 2.95 (m, 4H), 2.54 (s, 3H), 2.40 (m, 2H), 1.87 (m, 1H), 1.69 (m, 1H).

EXAMPLE 7

Compound 7

N-{[3,5-bis(trifluoromethyl)phenyl]methyl}-N-methyl-1-(2-methylphenyl)-7-oxo-octahydro-1H-pyrrolo[1,2-a][1,4]diazepine-2-carboxamide (Diastereomeric Mixture)

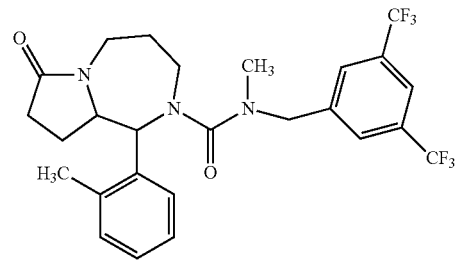 [SMILES: Cc1ccccc1C1C2CCC(=O)N2CCCN1C(=O)N(C)Cc1cc(C(F)(F)F)cc(C(F)(F)F)c1]

Triphosgene (12 mg) was dissolved in ETOAc (0.5 mL) at 0° C. A solution of 1-(2-methylphenyl)-octahydro-1H-pyrrolo[1,2-a][1,4]diazepin-7-one (Intermediate 8, 20 mg, 0.08 mmol) and TEA (15 mL, 0.11 mmol) in EtOAc (0.5 mL), was added. The reaction mixture was stirred at room temperature for 2 h, then a solution of {[3,5-bis(trifluoromethyl)phenyl]methyl}(methypamine (Intermediate 18, 29 mg, 0.1 mmol) and TEA (15 mL, 0.11 mmol) in EtOAc (0.5 mL), was added.

The reaction mixture was stirred 4 h at room temperature. NaOH 1M and EtOAc were added. The organic layer was dried over Na₂SO₄, filtered and evaporated under vacuo to give a yellow oil that was purified on biotage KP-Sil cartridge (CH/EtOAc and then DCM/MeOH as eluent). Collected fractions were evaporated to give a yellow oil (11 mg). ¹H NMR (500 MHz, CDCl₃) δ ppm 7.78 (s, 1H), 7.64 (s, 2H), 5.33 (d, J=3.4 Hz, 1H), 4.53 (m, 1H), 4.47 (s, 2H), 4.01 (ddd, J=13.7, 8.3, 3.9 Hz, 1H), 3.62 (m, 1H), 3.32 (ddd, J=13.9, 7.8, 3.4 Hz, 1H), 3.26 (ddd, J=14.9, 6.8, 3.7 Hz, 1H), 2.77 (s, 3H), 2.38 (d, J=6.6 Hz, 3H), 2.20 (m, 2H), 2.10 (m, 1H), 1.98 (m, 1H), 1.87 (m, 1H), 1.70 (m, 1H); UPLC-MS: Rt=1.21 min and 1.24 min; m/z (ES+): 528.3 [M+H]⁺.

EXAMPLE 8

Compound 8

2-({[3,5-bis(trifluoromethyl)phenyl]methyl}(methyl)carbamoyl)-7-methyl-1-(2-methylphenyl)-6-oxo-octahydropyrrolo[1,2-a]piperazine-7-carboxylic acid (Diastereomeric Mixture with ANTI Configuration at C1-C8a)

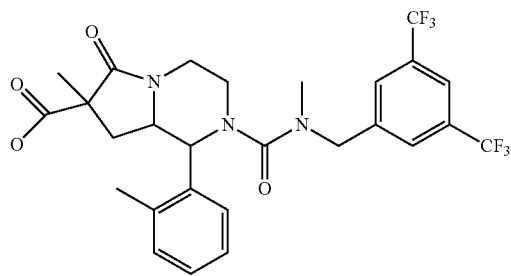 [SMILES: Cc1ccccc1C1C2CC(C)(C(=O)O)C(=O)N2CCN1C(=O)N(C)Cc1cc(C(F)(F)F)cc(C(F)(F)F)c1]

Intermediate 19 (6 mg, 0.010 mmol) was dissolved in a mixture of THF/H₂O/MeOH (0.2 mL each) and LiOH.H₂O (1.2 mg, 0.02 mmol) was added. The mixture was heated at 60° C. for 2 h, then the solution was concentrated and DCM and HCl 1M aq were added. The phases were separated and the organic layer was filtered through a phase separator and concentrated to give the title compound (5.8 mg). ¹H NMR (500 MHz, DMSO-d6) δ ppm 12.86 (br s, 1H), 7.95 (s, 1H), 7.58 (s, 2H), 7.34 (m, 1H), 7.09 (m, 3H), 4.58 (d, 1H), 4.48 (d, 1H), 4.12 (d, 1H), 3.88 (m, 1H), 3.76 (m, 1H), 3.48 (m, 1H), 3.23 (m, 1H), 2.87 (s, 3H), 2.75 (m, 1H), 2.00 (m, 2H), 1.60 (m, 3H), 1.23 (s, 3H). UPLC-MS: Rt=1.20 min; m/z (ES+): 572 [M+H]⁺.

EXAMPLE 9

Compound 9 and Example 10

Compound 10

N-[(1R)-1-[3,5-bis(trifluoromethyl)phenyl]ethyl]-N-methyl-1-(2-methylphenyl)-6-oxo-octahdropyrrolo[1,2a]piperazine-2-carboxamide

EXAMPLE 9

Compound 9

(1S,8aS)-N-[(1R)-1-[3,5-bis(trifluoromethyl)phenyl]ethyl]-N-methyl-1-(2-methylphenyl)-6-oxo-octahydropyrrolo[1,2-a]piperazine-2-carboxamide (Enantiomer 1, Single Isomer with ANTI Configuration at C1-C8a)

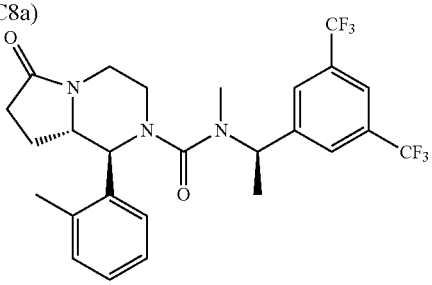

Triphosgene (204.45 mg, 0.6 mmol) was dissolved in EtOAc (10 mL), this solution was cooled at 0° C. and a solution of Intermediate 13 (480 mg, 70% purity, 1.46 mmol) and TEA (400 µL, 2.88 mmol) in EtOAc (20 mL) was added. The resulting mixture was left stirring at this temperature for 2 h, then TEA (400 µL, 2.88 mmol) and Intermediate 1 (554.27 mg, 2.044 mmol) in EtOAc (20 mL) were added and the mixture was left stirring for 3 h. Further 600 mg of Intermediate 1 in 10 mL of EtOAc were added and the mixture was left stirring for 36 h. NaOH 1M was added to the mixture, the phases were separated and the aqueous one was extracted with EtOAc. The organic layer was dried over Na₂SO₄ and concentrated in vacuo to obtain 1.56 g of a crude which was subjected to chiral preparative HPLC. Two fractions were obtained. After evaporation two products were obtained: enantiomer 1 and enantiomer 2 (see experimental below). (1S,8aS)-N-[(1R)-1-[3,5-bis(trifluoromethyl)phenyl]ethyl]-N-methyl-1-(2-methylphenyl)-6-oxo-octahydropyrrolo[1,2-a]piperazine-2-carboxamide, (Enantiomer 1): (white solid, 47 mg). Chiral column: Chiralpak AS-H (25× 0.46 cm), 5µ Mobile phase: n-Hexane/Ethanol 80/20 v/v Flow rate: 0.8 mL/min Detection: DAD at 220 nm, Rt=10.3 min; ¹H NMR (400 MHz, CDCl₃) δ ppm 7.79 (s, 1H), 7.55 (s, 2H), 7.25 (d, 1H), 7.16 (m, 3H), 5.55 (q, 1H), 4.16 (dt, 1H), 4.08 (d, 1H), 3.74 (m, 1H), 3.27 (dt, 1H), 3.12 (td, 1H), 2.98 (td, 1H), 2.71 (s, 3H), 2.54 (s, 3H), 2.43 (m, 1H), 2.34 (m, 1H), 1.86 (m, 1H), 1.68 (m, 1H), 1.41 (d, 3H). Rt=1.24 min; m/z (ES+) 528.3 [M+H]⁺.

EXAMPLE 10

Compound 10

(1R,8aR)-N-[(1R)-1-[3,5-bis(trifluoromethyl)phenyl]ethyl]-N-methyl-1-(2-methylphenyl)-6-oxo-octahydropyrrolo[1,2-a]piperazine-2-carboxamide (Enantiomer 2, Single Isomer with ANTI Configuration at C1-C8a)

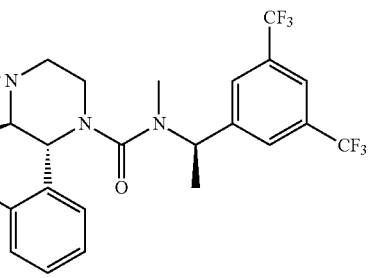

(1R,8aR)-N-[(1R)-1-[3,5-bis(trifluoromethyl)phenyl]ethyl]-N-methyl-1-(2-methylphenyl)-6-oxo-octahydropyrrolo[1,2-a]piperazine-2-carboxamide (Enantiomer 2) (50 mg) was isolated and characterized as follows. Chiral HPLC (from the above described experimental): Chiral column Chiralpak AS-H (25×0.46 cm), 5μ Mobile phase: n-Hexane/Ethanol 80/20 v/v Flow rate: 0.8 mL/min Detection: DAD at 220 nm Rt=14.7 min. $^1$H NMR (500 MHz, CDCl$_3$)) δ ppm 7.72 (s, 1H), 7.36 (s, 2H), 7.24 (d, J=7.1 Hz, 1H), 7.16 (m, 3H), 5.59 (q, J=7.1 Hz, 1H), 4.18 (dt, J=12.6, 2.8 Hz, 1H), 4.08 (d, =10.0 Hz, 1H), 3.69 (dt, J=9.7, 7.4 Hz, 1H), 3.33 (m, 1H), 3.13 (td, J=12.3, 2.9 Hz, 1H), 2.93 (td, J=12.0, 3.3 Hz, 1H), 2.83 (s, 3H), 2.53 (s, 3H), 2.44 (m, 1H), 2.34 (m, 1H), 1.85 (m, 1H), 1.71 (m, 1H), 1.51 (d, J=7.3 Hz, 3H).

EXAMPLE 11

Compound 11

Methyl 2-({[3,5-bis(trifluoromethyl)phenyl]methyl}(methyl)carbamoyl)-7-methyl-1-(2-methylphenyl)-6-oxo-octahydropyrrolo{1,2-a}piperazine-7-carboxylate (Diastereomeric Mixture with ANTI Configuration at C1-C8a)

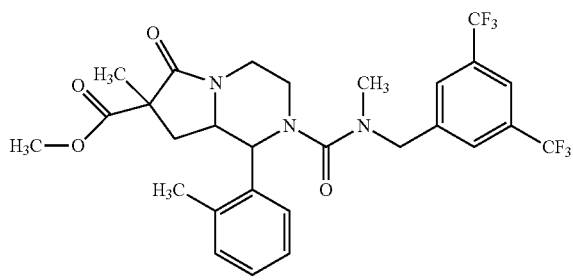 [SMILES: COC(=O)C1(C)CC2C(c3ccccc3C)N(C(=O)N(C)Cc3cc(C(F)(F)F)cc(C(F)(F)F)c3)CCN2C1=O]

Triphosgene (23.44 mg, 0.07 mmol) was dissolved in EtOAc (1 mL), the solution was cooled at 0° C. and a solution of Intermediate 17 (52 mg, 0.172 mmol) and TEA (40 μL, 0.46 mmol) in EtOAC (2 mL) was added. The resulting mixture was left stirring at this temperature for 2 h, then TEA (40 μL, 0.46 mmol) and Intermediate 18 (61.91 mg, 0.240 mmol) in EtOAc (2 mL) were added and the mixture was left stirring for 3 h. NaOH 1M was added to the mixture, the phases were separated and the organic layer was washed with HCl 1M and brine, dried aver Na$_2$SO$_4$ and concentrated in vacuo. The crude material was purified on SP1 (snap-NH cartridge, 11 g, CH/EtOAc 9:1 to 0:1 as eluent) to give the title compound as a white foam (70 mg). $^1$H NMR (500 MHz, CDCl$_3$) δ ppm 7.67 (s, 1H), 7.29 (s, 2H), 7.19 (s, 2H), 7.10 (s, 2H), 4.62 (d, 1H), 4.28 (d, 1H), 4.17 (d, 1H), 4.13 (dt, 1H), 3.73 (s, 3H), 3.68 (m, 1H), 3.30 (m, 1H), 3.12 (m, 1H), 2.96 (m, 1H), 2.89 (s, 3H), 2.17 (m, 1H), 1.69 (m, 1H), 1.31 (s, 2H). UPLC-MS: Rt=1.30 min; m/z (ES+): 586 [M+H]$^+$.

EXAMPLE 12

Compound 12

Methyl 2-({[3,5-bis(trifluoromethyl)phenyl]methyl}(methyl)carbamoyl)-7-methyl-1-(2-methylphenyl)-6-oxo-octahydropyrrolo{1,2-a}piperazine-7-carboxylate (Enantiomer 1 of Diastereoisomer 2, Single Isomer with ANTI Configuration at C1-C8a)

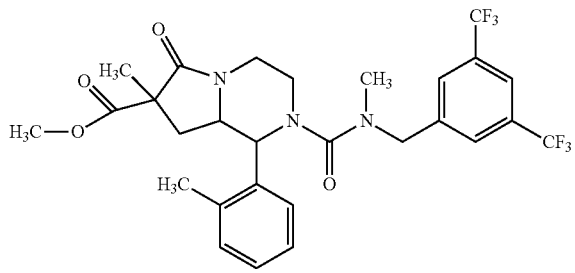 [SMILES: COC(=O)C1(C)CC2C(c3ccccc3C)N(C(=O)N(C)Cc3cc(C(F)(F)F)cc(C(F)(F)F)c3)CCN2C1=O]

Compound 11 was separated by chiral preparative chromatography obtaining the title compound (Compound 12, 19.5 mg). Column: Chiralpak IC (25×0.46 cm), 5μ Mobile phase: n-Hexane/Ethanol 70/30 v/v Flow rate: 0.8 mL/min Detection: DAD at 220 nm; Rt=10.3 min. $^1$H NMR (500 MHz, CDCL$_3$) δ ppm 7.75 (s, 1H), 7.37 (s, 2H), 7.27 (s, 1H), 7.18 (m, 3H), 4.70 (d, J=14.7 Hz, 1H), 4.36 (d, J=16.0 Hz, 1H), 4.25 (d, J=10.0 Hz, 1H), 4.20 (m, 1H), 3.81 (s, 3H), 3.76 (m, 1H), 3.38 (m, 1H), 3.20 (td, J=13.0, 3.5 Hz, 1H), 3.03 (td, J=12.0, 3.2 Hz, 1H), 2.97 (s, 3H), 2.53 (s, 3H), 2.25 (dd, J=13.7, 6.6 Hz, 1H), 1.78 (dd, J=13.2, 8.1 Hz, 1H), 1.39 (s, 3H).

EXAMPLE 13

Compound 13

Methyl 2-({[3,5-bis(trifluoromethyl)phenyl]methyl}(methyl)carbamoyl)-7-methyl-1-(2-methyl phenyl)-6-oxo-octahydropyrrolo{1,2-a}piperazine-7-carboxylate (Enantiomer 2 of Diastereoisomer 1, Single Isomer with ANTI Configuration at C1-C8a)

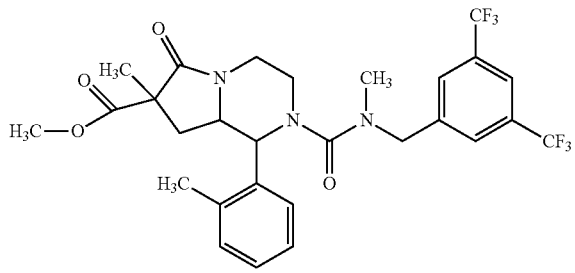 [SMILES: COC(=O)C1(C)CC2C(c3ccccc3C)N(C(=O)N(C)Cc3cc(C(F)(F)F)cc(C(F)(F)F)c3)CCN2C1=O]

Compound 11 was separated by chiral preparative chromatography obtaining the title compound (Compound 13, 5.8 mg). Column: Chiralpak IC (25×0.46 cm), 5μ Mobile phase: n-Hexane/Ethanol 70/30 v/v Flow rate: 0.8 mL/min Detection: DAD at 220 nm; Rt=11.8 min. $^1$H NMR (500 MHz, CDCl$_3$) δ ppm 7.75 (s, 1H), 7.37 (s, 2H), 7.27 (s, 2H), 7.17 (s, 2H), 4.69 (d, J=14.9 Hz, 1H), 4.36 (d, J=15.9 Hz, 1), 4.18 (m, 1H), 4.04 (d, J=9.8 Hz, 1H), 3.85 (q, J=8.3 Hz, 1H), 3.68 (s, 3H), 3.41 (m, 1H), 3.24 (td, J=10.8, 3.4 Hz, 1H), 3.00 (dd, J=12.2, 3.7 Hz, 1H), 2.97 (s, 3H), 2.52 (s, 3H), 2.33 (dd, J=13.0, 6.4 Hz, 1H), 1.59 (m, 1H), 1.51 (s, 3H).

EXAMPLE 14

Compound 14

Methyl 2-({[3,5-bis(trifluoromethyl)phenyl]methyl}(methyl)carbamoyl)-7-methyl-1-(2-methylphenyl)-6-oxo-octahydropyrrolo{1,2-a}piperazine-7-carboxylate (Enantiomer 2 of Diastereoisomer 2, Single Isomer with ANTI Configuration at C1-C8a)

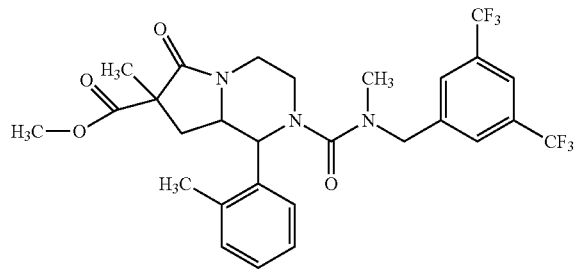 [SMILES: COC(=O)C1(C)CC2C(c3ccccc3C)N(C(=O)N(C)Cc3cc(C(F)(F)F)cc(C(F)(F)F)c3)CCN2C1=O]

Compound 11 was separated by chiral preparative chromatography obtaining the title compound (Compound 14, 19 mg). Column: Chiralpak IC (25×0.46 cm), 5μ Mobile phase: n-Hexane/Ethanol 70/30 v/v Flow rate: 0.8 mL/min Detection: DAD at 220 nm; Rt=26.4 min. $^1$H NMR (500 MHz, CDCl$_3$) δ ppm 7.74 (m, 1H), 7.37 (s, 2H), 7.25 (m, 2H), 7.18 (s, 2H), 4.70 (d, J=15.4 Hz, 1H), 4.36 (d, J=15.2 Hz, 1H), 4.25 (d, J=10.0 Hz, 1H), 4.20 (m, 1H), 3.81 (s, 3H), 3.76 (m, 1H), 3.38 (m, 1H), 3.20 (td, J=12.4, 3.4 Hz, 1H), 3.03 (td, J=12.0, 3.2 Hz, 1H), 2.97 (s, 3H), 2.53 (s, 3H), 2.25 (dd, J=13.4, 6.8 Hz, 1H), 1.78 (dd, J=13.5, 7.2 Hz, 1H), 1.39 (s, 3H).

EXAMPLE 15

Compound 15

Methyl 2-({[3,5-bis(trifluoromethyl)phenyl]methyl}(methyl)carbamoyl)-7-methyl-1-(2-methylphenyl)-6-oxo-octahydropyrrolo{1,2-a}piperazine-7-carboxylate (Enantiomer 1 of Diastereoisomer 1, Single Isomer with ANTI Configuration at C1-C8a)

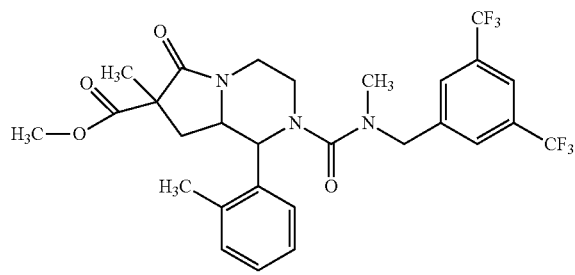 [SMILES: COC(=O)C1(C)CC2C(c3ccccc3C)N(C(=O)N(C)Cc3cc(C(F)(F)F)cc(C(F)(F)F)c3)CCN2C1=O]

Compound 11 was separated by chiral preparative chromatography obtaining the title compound (Compound 15, 2.7 mg). Column: Chiralpak IC (25×0.46 cm), 5μ Mobile phase: n-Hexane/Ethanol 70/30 v/v Flow rate: 0.8 mL/min. Detection: DAD at 220 nm; Rt=9.1 min. $^1$H NMR (500 MHz, CDCl$_3$) δ ppm 7.75 (s, 1H), 7.37 (s, 2), 7.28 (m, 2H), 7.17 (m, 2H), 4.69 (d, J=15.7 Hz, 1H), 4.36 (d, J=15.7 Hz, 1H), 4.17 (m, 1H), 4.04 (d, J=10.0 Hz, 1H), 3.85 (q, J=8.8 Hz, 1H), 3.68 (s, 3H), 3.40 (m, 1H), 3.24 (td, J=12.5, 3.2 Hz, 1H), 3.00 (dd, J=13.0, 2.9 Hz, 2H), 2.97 (s, 3H), 2.53 (m, 3H), 2.33 (dd, J=13.2, 6.8 Hz, 1H), 1.59 (d, J=8.1 Hz, 1H), 1.51 (s, 3H).

EXAMPLE 16

Compound 16

N-{[3,5-bis(trifluoromethyl)phenyl]methyl}-N-methyl-1-(2-methylphenyl)-6-oxo-octahydropyrrolo[1,2-a]piperazine-2-carboxamide (Racemic Mixture with ANTI Configuration at C1-C8a)

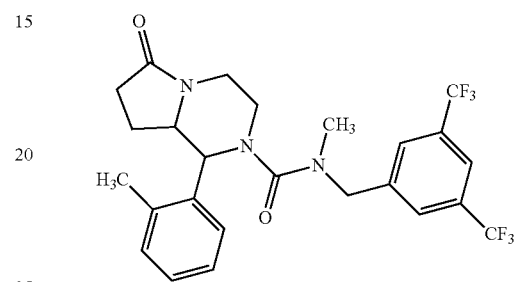

Triphosgene (30.7 mg, 0.09 mmol) was dissolved in EtOAc (1 mL). The solution was cooled to 0° C. and a solution of Intermediate 13 (51.8 mg, 0.22 mmol) in EtOAc (1 mL) and TEA (50 μL, 0.6 mmol) were added. The reaction mixture was stirred at this temperature for 2 h, then EtOAc (2 mL), TEA (50 μL) and Intermediate 18 (81 mg, 0.31 mmol) were added. The reaction was stirred at 25° C. for 2 h, then NaOH 1M was added and the organic layer was washed with water, dried over sodium sulphate, filtered and concentrated in vacuo to give a crude that was purified on SP1 (snap cartridge, 10 g, CH/EtOAc 7:3 to DCM/MeOH 9:1 as eluent) to give the title compound (57 mg). $^1$H NMR (600 MHz, DMSO-d6) δ ppm 7.93 (s, 1H), 7.57 (s, 2H), 7.30 (dd, 1H), 7.07 (m, 3H), 4.55 (d, 1H), 4.46 (d, 1H), 3.96 (d, 1H), 3.85 (dt, 1H), 3.66 (dt, 1H), 3.44 (dt, 1H), 3.12 (m, 1H), 2.86 (s, 3H), 2.73 (td, 1H), 2.40 (s, 3H), 2.20 (m, 2H), 1.62 (m, 1H), 1.52 (m, 1H). HPLC-MS: Rt=1.25 min; m/z (ES+): 514.3 [M+H]$^+$.

EXAMPLE 17

Compound 17

N-{[3,5-bis(trifluoromethyl)phenyl]methyl}-N-methyl-1-(2-methylphenyl)-6-oxo-octahydropyrrolo[1,2-a]piperazine-2-carboxamide (Enantiomer 1, Single Isomer with ANTI Configuration at C1-C8a)

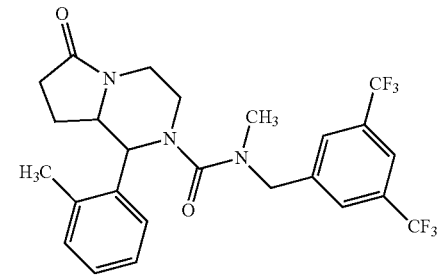 [SMILES: Cc1ccccc1C1C2CCC(=O)N2CCN1C(=O)N(C)Cc1cc(C(F)(F)F)cc(C(F)(F)F)c1]

Separation by chiral chromatography of Compound 16, from the above described experimental, provided 20.8 mg of the title compound (enantiomer 1). ¹H NMR (500 MHz, CDCl₃) δ ppm 7.74 (s, 1H), 7.37 (s, 2H), 7.26 (m, 1H), 7.15 (m, 3H), 4.69 (d, 1H), 4.36 (d, 1H), 4.18 (dt, 1H), 4.09 (d, 1H), 3.73 (m, 1H), 3.37 (m, 1H), 3.15 (m, 1H), 2.96 (s, 3H), 2.96 (m, 1H), 2.53 (s, 3H), 2.44 (m, 1H), 2.35 (m, 1H), 1.87 (dddd, 1H), 1.69 (m, 1H). Chiral HPLC: Rt=15.3 min.

EXAMPLE 18

Compound 18

N-{[3,5-bis(trifluoromethyl)phenyl]methyl}-N-methyl-1-(2-methylphenyl)-6-oxo-octahydropyrrolo[1,2-a]piperazine-2-carboxamide (Enantiomer 2, Single Isomer with ANTI Configuration at C1-C8a)

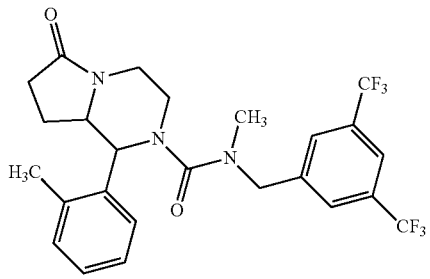 [SMILES: Cc1ccccc1C1C2CCC(=O)N2CCN1C(=O)N(C)Cc1cc(C(F)(F)F)cc(C(F)(F)F)c1]

Separation by chiral chromatography of Compound 16, from the above described experimental, provided 19.6 mg of the title compound (enantiomer 2). ¹H NMR (500 MHz, CDCl₃) δ ppm 7.74 (s, 1H), 7.37 (s, 2H), 7.26 (m, 1H), 7.16 (m, 3H), 4.69 (d, 1H), 4.36 (d, 1H), 4.18 (dt, 1H), 4.09 (d, 1H), 3.73 (dt, 1H), 3.37 (dt, 1H), 3.15 (td, 1H), 2.96 (s, 3H), 2.96 (m, 1H), 2.53 (s, 3H), 2.44 (m, 1H), 2.35 (m, 1H), 1.87 (dddd, 1H), 1.69 (m, 1H). Chiral HPLC: Rt=20.8 min.

EXAMPLE 19

Compound 19

N-{[3,5-bis(trifluoromethyl)phenyl]methyl}-7-(hydroxymethyl)-N-methyl-1-(2-methylphenyl)-6-oxo-octahydropyrrolo[1,2-a]piperazine-2-carboxamide (Enantiomer 1 of Diastereoisomer 1, Single Isomer with ANTI Configuration at C1-C8a)

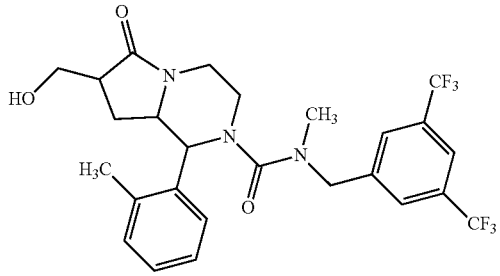 [SMILES: Cc1ccccc1C1C2CC(CO)C(=O)N2CCN1C(=O)N(C)Cc1cc(C(F)(F)F)cc(C(F)(F)F)c1]

To a stirred solution of Intermediate 21 (59 mg, 0.1 mmol) in MeOH (3 mL) was added calcium chloride (17 mg, 0.15 mmol). The resulting suspension was cooled to 0° C. and sodium borohydride (12 mg, 0.31 mmol) was added. The reaction mixture was stirred at 25° C. for 2 h, then HCl 1M and DCM were added. The aqueous layer was extracted several times with DCM and the combined organic layers were filtered through a phase separator and concentrated in vacuo to give a crude (45 mg) which was subjected to chiral preparative HPLC. Compound 19 (13 mg) was then isolated as single enantiomer. Column: Chiralpak AD-H (25×0.46 cm), 5μ Mobile phase: n-Hexane/2-Propanol 90/10 v/v Flow rate: 1 mL/min Detection: DAD at 220 nm. Rt=9.4 min. ¹H NMR (500 MHz, CDCl₃) δ ppm 7.75 (s, 1H), 7.37 (s, 2H), 7.22 (m, 4H), 4.69 (d, 1H), 4.36 (d, 1H), 4.17 (dt, 1H), 4.10 (d, 1H), 3.95 (br. s, 1H), 3.73 (m, 2H), 3.40 (dt, 1H), 3.17 (td, 1H), 3.00 (td, 1H), 2.96 (s, 3H), 2.63 (spt, 1H), 2.53 (s, 3H), 1.96 (ddd, 1H), 1.55 (m, 1H). UPLC-MS: Rt=1.15 min; m/z (ES+): 544.28 [M+H]⁺.

EXAMPLE 20

Compound 20

N-{[3,5-bis(trifluoromethyl)phenyl]methyl}-7-(hydroxymethyl)-N-methyl-1-(2-methylphenyl)-6-oxo-octahydropyrrolo[1,2-a]piperazine-2-carboxamide (Enantiomer 1 of Diastereoisomer 2, Single Isomer with ANTI Configuration at C1-C8a)

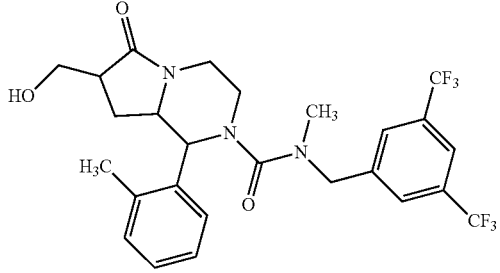 [SMILES: Cc1ccccc1C1C2CC(CO)C(=O)N2CCN1C(=O)N(C)Cc1cc(C(F)(F)F)cc(C(F)(F)F)c1]

From the same preparation where Compound 19 is described, Compound 20 (3.5 mg) was isolated as single enantiomer. UPLC-MS: Rt=1.14 min; m/z (ES+): 544.30 [M+H]⁺. Column: Chiralpak AD-H (25×0.46 cm), 5μ Mobile phase: n-Hexane/2-Propanol 90/10 v/v Flow rate: 1 mL/min Detection: DAD at 220 nm. Rt=12.4 min. ¹H NMR (500 MHz, CDCl₃) δ ppm 7.74 (s, 1H), 7.36 (s, 2H), 7.18 (m, 3H), 4.69 (d, 1H), 4.35 (d, 1H), 4.21 (ddd, 1H), 4.08 (d, 1H), 3.87 (dd, 1H), 3.77 (ddd, 1H), 3.67 (dd, 1H), 3.35 (ddd, 1H), 3.21 (td, 1H), 2.97 (s, 3H), 2.95 (td, 1H), 2.76 (dtd, 1H), 2.53 (s, 3H), 1.83 (ddd, 1H), 1.72 (ddd, 1H).

EXAMPLE 21

Compound 21

N-{[3,5-bis(trifluoromethyl)phenyl]methyl}-7-(hydroxymethyl)-N-methyl-1-(2-methylphenyl)-6-oxo-octahydropyrrolo[1,2-a]piperazine-2-carboxamide diastereomeric mixture of diastereoisomers (Mixture of Enantiomer 2 of Diastereoisomer 1 Plus Enantiomer 2 of Diastereoisomer 2, Single Isomer with ANTI Configuration at C1-C8a)

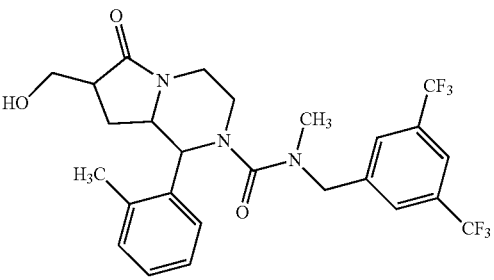 [SMILES: Cc1ccccc1C1C2CC(CO)C(=O)N2CCN1C(=O)N(C)Cc1cc(C(F)(F)F)cc(C(F)(F)F)c1]

From the same preparation where Compound 19 is described, Compound 21 (17.6 mg) was isolated. UPLC-MS: Rt=1.13; m/z (ES): 544.33 [M+H]+; Rt=1.14; m/z (ES+): 544.30 [M+H]+. Column: Chiralpak AD-H (25×0.46 cm), 5μ Mobile phase: n-Hexane/2-Propanol 90/10 v/v. Flow rate: 1 mL/min. Detection: DAD at 220 nm. Rt=16.1 min and 16.8 min.

EXAMPLE 22

Compound 22

N-{[3,5-bis(trifluoromethyl)phenyl]methyl}-7-(hydroxymethyl)-N-methyl-1-(2-methylphenyl)-6-oxo-octahydropyrrolo[1,2-a]piperazine-2-carboxamide (Single Isomer, Enantiomer 2 of Diastereoisomer 1 in Compound 21)

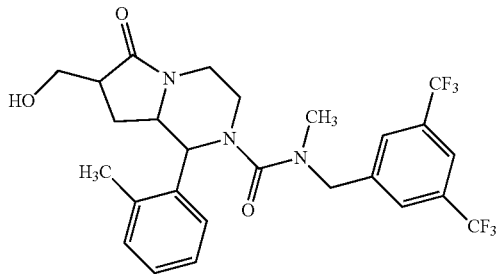 [SMILES: Cc1ccccc1C1C2CC(CO)C(=O)N2CCN1C(=O)N(C)Cc1cc(C(F)(F)F)cc(C(F)(F)F)c1]

Separation by chiral chromatography of Compound 21 provided 9.5 mg of Compound 22 (enantiomer 1). 1H NMR (500 MHz, CDCl3) δ ppm 7.75 (s, 1H), 7.37 (s, 2H), 7.22 (m, 4H), 4.69 (d, 1H), 4.36 (d, 1H), 4.17 (dt, 1H), 4.11 (d, 1H), 3.73 (m, 2H), 3.40 (ddd, 1H), 3.17 (m, 1H), 3.00 (td, 4H), 2.96 (s, 3H), 2.63 (m, 1H), 2.53 (s, 3H), 1.96 (ddd, 1H), 1.55 (m, 1H). Column: Chiralpak AS-H (25×0.46 cm), 5μ Mobile phase: n-Hexane/Ethanol 90/10 v/v Flow rate: 1 mL/min Detection: DAD at 220 nm. Rt=10.4 min.

EXAMPLE 23

Compound 23

N-{[3,5-bis(trifluoromethyl)phenyl]methyl}-7-(hydroxymethyl)-N-methyl-1-(2-methylphenyl)-6-oxo-octahydropyrrolo[1,2-a]piperazine-2-carboxamide (Single Isomer, Enantiomer 2 of Diastereoisomer 2 in Compound 21)

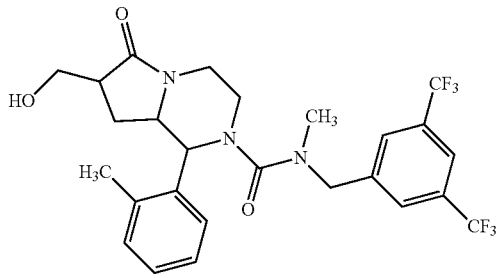 [SMILES: Cc1ccccc1C1C2CC(CO)C(=O)N2CCN1C(=O)N(C)Cc1cc(C(F)(F)F)cc(C(F)(F)F)c1]

Separation by chiral chromatography of Compound 21 provided 2.5 mg of Compound 23 (enantiomer 2). Column: Chiralpak AS-H (25×0.46 cm), 5μ Mobile phase: n-Hexane/Ethanol 90/10 v/v Flow rate: 1 mL/min Detection: DAD at 220 nm. Rt=14.7 min. 1H NMR (500 MHz, CDCl3) δ ppm 7.74 (s, 1H), 7.36 (s, 2H), 7.18 (m, 3H), 4.69 (d, 1H), 4.35 (d, 1H), 4.21 (ddd, 1H), 4.08 (d, 1H), 3.87 (dd, 1H), 3.77 (ddd, 1H), 3.67 (dd, 1H), 3.35 (ddd, 1H), 3.21 (td, 1H), 2.97 (s, 3H), 2.95 (td, 1H), 2.76 (dtd, 1H), 2.53 (s, 3H), 1.83 (ddd, 1H), 1.72 (ddd, 1H).

EXAMPLE 24

Compound 24

N-{[3,5-bis(trifluoromethyl)phenyl]methyl}-N-methyl-1-(2-methylphenyl)-octahydropyrrolo[1,2-a]piperazine-2-carboxamide (Mixture of Enantiomers, with ANTI Configuration at C1-C8a)

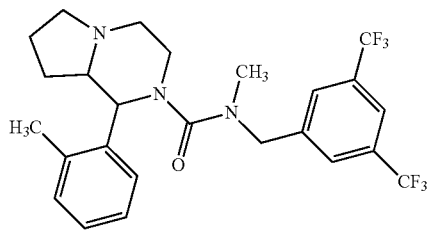 [SMILES: Cc1ccccc1C1C2CCCN2CCN1C(=O)N(C)Cc1cc(C(F)(F)F)cc(C(F)(F)F)c1]

Triphosgene (30 mg, 0.088 mmol) was dissolved in EtOAc (1 mL). The solution was cooled to 0° C. and a solution of Intermediate 23 (48 mg, 0.22 mmol) in EtOAc (2 mL) and TEA (100 μL) were added. The reaction mixture was stirred for 1.5 h, then Intermediate 3 (80 mg, 0.3 mmol) in EtOAc (2 mL) and TEA (50 μL) were added. The reaction was stirred at 25° C. for 2 h. To the mixture was added NaOH 1M and the organic layer was dried over sodium sulphate, filtered and concentrated in vacuo. The crude was purified by SP1 (SNAP-NH cartridge, 11 g, CH/EtOAc 9:1 to EtOAc as eluent), to give the title compound (50 mg). 1H NMR (400 MHz, CDCl3) δ ppm 7.73 (br, 1H), 7.41 (br, 2H), 7.26-7.24 (m, 1H), 7.15-7.07 (m, 3H), 4.63 (d, 1H), 4.46 (d, 1H), 4.27 (d, 1H), 3.42-3.36 (m, 1H), 3.20-3.12 (m, 3H), 2.93 (s, 3H), 2.52 (s, 3H), 2.51-2.44 (m, 1H), 2.25-2.10 (m, 2H), 1.88-1.75 (m, 1H), 1.66-1.48 (m, 2H), 1.44-1.34 (m, 1H). UPLC-MS: Rt=0.90 min; m/z (ES+): 500.33 [M+H]+.

EXAMPLE 25

Compound 25

2-N-{[3,5-bis(trifluoromethyl)phenyl]methyl}-2-N,7-N,7-N,7-tetramethyl-1-(2-methylphenyl)-6-oxo-octahydropyrrolo[1,2-a]piperazine-2,7-dicarboxamide (Pure Enantiomer, with ANTI Configuration at C1-C8a)

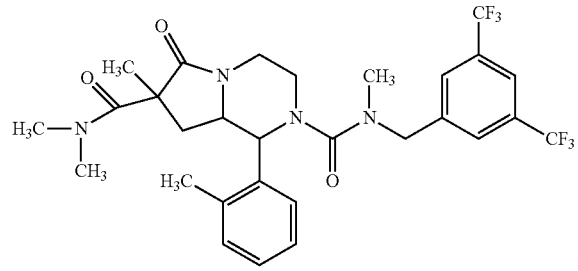 [SMILES: Cc1ccccc1C1C2CC(C)(C(=O)N(C)C)C(=O)N2CCN1C(=O)N(C)Cc1cc(C(F)(F)F)cc(C(F)(F)F)c1]

A solution of Compound 8 (13 mg, 0.023 mmol), in DCM (1 mL), was added to a solution of EDCI.HCl (8.62 mg, 0.045 mmol) and HOBT.H$_2$O (6.1 mg, 0.045 mmol) in DCM (2 mL). To this stirring mixture was added a solution of (CH$_3$)$_2$NH.HCl (3 mg, 0.034 mmol) and TEA (12.7 mL, 0.091 mmol) in 1 mL of DCM. The reaction was left stirring at RT for 2 h, then the mixture was diluted with DCM, water was added and the phases were separated. The organic layer was washed with HCl 1M, then an aqueous saturated solution of NaHCO$_3$ and brine. The organic layer was filtered through a phase separator and the solvent was evaporated. The crude was purified by flash chromatography (SNAP 10 g, eluting from CH/EtOAc 9:1 to EtOAc 100%). The fractions were collected and the solvent removed in vacuo to give the title compound (9 mg). UPLC-MS: Column: Acquity UPLC BEH C18 column; m/z (ES+): 599.3 [M+H]$^+$ Rt=1.2 min. $^1$H NMR (500 MHz, CDCl$_3$) δ ppm 7.75 (s, 1H), 7.37 (s, 2H), 7.29 (s, 2H), 7.18 (m, 2H), 4.69 (d, J=15.4 Hz, 1H), 4.38 (d, J=15.4 Hz, 1H), 4.19 (m, 2H), 3.75 (q, J=7.8 Hz, 1H), 3.42 (dt, J=11.7, 2.9 Hz, 1H), 3.18 (td, J=12.5, 3.7 Hz, 1H), 3.06 (br s, 6H), 3.00 (m, 4H), 2.53 (s, 3H), 2.13 (dd, J=12.7, 9.5 Hz, 1H), 1.77 (dd, J=13.4, 7.1 Hz, 1H), 1.39 (s, 3H).

EXAMPLE 26

Compound 26

2-N-{[3,5-bis(trifluoromethyl)phenyl]methyl}-2-N,7-N,7-N,7-tetramethyl-1-(2-methylphenyl)-6-oxo-octahydropyrrolo[1,2-a]piperazine-2,7-dicarboxamide (Pure Enantiomer, with ANTI Configuration at C1-C8a)

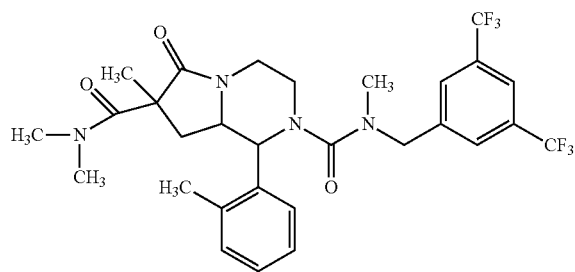 [SMILES: Cc1ccccc1C1C2CC(C)(C(=O)N(C)C)C(=O)N2CCN1C(=O)N(C)Cc1cc(C(F)(F)F)cc(C(F)(F)F)c1]

A solution of Compound 8 (12 mg, 0.021 mmol), in DCM (1 mL), was added to a solution of EDCI.HCl (8 mg, 0.042 mmol) and HOBT.H$_2$O (5.6 mg, 0.042 mmol) in DCM (2 mL). To this stirring mixture was added a solution of (CH$_3$)$_2$NH.HCl (2.6 mg, 0.031 mmol) and TEA (11.7 mL, 0.083 mmol) in 1 mL of DCM. The reaction was left stirring at RT for 2 h, then the mixture was diluted with DCM, water was added and the phases were separated. The organic layer was washed with HCl 1M, then an aqueous saturated solution of NaHCO$_3$ and brine. The organic layer was filtered through a phase separator and the solvent was evaporated. The crude was purified by flash chromatography (SNAP 10 g, eluting from CH/EtOAc 9:1 to EtOAc 100% to DCM/EtOAc 9:1). The fractions were collected and the solvent removed in vacuo to give the title compound (9 mg). UPLC-MS: Column: Acquity UPLC BEH C18 column; m/z (ES+): 599.3 [M+H]$^+$ Rt=1.19 min. 1H NMR (500 MHz, CDCl$_3$)) δ ppm 7.75 (s, 1H), 7.37 (s, 2H), 7.28 (m, 2H), 7.18 (m, 2H), 4.69 (d, J=15.4 Hz, 1H), 4.37 (d, J=14.9 Hz, 1H), 4.19 (m, 2H), 3.75 (q, J=7.8 Hz, 1H), 3.42 (dt, J=11.0, 0.5 Hz, 1H), 3.18 (td, J=11.5, 2.9 Hz, 1H), 3.06 (br s, 6H), 3.00 (m, 4H), 2.52 (s, 3H), 2.13 (dd, J=12.7, 8.8 Hz, 1H), 1.77 (dd, J=13.2, 6.8 Hz, 1H), 1.39 (s, 3H).

EXAMPLE 27

Compound 27

N-{[3,5-bis(trifluoromethyl)phenyl]methyl}-7-(hydroxymethyl)-N-methyl-1-(2-methylphenyl)-octahydropyrrolo[1,2-a]piperazine-2-carboxamide; methanesulfonic acid salt (Enantiomer 1, Single Enantiomer with ANTI Configuration at C1-C8a)

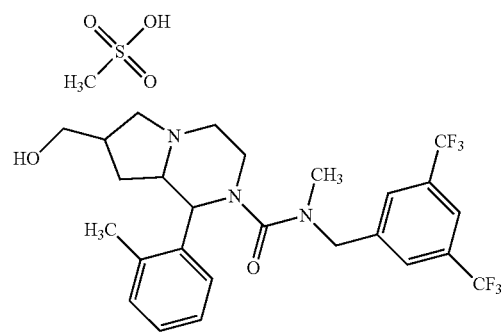

Intermediate 26 (270 mg, 0.5 mmol), was dissolved in dry THF (20 mL) at 0° C., BH$_3$.Me$_2$S (2M in THF) (1 mL), was added dropwise. The reaction mixture was stirred at RT for 16 h. BH$_3$.Me$_2$S (2 M in THF) (1 mL) was added again and the reaction was left stirring at RT for a further 8 h. HCl (1M) (2 mL) and MeOH (2 mL) were then added and the reaction mixture was stirred overnight. The reaction mixture was concentrated in vacuo, DCM (20 mL) was added followed by a aqueous saturated solution of NaHCO$_3$ (30 mL). The organic layer was dried over sodium sulphate, filtered and evaporated in vacuo to give a colourless oil (210 mg) which was subjected to chiral prep. HPLC. Column Chiralpak AD-H (25×0.46 cm), 5 um; Mobile phase: n-Hexane/2-Propanol 90/10% v/v; Flow rate (ml/min): 1.0; DAD detection: 220 nm; Loop: 20 μL; enantiomer 1: 50% a/a by UV (5.9 min); enantiomer 2: 50% a/a by UV (12.2 min). Thus, two fractions were recovered (fraction 1 containing the first eluting enantiomer, enantiomer 1, 95 mg) and fraction 2 (containing the second eluting enantiomer: enantiomer 2, 105 mg, described below). Fraction 1 (95 mg, 0.18 mmol) was dissolved in THF (3 mL) and a solution of methanesulfonic acid (11.7 mL, 0.18 mmol) in dry THF (1 mL) was added at 0° C. and the reaction mixture was stirred 30' at this temperature. The solvents were evaporated in vacuo to give 102 mg of a white solid. UPLC/MS (ES+/ES−) 2.0 Minute; Method: LC/MS System: Acquity UPLC coupled with SQD mass spectrometer: LC/MS Conditions: Column: Acquity UPLC BEH C18 column. MS Conditions: Ionisation mode: alternate Positive/Negative Electrospray (ES+/ES−); Rt=1.22 min a/a. m/z (ES+): 530 [M+H]$^+$. $^1$H NMR (500 MHz, CDCl$_3$) δ ppm 10.59 (br. s, 1H), 7.67 (s, 1H), 7.27 (s, 2H), 7.09 (m, 4H), 4.70 (m, J=10.3 Hz, 2H), 4.14 (m, J=14.2 Hz, 2H), 4.02 (d, J=11.2 Hz, 1H), 3.61 (m, 3H), 3.46 (d, J=13.7 Hz, 1H), 3.23 (m, 1H), 2.99 (m, 2H), 2.87 (s, 3H), 2.81 (s, 3H), 2.49 (m, 1H), 2.46 (s, 3H), 1.75 (m, J=8.3, 2.9 Hz, 2H).

EXAMPLE 28

Compound 28

N-{[3,5-bis(trifluoromethyl)phenyl]methyl}-7-(hydroxymethyl)-N-methyl-1-(2-methylphenyl)-octahydropyrrolo[1,2-a]piperazine-2-carboxamide; methanesulfonic acid salt (Enantiomer 2, Single Enantiomer with ANTI Configuration at C1-C8a)

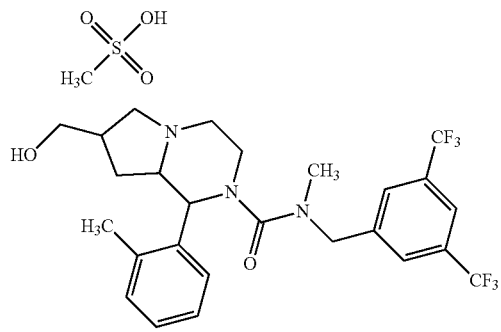

Fraction 2 (from the above described experimental), (105 mg, 0.2 mmol) containing the second eluting enantiomer, enantiomer 2, was dissolved in THF (3 mL) and a solution of methanesulfonic acid (13 mL, 0.18 mmol) in dry THF (1 mL) was added at 0° C. and the reaction mixture was stirred 30' at this temperature. The solvents were evaporated in vacuo to give 98 mg of a white solid. $^1$H NMR (500 MHz, CHLOROFORM-d) δ ppm 10.66 (br. s, 1H), 7.74 (s, 1H), 7.34 (s, 2H), 7.17 (m, 4H), 4.77 (m, J=10.3 Hz, 2H), 4.22 (m, J=14.2 Hz, 2H), 4.10 (d, J=11.2 Hz, 1H), 3.69 (m, 3H), 3.54 (d, J=13.7 Hz, 1H), 3.31 (m, 1H), 3.07 (m, 2H), 2.94 (s, 3H), 2.89 (s, 3H), 2.57 (m, 1H), 2.54 (s, 3H), 1.83 (m, J=8.3, 2.9 Hz, 2H) UPLC/MS Electrospray (ES+/ES−); Rt=1.22 min a/a. (ES+): 530.2 [M+H]$^+$.

EXAMPLE 29

Compound 29

N-{[3,5-bis(trifluoromethyl)phenyl]methyl}-N-methyl-1-(2-methylphenyl)-7-(morpholin-4-ylmethyl)-6-oxo-octahydropyrrolo[1,2-a]piperazine-2-carboxamide (Mixture of Enantiomer 2 of Diastereoisomer 1 Plus Enantiomer 2 of Diastereoisomer 2, Single Stereoisomer with ANTI Configuration at C1-C8a)

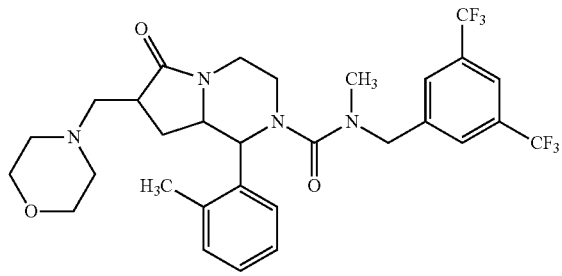 [SMILES: Cc1ccccc1C1C2CC(CN3CCOCC3)C(=O)N2CCN1C(=O)N(C)Cc1cc(C(F)(F)F)cc(C(F)(F)F)c1]

A solution of Intermediate 33 (68 mg, 0.109 mmol) and morpholine (96 μL, 1.09 mmol) in dry THF (1.5 mL) was heated at 65° C. under stirring for 48 h. The solvent was removed in vacuo and the residue was dissolved in EtOAc (10 mL) and washed with saturated NaHCO$_3$ (3×5 mL). The organic layer was dried over Na$_2$SO$_4$, filtered and concentrated in vacuo. The residue was dissolved in 1 mL of meOH and filtered through a SCX cartridge (Strata-SCX, 100 mg, Phenomenex, eluting with ammonia 2M solution in MeOH). Concentration of opportune fractions provided 29 mg of a crude which was purified by preparative HPLC.LC/MS System: Fractionlynx (Waters) with ZQ MS detector. UV Conditions: UV detection range: 210 nm to 350 nm; Acquisition rate: 1.0 spectra/s; MS Conditions: Ionisation mode: Positive Electrospray (ES+); Scan Range: ES+100 to 900 AMU: Scan Duration: 0.50 seconds; Columns: XBridge Prep. C18 5 μm OBD (100 mm×19.0; mm) at RT; 9 mg of the title compound were recovered as a 75:25 mixture of diastereoisomers. $^1$H NMR (400 MHz, CDCl$_3$) δ ppm 7.74 (br s), 7.37 (br s), 7.27-7.10 (m), 4.68 (d), 4.40-4.33 (m), 4.22-4.15 (m), 4.06 (d), 3.80-3.60 (m), 3.40-3.30 (m), 3.20-3.10 (m), 3.00-2.90 (m), 2.88-2.80 (m), 2.75-2.30 (m), 2.05-1.95 (m), 1.92-1.75 (m), 1.70-1.60 (m) UPLC-MS: Rt=1.22; m/z (ES+): 613 [M+H]$^+$; Rt=1.23; m/z (ES+): 613 [M+H]$^+$; Rt=1.24 min; m/z (ES+): 613 [M+H]$^+$.

EXAMPLE 30

Compound 30

N-{[3,5-bis(trifluoromethyl)phenyl]methyl}-N-methyl-1-(2-methylphenyl)-6-oxo-7-(pyrrolidin-1-ylmethyl)-octahydropyrrolo[1,2-a]piperazine-2-carboxamide (Diastereoisomer 1, ANTI Stereochemistry at C1-C8a, ANTI Stereochemistry at C1-C7)

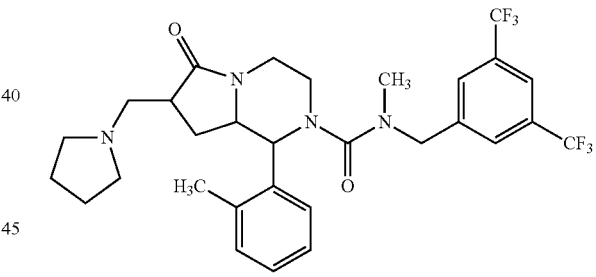

A solution of Intermediate 33 (97 mg, 0.156 mmol0 and pyrrolidine (130 μL, 1.56 mmol) in dry THF (2 mL) was heated at 65° C. under stirring for 20 h. Solvent was removed in vacuo and the residue was dissolved in EtOAc and washed with saturated NaHCO$_3$ solution (3×5 mL). the organic layer was dried over Na$_2$SO$_4$, filtered and concentrated in vacuo. The residue was dissolved in 1 mL of MeOH and filtered through a SCX (Phenomenex, 2000 mg). Elution with only MeOH provided a first fraction which was subjected to preparative HPLC: Column: X-Bridge Prep C-18 (19×100 mm), 5μ; Mobile phase Amm Bicarbonate, pH=10/Acn 65/35% v/v->25/75 in 10 min; Flow rate (ml/min) 17 mL/min; DAD detection 220 nm; Loop 1000 μL; Total amount 40 mg; Solubilization 40 mg/mL in 3 mL Acn=13.3 mg/mL; Rt=9.36 min to provide a crude which was further purified as follows: elution with solution of ammonia 2M in MeOH, gave a fraction which was further purified by preparative HPLC. Column: BEH C-18 (2.1×50 mm), 1.7 um; Mobile phase: Amm.Bicarbonate, pH=10/Acn 97/3% v/v->0/100 in 1.5 min; Flow rate (mL/min): 1.0; DAD detection: 210-350 nm;

Loop: 20 μL; diastereoisomer 1, 21.8% ee (1.33 min); diastereoisomer 2, 41% ee (1.38 min). After evaporation of the two fractions obtained, two products were obtained: isomer 1 (Compound 30) and isomer 2 (Compound 31, described below). Compound 30 (16 mg): $^1$H NMR (400 MHz, CDCl$_3$) δ ppm 7.66 (s, 1H), 7.29 (s, 2H), 7.07 (m, 3H), 4.60 (d, J=15.3 Hz, 1H), 4.29 (d, J=15.3 Hz, 1H), 4.08 (dt, J=12.9, 2.7 Hz, 1H), 3.99 (d, Hz, 1H), 3.58 (dt, J=9.8, 7.8 Hz, 1H), 3.30 (dt, J=11.7, 2.7 Hz, 1H), 3.07 (td, J=12.3, 3.1 Hz, 1H), 2.89 (m, 5H), 2.48 (m, 9H), 1.99 (dt, J=13.1, 7.7 Hz, 1H), 1.62 (m, 5H). UPLC-MS: Rt=1.31 min; m/z (ES+): 597.3 [M+H]$^+$

EXAMPLE 31

Compound 31

N-{[3,5-bis(trifluoromethyl)phenyl]methyl}-N-methyl-1-(2-methylphenyl)-6-oxo-7-(pyrrolidin-1-ylmethyl)-octahydropyrrolo[1,2-a]piperazine-2-carboxamide (Diastereoisomer 2, ANTI Stereochemistry at C1-C8a, SYN Stereochemistry at C1-C7)

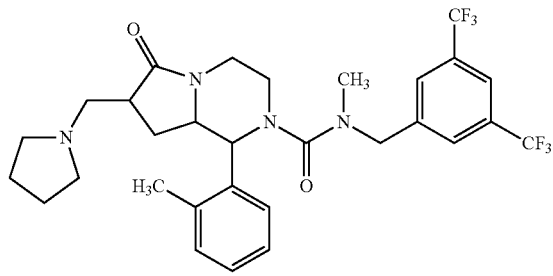 [SMILES: Cc1ccccc1C1C2CC(CN3CCCC3)C(=O)N2CCN1C(=O)N(C)Cc1cc(C(F)(F)F)cc(C(F)(F)F)c1]

After evaporation of fraction collected by preparative HPLC from the above described experimental, Compound 31 was obtained (5 mg). $^1$H NMR (400 MHz, CDCl$_3$) δ ppm 7.74 (s, 1H), 7.37 (s, 2H), 7.15 (m, 3H), 4.67 (d, J=15.7 Hz, 1H), 4.36 (d, J=15.7 Hz, 1H), 4.20 (dt, J=12.9, 2.7 Hz, 1H), 4.06 (d, J=10.2 Hz, 1H), 3.74 (ddd, J=9.4, 8.2, 5.9 Hz, 1H), 3.33 (dt, J=12.1, 2.3 Hz, 1H), 3.15 (td, J=12.9, 3.5 Hz, 1H), 2.95 (m, 4H), 2.73 (m, 2H), 2.52 (m, 8H), 1.87 (m, 2H), 1.74 (m, 4H). UPLC-MS: Rt=1.33 min; m/z (ES+): 597.3 [M+H]$^+$.

EXAMPLE 32

Compound 32

N-{[3,5-bis(trifluoromethyl)phenyl]methyl}-N-methyl-7-methylidene-1-(2-methylphenyl)-6-oxo-octahydropyrrolo[1,2-a]piperazine-2-carboxamide (Pure Enantiomer, with ANTI Configuration at C1-C8a)

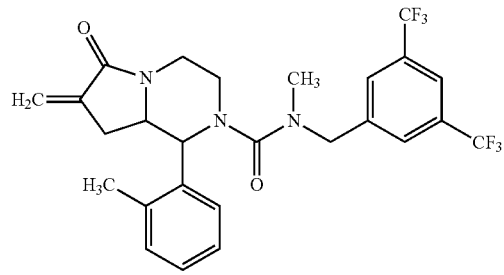 [SMILES: C=C1CC2C(c3ccccc3C)N(C(=O)N(C)Cc3cc(C(F)(F)F)cc(C(F)(F)F)c3)CCN2C1=O]

After evaporation of fraction collected by preparative HPLC, Compound 32 was obtained (5 mg). $^1$H NMR (400 MHz, CDCl$_3$) δ ppm 7.66 (s, 1H), 7.29 (s, 2H), 7.10 (m, 3H), 5.96 (t, 1H), 5.26 (t, 1H), 4.62 (d, 1H), 4.27 (d, 1H), 4.23 (dt, 1H), 3.97 (d, 1H), 3.71 (m, 1H), 3.31 (m, 1H), 3.17 (td, 1H), 2.92 (td, 1H), 2.89 (s, 3H), 2.51 (m, 1H), 2.44 (s, 3H), 2.29 (m, 1H). UPLC-MS: Rt=1.28 min; m/z (ES+): 526.2 [M+H]$^+$

EXAMPLE 33

Compound 33

N-{1-[3,5-bis(trifluoromethyl)phenyl]-3-hydroxypropyl}-7-(2-hydroxyethyl)-N-methyl-1-(2-methylphenyl)-6-oxo-octahydropyrrolo[1,2-a]piperazine-2-carboxamide (Mixture of Stereoisomers with ANTI Configuration at C1-C8a and SYN Configuration at C1-C7)

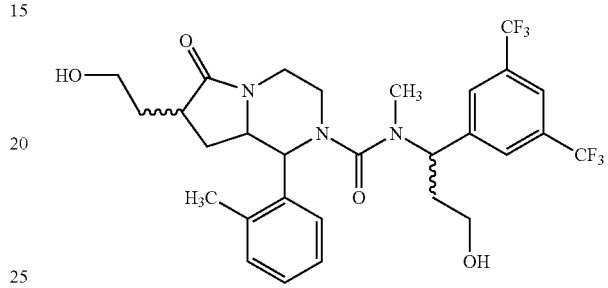

NaBH$_4$ (10 mg, 0.268 mmol) was added to an ice cooled solution of Intermediate 32 (80 mg, 0.134 mmol) in MeOH (5 mL), the resulting solution was stirred for 30 min. MeOH was evaporated in vacuo, the residue was dissolved with DCM and washed with NH$_4$Cl ss. The organic phase was filtered through a phase separator and the solvent was evaporated. The crude was purified by flash chromatography (SNAP 10 g, eluting from DCM 100% to DCM/MeOH 85:15). The fractions were collected and the solvent removed in vacuo to give the title compound as white solid (50 mg). $^1$H NMR (400 MHz, CDCl$_3$) δ ppm 7.68 (s, 1H), 7.29 (s, 2H), 7.12 (m, 5H), 5.57 (dd, J=11.3, 3.5 Hz, 1H), 4.13 (ddd, J=13.3, 3.1, 2.0 Hz, 1H), 3.98 (d, J=10.2 Hz, 1H), 3.70 (m, 4H), 3.38 (m, 1H), 3.43 (dd, J=6.7, 4.7 Hz, 1H), 3.22 (ddd, J=12.1, 3.5, 1.6 Hz, 1H), 3.10 (td, J=12.5, 3.9 Hz, 1H), 2.85 (td, J=12.1, 3.1 Hz, 1H), 2.69 (s, 3H), 2.64 (m, 1H), 2.43 (s, 3H), 2.08 (m, 1H), 1.95 (m, 1H), 1.80 (m, 2H), 1.59 (m, 2H) UPLC-MS: Rt=1.07 min; m/z (ES+): 602.3 [M+H]$^+$.

EXAMPLE 34

Compound 34

N-{1-[3,5-bis(trifluoromethyl)phenyl]-3-hydroxypropyl}-7-(2-hydroxyethyl)-N-methyl-1-(2-methylphenyl)-6-oxo-octahydropyrrolo[1,2-a]piperazine-2-carboxamide (Enantiomeric Pair with ANTI Configuration at C1-C8a and Syn Configuration at C1-C7)

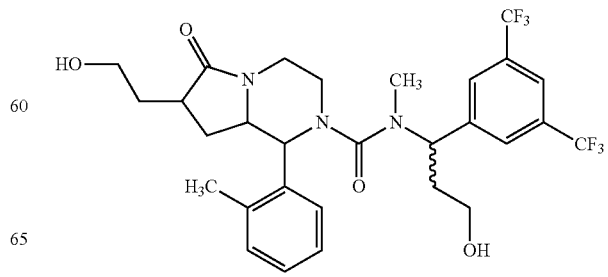

Separation by chiral chromatography of 22 mg of Compound 33 provided 5.3 mg of Compound 34 Column: Chiralcel OD-H (25×0.46 cm), 5μ Mobile phase: n-Hexane/Ethanol 90/10 v/v Flow rate: 1 mL/min Detection: DAD at 220 nm. Rt=25.1 min. $^1$H NMR (400 MHz, CDCl$_3$) δ ppm 7.68 (s, 1H), 7.29 (s, 2H), 7.12 (m, 5H), 5.57 (dd, J=11.3, 3.5 Hz, 1H), 4.13 (ddd, J=13.3, 3.1, 2.0 Hz, 1H), 3.98 (d, J=10.2 Hz, 1H), 3.70 (m, 4H), 3.38 (m, 1H), 3.43 (dd, J=6.7, 4.7 Hz, 1H), 3.22 (ddd, J=12.1, 3.5, 1.6 Hz, 1H), 3.10 (td, J=12.5, 3.9 Hz, 1H), 2.85 (td, J=12.1, 3.1 Hz, 1H), 2.69 (s, 3H), 2.64 (m, 1H), 2.43 (s, 3H), 2.08 (m, 1H), 1.95 (m, 1H), 1.80 (m, 2H), 1.59 (m, 2H).

EXAMPLE 35

Compound 35

N-{1-[3,5-bis(trifluoromethyl)phenyl]-3-hydroxypropyl}-7-(2-hydroxyethyl)-N-methyl-1-(2-methylphenyl)-6-oxo-octahydropyrrolo[1,2-a]piperazine-2-carboxamide (Enantiomeric Pair with ANTI Configuration at C1-C8a and Syn Configuration at C1-C7)

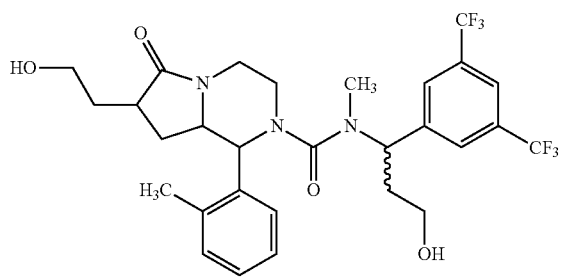 [SMILES: Cc1ccccc1C1C2CC(CCO)C(=O)N2CCN1C(=O)N(C)C(CCO)c1cc(C(F)(F)F)cc(C(F)(F)F)c1]

Separation by chiral chromatography of 22 mg of Compound 33 provided 7.2 mg of Compound 35. Column: Chiralcel OD-H (25×0.46 cm), 5μ Mobile phase: n-Hexane/Ethanol 90/10 v/v Flow rate: 1 mL/min Detection: DAD at 220 nm. Rt=32.8 min. $^1$H NMR (400 MHz, CDCl$_3$) δ ppm 7.68 (s, 1H), 7.29 (s, 2H), 7.12 (m, 5H), 5.57 (dd, J=11.3, 3.5 Hz, 1H), 4.13 (ddd, J=13.3, 3.1, 2.0 Hz, 1H), 3.98 (d, J=10.2 Hz, 1H), 3.70 (m, 4H), 3.38 (m, 1H), 3.43 (dd, J=6.7, 4.7 Hz, 1H), 3.22 (ddd, J=12.1, 3.5, 1.6 Hz, 1H), 3.10 (td, J=12.5, 3.9 Hz, 1H), 2.85 (td, J=12.1, 3.1 Hz, 1H), 2.69 (s, 3H), 2.64 (m, 1H), 2.43 (s, 3H), 2.08 (m, 1H), 1.95 (m, 1H), 1.80 (m, 2H), 1.59 (m, 2H).

EXAMPLE 36

Compound 36

N-{1-[3,5-bis(trifluoromethyl)phenyl]-3-hydroxypropyl}-7-(2-hydroxyethyl)-N-methyl-1-(2-methylphenyl)-octahydropyrrolo[1,2-a]piperazine-2-carboxamide (Mixture of Stereoisomers with ANTI Configuration at C1-C8a and SYN Configuration at C1-C7)

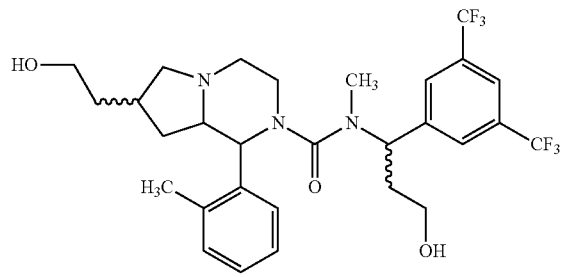 [SMILES: Cc1ccccc1C1C2CC(CCO)CN2CCN1C(=O)N(C)C(CCO)c1cc(C(F)(F)F)cc(C(F)(F)F)c1]

To a 0° C. cooled solution of Compound 33 (30 mg, 0.05 mmol) in THF (3 mL), a solution of borane dimethylsulfide complex 2M in THF (0.100 mL, 0.2 mmol) was added dropwise. The reaction mixture was stirred overnight at 25° C. MeOH (1 mL) and HCl 1N (1 ml) were carefully added and the reaction mixture was stirred at 25° C. for 2 h. HCl 1M was added and the mixture was stirred 6 h. The solution was evaporated and the crude material was charged the residue was filtered through an SCX cartridge eluting with NH$_3$ in MeOH 2M solution. The solvent was removed in vacuo to give the title compound as white solid (15 mg). $^1$H NMR (400 MHz, CD$_3$OD) δ ppm 7.78 (s, 1H), 7.55 (s, 2H), 7.23 (d, J=7.0 Hz, 1H), 7.05 (m, 3H), 5.50 (t, J=7.4 Hz, 1H), 4.30 (d, J=9.8 Hz, 1H), 3.53 (m, 6H), 3.08 (t, J=12.5 Hz, 1H), 2.90 (s, 3H), 2.74 (m, 1H), 2.59 (m, 1H), 2.48 (s, 3H), 2.34 (m, 1H), 2.17 (m, 3H), 1.81 (q, J=11.0 Hz, 1H), 1.50 (quin, J=6.7 Hz, 2H), 1.09 (m, 1H). HPLC-MS: Rt=1.14 min; m/z (ES+): 588.3 [M+H]$^+$.

EXAMPLE 37

Compound 37

7-[(4-acetylpiperazin-1-yl)methyl]-N-{[3,5-bis(trifluoromethyl)phenyl]methyl}-N-methyl-1-(2-methylphenyl)-6-oxo-octahydropyrrolo[1,2-a]piperazine-2-carboxamide (Diastereoisomeic Mixture with ANTI Configuration at C1-C8a)

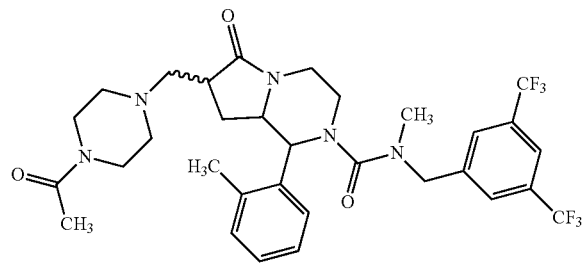 [SMILES: CC(=O)N1CCN(CC2CC3C(c4ccccc4C)N(C(=O)N(C)Cc4cc(C(F)(F)F)cc(C(F)(F)F)c4)CCN3C2=O)CC1]

A solution of Intermediate 33 (34 mg, 0.055 mmol) and N-acetylpiperazine (70 mg, 0.55 mmol) in THF (3 mL) was heated at reflux for 72 h. The solvent was removed in vacuo and the residue was purified by HPLC preparative column in acid conditions to obtain the title compound as a pale yellow solid (9 mg): $^1$H NMR (400 MHz, CDCl$_3$) δ ppm 7.67 (s, 1H), 7.29 (s, 2H), 7.09 (m, 3H), 4.61 (d, J=15.7 Hz, 1H), 4.28 (d, J=14.1 Hz, 1H), 4.08 (dt, J=13.3, 2.7 Hz, 1H), 3.98 (d, J=10.2 Hz, 1H), 3.63 (m, 2H), 3.37 (m, 4H), 3.08 (td, J=12.3, 3.1 Hz, 1H), 2.88 (s, 3H), 2.84 (m, 2H), 2.48 (s, 3H), 2.50 (m, 2H), 2.32 (m, 4H), 2.00 (s, 3H), 1.97 (m, 1H). HPLC-MS: Rt=1.14 min; m/z (ES+): 654 [M+H]$^+$.

EXAMPLE 38

Compound 38

N-{[3,4-bis(trifluoromethyl)phenyl]methyl}-N-methyl-1-(2-methylphenyl)-7-(morpholin-4-ylmethyl)-6-oxa-octahydropyrrolo[1,2-a]piperazine-2-carboxamide Methansulfonic Acid Salt (Enantiomer 1 of Diastereoisomer 1, Single Isomer with ANTI Configuration at C1-C8a)

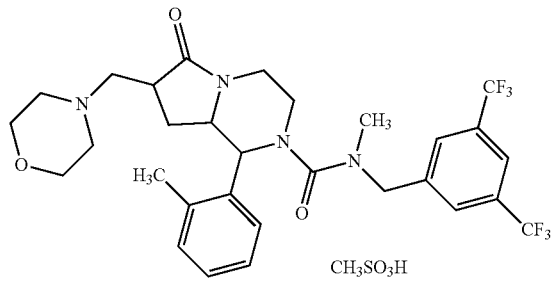

Compound 29 was subjected to chiral prep. HPLC and four fractions were recovered: Compound 38, described here, and Compound 39, 40 and 41, described below. Compound 38: column: Chiralpak AD-H (25×0.46 cm), 5μ Mobile phase: n-Hexane/2-Propanol 88/12 v/v Flow rate: 1 mL/min Detection: DAD at 220 nm. Rt=10.6 min. The sample recovered (150 mg, 0.245 mmol) was dissolved in THF (3 ml) and the solution was cooled at 0° C., then a solution of methansulfonic acid (16 μL, 0.245 mmol) in THF (1 mL) was added dropwise. The resulting solution was stirred for 30 min then the solvent was evaporated, the solid was triturated with $Et_2O$ and dried overnight in the vacuum pump at 50° C. to obtain the title compound as pale yellow-white solid (163 mg) $^1$H NMR (500 MHz, DMSO-$d_6$) δ ppm 9.41 (br s, 1H), 7.96 (s, 1H), 7.60 (s, 2H), 7.34 (m, 1H), 7.11 (m, 3H), 4.58 (d, J=15.7 Hz, 1H), 4.48 (d, J=15.7 Hz, 1H), 4.02 (d, J=10.3 Hz, 1H), 3.94 (br. d, J=12.2 Hz, 2H), 3.86 (dt, J=13.2, 2.9 Hz, 1H), 3.70 (td, J=9.4, 6.6 Hz, 1H), 3.55 (m, 5H), 3.37 (m, 1H), 3.23 (m, 2H), 3.13 (m, 1H), 3.02 (m, 1H), 2.88 (s, 3H), 2.87 (m, 2H), 2.47 (s, 3H), 2.30 (s, 3H), 2.03 (ddd, J=12.2, 7.8, 6.4 Hz, 1H), 1.52 (q, J=10.7 Hz, 1H). HPLC-MS: Rt=1.23 min; m/z (ES+): 613 [M+H]$^+$.

EXAMPLE 39

Compound 39

N-{[3,4-bis(trifluoromethyl)phenyl]methyl}-N-methyl-1-(2-methylphenyl)-7-(morpholin-4-ylmethyl)-6-oxa-octahydropyrrolo[1,2-a]piperazine-2-carboxamide as Methansulfonic Salt (Enantiomer 2 of Diastereoisomer 1, Single Isomer with ANTI Configuration at C1-C8a)

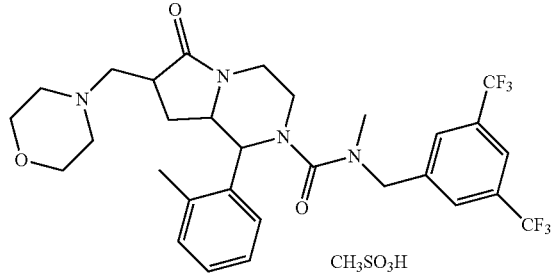

From the above described chiral prep. Chromatography on Compound 29, Compound 39 was also obtained. Column: Chiralpak AD-H (25×0.46 cm), 5μ Mobile phase: n-Hexane/2-Propanol 88/12 v/v Flow rate: 1 mL/min Detection: DAD at 220 nm. Rt=18.9. The sample recovered (150 mg, 0.245 mmol) was dissolved in THF (3 mL) and the solution was cooled at 0° C., then a solution of methansulfonic acid (16 μL, 0.245 mmol) in THF (1 mL) was added dropwise. The resulting solution was stirred for 30 min then the solvent was evaporated, the solid was triturated with $Et_2O$ and dried overnight in the vacuum pump at 50° C. to obtain the title compound as pale yellow-white solid (156 mg) $^1$H NMR (500 MHz, DMSO-$d_6$) δ ppm 9.41 (br s, 1H), 7.96 (s, 1H), 7.59 (s, 2H), 7.34 (m, 1H), 7.10 (m, 3H), 4.58 (d, J=15.7 Hz, 1H), 4.48 (d, J=15.7 Hz, 1H), 4.02 (d, J=9.8 Hz, 1H), 3.94 (d, J=12.7 Hz, 2H), 3.86 (dt, J=12.7, 2.5 Hz, 1H), 3.70 (m, 1H), 3.55 (m, 5H), 3.36 (m, 1H), 3.23 (m, 2H), 3.15 (m, 1H), 3.03 (m, 1H), 2.88 (s, 3H), 2.84 (m, 2H), 2.47 (s, 3H), 2.29 (s, 3H), 2.03 (m, 1H), 1.52 (m, 1H). HPLC-MS: Rt=1.23; m/z (ES+): 613 [M+H]$^+$.

EXAMPLE 40

Compound 40

N-{[3,4-bis(trifluoromethyl)phenyl]methyl}-N-methyl-1-(2-methylphenyl)-7-(morpholin-4-ylmethyl)-6-oxa-octahydropyrrolo[1,2-a]piperazine-2-carboxamide as methansulfonic salt (Enantiomer 1 of Diastereoisomer 2, Single Isomer with ANTI Configuration at C1-C8a)

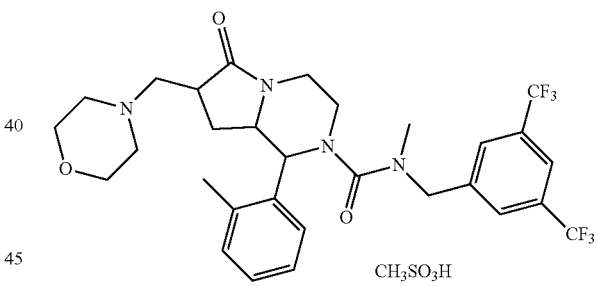

From the above described chiral prep. Chromatography on Compound 29, Compound 40 was also obtained. Column: Chiralpak AD-H (25×0.46 cm), 5μ Mobile phase: n-Hexane/2-Propanol 88/12 v/v Flow rate: 1 mL/min Detection: DAD at 220 nm. Rt=13.8 min. The sample recovered (62 mg, 0.101 mmol) was dissolved in THF (3 ml) and the solution was cooled at 0° C., then a solution of methansulfonic acid (6.5 μL, 0.101 mmol) in THF (1 mL) was added dropwise. The resulting solution was stirred for 30 min then the solvent was evaporated, the solid was triturated with $Et_2O$ and dried overnight in the vacuum pump at 50° C. to obtain the title compound as pale yellow-white solid (73 mg) $^1$H NMR (500 MHz, DMSO-$d_6$) δ ppm 9.31 (br s, 1H), 7.96 (s, 1H), 7.59 (s, 2H), 7.34 (m, 1H), 7.11 (m, 3H), 4.57 (d, J=15.7 Hz, 1H), 4.47 (d, J=15.7 Hz, 1H), 4.04 (d, J=10.3 Hz, 1H), 3.94 (m, 3H), 3.80 (td, J=9.2, 4.6 Hz, 1H), 3.63 (m, 2H), 3.47 (m, 2H), 3.38 (m, 2H), 3.25 (m, 1H), 3.17 (m, 3H), 3.04 (m, J=12.2 Hz, 1H), 2.89 (s, 3H), 2.76 (td, J=11.7, 2.9 Hz, 1H), 2.45 (s, 3H), 2.30 (s, 3H), 1.82 (ddd, J=13.6, 9.2, 4.6 Hz, 1H), 1.72 (m, 1H). HPLC-MS: Rt=1.24 min; m/z (ES+): 613 [M+H]$^+$.

EXAMPLE 41

Compound 41

N-{[3,4-bis(trifluoromethyl)phenyl]methyl}-N-methyl-1-(2-methylphenyl)-7-(morpholin-4-ylmethyl)-6-oxa-octahydropyrrolo[1,2-a]piperazine-2-carboxamide as Methansulfonic Salt (Enantiomer 2 of Diastereoisomer 2, Single Isomer with ANTI Configuration at C1-C8a)

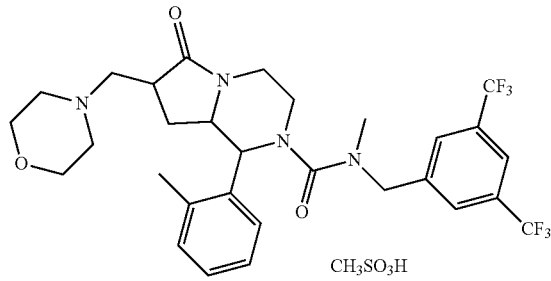

From the above described chiral prep. Chromatography on Compound 29, Compound 39 was also obtained. Column: Chiralpak AD-H (25×0.46 cm), 5μ Mobile phase: n-Hexane/2-Propanol 88/12 v/v Flow rate: 1 mL/min Detection: DAD at 220 nm. Rt=15.4 min. The sample recovered (62 mg, 0.101 mmol) was dissolved in THF (3 ml) and the solution was cooled at 0° C., then a solution of methansulfonic acid (6.5 μL, 0.101 mmol) in THF (1 mL) was added dropwise. The resulting solution was stirred for 30' then the solvent was evaporated, the solid was triturated with $Et_2O$ and dried overnight in the vacuum pump at 50° C. to obtain the title compound as pale yellow-white solid (67 mg) $^1$H NMR (500 MHz, DMSO-$d_6$) δ ppm 9.30 (br s, 1H), 7.96 (s, 1H), 7.59 (s, 2H), 7.34 (m, 1H), 7.11 (m, 3H), 4.57 (d, J=15.7 Hz, 1H), 4.47 (d, J=15.7 Hz, 1H), 4.04 (d, J=10.3 Hz, 1H), 3.95 (m, 3H), 3.80 (td, J=9.0, 4.9 Hz, 2H), 3.63 (m, 2H), 3.46 (m, 2H), 3.37 (m, J=10.8 Hz, 2H), 3.25 (m, 1H), 3.15 (m, 3H), 3.04 (m, 1H), 2.89 (s, 3H), 2.76 (td, J=11.6, 3.2 Hz, 1H), 2.46 (s, 3H), 2.29 (s, 3H), 1.82 (ddd, J=13.6, 9.2, 4.6 Hz, 1H), 1.72 (m, 1H). HPLC-MS: Rt=1.24 min; m/z (ES+): 613 [M+H]$^+$.

EXAMPLE 42

Compound 42

N-{[3,5-bis(trifluoromethyl)phenyl]methyl}-7,7-bis(2-hydroxyethyl)-N-methyl-1-(2-methylphenyl)-6-oxo-octahydropyrrolo[1,2-a]piperazine-2-carboxamide (Racemic Mixture, ANTI Configuration at C1-C8a)

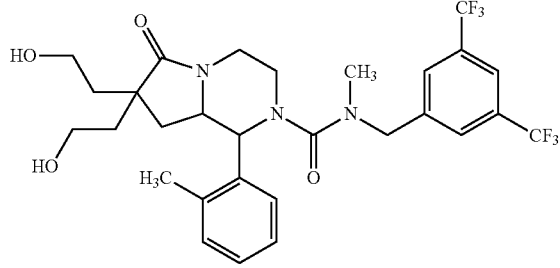 [SMILES: Cc1ccccc1C1C2CC(CCO)(CCO)C(=O)N2CCN1C(=O)N(C)Cc1cc(C(F)(F)F)cc(C(F)(F)F)c1]

Intermediate 37 (43 mg) was dissolved in MeOH (5 mL) and NaBH$_4$ (10 mg) was added at 0° C. The reaction was left stirring at this temperature for 30 min, then the solvent was removed in vacuo and the residue was taken up with HCl 1N and DCM. The organic layer was filtered through a phase separator and concentrated in vacuo. The crude was purified by flash chromatography (10 g SNAP cartridge, eluting from Cy/EtOAc 8:2 to 0:1 and DCM/MeOH 9:1). The fractions were collected and the solvent removed to give 35 mg of title compound. UPLC/MS: m/z (ES+): 601.92 [M+H]$^+$ Rt=1.05 min. $^1$H NMR (400 MHz, CDCl$_3$) δ ppm 7.73 (s, 1H), 7.36 (s, 2H), 7.16 (m, 3H), 4.67 (d, J=15.3 Hz, 1H), 4.34 (d, J=15.3 Hz, 1H), 4.14 (d, J=13.3 Hz, 1H), 4.07 (d, J=9.8 Hz, 1H), 3.72 (m, 5H), 3.38 (d, J=12.1 Hz, 1H), 3.15 (td, J=12.7, 4.1 Hz, 1H), 2.95 (s, 3H), 2.98 (td, J=12.1, 2.7 Hz, 1H), 2.91 (m, 1H), 2.52 (s, 3H), 2.04 (m, 1H), 1.81 (m, 6H).

EXAMPLE 43

Compound 43

N-{[3,5-bis(trifluoromethyl)phenyl]methyl}-7,7-bis(2-hydroxyethyl)-N-methyl-1-(2-methylphenyl)-6-oxo-octahydropyrrolo[1,2-a]piperazine-2-carboxamide (Enantiomer 1, ANTI Stereochemistry at C1-C8a, Single Unknown Stereoisomer)

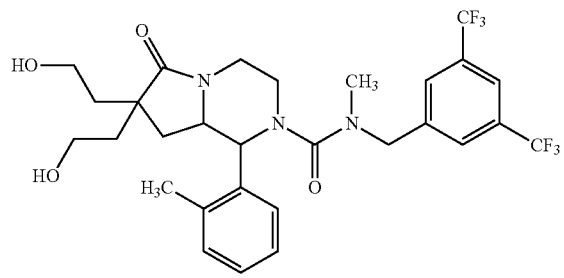 [SMILES: Cc1ccccc1C1C2CC(CCO)(CCO)C(=O)N2CCN1C(=O)N(C)Cc1cc(C(F)(F)F)cc(C(F)(F)F)c1]

35 mg of Compound 42 were purified by chiral preparative HPLC obtaining two fractions. After evaporation two products were obtained: enantiomer 1 (Compound 43, described here) and enantiomer 2 (Compound 44, described below). Compound 43: white foam, 12.3 mg. Chiral HPLC, Chiralpak AD-H column (25×0.46 cm), 5 μm, Mobile phase: n-Hexane/2-Propanol 85/15 v/v, Flow rate: 1 mL/min; Detection: DAD at 220 nm. Rt=6.5 min $^1$H NMR (400 MHz, CDCl$_3$) δ ppm 7.73 (s, 1H), 7.36 (s, 2H), 7.16 (m, 3H), 4.67 (d, J=15.3 Hz, 1H), 4.34 (d, J=15.3 Hz, 1H), 4.14 (d, J=13.3 Hz, 1H), 4.07 (d, J=9.8 Hz, 1H), 3.72 (m, 5H), 3.38 (d, J=12.1 Hz, 1H), 3.15 (td, J=12.7, 4.1 Hz, 1H), 2.95 (s, 3H), 2.98 (td, J=12.1, 2.7 Hz, 1H), 2.91 (m, 1H), 2.52 (s, 3H), 2.04 (m, 1H), 1.81 (m, 6H).

EXAMPLE 44

Compound 44

N-{[3,5-bis(trifluoromethyl)phenyl]methyl}-7,7-bis(2-hydroxyethyl)-N-methyl-1-(2-methylphenyl)-6-oxo-octahydropyrrolo[1,2-a]piperazine-2-carboxamide (Enantiomer 2, ANTI Stereochemistry at C1-C8a, Single Unknown Stereoisomer)

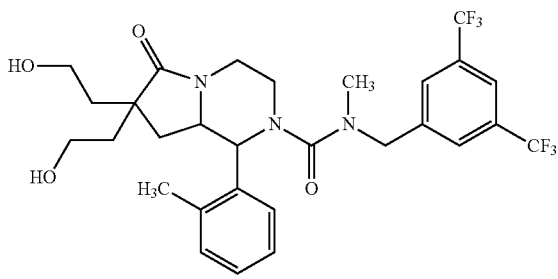 [SMILES: Cc1ccccc1C1C2CC(CCO)(CCO)C(=O)N2CCN1C(=O)N(C)Cc1cc(C(F)(F)F)cc(C(F)(F)F)c1]

After evaporation of collected fraction from chiral preparative HPLC from the above described experimental, Compound 44 was obtained (white foam, 11.3 mg). Chiral HPLC: Chiralpak AD-H column (25×0.46 cm), 5 µm. Mobile phase: n-Hexane/2-Propanol 85/15 v/v, Flow rate: 1 mL/min. Detection: DAD at 220 nm. Rt=11.4 min. $^1$H NMR (400 MHz, CDCl$_3$) δ ppm 7.73 (s, 1H), 7.36 (s, 2H), 7.16 (m, 3H), 4.67 (d, J=15.3 Hz, 1H), 4.34 (d, J=15.3 Hz, 1H), 4.14 (d, J=13.3 Hz, 1H), 4.07 (d, J=9.8 Hz, 1H), 3.72 (m, 5H), 3.38 (d, J=12.1 Hz, 1H), 3.15 (td, J=12.7, 4.1 Hz, 1H), 2.95 (s, 3H), 2.98 (td, J=12.1, 2.7 Hz, 1H), 2.91 (m, 1H), 2.52 (s, 3H), 2.04 (m, 1H), 1.81 (m, 6H). [M+H]+ CALC: 602.2454; OBSERVED: 602.2450.

EXAMPLE 45

Compound 45

N-{[3,5-bis(trifluoromethyl)phenyl]methyl}-N,1-dimethyl-4'-(2-methylphenyl)-1'-oxo-hexahydro-1'H-spiro[piperidine-4,2'-pyrrolo[1,2-a]piperazine]-5'-carboxamide (Racemic Mixture with ANTI Configuration at C1-C8a)

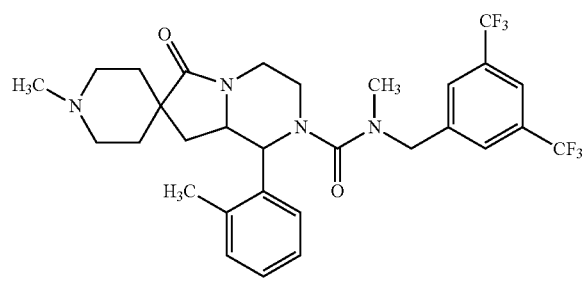 [SMILES: Cc1ccccc1C1C2CC3(CCN(C)CC3)C(=O)N2CCN1C(=O)N(C)Cc1cc(C(F)(F)F)cc(C(F)(F)F)c1]

Intermediate 37 (16 mg, 0.027 mmol) was dissolved in MeOH (1 mL). MeNH$_2$HCl (1.8 mg, 0.027 mmol) and AcOH (1 drop) were added to the solution and the reaction was left stirring at RT for 10 min, then NaBH$_3$(CN) was added and the reaction was left stirring at RT overnight. The solution was filtered through a SCX cartridge, eluting with NH$_3$ 2M solution in MeOH. The solvent was removed in vacuo, obtaining 11.6 mg of a residue which was dissolved in DCM and washed with NaOH 1M. The organic phase was filtered through a phase separator and concentrated, obtaining 7.8 mg of the title compound. UPLC-MS, m/z (ES+): 596.98 [M+H]$^+$ Rt=0.94 min. $^1$H NMR (400 MHz, CDCl$_3$) δ ppm 7.73 (s, 1H), 7.36 (s, 2H), 7.20 (m, 3H), 4.68 (d, J=15.7 Hz, 1H), 4.34 (d, J=15.7 Hz, 1H), 4.17 (dt, J=13.7, 2.7 Hz, 1H), 4.02 (d, J=9.8 Hz, 1H), 3.67 (dt, J=9.4, 7.4 Hz, 1H), 3.36 (dt, J=11.7, 2.7 Hz, 1H), 3.14 (td, J=11.7, 3.1 Hz, 1H), 2.95 (td, J=11.7, 3.5 Hz, 1H), 2.95 (s, 3H), 2.83 (m, 1H), 2.69 (m, 1H), 2.52 (s, 3H), 2.24 (s, 3H), 2.20 (m, 1H), 1.91 (m, 4H), 1.46 (m, 2H), 1.33 (m, 1H).

EXAMPLE 46

Compound 46

N-{[3,5-bis(trifluoromethyl)phenyl]methyl}-N,1-dimethyl-4'-(2-methylphenyl)-1'-oxo-hexahydro-1'H-spiro[piperidine-4,2'-pyrrolo[1,2-a]piperazine]-5'-carboxamide (Enantiomer 1, ANTI Stereochemistry at C1-C8a, Single Unknown Stereoisomer)

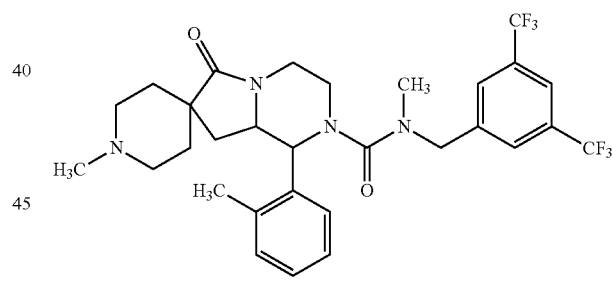

Compound 45 was separated in the corresponding isomers by chiral chromatography, two fractions were obtained, Compound 46 (described here) and Compound 47 (described below). After evaporation of collected fractions from chiral preparative HPLC, Compound 46 was obtained (isomer 1, 68 mg). Chiral HPLC: Chiralpak AD-H column (25×0.46 cm), 5 µm, n-Hexane/(Ethanol+0.1% isopropylamine) 90/10% v/v, Flow rate: 0.8 mL/min. Detection: DAD at 220 nm, Circular Dichroism detector: 230 nm, Rt=9.0 min. $^1$H NMR (400 MHz, CDCl$_3$) δ ppm 7.73 (s, 1H), 7.36 (s, 2H), 7.20 (m, 3H), 4.68 (d, J=15.7 Hz, 1H), 4.34 (d, J=15.7 Hz, 1H), 4.17 (dt, J=13.7, 2.7 Hz, 1H), 4.02 (d, J=9.8 Hz, 1H), 3.67 (dt, J=9.4, 7.4 Hz, 1H), 3.36 (dt, J=11.7, 2.7 Hz, 1H), 3.14 (td, J=11.7, 3.1 Hz, 1H), 2.95 (td, J=11.7, 3.5 Hz, 1H), 2.95 (s, 3H), 2.83 (m, 1H), 2.69 (m, 1H), 2.52 (s, 3H), 2.24 (s, 3H), 2.20 (m, 1H), 1.91 (m, 4H), 1.46 (m, 2H), 1.33 (m, 1H).

141

EXAMPLE 47

Compound 47

N-{[3,5-bis(trifluoromethyl)phenyl]methyl}-N,1-dimethyl-4'-(2-methylphenyl)-1'-oxo-hexahydro-1'H-spiro[piperidine-4,2'-pyrrolo[1,2-a]piperazine]-5'-carboxamide (Enantiomer 2, ANTI Stereochemistry at C1-C8a, Single Unknown Stereoisomer)

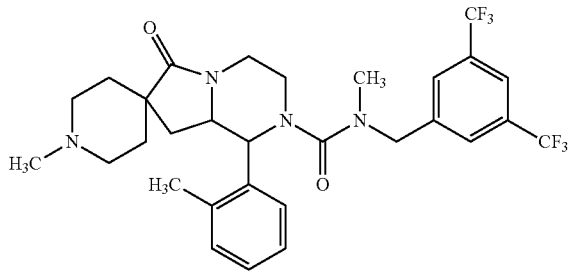 [SMILES: Cc1ccccc1C1C2CC3(CCN(C)CC3)C(=O)N2CCN1C(=O)N(C)Cc1cc(C(F)(F)F)cc(C(F)(F)F)c1]

After evaporation of the second collected fraction from chiral preparative HPLC of the above described experimental, Compound 47 was obtained (isomer 2, 73 mg). Chiral HPLC: Chiralpak AD-H column (25×0.46 cm), 5 µm, n-Hexane/(Ethanol+0.1% isopropylamine) 90/10% v/v, Flow rate: 0.8 mL/min. Detection: DAD at 220 nm, Circular Dichroism detector: 230 nm, Rt=12.5 min. $^1$H NMR (400 MHz, CDCl$_3$) δ ppm 7.73 (s, 1H), 7.36 (s, 2H), 7.20 (m, 3H), 4.68 (d, J=15.7 Hz, 1H), 4.34 (d, J=15.7 Hz, 1H), 4.17 (dt, J=13.7, 2.7 Hz, 1H), 4.02 (d, J=9.8 Hz, 1H), 3.67 (dt, J=9.4, 7.4 Hz, 1H), 3.36 (dt, J=11.7, 2.7 Hz, 1H), 3.14 (td, J=11.7, 3.1 Hz, 1H), 2.95 (td, J=11.7, 3.5 Hz, 1H), 2.95 (s, 3H), 2.83 (m, 1H), 2.69 (m, 1H), 2.52 (s, 3H), 2.24 (s, 3H), 2.20 (m, 1H), 1.91 (m, 4H), 1.46 (m, 2H), 1.33 (m, 1H).

EXAMPLE 48

Compound 48

N-{[3,5-bis(trifluoromethyl)phenyl]methyl}-7-(hydroxymethyl)-N-methyl-1-(2-methylphenyl)-octahydropyrrolo[1,2-a]piperazine-2-carboxamide (Enantiomeric Pair, ANTI at C2-C8a, Diastereoisomer 1)

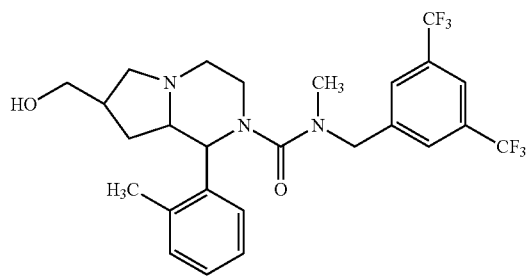 [SMILES: Cc1ccccc1C1C2CC(CO)CN2CCN1C(=O)N(C)Cc1cc(C(F)(F)F)cc(C(F)(F)F)c1]

Separation by HPLC chromatography of Intermediate 38 provided two fractions, Compound 48, described here, and Compound 49, described below. Compound 48: 4.5 mg, isomer 1: column: X Bridge C-18 BOD (19×100 mm), 5µ Mobile phase: Ammonium Bicarbonate, pH+10, 10 mM/ACN 80/20% v/v>25/75 in 10 min>0/100 in 1 min. Flow rate 17 mL/min Detection: DAD at 225 nm. $^1$H NMR (400 MHz, CDCl$_3$) δ ppm 7.66 (s, 1H), 7.32 (s, 2 H), 7.16 (m, 1 H), 7.05 (m, 3 H), 4.55 (d, J=15.3 Hz, 1 H), 4.37 (m, 1 H), 4.18 (d, J=9.0 Hz, 1 H), 3.38 (m, 2 H), 3.27 (m, 2H), 3.08 (m, 2H), 2.85 (s, 3 H), 2.44 (s, 3 H), 2.41 (m, 2 H), 2.16 (m, 1 H), 1.97 (m, 1 H), 1.65 (q, J=11.0 Hz, 1 H), 1.10 (m, 1 H). HPLC-MS: Rt=1.16 min, m/z (ES+): 530.03 [M+H]$^+$.

EXAMPLE 49

Compound 49

N-{[3,5-bis(trifluoromethyl)phenyl]methyl}-7-(hydroxymethyl)-N-methyl-1-(2-methylphenyl)-octahydropyrrolo[1,2-a]piperazine-2-carboxamide (Enantiomeric Pair, ANTI at C1-C8a, Diastereoisomer 2)

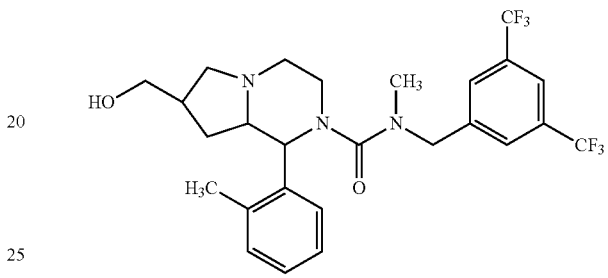

Separation by HPLC chromatography of Intermediate 38 provided 9.8 mg of the title compound. Column: X Bridge C-18 BOD (19×100 mm), 5µ Mobile phase: Ammonium Bicarbonate, pH+10, 10 mM/ACN 80/20% v/v>25/75 in 10 min>0/100 in 1 min. Flow rate 17 mL/min Detection: DAD at 225 nm. $^1$H NMR (400 MHz, CDCl$_3$) δ ppm 7.65 (s, 1H), 7.32 (s, 2H), 7.16 (d, J=2.0 Hz, 1H), 7.05 (s, 3H), 4.55 (d, J=14.9 Hz, 1H), 4.37 (m, 1H), 4.20 (d, J=9.4 Hz, 1H), 3.59 (dd, J=10.6, 4.3 Hz, 1H), 3.46 (dd, J=11.0, 6.3 Hz, 1H), 3.28 (m, 1H), 3.07 (m, 2H), 2.97 (d, J=10.5 Hz, 1H), 2.85 (s, 3H), 2.46 (s, 3H), 2.34 (m, 2H), 2.13 (m, 2H), 1.53 (br s, 1H), 1.28 (m, 1H). HPLC-MS: Rt=1.22 min, m/z (ES+): 530.03 [M+H]$^+$.

EXAMPLE 50

Compound 50

N-{[3,4-bis(trifluoromethyl)phenyl]methyl}-N-methyl-1-(2-methylphenyl)-7-(morpholin-4-ylmethyl)-6-oxa-octahydropyrrolo[1,2-a]piperazine-2-carboxamide (Enantiomer 2 of Diastereoisomer 2, Single Isomer)

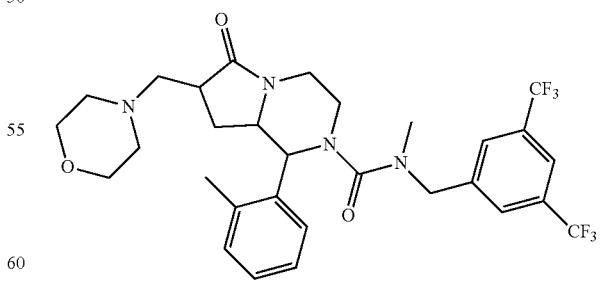

Compound 41 (67 mg) was treated with NaOH 1N and the free base was extracted several times with DCM. After evaporation of the organic phase 60 mg of a pale yellow foam were obtained. Separation by chiral chromatography provided 33 mg of the title compound (6 mg of a previously prepared batch of the same compound were also added) to obtain 39 mg of Compound 50 as a white solid. Column: Chiralpak AD-H (25×0.46 cm), 5μ Mobile phase: n-Hexane/Ethanol 70/30% v/v Flow rate: 0.8 mL/min Detection: DAD at 220 nm. Rt=9.2. ¹H NMR (400 MHz, CDCl₃) δ ppm 7.74 (s, 1H), 7.36 (s, 2H), 7.28 (m, 1H), 7.17 (m, 3H), 4.69 (d, J=15.7 Hz, 1H), 4.35 (d, J=15.7 Hz, 1H), 4.21 (m, 1H), 4.06 (d, J=9.8 Hz, 1H), 3.77 (m, 1H), 3.64 (m, 4H), 3.34 (m, 1H), 3.15 (td, J=12.3, 3.7 Hz, 1H), 2.94 (m, 4H), 2.71 (m, 2H), 2.52 (s, 3H), 2.41 (m, 5H), 1.89 (m, 1H), 1.79 (m, 1H). HPLC-MS: Rt=1.22; m/z (ES+): 613 [M+H]⁺.

EXAMPLE 51

Compound 51

N-{[3,4-bis(trifluoromethyl)phenyl]methyl}-N-methyl-1-(2-methylphenyl)-7-(morpholin-4-ylmethyl)-6-oxa-octahydropyrrolo[1,2-a]piperazine-2-carboxamide (Enantiomer 1 of Diastereoisomer 1, Single Isomer)

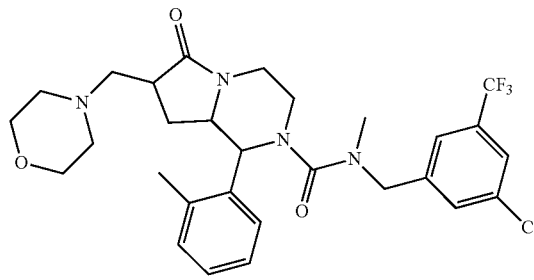

Separation by HPLC chromatography of Compound 38 provided 35 mg of the title compound as a white solid. ¹H NMR (400 MHz, CDCl₃) δ ppm 7.74 (s, 1H), 7.37 (s, 2H), 7.18 (m, 4H), 4.68 (d, J=15.7 Hz, 1H), 4.36 (d, J=15.7 Hz, 1H), 4.16 (d, J=13.2 Hz, 1H), 4.06 (d, J=9.8 Hz, 1H), 3.67 (m, 5H), 3.39 (d, J=11.7 Hz, 1H), 3.15 (td, J=1.0 Hz, 1H), 2.94 (m, 1H), 2.94 (s, 3H), 2.85 (dd, J=12.2, 3.4 Hz, 1H), 2.56 (s, 3H), 2.49 (m, 6H), 2.02 (m, J=13.0, 7.9, 7.9 Hz, 1H), 1.67 (m, J=13.0, 8.7, 8.7 Hz, 1H). HPLC-MS: Rt=1.22; m/z (ES+): 613 [M+H]⁺. Column: Chiralpak AD-H (25×0.46 cm), 5μ Mobile phase: n-Hexane/2-Propanol 88/12 v/v Flow rate: 1 mL/min Detection: DAD at 220 nm. Rt=11.9.

EXAMPLE 52

Compound 52

N-{[3,5-bis(trifluoromethyl)phenyl]methyl}-7-(hydroxymethyl)-N-methyl-1-(2-methylphenyl)-octahydropyrrolo[1,2-a]piperazine-2-carboxamide; methanesulfonic acid salt (Single Enantiomer with ANTI Configuration at C1-C8a)

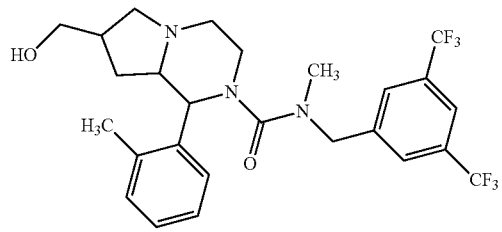 [SMILES: Cc1ccccc1C1C2CC(CO)CN2CCN1C(=O)N(C)Cc1cc(C(F)(F)F)cc(C(F)(F)F)c1]

Compound 28 (96 mg) was treated with DCM (20 mL) and NaHCO₃ aq sat. sol. (20 mL). The organic layer was separated, dried over sodium sulphate, filtered and evaporated under vacuo to give the title compound as a white solid (75 mg). Chiral preparative HPLC: Column: Chiralpak AD-H (25×0.46 cm), 5 um; Mobile phase: n-Hexane/2-Propanol 90/10% v/v; Flow rate (mL/min): 1.0; DAD: 220 nm; 100% e.e. UV (Rt=14.87 min). ¹H NMR (500 MHz, CHLOROFORM-d) δ ppm 7.73 (s, 1H), 7.40 (s, 2H), 7.15 (m, 4H), 4.63 (d, J=15.2 Hz, 1H), 4.44 (m, 1H), 4.28 (d, J=9.3 Hz, 1H), 3.66 (dd, J=10.3, 4.4 Hz, 1H), 3.54 (dd, J=10.0, 5.6 Hz, 1H), 3.35 (m, 1H), 3.14 (m, 2H), 3.05 (dd, J=8.8, 1.0 Hz, 1H), 2.93 (s, 3H), 2.54 (s, 3H), 2.42 (m, 2H), 2.22 (m, 2H), 1.61 (m, 1H), 1.36 (m, 1H). UPLC/MS Electrospray (ES+/ES−); Rt=1.21 min a/a. (ES+): 530.2 [M+H]⁺.

EXAMPLE 53

Compound 53

N-[(1R)-1-[3,5-bis(trifluoromethyl)phenyl]ethyl]-7,7-bis(2-hydroxyethyl)-N-methyl-1-(2-methylphenyl)-6-oxo-octahydropyrrolo[1,2-a]piperazine-2-carboxamide (Pure Enantiomer, with ANTI Configuration at C1-C8a)

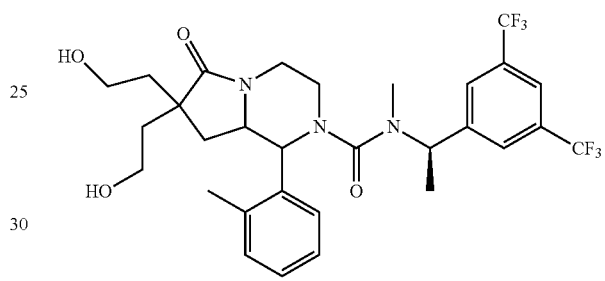

300 mg of Compound Intermediate 41 were purified by chiral preparative HPLC obtaining two fractions. After evaporation two products were obtained: diastereoisomer 1 (Compound 53, described here) and diastereoisomer 2 (Compound 54, described below). Compound 53: white foam, 160 mg. Chiralpak IC column (25×0.46 cm), 5 μm. Mobile phase: n-Hexane/Ethanol; 73/27 v/v, Flow rate: 0.8 mL/min. Detection: DAD at 220 nm. Rt=13.3 min. ¹H NMR (500 MHz, CDCl₃) δ ppm 7.64 (s, 1H), 7.27 (s, 2H), 7.16 (d, J=7.3 Hz, 1H), 7.07 (m, 3H), 5.51 (q, J=7.3 Hz, 1H), 4.07 (d, J=12.7 Hz, 1H), 3.99 (d, J=9.8 Hz, 1H), 3.71 (m, 4H), 3.53 (m, 1H), 3.27 (m, 1H), 3.07 (td, J=12.7, 5.9 Hz, 1H), 2.88 (td, J=12.2, 3.4 Hz, 1H), 2.88 (br. s, 1H), 2.74 (s, 3H), 2.46 (s, 3H), 2.00 (br. s, 1H), 1.74 (m, 6H), 1.43 (d, J=6.8 Hz, 3H).

EXAMPLE 54

Compound 54 N-[(1R)-1-[3,5-bis(trifluoromethyl)phenyl]ethyl]-7,7-bis(2-hydroxyethyl)-N-methyl-1-2-methylphenyl)-6-oxo-octahydropyrrolo[1,2-a]piperazine-2-carboxamide (Pure Enantiomer, with ANTI Configuration at C1-C8a)

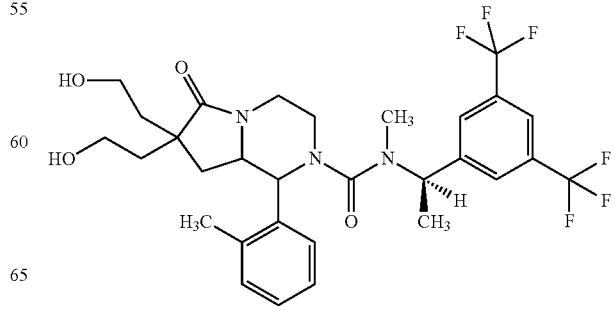

Compound 54: white foam 120 mg. Chiralpak IC column (25×0.46 cm), 5 μm. Mobile phase: n-Hexane/Ethanol; 73/27 v/v, Flow rate: 0.8 mL/min. Detection: DAD at 220 nm. Rt=16.2 min. ¹H NMR (500 MHz, CDCl₃) δ ppm 7.70 (s, 1H), 7.46 (s, 2H), 7.17 (d, J=8.3 Hz, 1H), 7.10 (m, 3H), 5.47 (quin, J=5.0 Hz, 1H), 4.06 (d, J=12.7 Hz, 1H), 3.99 (d, J=9.8 Hz, 1H), 3.75 (m, 3H), 3.64 (m, 1H), 3.52 (m, 1H), 3.22 (d, J=10.8 Hz, 1H), 3.06 (td, J=13.7, 2.9 Hz, 1H), 2.94 (td, J=12.2, 2.0 Hz, 1H), 2.86 (m, 1H), 2.62 (s, 3H), 2.46 (s, 3H), 1.99 (m, 1H), 1.75 (m, 6H), 1.33 (d, J=6.8 Hz, 3H). [M+H]+ CALC: 616.2610; OBS: 616.2601

EXAMPLE 55

Compound 55

N-[(1R)-1-[3,5-bis(trifluoromethyl)phenyl]ethyl]-7-(hydroxymethyl)-N-methyl-1-(2-methylphenyl)-6-oxo-octahydropyrrolo[1,2-a]piperazine-2-carboxamide (Pure Enantiomer, with ANTI Configuration at C1-C8a)

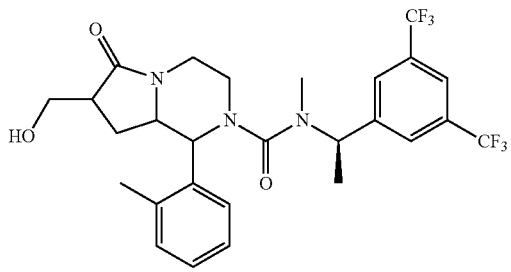 [SMILES: Cc1ccccc1C1C2CC(CO)C(=O)N2CCN1C(=O)N(C)[C@H](C)c1cc(C(F)(F)F)cc(C(F)(F)F)c1]

Intermediate 47 (300 mg) was separated in the corresponding isomers by chiral chromatography. After evaporation of collected fraction from chiral preparative HPLC, Compound 55 was obtained (isomer 1, 56 mg). Chiral HPLC: Chiralpak AD-H column (25×0.46 cm), 5 μm, n-Hexane/Ethanol 85/15% v/v, Flow rate: 0.8 mL/min. Detection: DAD at 220 nm, Rt=22.5 min. ¹H NMR (500 MHz, CHLOROFORM-d) δ ppm 7.71 (s, 1H), 7.47 (s, 2H), 7.16 (d, J=7.8 Hz, 1H), 7.08 (m, 3H), 5.47 (q, J=6.8 Hz, 1H), 4.11 (d, J=12.2 Hz, 1H), 3.99 (d, J=9.8 Hz, 1H), 3.78 (m, 1H), 3.70 (m, 1H), 3.59 (m, 1H), 3.16 (d, J=11.7 Hz, 1H), 3.09 (td, J=13.2, 3.9 Hz, 1H), 2.88 (td, J=12.2, 3.4 Hz, 1H), 2.68 (m, 1H), 2.63 (s, 3H), 2.46 (s, 3H), 2.44 (dd, J=7.8, 3.9 Hz, 1H), 1.74 (m, 1H), 1.65 (m, J=5.9 Hz, 1H), 1.32 (q, J=6.8 Hz, 3H).

EXAMPLE 56

Compound 56

N-[(1R)-1-[3,5-bis(trifluoromethyl)phenyl]ethyl]-7-(hydroxymethyl)-N-methyl-1-(2-methylphenyl)-6-oxo-octahydropyrrolo[1,2-a]piperazine-2-carboxamide (Pure Enantiomer, with ANTI Configuration at C1-C8a)

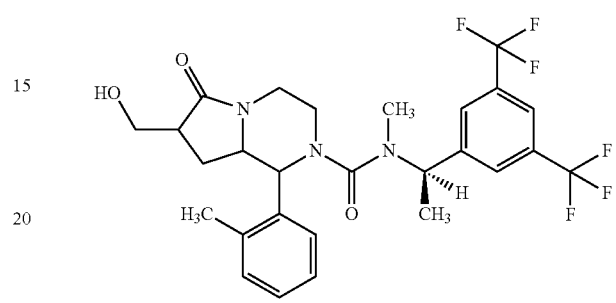

After evaporation of the second collected fraction from chiral preparative HPLC, Compound 56 was obtained (isomer 2, 172 mg). Chiral HPLC: Chiralpak AD-H column (25×0.46 cm), 5 μm, n-Hexane/Ethanol 85/15% v/v, Flow rate: 0.8 mL/min. Detection: DAD at 220 nm, 99.4% a/a by UV Rt=24.5 min. ¹H NMR (500 MHz, CHLOROFORM-d) δ ppm 7.70 (s, 1H), 7.47 (s, 2H), 7.17 (d, J=7.8 Hz, 1H), 7.09 (m, 3H), 5.47 (q, J=6.7 Hz, 1H), 4.07 (d, J=12.7 Hz, 1H), 4.01 (d, J=9.8 Hz, 1H), 3.83 (m, 1H), 3.67 (m, 2H), 3.22 (d, J=10.8 Hz, 1H), 3.06 (t, J=12.7 Hz, 1H), 2.90 (m, 2H), 2.62 (s, 3H), 2.55 (m, 1H), 2.46 (s, 3H), 1.88 (m, 1H), 1.43 (m, 1H), 1.33 (d, J=7.3 Hz, 3H).

EXAMPLE 57

Compound 57

N-[(1R)-1-[3,5-bis(trifluoromethyl)phenyl]ethyl]-7-(hydroxymethyl)-N-methyl-1-(2-methylphenyl)-6-oxo-octahydropyrrolo[1,2-a]piperazine-2-carboxamide (Pure Enantiomer, with ANTI Configuration at C1-C8a)

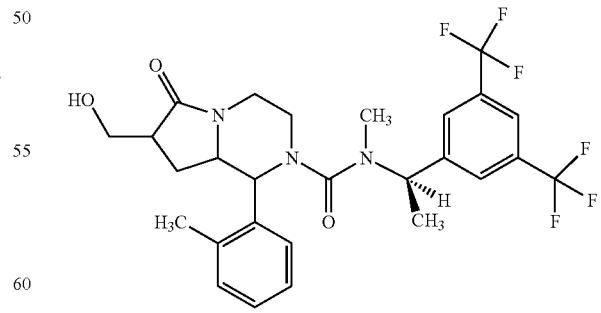

Intermediate 48 (350 mg) was separated in the corresponding isomers by chiral chromatography. After evaporation of collected fraction from chiral preparative HPLC, Compound 57 was obtained (isomer 1, 199 mg). Chiral HPLC: Chiralpak AD-H column (25×0.46 cm), 5 μm, n-Hexane/2-propanol 90/10% v/v, Flow rate: 1 mL/min. Detection: DAD at 220 nm, Rt=7 min ¹H NMR (500 MHz, CHLOROFORM-d) δ ppm 7.72 (br s, 1H), 7.36 (br s, 2H), 7.23 (d, J=7.3 Hz, 1H), 7.15 (m, 3H), 5.58 (m, 1H), 4.17 (d, J=12.7 Hz, 1H), 4.09 (d, J=9.8 Hz, 1H), 3.91 (m, 1H), 3.74 (m, 1H), 3.69 (q, J=7.3 Hz, 1H), 3.35 (d, J=12.2 Hz, 1H), 3.15 (m, 1H), 2.97 (m, 2H), 2.82 (s, 3H), 2.64 (m, 1H), 2.53 (s, 3H), 1.94 (m, 1H), 1.55 (m, 1H), 1.51 (d, J=6.8 Hz, 3H).

EXAMPLE 58

Compound 58 N-[(1R)-1-[3,5-bis(trifluoromethyl) phenyl]ethyl]-7-(hydroxymethyl)-N-methyl-1-(2-methylphenyl)-6-oxo-octahydropyrrolo[1,2-a]piperazine-2-carboxamide (Pure Enantiomer, with ANTI Configuration at C1-C8a)

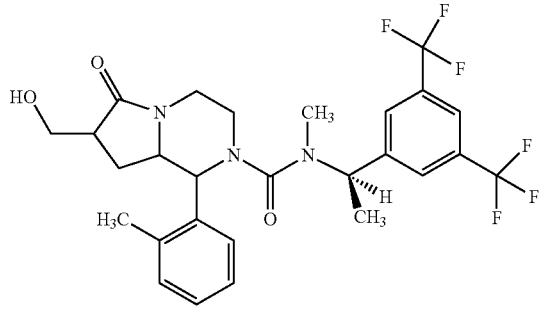 [SMILES: Cc1ccccc1C1C2CC(CO)C(=O)N2CCN1C(=O)N(C)[C@H](C)c1cc(C(F)(F)F)cc(C(F)(F)F)c1]

After evaporation of the second collected fraction from chiral preparative HPLC, Compound 58 was obtained (isomer 2, 49.5 mg). Chiral HPLC: Chiralpak AD-H column (25×0.46 cm), 5 μm, n-Hexane/2-propanol 90/10% v/v, Flow rate: 1 mL/min. Detection: DAD at 220 nm, Rt=8.6 min. ¹H NMR (500 MHz, CHLOROFORM-d) δ ppm 7.72 (br s, 1H), 7.35 (s, 2H), 7.23 (d, J=7.3 Hz, 1H), 7.16 (m, 3H), 5.58 (m, 1H), 4.21 (d, J=13.2 Hz, 1H), 4.06 (d, J=10.3 Hz, 1H), 3.86 (m, 1H), 3.74 (m, 1H), 3.67 (m, 1H), 3.30 (d, J=12.2 Hz, 1H), 3.19 (m, 1H), 2.91 (m, 1H), 2.82 (s, 3H), 2.76 (m, 1H), 2.52 (m, 4H), 1.83 (m, 1H), 1.71 (m, 1H), 1.51 (d, J=6.8 Hz, 3H).

EXAMPLE 59

Compound 59 N-[(1R)-1-[3,5-bis(trifluoromethyl) phenyl]ethyl]-7,7-bis(2-hydroxyethyl)-N-methyl-1-(2-methylphenyl)-octahydropyrrolo[1,2-a]piperazine-2-carboxamide (Pure Enantiomer, Isomer 1, with ANTI Configuration at C1-C8a)

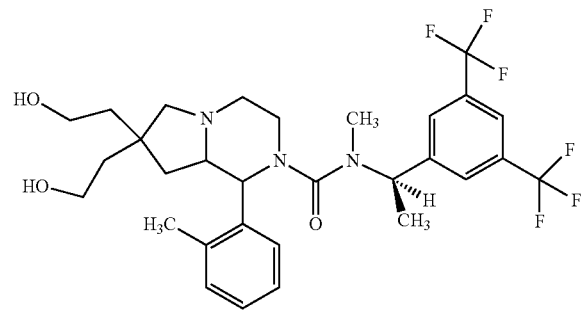 [SMILES: Cc1ccccc1C1C2CC(CCO)(CCO)CN2CCN1C(=O)N(C)[C@H](C)c1cc(C(F)(F)F)cc(C(F)(F)F)c1]

620 mg of Intermediate 42 were purified by chiral preparative HPLC obtaining two fractions. After evaporation, two products were obtained: diasteroisomer 1 (Compound 59, described here) and diasteroisomer 2 (Compound 60, described below). Compound 59: white foam, 166 mg. Chiral HPLC: Chiralpak IC column (25×0.46 cm), 5 μm. Mobile phase: n-Hexane/Ethanol 85/15 v/v, Flow rate: 0.8 mL/min. Detection: DAD at 220 nm. Rt=14.3 min. ¹H NMR (500 MHz, CDCl₃) δ ppm 7.62 (s, 1H), 7.29 (s, 2H), 7.13 (m, 1H), 7.04 (m, 3H), 5.51 (q, J=7.3 Hz, 1H), 4.97 (br s, 2H), 4.27 (d, J=10.8 Hz, 1H), 3.83 (td, J=9.8, 2.4 Hz, 1H), 3.68 (s, 1H), 3.57 (d, J=4.4 Hz, 2H), 3.26 (d, J=12.7 Hz, 1H), 3.04 (m, 3H), 2.70 (s, 3H), 2.48 (s, 3H), 2.39 (m, 2H), 2.13 (d, J=9.3 Hz, 1H), 1.73 (m, 1H), 1.64 (t, J=12.2 Hz, 1H), 1.55 (t, J=7.8 Hz, 2H), 1.42 (d, J=6.8 Hz, 3H), 1.36 (m, 1H), 1.16 (dd, J=13.7, 5.4 Hz, 1H).

EXAMPLE 60

Compound 60 N-[(1R)-1-[3,5-bis(trifluoromethyl) phenyl]ethyl]-7,7-bis(2-hydroxyethyl)-N-methyl-1-(2-methylphenyl)-octahydropyrrolo[1,2-a]piperazine-2-carboxamide (Pure Enantiomer, Isomer 2, with ANTI Configuration at C1-C8a)

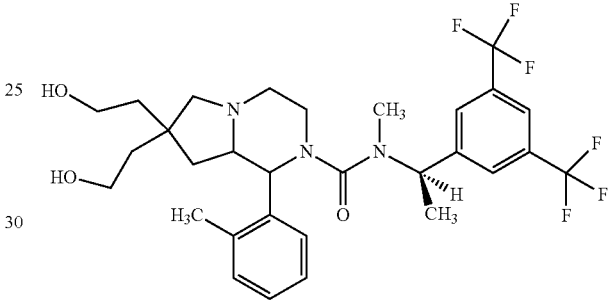

Compound 60: white foam 160 mg. Chiral HPLC: Chiralpak IC column (25×0.46 cm), 5 μm. Mobile phase: n-Hexane/Ethanol 85/15 v/v, Flow rate: 0.8 mL/min. Detection: DAD at 220 nm. Rt=17.3 min. ¹H NMR (500 MHz, CDCl₃) δ ppm 7.77 (s, 1H), 7.56 (s, 2H), 7.21 (d, J=7.8 Hz, 1H), 7.13 (m, 3H), 5.53 (q, J=6.8 Hz, 1H), 4.95 (br s, 2H), 4.35 (d, J=8.8 Hz, 1H), 3.91 (m, 1H), 3.75 (m, 1H), 3.64 (d, J=3.9 Hz, 2H), 3.28 (d, J=12.2 Hz, 1H), 3.11 (d, J=8.8 Hz, 3H), 2.67 (br s, 3H), 2.58 (s, 3H), 2.45 (m, 2H), 2.20 (d, J=8.3 Hz, 1H), 1.81 (m, 1H), 1.70 (dd, J=13.7, 10.5 Hz, 1H), 1.63 (t, J=7.3 Hz, 2H), 1.41 (br s, 4H), 1.23 (dd, J=12.7, 8.3 Hz, 1H). [M+H]+ CALC: 602.2812; OBS: 602.2814.

EXAMPLE 61

Compound 61

N-{[3,5-bis(trifluoromethyl)phenyl]methyl}-N-methyl-1-(2-methylphenyl)-octahydropyrrolo[1,2-a]piperazine-2-carboxamide (Pure Enantiomer, with ANTI Configuration at C1-C8a)

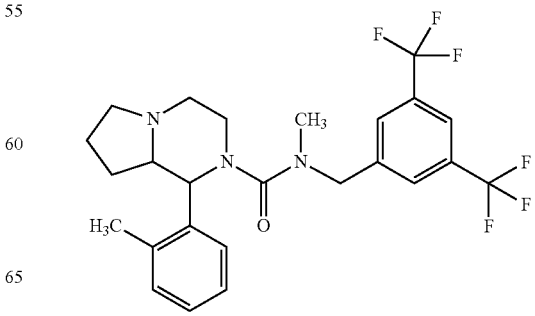

Compound 24 was separated in the corresponding isomers by chiral chromatography. After evaporation of collected fractions from chiral preparative HPLC, two isomers were obtained (isomer 1, described here and isomer 2, described in the next experimental part). Isomer 1 (15.5 mg): Chiral HPLC: Chiralpak AD-H column (25×0.46 cm), 5 μm, n-Hexane/2-propanol 90/10% v/v, Flow rate: 1 mL/min. Detection: DAD at 220 nm, Circular Dichroism detector: 230 nm, Rt=3.9 min $^1$H NMR (500 MHz, CHLOROFORM-d) δ ppm 7.73 (s, 1H), 7.41 (s, 2H), 7.15 (m, 4H), 4.63 (d, J=15.7 Hz, 1H), 4.46 (m, 1H), 4.26 (d, J=9.3 Hz, 1H), 3.38 (m, 1H), 3.18 (m, 3H), 2.93 (s, 3H), 2.52 (s, 3H), 2.47 (m, 1H), 2.22 (q, J=9.1 Hz, 1H), 2.14 (m, 1H), 1.82 (m, 1H), 1.58 (m, 2H), 1.39 (m, 1H).

EXAMPLE 62

Compound 62

N-{[3,5-bis(trifluoromethyl)phenyl]methyl}-N-methyl-1-(2-methylphenyl)-octahydropyrrolo[1,2-a]piperazine-2-carboxamide (Pure Enantiomer, with ANTI Configuration at C1-C8a)

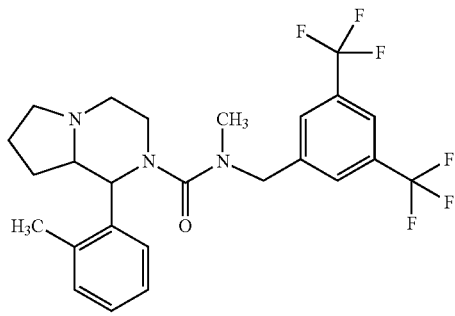 [SMILES: Cc1ccccc1C1C2CCCN2CCN1C(=O)N(C)Cc1cc(C(F)(F)F)cc(C(F)(F)F)c1]

After evaporation of the second collected fraction from chiral preparative HPLC as described in the previous experimental, Compound 62 was obtained (isomer 2, 16.7 mg). Chiral HPLC: Chiralpak AD-H column (25×0.46 cm), 5 μm, n-Hexane/2-propanol 90/10% v/v, Flow rate: 1 mL/min. Detection: DAD at 220 nm, Circular Dichroism detector: 230 nm, Rt=5.4 min $^1$H NMR (500 MHz, CHLOROFORM-d) δ ppm 7.73 (s, 1H), 7.41 (s, 2H), 7.15 (m, 4H), 4.63 (d, J=15.7 Hz, 1H), 4.46 (m, 1H), 4.26 (d, J=9.3 Hz, 1H), 3.38 (m, 1H), 3.18 (m, 3H), 2.93 (s, 3H), 2.52 (s, 3H), 2.47 (m, 1H), 2.22 (q, J=9.1 Hz, 1H), 2.14 (m, 1H), 1.82 (m, 1H), 1.58 (m, 2H), 1.39 (m, 1H).

EXAMPLE 63

Compound 63

N-[(1R)-1-[3,5-bis(trifluoromethyl)phenyl]ethyl]-N-methyl-1-(2-methylphenyl)-octahydropyrrolo[1,2-a]piperazine-2-carboxamide (Pure Enantiomer, Isomer 1, with ANTI Configuration at C1-C8a)

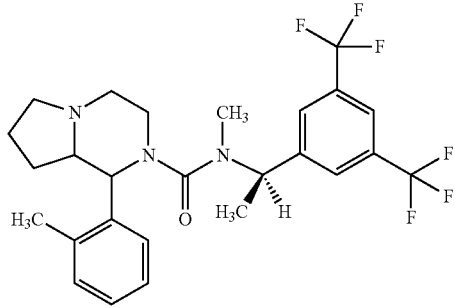 [SMILES: Cc1ccccc1C1C2CCCN2CCN1C(=O)N(C)[C@H](C)c1cc(C(F)(F)F)cc(C(F)(F)F)c1]

Intermediate 43 was purified by chiral preparative HPLC. After evaporation of collected fractions from chiral prepara-tive HPLC, Compound 63 was obtained (isomer 1, 101.1 mg). Chiral HPLC: Chiralpak AD-H column (25×0.46 cm), 5 μm, n-Hexane/2-propanol 90/10% v/v, Flow rate: 1 mL/min. Detection: DAD at 220 nm, Circular Dichroism detector: 230 nm, Rt=3.9 min. $^1$H NMR (400 MHz, CHLOROFORM-d) δ ppm 7.73 (s, 1H), 7.36 (s, 2H), 7.20 (m, 3H), 4.68 (d, J=15.7 Hz, 1H), 4.34 (d, J=15.7 Hz, 1H), 4.17 (dt, J=13.7, 2.7 Hz, 1H), 4.02 (d, J=9.8 Hz, 1H), 3.67 (dt, J=9.4, 7.4 Hz, 1H), 3.36 (dt, J=11.7, 2.7 Hz, 1H), 3.14 (td, J=11.7, 3.1 Hz, 1H), 2.95 (td, J=11.7, 3.5 Hz, 1H), 2.95 (s, 3H), 2.83 (m, 1H), 2.69 (m, 1H), 2.52 (s, 3H), 2.24 (s, 3H), 2.20 (m, 1H), 1.91 (m, 4H), 1.46 (m, 2H), 1.33 (m, 1H).

EXAMPLE 64

Compound 64

N-[(1R)-1-[3,5-bis(trifluoromethyl)phenyl]ethyl]-N-methyl-1-(2-methylphenyl)-octahydropyrrolo[1,2-a]piperazine-2-carboxamide (Pure Enantiomer, Isomer 2, with ANTI Configuration at C1-C8a)

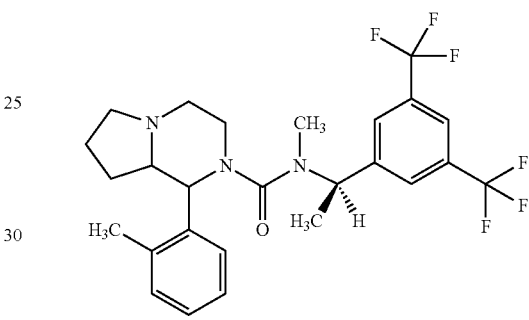

After evaporation of the second collected fraction from chiral preparative HPLC Compound 64 was obtained (isomer 2, 150 mg). Chiral HPLC: Chiralpak AD-H column (25×0.46 cm), 5 μm, n-Hexane/2-propanol 90/10% v/v; Flow rate: 1 mL/min. Detection: DAD at 220 nm, Circular Dichroism detector: 230 nm, Rt=3.9 min. $^1$H NMR (400 MHz, CHLOROFORM-d) δ ppm 7.73 (s, 1H), 7.36 (s, 2H), 7.20 (m, 3H), 4.68 (d, J=15.7 Hz, 1H), 4.34 (d, J=15.7 Hz, 1H), 4.17 (dt, J=13.7, 2.7 Hz, 1H), 4.02 (d, J=9.8 Hz, 1H), 3.67 (dt, J=9.4, 7.4 Hz, 1H), 3.36 (dt, J=11.7, 2.7 Hz, 1H), 3.14 (td, J=11.7, 3.1 Hz, 1H), 2.95 (td, J=11.7, 3.5 Hz, 1H), 2.95 (s, 3H), 2.83 (m, 1H), 2.69 (m, 1H), 2.52 (s, 3H), 2.24 (s, 3H), 2.20 (m, 1H), 1.91 (m, 4H), 1.46 (m, 2H), 1.33 (m, 1H).

EXAMPLE 65

Compound 65

N-{[3,5-bis(trifluoromethyl)phenyl]methyl}-7,7-bis(2-hydroxyethyl)-N-methyl-1-(2-methylphenyl)-octahydropyrrolo[1,2-a]piperazine-2-carboxamide (Pure Enantiomer, with ANTI Configuration at C1-C8a)

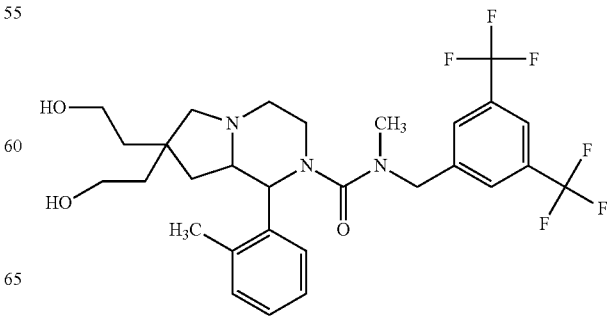

To a 0° C. cooled solution of Intermediate 49 (2.09 g, 3.47 mmol) in dry THF (30 mL) under nitrogen, a solution of BH$_3$.SMe$_2$ (2M, THF) was added (6.94 mL, 13.88 mmol) and the resulting mixture was stirred at RT 17 h. The mixture was cooled again at 0° C. and a second amount of BH$_3$.SMe$_2$ (2M, THF) was added dropwise (3.47 mL, 6.94 mmol) and the mixture was stirred at RT for 6 h, then it was quenched by adding HCl 1M (15 mL) and MeOH (15 mL). The resulting mixture was stirred at RT for 17 h, then it was concentrated in vacuo. The residue was diluted with water (50 mL) and the PH adjusted to 9 by addition of NaHCO$_3$ aq. sat. sol., followed by extraction with DCM (3×50 mL). The combined organic layers were dried over Na$_2$SO$_4$, filtered and concentrated in vacuo. The residue was dissolved in 15 mL of MeOH then loaded on SCX cartridge (Strata 20 g, Phenomenex). The cartridge was washed with MeOH, then diluted with ammonia 2M in MeOH. After evaporation of the fractions, 1.63 g of a white solid were obtained. This material was purified by chiral preparative HPLC (Column: Chiralpak IC (25×3.0 cm), 5µ; Mobile phase: n-Hexane/2-Propanol 90/10% v/v; Flow rate (ml/min) 32 ml/min; DAD detection 220 nm) to give two fractions, which, after evaporation gave two products: Enantiomer 1 (Compound 65, described here) and enantiomer 2 (Compound 66, described below). Compound 65 (529 mg): (Column Chiralpak IC (25×0.46 cm), 5 um; Mobile phase n-Hexane/Ethanol 85/15% v/v; Flow rate (ml/min) 0.8; DAD 220 nm; CD 230 nm;) Rt=13.973 min., m/z (ES+): 588.3 [M+H]$^+$; $^1$H NMR (400 MHz, CHLOROFORM-d) δ ppm 7.73 (s, 2H), 7.38 (s, 3H), 7.24 (m, 2H), 7.13 (m, 4H), 5.02 (br s, 2H), 4.66 (m, 2H), 4.43 (br s, 2H), 4.35 (d, 2H), 3.91 (td, 2H), 3.75 (m, 2H), 7.65 (m, 3H), 3.37 (m, 2H), 3.14 (m, 5H), 2.92 (s, 4H), 2.56 (s, 4H), 2.46 (m, 4H), 2.20 (d, 2H), 1.81 (m, 2H), 1.71 (dd, 2H), 1.63 (t, 3H), 1.44 (m, 3H).

EXAMPLE 66

Compound 66

"N-{[3,5-bis(trifluoromethyl)phenyl]methyl}-7,7-bis (2-hydroxyethyl)-N-methyl-1-(2-methylphenyl)- octahydropyrrolo[1,2-a]piperazine-2-carboxamide (Pure Enantiomer, with ANTI Configuration at C1-C8a)

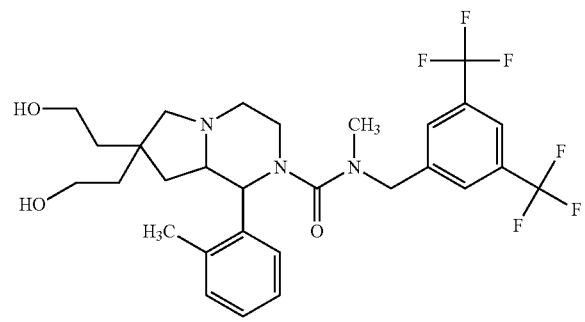 [SMILES: Cc1ccccc1C1C2CC(CCO)(CCO)CN2CCN1C(=O)N(C)Cc1cc(C(F)(F)F)cc(C(F)(F)F)c1]

Compound 66 (Enantiomer 2): (Column Chiralpak IC (25× 0.46 cm), 5 um; Mobile phase n-Hexane/Ethanol 85/15% v/v; Flow rate (ml/min) 0.8; DAD 220 nm; CD 230 nm;) Rt=19.318 min., m/z (ES+): 588.2 [M+H]$^+$; $^1$H NMR (400 MHz, CHLOROFORM-d) δ ppm 7.73 (m, 1H), 7.38 (s, 2H), 7.27 (s, 2H), 7.15 (d, 3H), 5.02 (m, 1H), 4.64 (d, 1H), 4.39 (m, 1H), 4.38 (m, 1H), 4.35 (d, 2H), 3.91 (m, 1H), 3.76 (m, 1H), 3.63 (m, 2H), 3.37 (m, 1H), 3.14 (s, 3H), 2.92 (s, 3H), 2.56 (s, 3H), 2.46 (m, 2H), 2.20 (d, 1H), 1.81 (m, 1H), 1.70 (m, 1H), 1.63 (t, 2H), 1.44 (m, 2H). 1.23 (m, 1H).

EXAMPLE 67

Compound 67

N-[(1R)-1-[3,5-bis(trifluoromethyl)phenyl]ethyl]-7- (hydroxymethyl)-N-methyl-1-(2-methylphenyl)- octahydropyrrolo[1,2-a]piperazine-2-carboxamide (Isomer 1, Pure Enantiomer, with ANTI Configuration at C1-C8a)

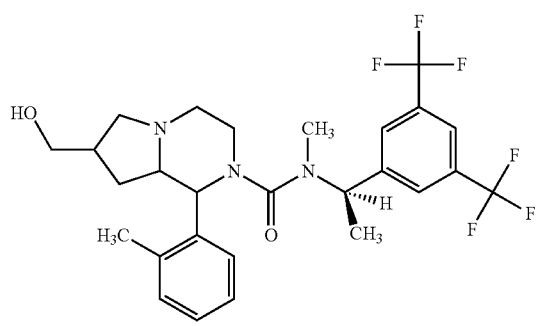 [SMILES: Cc1ccccc1C1C2CC(CO)CN2CCN1C(=O)N(C)[C@H](C)c1cc(C(F)(F)F)cc(C(F)(F)F)c1]

CaCl$_2$ (226.4 mg, 2.04 mmol) was added to a solution of Intermediate 44 (0.8 g, 1.36 mmol) in MeOH (40 mL), then it was cooled at 0° C. and NaBH$_4$ (154.3 mg, 4.08 mmol) was added portionwise. After stirring at 25° C. for 0.5 h, water (20 mL) was added, MeOH was evaporated and the aqueous layer was extracted with DCM (3×50 mL). The organic layer was separated, dried over Na$_2$SO$_4$, filtered and evaporated to give 0.7 g of a yellow oil. The same reaction was repeated on a different batch of starting material to give other 0.5 g of a yellow oil. Both crudes were purified by preparative HPLC (Fractionlynx (Waters) with ZQ MS detector; LC/MS Conditions: Columns: Phenomenex Luna C18 (2) 250×21.2 mm 10; µm @ RT; Solvents: H2O+0.1% HCOOH; Acetonitrile; UV detection range: 210 nm to 350 nm; Acquisition rate: 1.0 spectra/s) to give three fractions each; Rt=13.98 min (fraction A), Rt=14.32 min (fraction B), Rt=15.22 min (fraction C). Both chromatograms showed peaks having the same Rt, thus, the corresponding fractions were combined together. Fractions A (95 mg, containing mainly one isomer). Fraction B (200 mg, containing mainly two isomers) and Fraction C (120 mg, containing mainly one isomer). Elaboration of Fractions B and C will be described in the three next experimental parts. Fraction A (95 mg) was dissolved in dry THF (10 mL) and, at 0° C., BH$_3$.Me$_2$S (2 M in THF) (0.34 mL, 0.68 mmol) was added dropwise. The reaction mixture was stirred at RT for 16 h. BH$_3$.Me$_2$S (2 M in THF) (0.34 mL, 0.68 mmol) was added again and the reaction was left stirring at RT for 8 h. MeOH (2 mL) was added dropwise followed by HCl 1N (2 mL) and the reaction mixture was stirred overnight at RT, then it was concentrated in vacuo, diluted with DCM (30 mL) and washed with NaHCO$_3$ aq. sat. sol. (20 mL). The organic layer was separated, dried over Na$_2$SO$_4$, filtered and concentrated in vacuo to give 85 mg of a colourless oil which was purified by preparative HPLC (Rt=1.9 min). After evaporation of the fractions, the title compound (33.9 mg) was obtained as a white solid. HPLC-MS: Rt=1.20 min, m/z (ES+): 544.2 [M+H]$^+$. $^1$H NMR (500 MHz, CHLOROFORM-d) δ ppm 7.78 (s, 1H), 7.58 (s, 2H), 7.13 (m, 4H), 5.56 (d, J=6.8 Hz, 1H), 4.26 (d, J=9.3 Hz, 1H), 3.46 (m, 2H), 3.32 (m, 2H), 3.15 (m, 2H), 2.68 (s, 3H), 2.54 (s, 3H), 2.47 (m, 2H), 2.24 (d, J=5.9 Hz, 1H), 2.04 (t, J=8.6 Hz, 1H), 1.73 (m, 1H), 1.41 (d, J=6.4 Hz, 3H), 1.17 (td, J=6.4, 2.9 Hz, 1H).

EXAMPLE 68

Compound 68 N-[(1R)-1-[3,5-bis(trifluoromethyl)phenyl]ethyl]-7-(hydroxymethyl)-N-methyl-1-(2-methylphenyl)-octahydropyrrolo[1,2-a]piperazine-2-carboxamide (Isomer 2, Pure Enantiomer, with ANTI Configuration at C1-C8a)

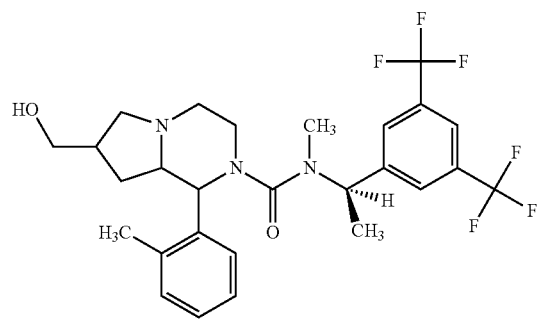 [SMILES: Cc1ccccc1C1C2CC(CO)CN2CCN1C(=O)N(C)[C@H](C)c1cc(C(F)(F)F)cc(C(F)(F)F)c1]

Fraction B mentioned in Example 67 (200 mg) was dissolved in dry THF (25 mL) and, at 0° C., BH$_3$.Me$_2$S (2 M in THF) (0.7 mL, 1.4 mmol) was added dropwise. The reaction mixture was stirred at RT for 16 h. BH$_3$.Me$_2$S (2 M in THF) (0.7 mL, 1.4 mmol) was added again and the reaction was left stirring RT for 8 h. MeOH (2 mL) was added dropwise followed by HCl 1N (2 mL) and the reaction mixture was stirred overnight at RT, then it was concentrated in vacuo, diluted with DCM (30 mL) and washed with NaHCO$_3$ aq. sat. sol. (20 mL). The organic layer was separated, dried over Na$_2$SO$_4$, filtered and concentrated in vacuo to give 180 mg of a colourless oil which was purified by preparative HPLC (LC/MS System: Fractionlynx (Waters) with ZQ MS detector LC/MS Conditions: Columns: Gemini 5 μm C18 110A AXIA 100×30 mm; Injection loop: 1 ml; Solvents: ammonium bicarbonate aqueous solution adjusted to pH 10 with ammonia, Acetonitrile; UV detection range: 210 nm to 350 nm; Rt=10.86 min and 11.95 min). After evaporation of the fractions, two isomers were isolated. Isomer 2 (described here) and isomer 3 (described below). The title compound (24 mg) was obtained as a white solid. HPLC-MS: Rt=1.22 min, m/z (ES+): 544.2 [M+H]$^+$. $^1$H NMR (500 MHz, CHLOROFORM-d) δ ppm 7.71 (s, 1H), 7.39 (s, 2H), 7.14 (m, 4H), 5.61 (d, J=6.8 Hz, 1H), 4.25 (d, J=9.8 Hz, 1H), 3.47 (dd, J=10.3, 6.8 Hz, 2H), 3.35 (m, 2H), 3.15 (m, 2H), 2.79 (s, 3H), 2.48 (m, 5H), 2.24 (m, 1H), 2.05 (t, J=8.6 Hz, 1H), 1.75 (m, 1H), 1.51 (d, J=6.8 Hz, 3H), 1.18 (m, 1H).

EXAMPLE 69

Compound 69

N-[(1R)-1-[3,5-bis(trifluoromethyl)phenyl]ethyl]-7-(hydroxymethyl)-N-methyl-1-(2-methylphenyl)-octahydropyrrolo[1,2-a]piperazine-2-carboxamide (Isomer 3, Pure Enantiomer, with ANTI Configuration at C1-C8a)

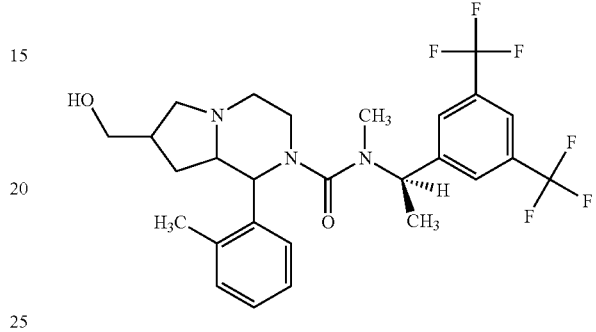

Compound 69 (Isomer 3 mentioned in the experimental of Compound 68) was obtained as a white solid (45.7 mg mg). HPLC-MS: Rt=1.26 min, m/z (ES+): 544.0 [M+H]$^+$. $^1$H NMR (500 MHz, CHLOROFORM-d) δ ppm 7.74 (s, 1H), 7.37 (s, 2H), 7.26 (m, 1H), 7.16 (m, 3H), 4.69 (d, J=15.7 Hz, 1H), 4.36 (d, J=15.4 Hz, 1H), 4.18 (dt, J=12.8, 2.8 Hz, 1H), 4.09 (d, J=10.0 Hz, 1H), 3.73 (dt, J=9.7, 7.4 Hz, 1H), 3.37 (dt, J=12.2, 2.8 Hz, 1H), 3.15 (td, J=12.5, 2.7 Hz, 1H), 2.96 (s, 3H), 2.96 (m, 1H), 2.53 (s, 3H), 2.44 (m, 1H), 2.35 (m, 1H), 1.87 (dddd, J=13.2, 9.6, 7.3, 3.9 Hz, 1H), 1.69 (m, 1H).

EXAMPLE 70

Compound 70

N-[(1R)-1-[3,5-bis(trifluoromethyl)phenyl]ethyl]-7-(hydroxymethyl)-N-methyl-1-(2-methylphenyl)-octahydropyrrolo[1,2-a]piperazine-2-carboxamide (Isomer 4, Pure Enantiomer, with ANTI Configuration at C1-C8a)

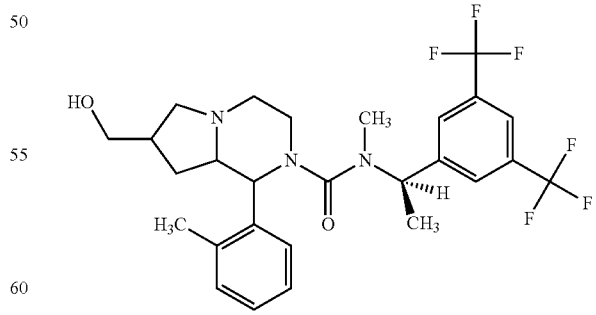

Fraction C mentioned in Example 67 (120 mg) was dissolved in dry THF (15 mL) and, at 0° C., BH$_3$.Me$_2$S (2 M in THF) (0.42 mL, 0.84 mmol) was added dropwise. The reaction mixture was stirred at RT for 16 h. BH$_3$.Me$_2$S (2 M in THF) (0.42 mL, 0.84 mmol) was added again and the reaction was left stirring RT for 8 h. MeOH (2 mL) was added dropwise followed by HCl 1N (2 mL) and the reaction mixture was stirred overnight at RT, then it was concentrated in vacuo, diluted with DCM (30 mL) and washed with NaHCO₃ aq. sat. sol. (20 mL). The organic layer was separated, dried over Na₂SO₄, filtered and concentrated in vacuo to give 120 mg of a colourless oil which was purified by chiral preparative HPLC (Column Chiralpak IC (25×3.0 cm), 5μ; Mobile phase: n-Hexane/2-Propanol 90/10% v/v; Flow rate (ml/min): 40 ml/min; DAD detection: 220 nm, Rt=10.86 min). After evaporation of the fractions, the title compound (48.6 mg) was obtained as a white solid. Column: Chiralpak IC (25× 0.46 cm), 5 um; Mobile phase: n-Hexane/2-Propanol 90/10% v/v; Flow rate (ml/min): 1.0; DAD: 220 nm; Rt=12.83; Rt=1.28 min, m/z (ES+): 544.5 [M+H]⁺. ¹H NMR (500 MHz, CHLOROFORM-d) δ ppm 7.70 (s, 1H), 7.38 (s, 2H), 7.13 (m, 4H), 5.61 (q, J=6.8 Hz, 1H), 4.28 (d, J=9.3 Hz, 1H), 3.67 (dd, J=10.0, 4.6 Hz, 1H), 3.54 (dd, J=10.0, 5.6 Hz, 1H), 3.32 (m, 1H), 3.09 (m, 3H), 2.79 (s, 3H), 2.54 (s, 3H), 2.42 (m, 2H), 2.22 (m, 2H), 1.60 (m, 1H), 1.51 (d, J=7.3 Hz, 3H), 1.37 (ddd, J=12.5, 10.5, 5.9 Hz, 1H).

EXAMPLE 71

Compound 71

N-[(1R)-1-[3,5-bis(trifluoromethyl)phenyl]ethyl]-N-methyl-1-(2-methylphenyl)-7-(morpholin-4-ylmethyl)-6-oxo-octahydropyrrolo[1,2-a]piperazine-2-carboxamide (Pure Enantiomer, with ANTI Configuration at C1-C8a)

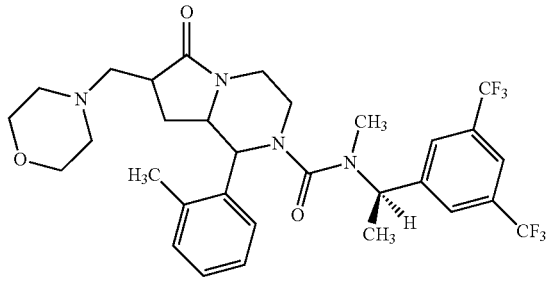 [SMILES: Cc1ccccc1C1C2CC(CN3CCOCC3)C(=O)N2CCN1C(=O)N(C)[C@H](C)c1cc(C(F)(F)F)cc(C(F)(F)F)c1]

To a solution of Intermediate 50 (2.31 g, 3.64 mmol) in dry THF (60 mL) was added morpholine (3.18 mL, 36.4 mmol) and the reaction mixture was stirred at 65° C. for 4 days. The mixture was allowed to cool to RT and the solvent was removed in vacuo. The residue was partitioned between EtOAc (50 mL) and NaHCO₃ aq. sat. sol. (40 mL), then dried over Na₂SO₄, filtered and concentrated in vacuo. The residue was dissolved in 8 mL of MeOH and loaded on a SCX cartridge (Strata 20 g, Phenomenex). Elution with ammonia 2M in MeOH and evaporation of the fractions provided 1.7 g of a crude as a pale orange oil. This crude was separated via chiral preparative HPLC, (Column Chiralpak AD-H (25×3.0 cm), 5μ Mobile phase n-Hexane/2-Propanol 90/10% v/v Flow rate (ml/min) 40 ml/min DAD detection 220 nm Loop 1000 μL Total amount 1743 mg Solubilization 1743 mg in 58 ml EtOH/n-Hexane 7/3=30 mg/ml), providing 3 fractions. The first collected fraction resulted in a mixture of two isomers, while the second one and the third one contained pure isomers. The second fraction was evaporated, to provide 220 mg of the title compound as a white solid. ¹H NMR (500 MHz, CDCl₃) δ ppm 7.72 (s, 1H), 7.35 (s, 2H), 7.18 (m, 4H), 5.58 (q, J=7.2 Hz, 1H), 4.21 (d, J=13.2 Hz, 1H), 4.04 (d, J=10.3 Hz, 1H), 3.74 (m, 1H), 3.64 (m, 4H), 3.29 (d, J=12.2 Hz, 1H), 3.14 (td, J=12.5, 3.9 Hz, 1H), 2.90 (td, J=12.0, 2.9 Hz, 1H), 2.82 (s, 3H), 2.73 (dt, J=9.3, 4.6 Hz, 1H), 2.69 (m, 1H), 2.52 (s, 3H), 2.47 (m, 2H), 2.41 (m, 1H), 2.37 (m, 2H), 1.88 (m, 1H), 1.80 (m, 1H), 1.51 (d, J=7.3 Hz, 3H). Chiral HPLC: 18.7 min Column Chiralpak AD-H (25×0.46 cm), 5 um Mobile phase n-Hexane/2-Propanol 90/10% v/v Flow rate (ml/min) 1.0 DAD 220 nm CD-nm Loop 20 μL. UPLC-MS: Rt=1.27; m/z (ES+): 627.2 [M+H]⁺.

EXAMPLE 72

Compound 72

N-[(1R)-1-[3,5-bis(trifluoromethyl)phenyl]ethyl]-N-methyl-1-(2-methylphenyl)-7-(morpholin-4-ylmethyl)-6-oxo-octahydropyrrolo[1,2-a]piperazine-2-carboxamide (Pure Enantiomer, with ANTI Configuration at C1-C8a)

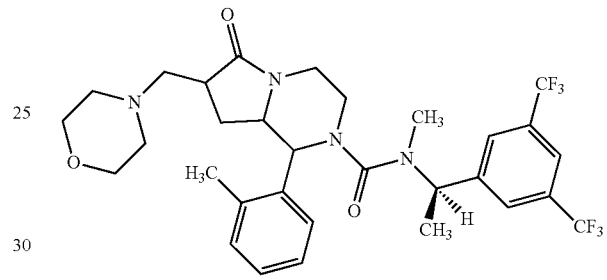

Evaporation of the third fraction provided 411 mg Compound 72 as a white solid. ¹H NMR (500 MHz, CDCl₃) δ ppm 7.72 (s, 1H), 7.35 (s, 2H), 7.18 (m, 4H), 5.59 (q, J=7.3 Hz, 1H), 4.15 (m, 1H), 4.05 (d, J=9.8 Hz, 1H), 3.66 (m, 5H), 3.34 (m, 1H), 3.14 (td, J=12.5, 2.9 Hz, 1H), 2.91 (td, J=12.1, 3.2 Hz, 1H), 2.85 (dd, J=12.0, 3.7 Hz, 1H), 2.82 (s, 3H), 2.58 (m, 4H), 2.52 (m, 1H), 2.47 (m, 2H), 2.42 (m, 2H), 2.01 (m, 1H), 1.68 (dt, J=13.1, 8.6 Hz, 1H), 1.51 (d, J=7.3 Hz, 3H). Chiral HPLC: 27.1 min Column Chiralpak AD-H (25×0.46 cm), 5 um Mobile phase n-Hexane/2-Propanol 90/10% v/v Flow rate (ml/min) 1.0 DAD 220 nm CD-nm Loop 20 μL. UPLC-MS: Rt=1.26; m/z (ES+): 627.2 [M+H]⁺.

EXAMPLE 73

Compound 73

N-[(1R)-1-[3,5-bis(trifluoromethyl)phenyl]ethyl]-N-methyl-1-(2-methylphenyl)-7-(morpholin-4-ylmethyl)-6-oxo-octahydropyrrolo[1,2-a]piperazine-2-carboxamide (Pure Enantiomer, with ANTI Configuration at C1-C8a)

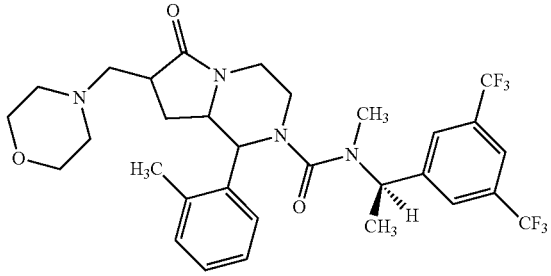 [SMILES: Cc1ccccc1C1C2CC(CN3CCOCC3)C(=O)N2CCN1C(=O)N(C)[C@H](C)c1cc(C(F)(F)F)cc(C(F)(F)F)c1]

The first fraction was subjected to a further purification by preparative chiral HPLC (Column Chiralpak AD-H (25×3.0 cm), 5μ Mobile phase n-Hexane/2-Propanol 90/10% v/v Flow rate (ml/min) 40 ml/min DAD detection 220 nm Loop 1000 μL Total amount 600 mg Solubilization 600 mg in 30 ml EtOH/n-Hexane 2/1=20 mg/ml), providing two fractions. The first fraction eluted was evaporated, providing 157 mg of Compound 73 as a white solid. $^1$H NMR (500 MHz, CDCl$_3$) δ ppm 7.78 (s, 1H), 7.55 (s, 2H), 7.18 (m, 4H), 5.56 (q, J=7.8 Hz, 1H), 4.14 (m, 1H), 4.06 (d, J=9.8 Hz, 1H), 3.68 (m, 5H), 3.28 (d, J=12.7 Hz, 1H), 3.12 (td, J=11.2, 5.4 Hz, 1H), 2.97 (td, J=13.7, 2.4 Hz, 1H), 2.85 (dd, J=13.7, 3.0 Hz, 1H), 2.70 (s, 3H), 2.57 (m, 4H), 2.52 (d, J=13.7 Hz, 1H), 2.44 (m, 4H), 2.02 (m, 1H), 1.65 (m, 1H), 1.40 (d, J=6.8 Hz, 3H). Chiral HPLC: Column Chiralpak AD-H (25×0.46 cm), 5μ Mobile phase n-Hexane/2-Propanol 90/10% v/v Flow rate (ml/min) 1.0 DAD 220 nm Loop 20 μL 100% e.e. (11.2 min). UPLC-MS: Rt=1.26; m/z (ES+): 627.2 [M+H]$^+$.

EXAMPLE 74

Compound 74

N-[(1R)-1-[3,5-bis(trifluoromethyl)phenyl]ethyl]-N-methyl-1-(2-methylphenyl)-7-(morpholin-4-ylmethyl)-6-oxo-octahydropyrrolo[1,2-a]piperazine-2-carboxamide (Pure Enantiomer, with ANTI Configuration at C1-C8a)

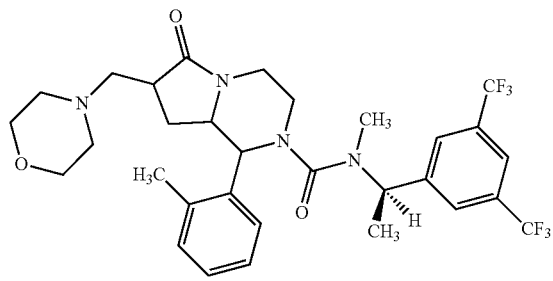 [SMILES: Cc1ccccc1C1C2CC(CN3CCOCC3)C(=O)N2CCN1C(=O)N(C)[C@H](C)c1cc(C(F)(F)F)cc(C(F)(F)F)c1]

From the same purification, the second fraction eluted was evaporated, providing 34 mg of Compound 74 as a white solid. $^1$H NMR (500 MHz, CDCl$_3$) δ ppm 7.71 (m, 1H), 7.46 (s, 2H), 7.12 (m, 4H), 5.46 (q, J=7.3 Hz, 1H), 4.11 (d, J=12.7 Hz, 1H), 3.97 (d, J=10.3 Hz, 1H), 3.71 (m, 1H), 3.56 (d, J=3.4 Hz, 4H), 3.16 (d, J=10.8 Hz, 1H), 3.04 (td, J=11.7, 4.4 Hz, 1H), 2.88 (td, J=13.0, 2.8 Hz, 1H), 2.66 (m, 1H), 2.62 (s, 3H), 2.60 (m, 1H), 2.45 (s, 3H), 2.39 (m, 2H), 2.33 (dd, J=12.7, 9.8 Hz, 1H), 2.28 (m, 1H), 1.81 (m, 1H), 1.70 (m, 1H), 1.32 (d, J=6.8 Hz, 3H) Chiral HPLC: Column Chiralpak AD-H (25×0.46 cm), 5μ Mobile phase n-Hexane/2-Propanol 90/10% v/v Flow rate (ml/min) 1.0 DAD 220 nm Loop 20 μL 93.6% e.e. (13.0 min). UPLC-MS: Rt=1.27; m/z (ES+): 627.2 [M+H]$^+$.

EXAMPLE 75

Compound 75

N-[(1R)-1-[3,5-bis(trifluoromethyl)phenyl]ethyl]-N-methyl-1-(2-methylphenyl)-6-oxo-octahydropyrrolo[1,2-a]piperazine 2 carboxamide (Enantiomer 1, Single Isomer with SYN Configuration at C1-C8a)

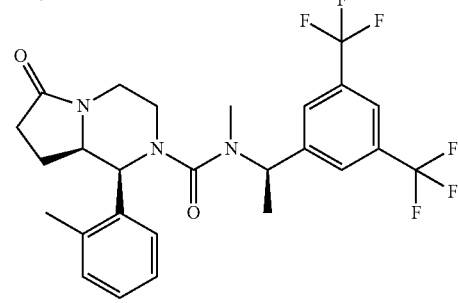

To a solution of triphosgene (63.6 mg, 0.22 mmol) in EtOAc (2 mL) at 0° C. was added solution of 1-(2-methylphenyl)-octahydropyrrolo[1,2-a]piperazin-6-one hydrochloride (racemic mixture with SYN configuration at C1-C8a, 100 mg, 0.43 mmol), DMAP (10.4 mg, 0.09 mmol) and TEA (90 mg, 0.86 mmol) in EtOAc (2 mL). The mixture was stirred for 1.5 h, followed by addition of 1-(3,5-bis(trifluoromethyl)phenyl)-N-methylmethanamine (163 mg, 0.6 mmol) in EtOAc (2 mL) and TEA (90 mg, 0.86 mmol). The reaction was stirred at 50° C. for 48 h and quenched with water. The resulting mixture was extracted with EtOAc and the organic layer was washed with 1 M aqueous HCl solution, dried over anhydrous Na$_2$SO$_4$ and then concentrated in high vacuum. The residue was purified by Prep-HPLC to give the compound 75 (20 mg, yield: 9%). $^1$H NMR (400 MHz, CDCl$_3$) δ ppm 7.80 (s, 1H), 7.68 (s, 2H), 7.37 (d, J=7.6 Hz, 1H), 7.22 (m, 3H), 5.54 (d, J=4.8 Hz, 1H), 5.11 (m, 1H), 4.30 (m, 1H), 4.20 (m, 1H), 3.45 (m, 2H), 3.02 (m, 1H), 2.51 (s, 3H), 2.38 (m, 2H), 2.29 (s, 3H), 1.74 (m, 1H), 1.70 (m, 3H); m/z (ES+): 528 [M+H]$^+$. Another enantiomer (single isomer with SYN configuration at C1-C8a, 12 mg, yield: 5%).

EXAMPLE 76

Compound 76

(1S,8aS)-N-(3-fluoro-5-(trifluoromethyl)benzyl)-7,7-bis(2-hydroxyethyl)-N-methyl-6-oxo-1-o-tolyl-hexahydropyrrolo[1,2-a]pyrazine-2(1H)-carboxamide

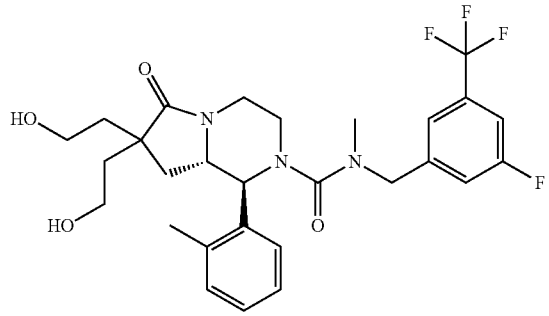 [SMILES: Cc1ccccc1[C@H]1[C@@H]2CC(CCO)(CCO)C(=O)N2CCN1C(=O)N(C)Cc1cc(F)cc(C(F)(F)F)c1]

A slow stream of O₃ in O₂ was passed through a cooled solution of Intermediate 56 (20 mg, 0.037 mmol) in DCM (10 mL) at −78° C. until a pale blue colour persisted. The reaction was purged with N₂ to remove the excess of O₃ followed by addition of NaBH₄ (20 mg, 0.53 mmol). The reaction mixture was allowed to warm to room temperature and stirred for 20 h. After quenched with water, the resulting mixture was extracted with DCM. The organic layer was washed with brine, dried over anhydrous Na₂SO₄ and then concentrated in high vacuum. The residue was purified by Prep-HPLC to give the compound 76 (4 mg, yield: 20%). ¹H NMR (400 MHz, CDCl₃) δ ppm 7.28 (s, 1H), 7.21 (m, 4H), 7.04 (s, 1H), 6.56 (d, J=8.8 Hz, 1H), 4.66 (d, J=15.6 Hz, 1H), 4.20 (m, 1H), 4.17 (m, 1H), 4.06 (m, 1H), 3.80 (m, 4H), 3.60 (m, 1H), 3.38 (m, 1H), 3.16 (m, 1H), 2.96 (m, 4H), 2.55 (s, 3H), 1.74 (m, 1H), 1.80 (m, 7H). m/z (ES+): 552 [M+H]⁺.

EXAMPLE 77

Compound 77

(1S,8aS)-7,7-bis(2-hydroxyethyl)-N-methyl-N-(3-methyl-5-(trifluoromethyl)benzyl)-6-oxo-1-o-tolyl-hexahydropyrrolo[1,2-a]pyrazine-2(1H)-carboxamide

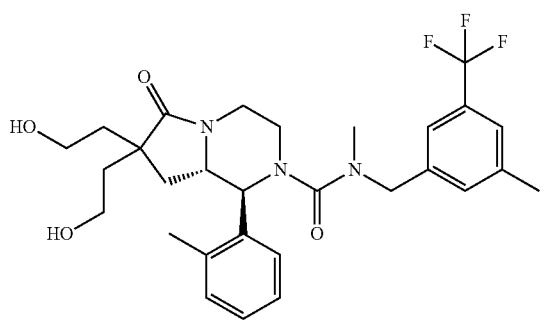 [SMILES: Cc1cc(CN(C)C(=O)N2CCN3C(=O)C(CCO)(CCO)C[C@H]3[C@@H]2c2ccccc2C)cc(C(F)(F)F)c1]

A slow stream of O₃ in O₂ was passed through a cooled solution of Intermediate 57 (130 mg, 0.22 mmol) in DCM (10 mL) at −78° C. until a pale blue colour persisted. The reaction was purged with N₂ to remove the excess of O₃ followed by addition of NaBH₄ (114 mg, 3.0 mmol). The reaction mixture was allowed to warm to room temperature and stirred for 20 h. After quenched with water, the resulting mixture was extracted with water and the resulting mixture was extracted with DCM. The organic layer was washed with brine, dried over anhydrous Na₂SO₄ and then concentrated in high vacuum. The residue was purified by Prep-HPLC to give the compound 77 (15 mg, yield: 18.3%). ¹H NMR (400 MHz, DMSO) δ ppm 7.40 (m, 2H), 7.15 (m, 4H), 6.87 (s, 1H), 4.35 (m, 4H), 3.88 (dd, J=9.8, 5.9 Hz, 2H), 3.63 (d, J=9.3 Hz, 1H), 3.50 (m, 3H), 3.28 (m, 2H), 3.10 (m, 1H), 2.78 (m, 4H), 2.45 (s, 3H), 2.27 (s, 3H), 1.60 (m, 6H). m/z (ES+): 548 [M+H]⁺.

EXAMPLE 78

Compound 78

(1S,8aS)-7,7-bis(2-hydroxyethyl)-N-(3-methoxy-5-(trifluoromethyl)benzyl)-N-methyl-6-oxo-1-o-tolyl-hexahydropyrrolo[1,2-a]pyrazine-2(1H)-carboxamide

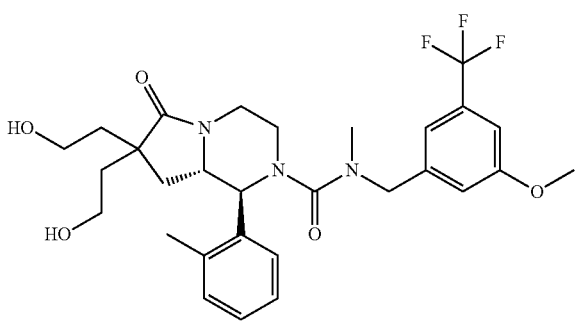 [SMILES: COc1cc(CN(C)C(=O)N2CCN3C(=O)C(CCO)(CCO)C[C@H]3[C@@H]2c2ccccc2C)cc(C(F)(F)F)c1]

A slow stream of O₃ in O₂ was passed through a cooled solution of Intermediate 58 (100 mg, 0.18 mmol) in DCM (10 mL) at −78° C. until a pale blue colour persisted. The reaction was purged with N₂ to remove the excess of O₃ followed by addition of NaBH₄ (137 mg, 3.6 mmol). The reaction mixture was allowed to warm to room temperature and stirred for 20 h. After quenched with water, the resulting mixture was extracted with DCM. The organic layer was washed with brine, dried over anhydrous Na₂SO₄ and then concentrated in high vacuum. The residue was purified by Prep-HPLC to give the compound 78 (40 mg, yield: 39.5%). ¹H NMR (400 MHz, DMSO) δ ppm 7.40 (m, 1H), 7.10 (dd, J=7.4, 4.8 Hz, 4H), 6.82 (d, J=17.5 Hz, 2H), 4.41 (m, 4H), 3.88 (t, J=11.9 Hz, 2H), 3.70 (m, 4H), 3.50 (m, 4H), 3.25 (m, 1H), 3.13 (t, J=10.3 Hz, 1H), 2.81 (m, 4H), 2.44 (s, 3H), 1.52 (m, 6H). m/z (ES+): 564 [M+H]⁺.

EXAMPLE 79

Compound 79

(1S,8aS)-N-(3-chloro-5-(trifluoromethyl)benzyl)-7,7-bis(2-hydroxyethyl)-N-methyl-6-oxo-1-o-tolyl-hexahydropyrrolo[1,2-a]pyrazine-2(1H)-carboxamide

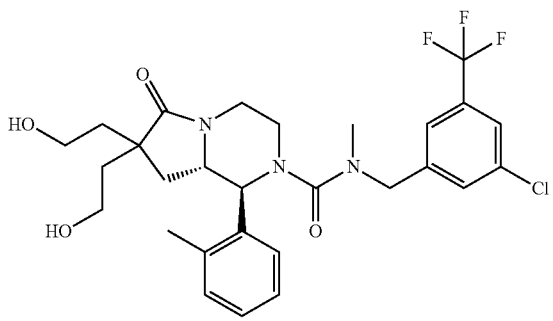 [SMILES: Cc1ccccc1[C@H]1[C@@H]2CC(CCO)(CCO)C(=O)N2CCN1C(=O)N(C)Cc1cc(Cl)cc(C(F)(F)F)c1]

A slow stream of O₃ in O₂ was passed through a cooled solution of Intermediate 58 (100 mg, 0.18 mmol) in DCM (10 mL) at −78° C. until a pale blue colour persisted. The reaction was purged with N₂ to remove the excess of O₃ followed by addition of NaBH₄ (137 mg, 3.6 mmol). The reaction mixture was allowed to warm to room temperature and stirred for 20 h. After quenched with water, the resulting mixture was extracted with DCM. The organic layer was washed with brine, dried over anhydrous Na₂SO₄ and then concentrated in high vacuum. The residue was purified by Prep-HPLC to give the compound 79 (15 mg, yield: 15%). ¹H NMR (400 MHz, CDCl₃) δ ppm 7.47 (s, 1H), 7.28 (s, 2H), 7.21 (s, 3H), 7.11 (s, 1H), 7.00 (s, 1H), 4.62 (d, J=15.2 Hz, 1H), 4.30 (m, 1H), 4.16 (m, 1H), 4.07 (m, 1H), 3.76 (m, 4H), 3.62 (m, 1H), 3.40 (m, 1H), 3.17 (m, 1H), 3.02 (m, 1H), 2.99 (s, 3H), 2.52 (s, 3H), 1.85 (m, 6H). m/z (ES+): 568 [M+H]⁺.

EXAMPLE 80

Compound 80

(1S,8aS)-7,7-bis(2-hydroxyethyl)-N-methyl-6-oxo-1-o-tolyl-N-(3-(trifluoromethyl)benzyl)hexahydro-pyrrolo[1,2-a]pyrazine-2(1H)-carboxamide

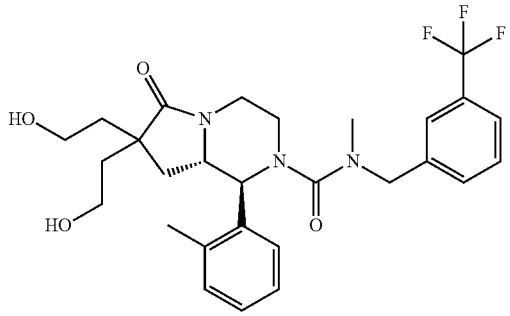 [SMILES: Cc1ccccc1[C@H]1[C@@H]2CC(CCO)(CCO)C(=O)N2CCN1C(=O)N(C)Cc1cccc(C(F)(F)F)c1]

A slow stream of O₃ in O₂ was passed through a cooled solution of Intermediate 58 (90 mg, 0.17 mmol) in DCM (10 mL) at −78° C. until a pale blue colour persisted. The reaction was purged with N₂ to remove the excess of O₃ followed by addition of NaBH₄ (194 mg, 5.1 mmol). The reaction mixture was allowed to warm to room temperature and stirred for 20 h. After quenched with water, the resulting mixture was extracted with DCM. The organic layer was washed with brine, dried over anhydrous Na₂SO₄ and then concentrated in high vacuum. The residue was purified by Prep-HPLC to give the compound 80 (10 mg, yield: 11%). ¹H NMR (400 MHz, CDCl₃) δ ppm 7.48 (d, J=7.6 Hz, 1H), 7.30 (m, 2H), 7.21 (m, 4H), 6.88 (d, J=8.0 Hz, 1H), 4.62 (d, J=15.2 Hz, 1H), 4.35 (m, 1H), 4.10 (m, 2H), 3.78 (m, 4H), 3.62 (m, 1H), 3.30 (m, 1H), 3.15 (m, 2H), 2.96 (m, 1H), 2.92 (s, 3H), 2.56 (s, 3H), 2.28 (s, 1H), 1.85 (m, 6H). m/z (ES+): 534 [M+H]⁺.

EXAMPLE 81 & EXAMPLE 82

Compound 81 & Compound 82

(1S,8aS)-N-(1-(3,5-bis(trifluoromethyl)phenyl)-3-hydroxypropyl)-7,7-bis(2-hydroxyethyl)-N-methyl-6-oxo-1-o-tolylhexahydropyrrolo[1,2-a]pyrazine-2(1H)-carboxamide

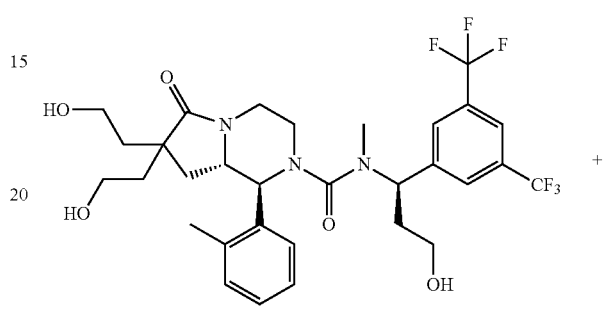

+

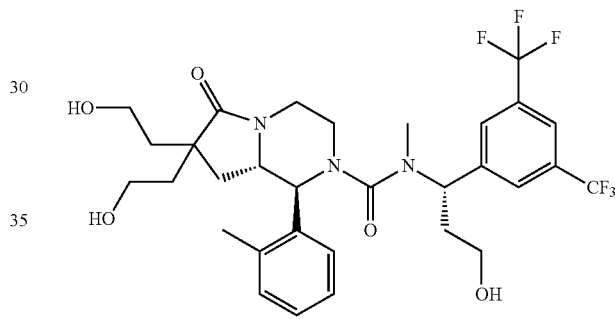

A slow stream of O₃ in O₂ was passed through a cooled solution of Intermediate 64 (30 mg, 0.05 mmol) in DCM (10 mL) at −78° C. until a pale blue colour persisted. The reaction was purged with N₂ to remove the excess of O₃ followed by addition of NaBH₄ (53 mg, 1.4 mmol). The reaction mixture was allowed to warm to room temperature and stirred for 20 h. After quenched with water, the resulting mixture was extracted with DCM. The organic layer was washed with brine, dried over anhydrous Na₂SO₄ and then concentrated in high vacuum. The residue was purified by Prep-HPLC to give the compound 81 (4 mg, yield: 11%) and the compound 82 (4 mg, yield: 11%).

¹H NMR (400 MHz, CDCl₃) δ ppm 7.83 (s, 1H), 7.63 (s, 2H), 7.40 (m, 1H), 7.20 (m, 1H), 5.58 (dd, J=15.2, 2.8 Hz, 1H), 4.15 (m, 2H), 4.12 (m, 1H), 3.83 (m, 3H), 3.64 (m, 1H), 3.31 (m, 2H), 3.14 (m, 1H), 3.06 (m, 3H), 2.68 (s, 3H), 2.56 (s, 3H), 2.47 (m, 1H), 2.21 (m, 6H), 1.90 (m, 6H). m/z (ES+): 646 [M+H]⁺.

¹H NMR (400 MHz, CDCl₃) δ ppm 7.80 (s, 1H), 7.41 (m, 2H), 7.28 (s, 1H), 7.21 (m, 1H), 7.15 (m, 3H), 6.88 (dd, J=11.2, 2.4 Hz, 1H), 4.16 (m, 2H), 4.07 (m, 6H), 3.83 (m, 2H), 3.14 (m, 1H), 3.03 (m, 2H), 2.15 (s, 3H), 2.00 (m, 10H). m/z (ES+): 646 [M+H]⁺.

EXAMPLE 83

Compound 83

(1S,8aS)-N-(1-(3,5-bis(trifluoromethyl)phenyl)propyl)-7,7-bis(2-hydroxyethyl)-N-methyl-6-oxo-1-o-tolylhexahydropyrrolo[1,2-a]pyrazine-2(1H)-carboxamide

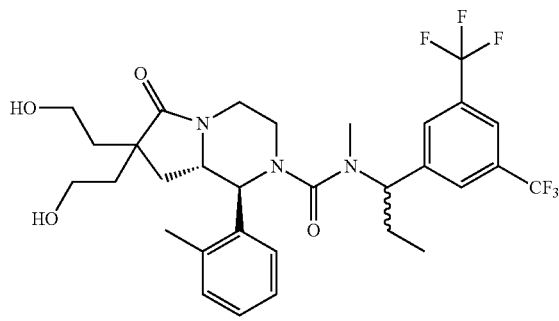 [SMILES: CCC(c1cc(C(F)(F)F)cc(C(F)(F)F)c1)N(C)C(=O)N1CCN2C(=O)C(CCO)(CCO)C[C@H]2[C@@H]1c1ccccc1C]

A slow stream of $O_3$ in $O_2$ was passed through a cooled solution of Intermediate 67 (50 mg, 0.08 mmol) in DCM (10 mL) at −78° C. until a pale blue colour persisted. The reaction was purged with $N_2$ to remove the excess of $O_3$ followed by addition of $NaBH_4$ (61 mg, 1.6 mmol). The reaction mixture was allowed to warm to room temperature and stirred for 20 h. After quenched with water, the resulting mixture was extracted with DCM. The organic layer was washed with brine, dried over anhydrous $Na_2SO_4$ and then concentrated in high vacuum. The residue was purified by Prep-HPLC to give the compound 83 (12 mg, yield: 23.8%). $^1$H NMR (400 MHz, CDCl$_3$) δ ppm 7.72 (s, 1H), 7.37 (s, 2H), 7.18 (m, 3H), 7.10 (dd, J=9.7, 4.2 Hz, 1H), 5.36 (dd, J=10.9, 4.9 Hz, 1H), 4.12 (dd, J=28.4, 11.2 Hz, 2H), 3.93 (m, 2H), 3.76 (m, 2H), 3.64 (m, 1H), 3.39 (d, J=10.8 Hz, 1H), 3.17 (td, J=12.5, 3.6 Hz, 1H), 2.98 (td, J=12.0, 3.2 Hz, 1H), 2.81 (s, 3H), 2.54 (d, J=7.8 Hz, 3H), 2.06 (m, 1H), 1.92 (dd, J=12.2, 6.1 Hz, 2H), 1.90 (m, 4H), 1.78 (m, 3H), 0.97 (t, J=7.2 Hz, 3H). m/z (ES+): 630 [M+H]$^+$.

EXAMPLE 84

Compound 84

(1S,8aS)-7,7-bis(2-hydroxyethyl)-N-methyl-N-((S)-1-(3-methyl-5-(trifluoromethyl)phenyl)ethyl)-6-oxo-1-o-tolylhexahydropyrrolo[1,2-a]pyrazine-2(1H)-carboxamide

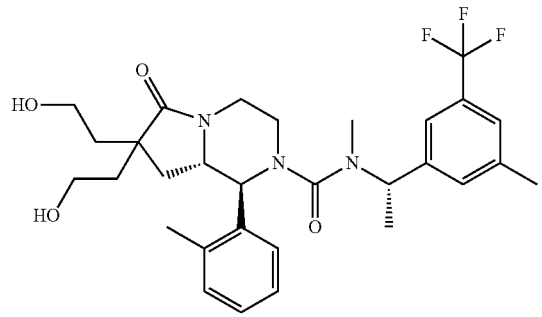 [SMILES: Cc1cc([C@H](C)N(C)C(=O)N2CCN3C(=O)C(CCO)(CCO)C[C@H]3[C@@H]2c2ccccc2C)cc(C(F)(F)F)c1]

A slow stream of $O_3$ in $O_2$ was passed through a cooled solution of Intermediate 81 (100 mg, 0.18 mmol) in DCM (30 mL) at −78° C. until a pale blue colour persisted. The reaction was purged with $N_2$ to remove the excess of $O_3$ followed by addition of $NaBH_4$ (137 mg, 3.6 mmol). The reaction mixture was allowed to warm to room temperature and stirred for 20 h. After quenched with water, the resulting mixture was extracted with DCM. The organic layer was washed with brine, dried over anhydrous $Na_2SO_4$ and then concentrated in high vacuum. The residue was purified by Prep-HPLC to give the compound 84 (12 mg, yield: 23.8%). $^1$H NMR (400 MHz, CDCl$_3$) δ ppm 7.32 (m, 2H), 7.22 (m, 3H), 7.05 (s, 1H), 6.73 (s, 1H), 5.53 (d, J=7.1 Hz, 1H), 4.10 (dd, J=25.2, 11.1 Hz, 2H), 3.89 (m, 1H), 3.76 (qd, J=11.4, 5.4 Hz, 3H), 3.64 (m, 1H), 3.33 (d, J=10.8 Hz, 1H), 3.14 (td, J=12.6, 3.6 Hz, 1H), 2.95 (td, J=12.1, 3.2 Hz, 1H), 2.77 (s, 3H), 2.55 (d, J=10.5 Hz, 3H), 2.25 (s, 3H), 1.92 (t, J=5.9 Hz, 2H), 1.89 (m, 3H), 1.78 (m, 3H), 1.46 (d, J=7.1 Hz, 3H). m/z (ES+): 562 [M+H]$^+$.

EXAMPLE 85

Compound 85

(1S,8aS)-7,7-bis(2-hydroxyethyl)-N-methyl-N-((R)-1-(3-methyl-5-(trifluoromethyl)phenyl)ethyl)-6-oxo-1-o-tolylhexahydropyrrolo[1,2-a]pyrazine-2(1H)-carboxamide

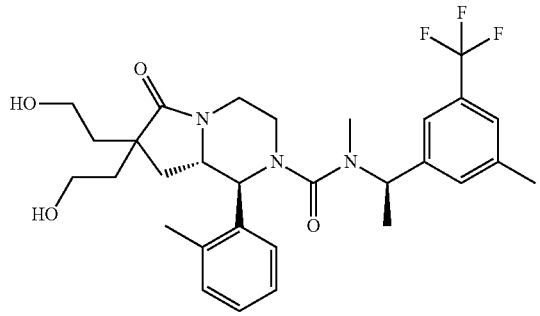 [SMILES: Cc1cc([C@@H](C)N(C)C(=O)N2CCN3C(=O)C(CCO)(CCO)C[C@H]3[C@@H]2c2ccccc2C)cc(C(F)(F)F)c1]

A slow stream of $O_3$ in $O_2$ was passed through a cooled solution of Intermediate 77 (100 mg, 0.18 mmol) in DCM (30 mL) at −78° C. until a pale blue colour persisted. The reaction was purged with $N_2$ to remove the excess of $O_3$ followed by addition of $NaBH_4$ (137 mg, 3.6 mmol). The reaction mixture was allowed to warm to room temperature and stirred for 20 h. After quenched with water, the resulting mixture was extracted with DCM. The organic layer was washed with brine, dried over anhydrous $Na_2SO_4$ and then concentrated in high vacuum. The residue was purified by Prep-HPLC to give the compound 85 (10 mg, yield: 20%). $^1$H NMR (400 MHz, CDCl$_3$) δ ppm 7.33 (s, 1H), 7.28 (m, 1H), 7.20 (m, 3H), 7.14 (m, 1H), 7.00 (s, 1H), 5.49 (d, J=7.8 Hz, 1H), 4.10 (m, 2H), 3.82 (m, 4H), 3.59 (m, 1H), 3.33 (m, 1H), 3.15 (m, 1H), 3.00 (m, 1H), 2.64 (s, 3H), 2.56 (s, 3H), 2.35 (s, 3H), 1.76 (m, 8H), 1.40 (m, 3H). m/z (ES+): 562 [M+H]$^+$.

EXAMPLE 86

Compound 86

(1S,8aS)-N-((S)-1-(3,5-bis(trifluoromethyl)phenyl)-2-hydroxyethyl)-7,7-bis(2-hydroxyethyl)-N-methyl-6-oxo-1-o-tolylhexahydropyrrolo[1,2-a]pyrazine-2(1H)-carboxamide

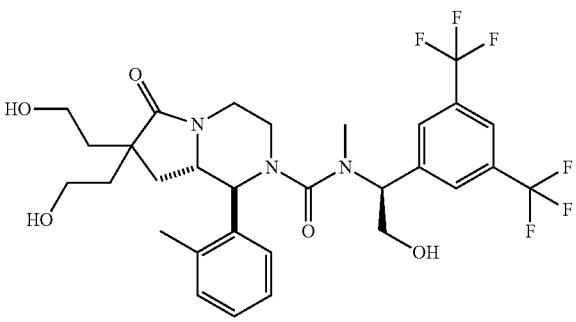

A slow stream of O₃ in O₂ was passed through a cooled solution of Intermediate 87 (100 mg, 0.16 mmol) in DCM (10 mL) at −78° C. until a pale blue colour persisted. The reaction was purged with N₂ to remove the excess of O₃ followed by addition of NaBH₄ (62 mg, 1.6 mmol). The reaction mixture was allowed to warm to room temperature and stirred for 20 h. After quenched with water, the resulting mixture was extracted with DCM. The organic layer was washed with brine, dried over anhydrous Na₂SO₄ and then concentrated in high vacuum. The residue was purified by Prep-HPLC to give the compound 86 (20 mg, yield: 51%). ¹H NMR (400 MHz, CDCl₃) δ ppm 7.71 (s, 1H), 7.31 (s, 2H), 7.26 (s, 1H), 7.15 (s, 2H), 5.37 (q, 1H), 4.06 (m, 3H), 3.71 (m, 5H), 3.47 (m, 3H), 3.15 (m, 2H), 2.93 (s, 3H), 2.52 (s, 4H), 1.93 (m, 1H), 1.77 (m, 6H). m/z (ES+): 632 [M+H]⁺.

EXAMPLE 87

Compound 87

(1S,8aS)-N-((R)-1-(3,5-bis(trifluoromethyl)phenyl)-2-hydroxyethyl)-7,7-bis(2-hydroxyethyl)-N-methyl-6-oxo-1-o-tolylhexahydropyrrolo[1,2-a]pyrazine-2(1H)-carboxamide

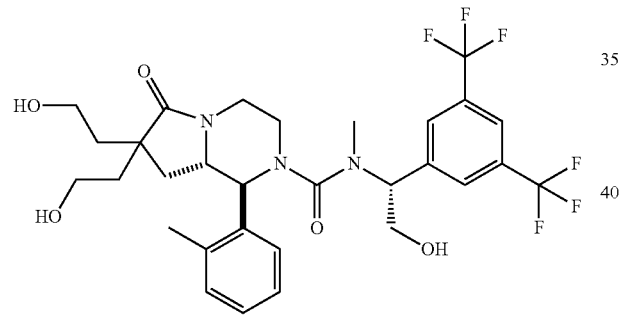

A slow stream of O₃ in O₂ was passed through a cooled solution of Intermediate 90 (70 mg, 0.11 mmol) in DCM (10 mL) at −78° C. until a pale blue colour persisted. The reaction was purged with N₂ to remove the excess of O₃ followed by addition of NaBH₄ (125 mg, 3.3 mmol). The reaction mixture was allowed to warm to room temperature and stirred for 20 h. After quenched with water, the resulting mixture was extracted with DCM. The organic layer was washed with brine, dried over anhydrous Na₂SO₄ and then concentrated in high vacuum. The residue was purified by Prep-HPLC to give the compound 87 (20 mg, yield: 51%). ¹H NMR (400 MHz, CDCl₃) δ ppm 7.79 (s, 1H), 7.51 (s, 2H), 7.26 (m, 1H), 7.18 (m, 2H), 7.15 (m, 1H), 5.22 (m, 1H), 4.10 (m, 3H), 3.97 (m, 2H), 3.87 (m, 2H), 3.60 (m, 4H), 3.20 (m, 3H), 2.70 (s, 3H), 2.65 (m, 1H), 2.52 (s, 3H), 1.88 (m, 4H). m/z (ES+): 632 [M+H]⁺.

EXAMPLE 88

Compound 88

(1S,8aS)-7,7-bis(2-hydroxyethyl)-N-methyl-6-oxo-1-o-tolyl-N-((R)-1-(3-(trifluoromethyl)phenyl)ethyl) hexa hydropyrrolo[1,2-a]pyrazine-2(1H)-carboxamide

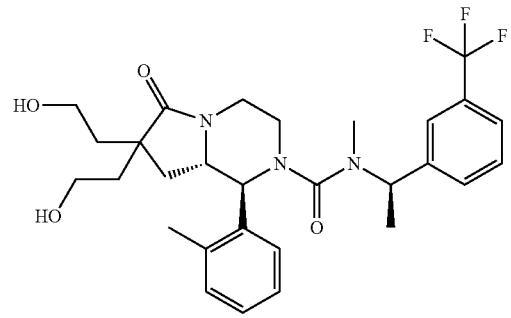 [SMILES: Cc1ccccc1[C@H]1[C@@H]2CC(CCO)(CCO)C(=O)N2CCN1C(=O)N(C)[C@H](C)c1cccc(C(F)(F)F)c1]

A slow stream of O₃ in O₂ was passed through a cooled solution of Intermediate 91 (82 mg, 0.15 mmol) in DCM (10 mL) at −78° C. until a pale blue colour persisted. The reaction was purged with N₂ to remove the excess of O₃ followed by addition of NaBH₄ (60 mg, 1.5 mmol). The reaction mixture was allowed to warm to room temperature and stirred for 20 h. After quenched with water, the resulting mixture was extracted with DCM. The organic layer was washed with brine, dried over anhydrous Na₂SO₄ and then concentrated in high vacuum. The residue was purified by Prep-HPLC to give the title compound (33 mg, yield: 40%). ¹H NMR (400 MHz, CDCl₃) δ ppm 7.54 (d, J=7.7 Hz, 1H), 7.45 (m, 2H), 7.28 (m, 5H), 5.52 (d, J=6.8 Hz, 1H), 4.10 (t, J=12.4 Hz, 2H), 3.79 (dtt, J=28.9, 11.4, 5.8 Hz, 4H), 3.65 (m, 1H), 3.32 (d, J=11.7 Hz, 1H), 3.15 (t, J=12.3 Hz, 1H), 3.00 (dd, J=11.8, 9.0 Hz, 1H), 2.67 (s, 3H), 2.57 (s, 3H), 1.92 (t, J=5.8 Hz, 2H), 1.88 (m, 2H), 1.71 (s, 4H), 1.38 (d, J=6.7 Hz, 3H); m/z (ES+): 548 [M+H]⁺.

EXAMPLE 89

Compound 89

(1S,8aS)-N-((R)-1-(3-chloro-5-(trifluoromethyl)phenyl)ethyl)-7,7-bis(2-hydroxyethyl)-N-methyl-6-oxo-1-o-tolylhexahydropyrrolo[1,2-a]pyrazine-2(1H)-carboxamide

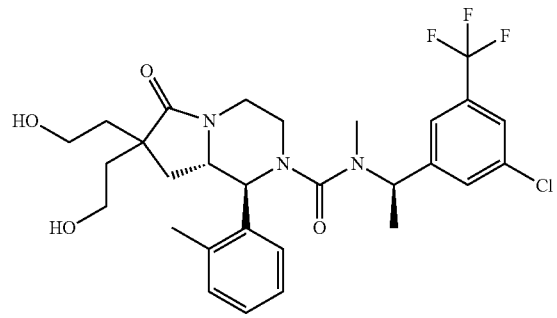 [SMILES: Cc1ccccc1[C@H]1[C@@H]2CC(CCO)(CCO)C(=O)N2CCN1C(=O)N(C)[C@H](C)c1cc(Cl)cc(C(F)(F)F)c1]

A slow stream of O₃ in O₂ was passed through a cooled solution of Intermediate 95 (65 mg, 0.11 mmol) in DCM (10 mL) at −78° C. until a pale blue colour persisted. The reaction was purged with N₂ to remove the excess of O₃ followed by addition of NaBH₄ (44 mg, 1.1 mmol). The reaction mixture was allowed to warm to room temperature and stirred for 20 h. After quenched with water, the resulting mixture was extracted with DCM. The organic layer was washed with brine, dried over anhydrous Na₂SO₄ and then concentrated in high vacuum. The residue was purified by Prep-HPLC to give the title compound (16.4 mg, yield: 25%). ¹H NMR (400 MHz, CDCl₃) δ ppm 7.52 (s, 1H), 7.26 (s, 2H), 7.23 (s, 1H), 7.19 (dd, J=3.9, 2.0 Hz, 2H), 7.18 (m, 1H), 5.49 (q, J=6.8 Hz, 1H), 4.10 (dd, J=18.9, 11.3 Hz, 2H), 3.80 (ddt, J=23.3, 11.3, 6.0 Hz, 4H), 3.64 (m, 1H), 3.32 (d, J=11.9 Hz, 1H), 3.18 (m, 1H), 3.04 (m, 1H), 2.68 (s, 3H), 2.55 (s, 3H), 1.91 (t, J=5.7 Hz, 2H), 1.83 (dd, J=6.2, 3.9 Hz, 3H), 1.75 (m, 2H), 1.38 (d, J=6.9 Hz, 3H); m/z (ES+): 582 [M+H]⁺.

EXAMPLE 90

Compound 90

(1S,8aS)-N-((S)-1-(3-chloro-5-(trifluoromethyl)phenyl)ethyl)-7,7-bis(2-hydroxyethyl)-N-methyl-6-oxo-1-o-tolylhexahydropyrrolo[1,2-a]pyrazine-2(1H)-carboxamide

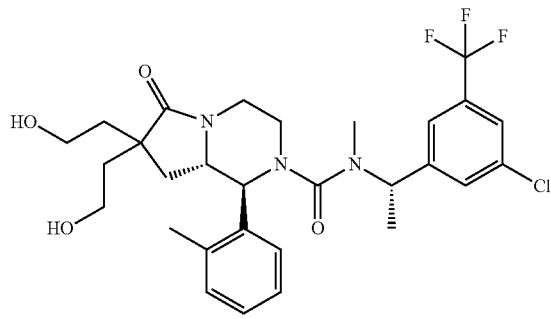 [SMILES: Cc1ccccc1[C@H]1[C@@H]2CC(CCO)(CCO)C(=O)N2CCN1C(=O)N(C)[C@@H](C)c1cc(Cl)cc(C(F)(F)F)c1]

A slow stream of O₃ in O₂ was passed through a cooled solution of Intermediate 96 (50 mg, 0.088 mmol) in DCM (10 mL) at −78° C. until a pale blue colour persisted. The reaction was purged with N₂ to remove the excess of O₃ followed by addition of NaBH₄ (67 mg, 1.75 mmol). The reaction mixture was allowed to warm to room temperature and stirred for 20 h. After quenched with water, the resulting mixture was extracted with DCM. The organic layer was washed with brine, dried over anhydrous Na₂SO₄ and then concentrated in high vacuum. The residue was purified by Prep-HPLC to give the title compound (10 mg, yield: 20%). ¹H NMR (400 MHz, CDCl₃) δ ppm 7.45 (s, 1H), 7.26 (d, J=3.5 Hz, 1H), 7.20 (d, J=2.8 Hz, 3H), 7.08 (s, 1H), 6.94 (s, 1H), 5.52 (q, J=7.0 Hz, 1H), 4.19 (m, 1H), 4.06 (d, J=9.7 Hz, 1H), 3.90 (m, 1H), 3.74 (ddd, J=16.3, 10.8, 5.8 Hz, 3H), 3.64 (m, 1H), 3.33 (d, J=11.5 Hz, 1H), 3.15 (td, J=12.5, 3.3 Hz, 1H), 2.95 (td, J=12.0, 2.9 Hz, 1H), 2.81 (s, 3H), 2.55 (s, 3H), 1.92 (t, J=6.1 Hz, 2H), 1.85 (dd, J=13.4, 7.3 Hz, 2H), 1.74 (ddd, J=26.5, 13.8, 7.1 Hz, 2H), 1.47 (d, J=7.1 Hz, 3H), 1.27 (m, J=8.5, 5.7 Hz, 1H); m/z (ES+): 582 [M+H]⁺.

EXAMPLE 91

Compound 91

(1S,8aS)-7,7-bis(2-hydroxyethyl)-N-((R)-1-(3-methoxy-5-(trifluoromethyl)phenyl)ethyl)-N-methyl-6-oxo-1-o-tolylhexahydropyrrolo[1,2-a]pyrazine-2(1H)-carboxamide

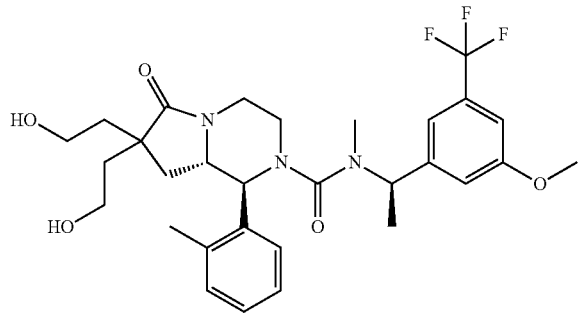 [SMILES: COc1cc([C@@H](C)N(C)C(=O)N2CCN3C(=O)C(CCO)(CCO)C[C@H]3[C@@H]2c2ccccc2C)cc(C(F)(F)F)c1]

A slow stream of O₃ in O₂ was passed through a cooled solution of Intermediate 100 (100 mg, 0.18 mmol) in DCM (10 mL) at −78° C. until a pale blue colour persisted. The reaction was purged with N₂ to remove the excess of O₃ followed by addition of NaBH₄ (137 mg, 3.6 mmol). The reaction mixture was allowed to warm to room temperature and stirred for 20 h. After quenched with water, the resulting mixture was extracted with DCM. The organic layer was washed with brine, dried over anhydrous Na₂SO₄ and then concentrated in high vacuum. The residue was purified by Prep-HPLC to give the title compound (10 mg, yield: 9.6%). ¹H NMR (400 MHz, CDCl₃) δ ppm 7.27 (d, J=6.9 Hz, 1H), 7.23 (m, 3H), 7.00 (d, J=18.1 Hz, 2H), 6.81 (s, 1H), 5.47 (q, J=6.8 Hz, 1H), 4.09 (dd, J=16.7, 11.4 Hz, 2H), 3.91 (m, 7H), 3.60 (dt, J=11.8, 6.0 Hz, 1H), 3.43 (m, 4H), 2.68 (s, 3H), 2.56 (s, 4H), 1.98 (m, 6H), 1.32 (t, J=13.3 Hz, 3H); m/z (ES+): 578 [M+H]⁺.

EXAMPLE 92

Compound 92

(1S,8aS)-N-((S)-1-(3-fluoro-5-(trifluoromethyl)phenyl)ethyl)-7,7-bis(2-hydroxyethyl)-N-methyl-6-oxo-1-o-tolylhexahydropyrrolo[1,2-a]pyrazine-2(1H)-carboxamide

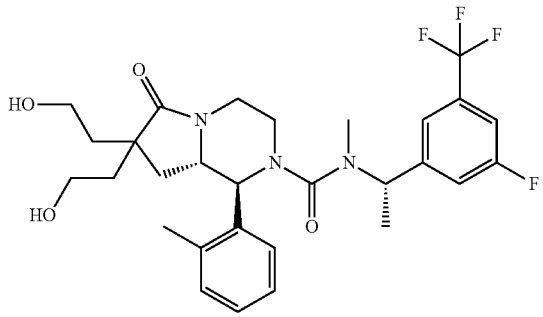 [SMILES: Cc1ccccc1[C@H]1[C@@H]2CC(CCO)(CCO)C(=O)N2CCN1C(=O)N(C)[C@@H](C)c1cc(F)cc(C(F)(F)F)c1]

A slow stream of O₃ in O₂ was passed through a cooled solution of Intermediate 103 (70 mg, 0.126 mmol) in DCM (10 mL) at −78° C. until a pale blue colour persisted. The reaction was purged with N₂ to remove the excess of O₃ followed by addition of NaBH₄ (96 mg, 2.52 mmol). The reaction mixture was allowed to warm to room temperature and stirred for 20 h. After quenched with water, the resulting mixture was extracted with DCM. The organic layer was washed with brine, dried over anhydrous Na₂SO₄ and then concentrated in high vacuum. The residue was purified by Prep-HPLC to give the title compound (20 mg, yield: 28%). ¹H NMR (400 MHz, CDCl₃) δ ppm 7.29 (s, 1H), 7.20 (s, 2H), 7.20 (m, 2H), 7.03 (s, 1H), 6.55 (d, J=9.4 Hz, 1H), 5.52 (q, J=7.0 Hz, 1H), 4.15 (d, J=12.7 Hz, 1H), 4.07 (d, J=9.7 Hz, 1H), 3.87 (dd, J=11.6, 5.9 Hz, 1H), 3.83 (m, 3H), 3.66 (m, 1H), 3.33 (d, J=11.8 Hz, 1H), 3.16 (t, J=12.4 Hz, 1H), 2.96 (dd, J=12.1, 9.4 Hz, 1H), 2.82 (s, 3H), 2.55 (s, 3H), 1.93 (t, J=5.8 Hz, 2H), 1.90 (m, 3H), 1.80 (m, 3H), 1.48 (d, J=7.1 Hz, 3H); m/z (ES+): 566 [M+H]⁺.

EXAMPLE 93

Compound 93

(1S,8aS)-N-((R)-1-(3-fluoro-5-(trifluoromethyl)phenyl)ethyl)-7,7-bis(2-hydroxyethyl)-N-methyl-6-oxo-1-o-tolylhexahydropyrrolo[1,2-a]pyrazine-2(1H)-carboxamide

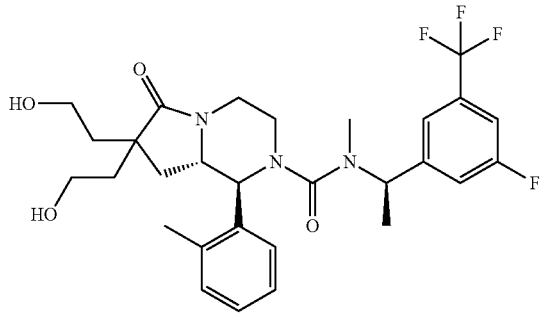 [SMILES: Cc1ccccc1[C@H]1[C@@H]2CC(CCO)(CCO)C(=O)N2CCN1C(=O)N(C)[C@H](C)c1cc(F)cc(C(F)(F)F)c1]

A slow stream of O₃ in O₂ was passed through a cooled solution of Intermediate 104 (65 mg, 0.11 mmol) in DCM (10 mL) at −78° C. until a pale blue colour persisted. The reaction was purged with N₂ to remove the excess of O₃ followed by addition of NaBH₄ (44 mg, 1.1 mmol). The reaction mixture was allowed to warm to room temperature and stirred for 20 h. After quenched with water, the resulting mixture was extracted with DCM. The organic layer was washed with brine, dried over anhydrous Na₂SO₄ and then concentrated in high vacuum. The residue was purified by Prep-HPLC to give the title compound (20 mg, yield: 28%). ¹H NMR (400 MHz, CDCl₃) δ ppm 7.29 (s, 1H), 7.25 (t, J=9.2 Hz, 2H), 7.20 (m, 2H), 7.14 (dd, J=9.4, 3.6 Hz, 1H), 6.94 (d, J=9.4 Hz, 1H), 5.61 (m, 1H), 4.10 (dd, J=19.0, 11.3 Hz, 2H), 3.86 (m, 4H), 3.64 (m, 1H), 3.32 (d, J=11.8 Hz, 1H), 3.18 (m, 1H), 3.02 (td, J=11.9, 3.1 Hz, 1H), 2.69 (s, 3H), 2.56 (s, 3H), 1.92 (d, J=5.8 Hz, 2H), 1.84 (dd, J=12.6, 5.6 Hz, 3H), 1.75 (m, 3H), 1.38 (d, J=6.9 Hz, 3H); m/z (ES+): 566 [M+H]⁺.

EXAMPLE 94

Compound 94

(1S,8aS)-N-((S)-1-(3-fluoro-5-(trifluoromethyl)phenyl)-2-hydroxyethyl)-7,7-bis(2-hydroxyethyl)-N-methyl-6-oxo-1-o-tolylhexahydropyrrolo[1,2-a]pyrazine-2(1H)-carboxamide

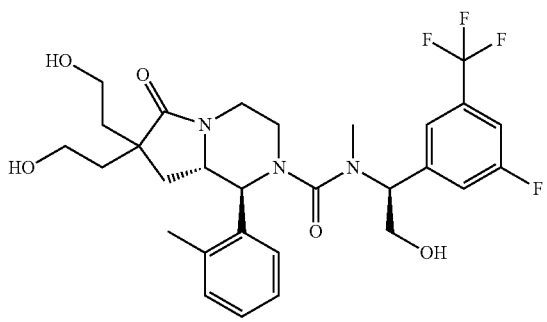 [SMILES: Cc1ccccc1[C@H]1[C@@H]2CC(CCO)(CCO)C(=O)N2CCN1C(=O)N(C)[C@H](CO)c1cc(F)cc(C(F)(F)F)c1]

A slow stream of O₃ in O₂ was passed through a cooled solution of Intermediate 105 (65 mg, 0.11 mmol) in DCM (10 mL) at −78° C. until a pale blue colour persisted. The reaction was purged with N₂ to remove the excess of O₃ followed by addition of NaBH₄ (44 mg, 1.1 mmol). The reaction mixture was allowed to warm to room temperature and stirred for 20 h. After quenched with water, the resulting mixture was extracted with DCM. The organic layer was washed with brine, dried over anhydrous Na₂SO₄ and then concentrated in high vacuum. The residue was purified by Prep-HPLC to give the title compound (28.8 mg, yield: 35%). ¹H NMR (400 MHz, CDCl₃) δ ppm 7.29 (s, 2H), 7.19 (t, J=7.6 Hz, 4H), 6.96 (s, 1H), 6.63 (d, J=9.1 Hz, 1H), 5.37 (s, 1H), 4.13 (s, 1H), 4.11 (s, 1H), 3.94 (m, 1H), 3.84 (m, 3H), 3.61 (s, 1H), 3.48 (d, J=12.1 Hz, 1H), 3.16 (d, J=11.5 Hz, 1H), 2.94 (s, 3H), 2.55 (s, 3H), 1.95 (s, 1H), 1.85 (d, J=4.6 Hz, 3H), 1.84 (s, 4H), 1.73 (d, J=13.9 Hz, 1H), 1.28 (s, 1H); m/z (ES+): 582 [M+H]⁺.

EXAMPLE 95

Compound 95

(1S,8aS)-N-((S)-2-hydroxy-1-(3-methoxy-5-(trifluoromethyl)phenyl)ethyl)-7,7-bis(2-hydroxyethyl)-N-methyl-6-oxo-1-o-tolylhexahydropyrrolo[1,2-a]pyrazine-2(1H)-carboxamide

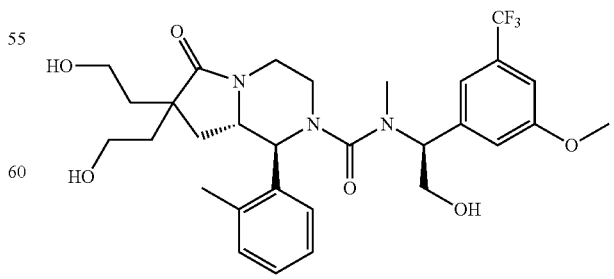

A slow stream of O₃ in O₂ was passed through a cooled solution of Intermediate 109 (60 mg, 0.103 mmol) in DCM (10 mL) at −78° C. until a pale blue colour persisted. The reaction was purged with $N_2$ to remove the excess of $O_3$ followed by addition of $NaBH_4$ (78 mg, 2.06 mmol). The reaction mixture was allowed to warm to room temperature and stirred for 20 h. After quenched with water, the resulting mixture was extracted with DCM. The organic layer was washed with brine, dried over anhydrous $Na_2SO_4$ and then concentrated in high vacuum. The residue was purified by Prep-HPLC to give the title compound (20 mg, yield: 32.7%). $^1$H NMR (400 MHz, CDCl$_3$) δ ppm 7.30 (d, J=7.0 Hz, 1H), 7.16 (d, J=2.9 Hz, 3H), 6.96 (s, 1H), 6.73 (d, J=12.6 Hz, 1H), 6.59 (s, 1H), 5.33 (dd, J=10.0, 4.9 Hz, 1H), 4.10 (dd, J=17.0, 7.1 Hz, 3H), 3.85 (dd, J=20.8, 9.4 Hz, 2H), 3.81 (m, 4H), 3.66 (s, 3H), 3.62 (m, 3H), 3.16 (t, J=10.8 Hz, 1H), 2.95 (d, J=12.2 Hz, 1H), 2.91 (s, 3H), 2.54 (s, 3H), 1.96 (dd, J=13.4, 4.8 Hz, 1H), 1.94 (m, 5H), 1.75 (m, 1H); m/z (ES+): 594 [M+H]$^+$.

EXAMPLE 96

Compound 96

(1S,8aS)-N-((S)-2-hydroxy-1-(3-(trifluoromethyl) phenyl)ethyl)-7,7-bis(2-hydroxyethyl)-N-methyl-6-oxo-1-o-tolylhexahydropyrrolo[1,2-a]pyrazine-2(1H)-carboxamide

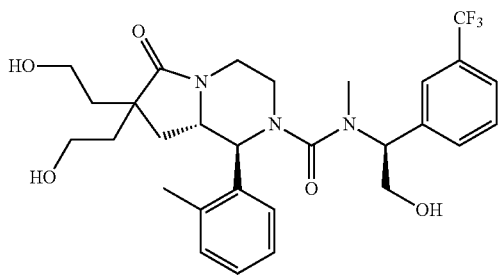 [SMILES: Cc1ccccc1[C@H]1[C@@H]2CC(CCO)(CCO)C(=O)N2CCN1C(=O)N(C)[C@H](CO)c1cccc(C(F)(F)F)c1]

A slow stream of $O_3$ in $O_2$ was passed through a cooled solution of Intermediate 114 (50 mg, 0.09 mmol) in DCM (10 mL) at −78° C. until a pale blue colour persisted. The reaction was purged with $N_2$ to remove the excess of $O_3$ followed by addition of $NaBH_4$ (70 mg, 1.8 mmol). The reaction mixture was allowed to warm to room temperature and stirred for 20 h. After quenched with water, the resulting mixture was extracted with DCM. The organic layer was washed with brine, dried over anhydrous $Na_2SO_4$ and then concentrated in high vacuum. The residue was purified by Prep-HPLC to give the title compound (10 mg, yield: 20%). $^1$H NMR (400 MHz, DMSO) δ ppm 7.54 (d, J=7.8 Hz, 1H), 7.36 (dd, J=9.9, 5.1 Hz, 2H), 7.22 (s, 1H), 7.12 (t, J=5.7 Hz, 3H), 6.99 (d, J=7.6 Hz, 1H), 5.20-5.11 (m, 1H), 5.02 (t, J=5.3 Hz, 1H), 4.50 (t, J=5.0 Hz, 1H), 4.37 (t, J=5.1 Hz, 1H), 3.95 (dt, J=11.3, 5.6 Hz, 1H), 3.87 (dd, J=16.7, 11.4 Hz, 2H), 3.77-3.68 (m, 1H), 3.63 (dd, J=16.9, 7.8 Hz, 1H), 3.48 (dd, J=19.0, 10.2 Hz, 3H), 3.32 (s, 2H), 3.12 (t, J=10.5 Hz, 1H), 2.86 (s, 3H), 2.68 (t, J=10.5 Hz, 1H), 2.43 (s, 3H), 1.70 (dd, J=15.0, 7.3 Hz, 2H), 1.50 (dt, J=20.3, 10.3 Hz, 2H), 1.24 (s, 1H), 0.93-0.83 (m, 1H); m/z (ES+): 564 [M+H]$^+$.

EXAMPLE 111

Compound 111

(1S,8aS)-N-((S)-2-hydroxy-1-(3-methyl-5-(trifluoromethyl)phenyl)ethyl)-7,7-bis(2-hydroxyethyl)-N-methyl-6-oxo-1-o-tolylhexahydropyrrolo[1,2-a]pyrazine-2(1H)-carboxamide

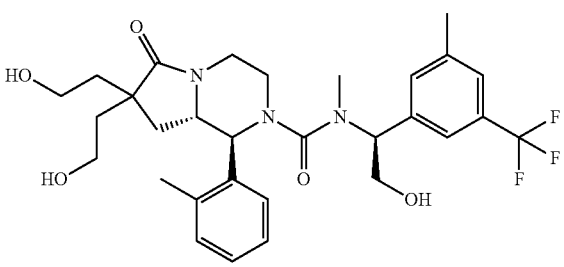 [SMILES: Cc1cc([C@@H](CO)N(C)C(=O)N2CCN3C(=O)C(CCO)(CCO)C[C@H]3[C@@H]2c2ccccc2C)cc(C(F)(F)F)c1]

A slow stream of $O_3$ in $O_2$ was passed through a cooled solution of Intermediate 117 (74 mg, 0.11 mmol) in DCM (10 mL) at −78° C. until a pale blue colour persisted. The reaction was purged with $N_2$ to remove the excess of $O_3$ followed by addition of $NaBH_4$ (70 mg, 1.8 mmol). The reaction mixture was allowed to warm to room temperature and stirred for 20 h. After quenched with water, the resulting mixture was extracted with DCM. The organic layer was washed with brine, dried over anhydrous $Na_2SO_4$ and then concentrated in high vacuum. The residue was purified by Prep-HPLC to give the title compound (17 mg, yield: 23%). $^1$H NMR (400 MHz, CDCl$_3$) δ ppm 7.30 (dd, J=15.0, 3.9 Hz, 3H), 7.18 (d, J=9.7 Hz, 3H), 6.95 (s, 1H), 6.74 (s, 1H), 5.36 (dd, J=9.9, 4.8 Hz, 1H), 4.13 (t, J=10.2 Hz, 3H), 3.93 (m, 2H), 3.76 (dd, J=15.1, 10.3 Hz, 3H), 3.65 (m, 1H), 3.48 (d, J=11.8 Hz, 1H), 3.15 (d, J=12.3 Hz, 1H), 2.95 (d, J=12.3 Hz, 1H), 2.91 (s, 3H), 2.56 (s, 3H), 2.27 (s, 3H), 2.01 (m, 2H), 1.86 (m, 4H), 1.77 (m, 1H), 1.27 (s, 1H); m/z (ES+): 578 [M+H]$^+$.

EXAMPLE 97

Compound 97

(1S,8aS)-N-((R)-1-(3-(difluoromethyl)-5-(trifluoromethyl)phenyl)ethyl)-7,7-bis(2-hydroxyethyl)-N-methyl-6-oxo-1-o-tolylhexahydropyrrolo[1,2-a]pyrazine-2(1H)-carboxamide

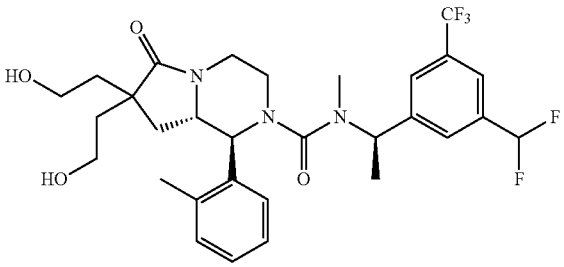 [SMILES: Cc1ccccc1[C@H]1[C@@H]2CC(CCO)(CCO)C(=O)N2CCN1C(=O)N(C)[C@H](C)c1cc(C(F)F)cc(C(F)(F)F)c1]

A slow stream of $O_3$ in $O_2$ was passed through a cooled solution of Intermediate 125 (70 mg, 0.12 mmol) in DCM (10 mL) at −78° C. until a pale blue colour persisted. The reaction was purged with N₂ to remove the excess of O₃ followed by addition of NaBH₄ (44 mg, 1.1 mmol). The reaction mixture was allowed to warm to room temperature and stirred for 20 h. After quenched with water, the resulting mixture was extracted with DCM. The organic layer was washed with brine, dried over anhydrous Na₂SO₄ and then concentrated in high vacuum. The residue was purified by Prep-HPLC to give the title compound (14 mg, yield: 20%). ¹H NMR (400 MHz, CDCl₃) δ ppm 7.67 (d, J=12.9 Hz, 1H), 7.48 (s, 1H), 7.35 (s, 1H), 7.25 (dd, J=20.3, 12.9 Hz, 2H), 7.22 (m, 2H), 7.17 (m, 1H), 6.59 (t, J=55.9 Hz, 1H), 5.53 (q, J=6.8 Hz, 1H), 4.10 (t, J=10.4 Hz, 2H), 3.89 (m, 4H), 3.64 (m, 1H), 3.32 (d, J=11.8 Hz, 1H), 3.15 (td, J=12.3, 3.2 Hz, 1H), 3.02 (dd, J=11.8, 9.0 Hz, 1H), 2.68 (s, 3H), 2.55 (s, 3H), 1.97 (m, 3H), 1.83 (dd, J=13.3, 6.3 Hz, 2H), 1.76 (m, 2H), 1.42 (d, J=6.8 Hz, 3H); m/z (ES+): 598 [M+H]⁺.

EXAMPLE 98

Compound 98

(1S,8aS)-N-((R)-1-(3-(difluoromethyl)-5-(trifluoromethyl)phenyl)ethyl)-7,7-bis(2-hydroxyethyl)-N-methyl-6-oxo-1-o-tolylhexahydropyrrolo[1,2-a]pyrazine-2(1H)-carboxamide

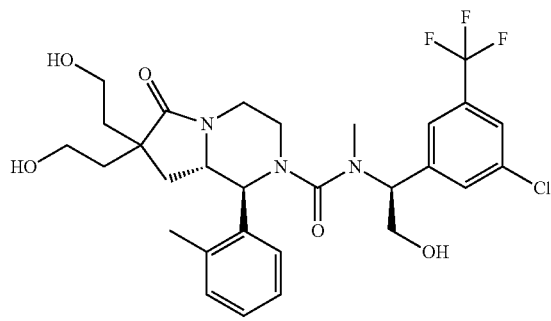 [SMILES: Cc1ccccc1[C@H]1[C@@H]2CC(CCO)(CCO)C(=O)N2CCN1C(=O)N(C)[C@H](CO)c1cc(Cl)cc(C(F)(F)F)c1]

A slow stream of O₃ in O₂ was passed through a cooled solution of Intermediate 130 (80 mg, 0.14 mmol) in DCM (10 mL) at −78° C. until a pale blue colour persisted. The reaction was purged with N₂ to remove the excess of O₃ followed by addition of NaBH₄ (44 mg, 1.1 mmol). The reaction mixture was allowed to warm to room temperature and stirred for 20 h. After quenched with water, the resulting mixture was extracted with DCM. The organic layer was washed with brine, dried over anhydrous Na₂SO₄ and then concentrated in high vacuum. The residue was purified by Prep-HPLC to give the title compound (14 mg, yield: 18%). ¹H NMR (400 MHz, CDCl₃) δ ppm 7.47 (s, 1H), 7.28 (s, 2H), 7.20 (s, 2H), 7.02 (d, J=17.5 Hz, 1H), 6.98 (s, 1H), 5.43 (m, 1H), 4.17 (m, 2H), 3.94 (m, 4H), 3.61 (s, 1H), 3.48 (d, J=11.8 Hz, 1H), 3.17 (t, J=10.9 Hz, 1H), 2.97 (d, J=9.8 Hz, 1H), 2.95 (s, 3H), 2.55 (s, 3H), 2.05 (m, 1H), 1.82 (dd, J=19.9, 7.1 Hz, 4H), 1.75 (s, 4H), 1.29 (s, 2H); m/z (ES+): 598 [M+H]⁺.

EXAMPLE 99

Compound 99

(1S,8aS)-N-((S)-1-(3,5-bis(trifluoromethyl)phenyl)ethyl)-7,7-bis(2-hydroxyethyl)-N-methyl-6-oxo-1-o-tolylhexahydropyrrolo[1,2-a]pyrazine-2(1H)-carboxamide

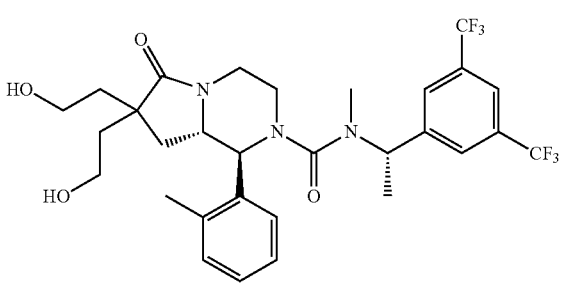 [SMILES: Cc1ccccc1[C@H]1[C@@H]2CC(CCO)(CCO)C(=O)N2CCN1C(=O)N(C)[C@@H](C)c1cc(C(F)(F)F)cc(C(F)(F)F)c1]

A slow stream of O₃ in O₂ was passed through a cooled solution of Intermediate 135 (40 mg, 0.066 mmol) in DCM (10 mL) at −78° C. until a pale blue colour persisted. The reaction was purged with N₂ to remove the excess of O₃ followed by addition of NaBH₄ (76 mg, 1.98 mmol). The reaction mixture was allowed to warm to room temperature and stirred for 20 h. After quenched with water, the resulting mixture was extracted with DCM. The organic layer was washed with brine, dried over anhydrous Na₂SO₄ and then concentrated in high vacuum. The residue was purified by Prep-HPLC to give the title compound (14 mg, yield: 35%). ¹H NMR (400 MHz, CDCl₃) δ ppm 7.73 (s, 1H), 7.36 (s, 2H), 7.28 (s, 1H), 7.25 (m, 1H), 7.17 (m, 2H), 5.60 (q, J=7.2 Hz, 1H), 4.17 (m, 2H), 3.87 (m, 4H), 3.61 (m, 1H), 3.37 (d, J=11.6 Hz, 1H), 3.19 (m, 2H), 3.00 (m, 1H), 2.82 (s, 3H), 2.54 (s, 3H), 2.32 (m, 1H), 1.87 (m, 6H), 1.29 (m, 3H); m/z (ES+): 616 [M+H]⁺.

EXAMPLE 100

Compound 100

(1'S,8a'S)-N-((R)-1-(3,5-bis(trifluoromethyl)phenyl)ethyl)-N-methyl-6'-oxo-1'-o-tolyloctahydro-1'H-spiro[pyran-4,7'-pyrrolo[1,2-a]pyrazine]-2'(6'H)-carboxamide

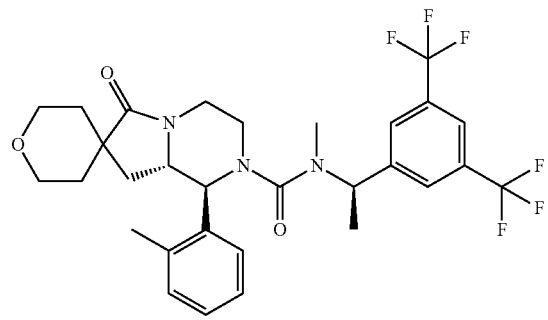 [SMILES: Cc1ccccc1[C@H]1[C@@H]2CC3(CCOCC3)C(=O)N2CCN1C(=O)N(C)[C@H](C)c1cc(C(F)(F)F)cc(C(F)(F)F)c1]

To a solution of (1S,8aS)-N-((R)-1-(3,5-bis(trifluoromethyl)phenyl)ethyl)-7,7-bis(2-hydroxyethyl)-N-methyl-6- oxo-1-o-tolylhexahydropyrrolo[1,2-a]pyrazine-2(1H)-carboxamide (70 mg, 0.11 mmol) in 5 mL of DCM, was added MsCl (38 mg, 0.33 mmol) at 0° C. The mixture was stirred for 1.5 h, and concentrated in high vacuum. The residue was treated with mixture of H$_2$O (5 mL) and TEA (0.5 mL) and then heated to 65° C. until the reaction was completed. The reaction mixture was extracted with DCM (2×15 mL) and the organic layers were dried over anhydrous Na$_2$Sa$_4$ and then concentrated in high vacuum. The residue was purified by Prep-HPLC to give the title compound (15 mg, yield: 23%). $^1$H NMR (400 MHz, CDCl$_3$) δ ppm 7.71 (s, 1H), 7.46 (s, 2H), 7.22 (m, 4H), 5.47 (d, J=7.0 Hz, 1H), 4.08 (d, J=12.8 Hz, 1H), 3.95 (d, J=9.7 Hz, 2H), 3.81 (dd, J=7.6, 4.0 Hz, 1H), 3.65 (d, J=9.1 Hz, 1H), 3.36 (dd, J=13.4, 6.3 Hz, 2H), 3.20 (d, J=11.6 Hz, 1H), 3.05 (td, J=12.3, 3.4 Hz, 1H), 2.91 (dt, J=11.8, 5.9 Hz, 1H), 2.63 (s, 3H), 2.46 (s, 3H), 2.11 (dd, J=17.6, 6.9 Hz, 1H), 1.89 (dd, J=13.1, 7.2 Hz, 1H), 1.79 (dd, J=17.0, 7.0 Hz, 1H), 1.49 (s, 2H), 1.31 (t, J=8.1 Hz, 6H), 1.18 (s, 3H), 0.86 (s, 2H); m/z (ES+): 598 [M+H]$^+$.

EXAMPLE 101

Compound 101

(1'S,8a'S)-N-((R)-1-(3,5-bis(trifluoromethyl)phenyl)ethyl)-N-methyl-6'-oxo-1'-o-tolyloctahydro-1'H-spiro[pyran-4,7'-pyrrolo[1,2-a]pyrazine]-2'(6'H)-carboxamide

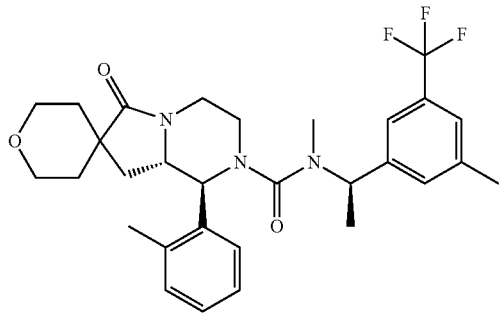 [SMILES: Cc1cc([C@@H](C)N(C)C(=O)N2CCN3C(=O)C4(CCOCC4)C[C@H]3[C@@H]2c2ccccc2C)cc(C(F)(F)F)c1]

To a solution of (1S,8aS)-7,7-bis(2-hydroxyethyl)-N-methyl-N-((R)-1-(3-methyl-5-(trifluoromethyl)phenyl)ethyl)-6-oxo-1-o-tolylhexahydropyrrolo[1,2-a]pyrazine-2(1H)-carboxamide (56 mg, 0.1 mmol) in 5 mL of DCM, was added MsCl (38 mg, 0.33 mmol) at 0° C. The mixture was stirred for 1.5 h, and concentrated in high vacuum. The residue was treated with mixture of H$_2$O (5 mL) and TEA (0.5 mL) and then heated to 65° C. until the reaction was completed. The reaction mixture was extracted with DCM (2×15 mL) and the organic layers were dried over anhydrous Na$_2$SO$_4$ and then concentrated in high vacuum. The residue was purified by Prep-HPLC to give the title compound (16 mg, yield: 29%). $^1$H NMR (400 MHz, CDCl$_3$) δ ppm 7.31 (s, 1H), 7.26 (s, 1H), 7.20 (m, 4H), 6.99 (s, 1H), 5.47 (d, J=7.2 Hz, 1H), 4.14 (d, J=13.2 Hz, 1H), 4.02 (m, 2H), 3.69 (q, J=8.0 Hz, 1H), 3.45 (m, 1H), 3.38 (m, 1H), 3.12 (m, 1H), 2.98 (m, 1H), 2.63 (s, 3H), 2.54 (s, 3H), 2.33 (s, 3H), 2.21 (m, 1H), 1.89 (m, 2H), 1.49 (m, 7H); m/z (ES+): 544 [M+H]$^+$.

EXAMPLE 102 & 103

Compound 102 & 103

(1S,8aS)-7-(hydroxymethyl)-N-methyl-N-((R)-1-(3-methyl-5-(trifluoromethyl)phenyl)ethyl)-6-oxo-1-o-tolylhexahydropyrrolo[1,2-a]pyrazine-2(1H)-carboxamide (1S,8aS)-7,7-bis(hydroxymethyl)-N-methyl-N-((R)-1-(3-methyl-5-(trifluoromethyl)phenyl)ethyl)-6-oxo-1-o-tolylhexahydropyrrolo[1,2-a]pyrazine-2(1H)-carboxamide

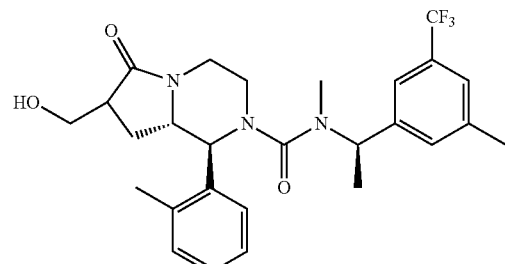

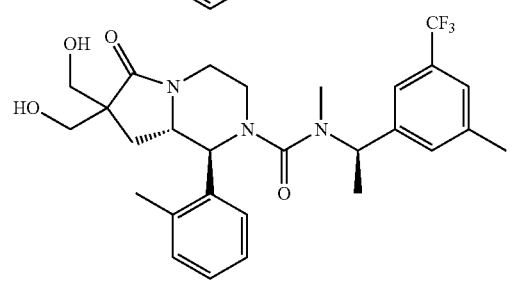

To a solution of Intermediate 136 (200 mg, 0.375 mmol) in THF (4 mL) at 0° C. was added LiBH$_4$ (16 mg, 0.75 mmol). The reaction mixture was allowed to warm to room temperature and stirred for 2 h. After quenched with water, the resulting mixture was extracted with EtOAc. The organic layer was washed with brine, dried over anhydrous Na$_2$SO$_4$ and then concentrated in high vacuum. The residue was purified by Prep-HPLC to give mono-hydroxymethyl substituted compound 102 (15 mg, yield: 8%) and bis-hydroxymethyl substituted compound 103 (8 mg, yield: 4%).

Compound 102: $^1$H NMR (400 MHz, CDCl$_3$) δ ppm 7.24 (s, 1H), 7.21 (m, 1H), 7.09 (d, J=5.8 Hz, 3H), 7.07 (m, 1H), 6.92 (s, 1H), 5.40 (q, J=6.8 Hz, 1H), 4.11 (m, 2H), 3.81 (dt, J=12.0, 6.0 Hz, 1H), 3.64 (dt, J=15.4, 7.7 Hz, 2H), 3.21 (t, J=16.7 Hz, 1H), 3.06 (t, J=12.3 Hz, 1H), 2.91 (td, J=11.8, 3.0 Hz, 1H), 2.55 (s, 3H), 2.51 (d, J=9.8 Hz, 1H), 2.47 (s, 3H), 2.26 (s, 3H), 1.85 (ddd, J=12.8, 9.0, 7.0 Hz, 1H), 1.50 (m, 1H), 1.29 (d, J=6.4 Hz, 3H); m/z (ES+): 504 [M+H]$^+$.

Compound 103: $^1$H NMR (400 MHz, CDCl$_3$) δ ppm 7.24 (s, 1H), 7.17 (s, 1H), 7.10 (s, 2H), 7.09 (m, 2H), 6.92 (s, 1H), 5.41 (d, J=7.0 Hz, 1H), 4.06 (t, J=12.0 Hz, 2H), 3.83-3.69 (m, 2H), 3.68 (m, 3H), 3.22 (d, J=12.0 Hz, 1H), 3.09 (dd, J=20.2, 7.9 Hz, 1H), 2.90 (dd, J=11.9, 8.8 Hz, 1H), 2.73 (s, 1H), 2.56 (s, 3H), 2.48 (d, J=14.3 Hz, 3H), 2.26 (s, 3H), 2.22 (m, 1H), 1.75 (dd, J=13.6, 7.9 Hz, 1H), 1.60 (m, 1H), 1.29 (d, J=6.3 Hz, 3H); m/z (ES+): 534 [M+H]$^+$.

Example 104

Compound 104

(1S,8aS)-N-((R)-1-(3,5-bis(trifluoromethyl)phenyl)ethyl)-7,7-bis(hydroxymethyl)-N-methyl-6-oxo-1-o-tolylhexahydropyrrolo[1,2-a]pyrazine-2(1H)-carboxamide

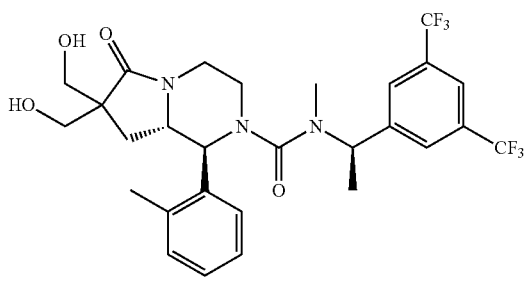 [SMILES: Cc1ccccc1[C@H]1[C@@H]2CC(CO)(CO)C(=O)N2CCN1C(=O)N(C)[C@H](C)c1cc(C(F)(F)F)cc(C(F)(F)F)c1]

To a solution of Intermediate 137 (166 mg, 0.26 mmol) in MeOH (5 mL) at 0° C. was added LiBH₄ (11 mg, 0.52 mmol). The reaction mixture was allowed to warm to room temperature and stirred for 2 h. After quenched with water, the resulting mixture was extracted with EtOAc. The organic layer was washed with brine, dried over anhydrous Na₂SO₄ and then concentrated in high vacuum. The residue was purified by Prep-HPLC to give the title compound (6 mg, yield: 3.9%). ¹H NMR (400 MHz, CDCl₃) δ ppm 7.70 (s, 3H), 7.47 (s, 6H), 7.19 (m, 13H), 5.47 (d, J=6.8 Hz, 3H), 4.06 (dd, J=20.7, 11.4 Hz, 6H), 3.92 (m, 15H), 3.30 (m, 10H), 2.65 (d, J=24.4 Hz, 11H), 2.46 (d, J=14.0 Hz, 9H), 2.15 (s, 3H), 1.77 (dd, J=13.5, 7.9 Hz, 4H), 1.62 (m, 3H), 1.32 (d, J=6.9 Hz, 10H); m/z (ES+): 588 [M+H]⁺.

Example 105

Compound 105

(1'S,8a'S)-N-((R)-1-(3,5-bis(trifluoromethyl)phenyl)ethyl)-N,1-dimethyl-6'-oxo-1'-o-tolyltetrahydro-1'H-spiro[piperidine-4,7'-pyrrolo[1,2-a]pyrazine]-2'(6'H)-carboxamide, formic acid salt

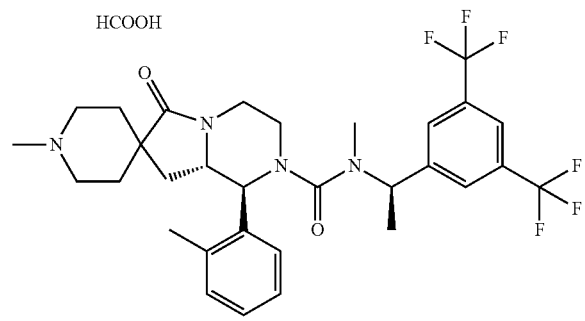 [SMILES: Cc1ccccc1[C@H]1[C@@H]2CC3(CCN(C)CC3)C(=O)N2CCN1C(=O)N(C)[C@H](C)c1cc(C(F)(F)F)cc(C(F)(F)F)c1 ; "HCOOH"]

To a solution of (1S,8aS)-N-((R)-1-(3,5-bis(trifluoromethyl)phenyl)ethyl)-7,7-bis(2-hydroxyethyl)-N-methyl-6-oxo-1-o-tolylhexahydropyrrolo[1,2-a]pyrazine-2(1H)-carboxamide (70 mg, 0.11 mmol) in DCM (5 mL), was added MsCl (38 mg, 0.33 mmol) at 0° C. The mixture was stirred for 1.5 h, and concentrated in high vacuum. The residue was treated with mixture of methanamine hydrochloride (10 mg, 0.15 mmol) in TEA (0.5 mL) and then heated to 65° C. until the reaction was completed. The reaction mixture was extracted with DCM (2×15 mL) and the organic layers were dried over anhydrous Na₂SO₄ and then concentrated in high vacuum. The residue was purified by Prep-HPLC to give the title compound (13 mg, yield: 20%). ¹H NMR (400 MHz, CDCl₃) δ ppm 7.79 (s, 1H), 7.55 (s, 2H), 7.28 (s, 1H), 7.19 (ddd, J=19.6, 11.8, 7.5 Hz, 4H), 5.56 (d, J=6.9 Hz, 1H), 4.11 (d, J=12.9 Hz, 1H), 4.03 (d, J=9.8 Hz, 1H), 3.76 (d, J=8.1 Hz, 2H), 3.39 (m, 2H), 3.20 (m, 2H), 2.99 (t, J=10.6 Hz, 1H), 2.72 (s, 6H), 2.52 (s, 3H), 2.24 (s, 1H), 2.06 (d, J=14.9 Hz, 2H), 1.87 (d, J=12.8 Hz, 1H), 1.84 (m, 1H), 1.60 (dd, J=13.5, 7.9 Hz, 1H), 1.40 (d, J=6.9 Hz, 3H); m/z (ES+): 611 [M−HCOOH+H]⁺.

Example 106

Compound 106

(1'S,8a'S)-N-((R)-1-(3,5-bis(trifluoromethyl)phenyl)ethyl)-N-methyl-6'-oxo-1'-o-tolyltetrahydro-1'H-spiro[piperidine-4,7'-pyrrolo[1,2-a]pyrazine]-2'(6'(6'H)-carboxamide, formic acid salt

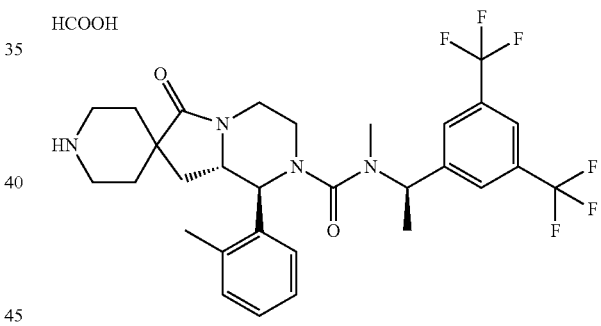

To a solution of (1S,8aS)-N-((R)-1-(3,5-bis(trifluoromethyl)phenyl)ethyl)-7,7-bis(2-hydroxyethyl)-N-methyl-6-oxo-1-o-tolylhexahydropyrrolo[1,2-a]pyrazine-2(1H)-carboxamide (70 mg, 0.11 mmol) in DCM (5 mL), was added MsCl (38 mg, 0.33 mmol) at 0° C. The mixture was stirred for 1.5 h, and concentrated in high vacuum. The residue was treated with NH₄OH (19 mg, 0.15 mmol) and then heated to 65° C. until the reaction was completed. The reaction mixture was extracted with DCM (2×20 mL) and the organic layers were dried over anhydrous Na₂SO₄ and then concentrated in high vacuum. The residue was purified by Prep-HPLC to give the title compound (13 mg, yield: 20%). ¹H NMR (400 MHz, CD₃OD) δ ppm 8.51 (s, 1H), 7.87 (s, 1H), 7.67 (s, 2H), 7.35 (d, J=7.3 Hz, 1H), 7.19 (m, 3H), 5.44 (d, J=6.8 Hz, 1H), 4.15 (d, J=10.0 Hz, 1H), 4.05 (m, 2H), 3.54 (dd, J=23.4, 8.7 Hz, 2H), 3.10 (m, 3H), 2.76 (s, 3H), 2.51 (s, 3H), 2.23 (m, 1H), 1.91 (dd, J=13.1, 5.4 Hz, 1H), 1.74 (m, 3H), 1.50 (d, J=7.0 Hz, 3H), 1.29 (s, 3H), 0.95 (dt, J=14.7, 7.3 Hz, 1H); m/z (ES+): 597 [M−HCOOH+H]⁺.

Example 107

Compound 107

(1S,8aS)-N-methyl-N-((R)-1-(3-methyl-5-(trifluoromethyl)phenyl)ethyl)-6-oxo-1-o-tolylhexahydropyrrolo[1,2-a]pyrazine-2(1H)-carboxamide

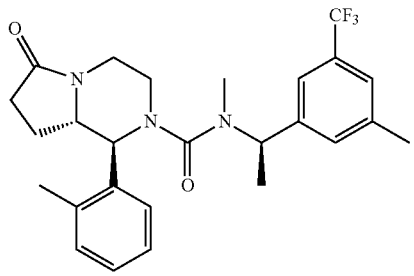 [SMILES: Cc1cc([C@@H](C)N(C)C(=O)N2CCN3C(=O)CC[C@H]3[C@@H]2c2ccccc2C)cc(C(F)(F)F)c1]

To a solution of triphosgene (254 mg, 0.87 mmol) in EtOAc (5 mL) at 0° C. was added solution of (1S,8aS)-1-o-tolylhexahydropyrrolo[1,2-a]pyrazin-6(7H)-one (400 mg, 1.73 mmol), DMAP (21 mg, 0.173 mmol) and TEA (524 mg, 5.19 mmol in EtOAc (5 mL). The mixture was stirred for 1.5 h, followed by addition of (R)-N-methyl-1-(3-methyl-5-(trifluoromethyl)phenyl)ethanamine (563 mg, 2.6 mmol) in EtOAc (2 mL) and TEA (524 mg, 5.19 mmol). The reaction was stirred at 50° C. for 48 h and quenched with water. The resulting mixture was extracted with EtOAc and the organic layer was washed with 1 M aqueous HCl solution, dried over anhydrous $Na_2SO_4$ and then concentrated in high vacuum. The residue was purified by silica gel chromatography (DCM/MeOH=20/1 to 10/1) to give the title compound (350 mg, yield: 85%). $^1$H NMR (400 MHz, CDCl$_3$) δ ppm 7.32 (s, 1H), 7.25 (d, J=8.0 Hz, 1H), 7.19 (d, J=7.4 Hz, 2H), 7.14 (ddd, J=17.5, 10.0, 4.2 Hz, 2H), 7.00 (s, 1H), 5.48 (q, J=6.9 Hz, 1H), 4.22 (m, 2H), 3.71 (dd, J=17.0, 7.3 Hz, 1H), 3.29 (d, J=11.8 Hz, 1H), 3.11 (td, J=12.4, 2.7 Hz, 1H), 2.95 (td, J=11.9, 3.2 Hz, 1H), 2.64 (s, 3H), 2.54 (s, 3H), 2.48 (m, 2H), 2.34 (s, 3H), 1.87 (m, 1H), 1.67 (ddd, J=17.1, 13.1, 9.4 Hz, 1H), 1.37 (d, J=6.7 Hz, 3H); m/z (ES+): 474 [M+H]$^+$.

Example 108

Compound 108

(1S,8aS)-N-((R)-1-(3-chloro-5-(trifluoromethyl)phenyl)ethyl)-7,7-bis(hydroxymethyl)-N-methyl-6-oxo-1-o-tolylhexahydropyrrolo[1,2-a]pyrazine-2(1H)-carboxamide

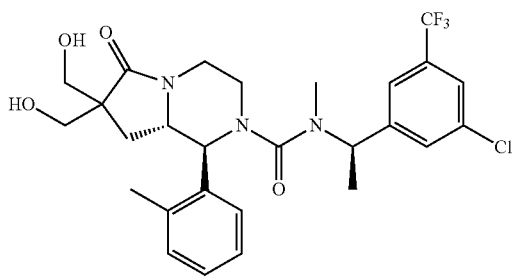 [SMILES: Cc1ccccc1[C@H]1[C@@H]2CC(CO)(CO)C(=O)N2CCN1C(=O)N(C)[C@H](C)c1cc(Cl)cc(C(F)(F)F)c1]

To a solution of Intermediate 138 (220 mg, 0.36 mmol) in MeOH (5 mL) at 0° C. was added LiBH$_4$(16 mg, 0.72 mmol). The reaction mixture was allowed to warm to room temperature and stirred for 2 h. After quenched with water, the resulting mixture was extracted with EtOAc. The organic layer was washed with brine, dried over anhydrous $Na_2SO_4$ and then concentrated in high vacuum. The residue was purified by Prep-HPLC to give the title compound (10 mg, yield: 5%). $^1$H NMR (400 MHz, CDCl$_3$) δ ppm 7.50 (s, 1H), 7.26 (m, 6H), 5.48 (d, J=6.0 Hz, 1H), 4.13 (dd, J=18.0, 11.7 Hz, 2H), 3.73 (ddd, J=31.7, 29.7, 10.8 Hz, 5H), 3.37 (m, 4H), 2.66 (s, 3H), 2.55 (s, 3H), 1.88 (m, 1H), 1.66 (d, J=6.2 Hz, 2H), 1.36 (d, J=4.8 Hz, 3H); m/z (ES+): 554 [M+H]$^+$.

Example 109

Compound 109

(1S,8aS)-N-((R)-1-(3-ethyl-5-(trifluoromethyl)phenyl)ethyl)-N-methyl-6-oxo-1-o-tolylhexahydropyrrolo[1,2-a]pyrazine-2(1H)-carboxamide

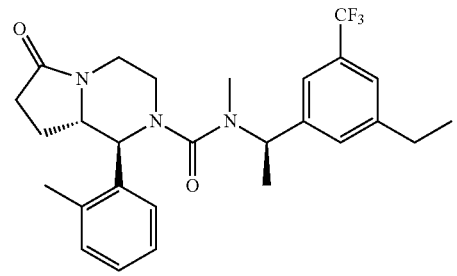 [SMILES: CCc1cc([C@@H](C)N(C)C(=O)N2CCN3C(=O)CC[C@H]3[C@@H]2c2ccccc2C)cc(C(F)(F)F)c1]

To a solution of triphosgene (47 mg, 0.16 mmol) in EtOAc (2 mL) at 0° C. was added solution of (1S,8aS)-1-o-tolylhexahydropyrrolo[1,2-a]pyrazin-6(7H)-one (74 mg, 0.32 mmol), DMAP (4 mg, 0.032 mmol) and TEA (49 mg, 0.48 mmol) in EtOAc (2 mL). The mixture was stirred for 1.5 h, followed by addition of (R)-1-(3-ethyl-5-(trifluoromethyl)phenyl)-N-methylethanamine (111 mg, 0.48 mmol) in EtOAc (2 mL) and TEA (97 mg, 0.963 mmol). The reaction was stirred at 50° C. for 48 h and quenched with water. The resulting mixture was extracted with EtOAc and the organic layer was washed with 1 M aqueous HCl solution, dried over anhydrous $Na_2SO_4$ and then concentrated in high vacuum. The residue was purified by Prep-HPLC to give the title compound (25 mg, yield: 17%). $^1$H NMR (400 MHz, CDCl$_3$) δ ppm 7.34 (s, 1H), 7.26 (d, J=7.8 Hz, 1H), 7.20 (s, 1H), 7.17 (d, J=4.8 Hz, 1H), 7.13 (dd, J=14.9, 7.3 Hz, 2H), 7.06 (s, 1H), 5.49 (q, J=6.8 Hz, 1H), 4.11 (dd, J=20.6, 11.3 Hz, 2H), 3.71 (dd, J=16.8, 7.4 Hz, 1H), 3.28 (d, J=11.9 Hz, 1H), 3.11 (t, J=12.3 Hz, 1H), 2.95 (td, J=11.8, 2.9 Hz, 1H), 2.66 (d, J=10.2 Hz, 4H), 2.61 (d, J=7.6 Hz, 1H), 2.55 (s, 3H), 2.47 (m, 1H), 2.38-2.26 (m, 1H), 1.84 (ddd, J=16.7, 13.0, 3.9 Hz, 1H), 1.67 (ddd, J=17.3, 13.1, 9.3 Hz, 1H), 1.36 (d, J=6.6 Hz, 3H), 1.21 (t, J=7.6 Hz, 3H); m/z (ES+): 488 [M+H]$^+$.

Example 110

Compound 110

(1S,8aS)-N-((R)-1-(3-ethyl-5-(trifluoromethyl)phenyl)ethyl)-7,7-bis(2-hydroxyethyl)-N-methyl-6-oxo-1-o-tolylhexahydropyrrolo[1,2-a]pyrazine-2(1H)-carboxamide

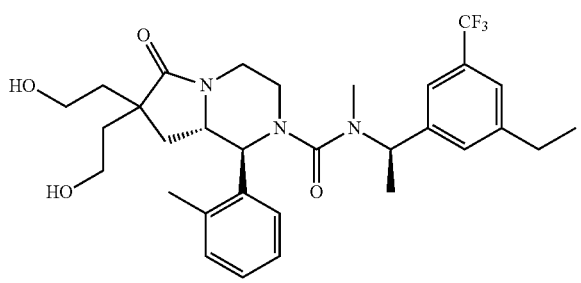 [SMILES: CCc1cc([C@@H](C)N(C)C(=O)N2CCN3C(=O)C(CCO)(CCO)C[C@H]3[C@@H]2c2ccccc2C)cc(C(F)(F)F)c1]

A slow stream of $O_3$ in $O_2$ was passed through a cooled solution of Intermediate 141 (78 mg, 0.14 mmol) in DCM (10 mL) at −78° C. until a pale blue colour persisted. The reaction was purged with $N_2$ to remove the excess of $O_3$ followed by addition of $NaBH_4$ (76 mg, 1.98 mmol). The reaction mixture was allowed to warm to room temperature and stirred for 20 h. After quenched with water, the resulting mixture was extracted with DCM. The organic layer was washed with brine, dried over anhydrous $Na_2SO_4$ and then concentrated in high vacuum. The residue was purified by Prep-HPLC to give the title compound (13 mg, yield: 16%). $^1$H NMR (400 MHz, $CDCl_3$) δ ppm 7.34 (s, 1H), 7.25 (m, 5H), 7.04 (s, 1H), 7.25 (m, 1H), 5.50 (q, J=6.8 Hz, 1H), 4.10 (m, 2H), 3.80 (m, 4H), 3.72 (m, 1H), 3.30 (d, J=4.4 Hz, 1H), 3.12 (m, 1H), 3.00 (m, 1H), 2.70 (m, 5H), 2.54 (s, 3H), 1.84 (m, 7H), 1.35 (m, 2H), 1.20 (m, 3H); m/z (ES+): 576 $[M+H]^+$.

Example 112

Compound 112

(1S,8aS)-N-((R)-1-(3-isopropyl-5-(trifluoromethyl)phenyl)ethyl)-N-methyl-6-oxo-1-o-tolylhexahydropyrrolo[1,2-a]pyrazine-2(1H)-carboxamide

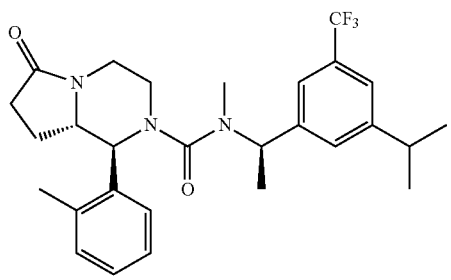 [SMILES: Cc1ccccc1[C@H]1[C@@H]2CCC(=O)N2CCN1C(=O)N(C)[C@H](C)c1cc(C(C)C)cc(C(F)(F)F)c1]

To a solution of triphosgene (72 mg, 0.242 mmol) in EtOAc (5 mL) at 0° C. was added solution of (1S,8aS)-1-o-tolylhexahydropyrrolo[1,2-a]pyrazin-6(7H)-one (112 mg, 0.484 mmol), DMAP (6.2 mg, 0.05 mmol) and TEA (151 mg, 1.5 mmol) in EtOAc (15 mL). The mixture was stirred for 1.5 h, followed by addition of (R)-1-(3-isopropyl-5-(trifluoromethyl)phenyl)-N-methylethanamine (142 mg, 0.58 mmol) in EtOAc (10 mL) and TEA (151 mg, 1.5 mmol). The reaction was then stirred at 50° C. for 48 h and quenched with water. The resulting mixture was extracted with EtOAc. The combined organic layer was washed with 1 N aqueous HCl solution, dried over anhydrous $Na_2SO_4$ and then concentrated in high vacuum. The residue was purified by silica gel chromatography (DCM/MeOH=20/1 to 10/1) to give the title compound (60 mg, yield: 25%) as yellow solid. $^1$H-NMR (400 MHz, $CDCl_3$) δ ppm 7.37 (s, 1H), 7.27 (d, J=6 Hz, 2H), 7.15 (m, 5H), 5.48 (m, 1H), 4.08 (m, 2H), 3.71 (m, 1H), 2.87 (m, 4H), 2.67 (s, 3H), 2.56 (s, 3H), 2.37 (m, 2H), 1.82 (m, 1H), 1.64 (m, 1H), 1.35 (d, 3H), 1.22 (m, 3H); m/z (ES+): 502 $[M+H]^+$.

Example 113

Compound 113

(1S,8aS)-7,7-bis(2-hydroxyethyl)-N-((R)-1-(3-isopropyl-5-(trifluoromethyl)phenyl)ethyl)-N-methyl-6-oxo-1-o-tolylhexahydropyrrolo[1,2-a]pyrazine-2(1H)-carboxamide

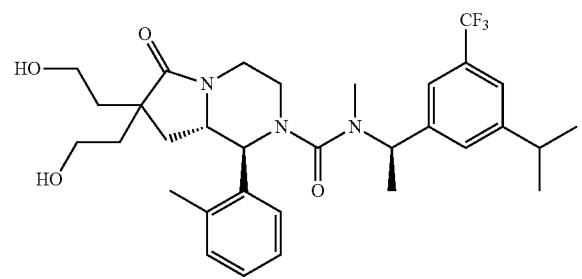 [SMILES: Cc1ccccc1[C@H]1[C@@H]2CC(CCO)(CCO)C(=O)N2CCN1C(=O)N(C)[C@H](C)c1cc(C(C)C)cc(C(F)(F)F)c1]

A slow stream of $O_3$ in $O_2$ was passed through a cooled solution of Intermediate 145 (100 mg, 0.172 mmol) in DCM (10 mL) at −78° C. until a pale blue colour persisted. The reaction was purged with $N_2$ to remove the excess of $O_3$ followed by addition of $NaBH_4$ (65 mg, 1.72 mmol). The reaction mixture was allowed to warm to room temperature and stirred for 20 h. The reaction was quenched with water and the resulting mixture was extracted with DCM. The organic layer was washed with brine, dried over anhydrous $Na_2SO_4$ and then concentrated in high vacuum. The residue was purified by Prep-HPLC to give the desired compound (20 mg, yield: 20%). $^1$H-NMR (400 MHz, $CDCl_3$) δ ppm 7.35 (s, 1H), 7.26 (s, 2H), 7.10 (m, 5H), 5.46 (m, 1H), 4.05 (m, 2H), 3.68 (m, 4H), 3.56 (m, 1H), 2.85 (m, 4H), 2.65 (s, 3H), 2.55 (s, 3H), 1.66 (m, 7H), 1.33 (m, 3H), 1.20 (m, 3H); m/z (ES+): 590 $[M+H]^+$.

Example 120

Measurement of NK1 Receptor Mediated Intracellular $[Ca^{2+}]$ Mobilization in U251 MG Cells Using FLIPR U251 MG cells were seeded into black walled clear-bottom 384-well plates (Greiner Bio-One GmbH, Frickenhausen, Germany) at a density of 15,000 cells/well in 50 µl culture medium and cultured overnight in a 37° C. 5% $CO_2$ incubator. The cells were then loaded with the calcium sensitive dye Fluo-4 (Invitrogen) at 1 µM in buffer, containing 0.04% Pluronic F-127 (Sigma-Aldrich), and 2.5 mM probenecid (Sigma-Aldrich) for 60 min in a humidified atmosphere of 5% $CO_2$. Thereafter, cells were washed three times in washing buffer containing 20 mM HEPES and 2.5 mM probenecid pH 7.3. Serial dilutions of test compounds in assay buffer containing 2% dimethyl sulfoxide (final concentration in the cell plate is 0.5% DMSO) and/or agonist were then automatically pipetted into each test well, and the peak fluorescence intensity was recorded ($l_{ex}$, 488 nm; $l_{em}$, 540 nm) by the FLIPR instrument (Molecular Devices) for approximately 5 min. To measure antagonist potency, cell plates were first incubated with the test compound and intracellular fluorescence recorded for 5 minutes to check a potential agonist effect of the test compound. Cell plates were quickly removed from the FLIPR instrument and incubated for additional 10 minutes at 37° C. before being moved back to the FLIPR instrument for Substance P ($EC_{80}$) addition. The response was measured as the peak relative fluorescence change after agonist addition.

Compound relative %-effect was normalized to the maximal response evoked by 100 nM Aprepitant in presence of the $EC_{80}$ of Substance P and the antagonist potency determined by non-linear regression using GraphPad Prism (version 5) or the four-parameter logistic model in XLfit (IDBS, Guilford, UK) for Microsoft Excel (Microsoft, Redmond, Wash.). The IC50 value is defined as the molar concentration of a test compound that produces a response midway between the fitted top and the fitted bottom. $pIC_{50}=-\log IC_{50}$ Formula is listed as follows:

Fit(% Effect calculated)=$(A+((B-A)/(1+((C/X)^{\wedge}D))))$

A: bottom value
B: top value
C: test compound concentration
X: Relative $IC_{50}$
D: Hill slope coefficient Ref: Sullivan E, Tucker E M, and Dale I L. Measurement of [$Ca^{2+}$] using the Fluorometric Imaging Plate Reader (FLIPR). Methods Mol Biol 114:125-133, 1999.

Compounds of the present invention were tested according to example 120. Results are reported in Table 1.

Example 121

Hepatic Extraction Ratio from Hepatic Intrinsic Clearance Following Incubation in Human Liver Microsomes The general procedure consists of an automated incubation system and LC-MS/MS analysis with human liver microsomes. Human liver microsomes are thawed rapidly in a waterbath at 37° C. and kept on ice until use. The human liver microsomes are diluted with 50 mM potassium phosphate buffer pH 7.4 to a protein concentration of 0.55 mg/mL. Test compounds and positive controls (Verapamil and Dextromethorphan, positive controls for CYP3A4 for CYP2D6 isoforms, respectively) are dissolved in methanol (or other appropriate solvent, if necessary) in order to obtain a 5 mM solution which is further diluted to the concentration of 50 µM. The stock solutions are prepared immediately before the test.

5 µL of 50 µM test compounds and controls are added to 445 µL-of the 0.55 mg/mL microsomes solution and the incubation mixture are pre-warmed at 37° C. for 5 minutes.

The incubation reactions are initiated by adding 50 µL of pre-warmed NADPH regenerating system to the incubation mixtures. 50 µL-aliquots will be taken from the incubation mixtures at: 0, 3, 6, 9, 15 and 30 minutes and the reactions are stopped by adding 100 µL of ACN containing Rolipram, used as generic Internal Standard (1S). Samples are then diluted with 120 µL of Milli-Q water and centrifuged at 3000 rpm for 10 minutes, prior the LC-MS/MS analysis.

Intrinsic Clearance.

The integrated peak areas for test compounds at the selected time points are divided by the respective peak areas of the IS and the percent of parent remaining is calculated by normalizing the peak area ratio of parent to IS at 0 min. Observed rate constant ($k_{obs}$) for parent degradation is calculated by determining the slope of the line of the graph of the natural log of percentage parent remaining versus time of incubation. From the rate of depletion (min-1) and volume of the incubation (mL), clearance is estimated. This is scaled for the protein in the incubation relative to that in the intact liver, for all species (mL/min/g liver).

$$Clint = Rate/min * \left(\frac{mL\ incubation}{0.5\ mg\ protein}\right) * \frac{52.5\ mean\ mg\ protein}{g\ liver}$$

Values for the Human in vitro Clint are expressed as mL/min/g liver.

Assuming a liver weight of 25.7 g/kg and a liver blood flow of 20.7 mL/min/kg, the hepatic extraction ratio, Eh, can be derived from the Human in vitro Clint:

$$Eh = \frac{(Clint*25.7)*20.7}{(Clint*25.7)+20.7} / 20.7$$

E.g. a Human in vitro Clint of 2.4 mL/min/g liver corresponds to a hepatic extraction ratio of 75%.

Some compounds of the present invention were tested according to example 121. Results are reported in Table 1

TABLE 1

| Compound | Name | U251MG (FLIPR $pIC_{50}$) | Human in vitro Clint (mL/min/g liver) |
|---|---|---|---|
| 1 | N-[(3,5-dimethylphenyl)methyl]-N-methyl-1-(2-methylphenyl)-6-oxo-octahydropyrrolo[1,2-a]piperazine-2-carboxamide | 8.19 | |
| 2 | N-[(3,5-dimethylphenyl)methyl]-N-methyl-1-(2-methylphenyl)-6-oxo-octahydropyrrolo[1,2-a]piperazine-2-carboxamide | 7.11 | |
| 3 | N-{[3-fluoro-5-trifluoromethyl)phenyl]methyl}-N-methyl-1-(2-methylphenyl)-6-oxo- | 8.86 | 9.5 |

TABLE 1-continued

| Compound | Name | U251MG (FLIPR pIC$_{50}$) | Human in vitro Clint (mL/min/g liver) |
|---|---|---|---|
| | octahydropyrrolo[1,2-a]piperazine-2-carboxamide | | |
| 4 | N-{[3-fluoro-5-(trifluoromethyl)phenyl]methyl}-N-methyl-1-(2-methylphenyl)-6-oxo-octahydropyrrolo[1,2-a]piperazine-2-carboxamide | 7.09 | |
| 5 | N-methyl-1-(2-methylphenyl)-6-oxo-N-{[3-(trifluoromethyl)phenyl]methyl}-octahydropyrrolo[1,2-a]piperazine-2-carboxamide | 8.13 | |
| 6 | N-methyl-1-(2-methylphenyl)-6-oxo-N-{[3-(trifluoromethyl)phenyl]methyl}-octahydropyrrolo[1,2-a]piperazine-2-carboxamide | <7 | |
| 7 | N-{[3,5-bis(trifluoromethyl)phenyl]methyl}-N-methyl-1-(2-methylphenyl)-7-oxo-octahydro-1H-pyrrolo[1,2-a][1,4]diazepine-2-carboxamide | 8.97 | |
| 8 | 2-({[3,5-bis(trifluoromethyl)phenyl]methyl}(methyl)carbamoyl)-7-methyl-1-(2-methylphenyl)-6-oxo-octahydropyrrolo[1,2-a]piperazine-7-carboxylic acid | 7.21 | |
| 9 | (1S,8aS)-N-[(1R)-1-[3,5-bis(trifluoromethyl)phenyl]ethyl]-N-methyl-1-(2-methylphenyl)-6-oxo-octahydropyrrolo[1,2-a] piperazine-2-carboxamide | 10.46 | 4.5 |
| 10 | (1R,8aR)-N-[(1R)-1-[3,5-bis(trifluoromethyl)phenyl]ethyl]-N-methyl-1-(2-methylphenyl)-6-oxo-octahydropyrrolo[1,2-a] piperazine-2-carboxamide | 7.89 | |
| 11 | Methyl 2-({[3,5-bis(trifluoromethyl)phenyl]methyl}(methyl)carbamoyl)-7-methyl-1-(2-methylphenyl)-6-oxo-octahydropyrrolo{1,2-a}piperazine-7-carboxylate | 9.09 | |
| 12 | Methyl 2-({[3,5-bis(trifluoromethyl)phenyl]methyl}(methyl)carbamoyl)-7-methyl-1-(2-methylphenyl)-6-oxo-octahydropyrrolo{1,2-a}piperazine-7-carboxylate | 8.75 | |
| 13 | Methyl 2-({[3,5-bis(trifluoromethyl)phenyl]methyl}(methyl)carbamoyl)-7-methyl-1-(2-methylphenyl)-6-oxo-octahydropyrrolo{1,2-a}piperazine-7-carboxylate | 8.38 | |
| 14 | Methyl 2-({[3,5-bis(trifluoromethyl)phenyl]methyl}(methyl)carbamoyl)-7-methyl-1-(2-methylphenyl)-6-oxo-octahydropyrrolo{1,2-a}piperazine-7-carboxylate | 10.16 | |
| 15 | Methyl 2-({[3,5-bis(trifluoromethyl)phenyl]methyl}(methyl)carbamoyl)-7-methyl-1-(2-methylphenyl)-6-oxo-octahydropyrrolo{1,2-a}piperazine-7-carboxylate | 10 | |
| 16 | N-{[3,5-bis(trifluoromethyl)phenyl]methyl}-N-methyl-1-(2-methylphenyl)-6-oxo-octahydropyrrolo[1,2-a]piperazine-2-carboxamide | 9.64 | |
| 17 | N-{[3,5-bis(trifluoromethyl)phenyl]methyl}-N-methyl-1-(2-methylphenyl)-6-oxo-octahydropyrrolo[1,2-a]piperazine-2-carboxamide | 7.55 | |
| 18 | N-{[3,5-bis(trifluoromethyl)phenyl]methyl}-N-methyl-1-(2-methylphenyl)-6-oxo-octahydropyrrolo[1,2-a]piperazine-2-carboxamide | 9.22 | 2.8 |
| 19 | N-{[3,5-bis(trifluoromethyl)phenyl]methyl}-7-(hydroxymethyl)-N-methyl-1-(2-methylphenyl)-6-oxo-octahydropyrrolo[1,2-a]piperazine-2-carboxamide | 8.43 | |

TABLE 1-continued

| Compound | Name | U251MG (FLIPR pIC$_{50}$) | Human in vitro Clint (mL/min/g liver) |
|---|---|---|---|
| 20 | N-{[3,5-bis(trifluoromethyl)phenyl]methyl}-7-(hydroxymethyl)-N-methyl-1-(2-methylphenyl)-6-oxo-octahydropyrrolo[1,2-a]piperazine-2-carboxamide | 8.78 | |
| 21 | N-{[3,5-bis(trifluoromethyl)phenyl]methyl}-7-(hydroxymethyl)-N-methyl-1-(2-methylphenyl)-6-oxo-octahydropyrrolo[1,2-a]piperazine-2-carboxamide | 10.39 | |
| 22 | N-{[3,5-bis(trifluoromethyl)phenyl]methyl}-7-(hydroxymethyl)-N-methyl-1-(2-methylphenyl)-6-oxo-octahydropyrrolo[1,2-a]piperazine-2-carboxamide | 10.29 | 0.8 |
| 23 | N-{[3,5-bis(trifluoromethyl)phenyl]methyl}-7-(hydroxymethyl)-N-methyl-1-(2-methylphenyl)-6-oxo-octahydropyrrolo[1,2-a]piperazine-2-carboxamide | 10.11 | |
| 24 | N-{[3,5-bis(trifluoromethyl)phenyl]methyl}-N-methyl-1-(2-methylphenyl)-octahydropyrrolo[1,2-a]piperazine-2-carboxamide | 8.87 | |
| 25 | 2-N-{[3,5-bis(trifluoromethyl)phenyl]methyl}-2-N,7-N,7-N,7-tetramethyl-1-(2-methylphenyl)-6-oxo-octahydropyrrolo[1,2-a]piperazine-2,7-dicarboxamide | 7.64 | |
| 26 | 2-N-{[3,5-bis(trifluoromethyl)phenyl]methyl}-2-N,7-N,7-N,7-tetramethyl-1-(2-methylphenyl)-6-oxo-octahydropyrrolo[1,2-a]piperazine-2,7-dicarboxamide | 9.18 | 1.0 |
| 27 | N-{[3,5-bis(trifluoromethyl)phenyl]methyl}-7-(hydroxymethyl)-N-methyl-1-(2-methylphenyl)-octahydropyrrolo[1,2-a]piperazine-2-carboxamide methanesulfonic acid salt | 7.23 | |
| 28 | N-{[3,5-bis(trifluoromethyl)phenyl]methyl}-7-(hydroxymethyl)-N-methyl-1-(2-methylphenyl)-octahydropyrrolo[1,2-a]piperazine-2-carboxamide methanesulfonic acid salt | 9.04 | |
| 29 | N-{[3,5-bis(trifluoromethyl)phenyl]methyl}-N-methyl-1-(2-methylphenyl)-7-(morpholin-4-ylmethyl)-6-oxo-octahydropyrrolo[1,2-a]piperazine-2-carboxamide | 9.4 | 6.4 |
| 30 | N-{[3,5-bis(trifluoromethyl)phenyl]methyl}-N-methyl-1-(2-methylphenyl)-6-oxo-7-(pyrrolidin-1-ylmethyl)-octahydropyrrolo[1,2-a]piperazine-2-carboxamide | 9.42 | 2.4 |
| 31 | N-{[3,5-bis(trifluoromethyl)phenyl]methyl}-N-methyl-1-(2-methylphenyl)-6-oxo-7-(pyrrolidin-1-ylmethyl)-octahydropyrrolo[1,2-a]piperazine-2-carboxamide | 9.29 | |
| 32 | N-{[3,5-bis(trifluoromethyl)phenyl]methyl}-N-methyl-7-methylidene-1-(2-methylphenyl)-6-oxo-octahydropyrrolo[1,2-a]piperazine-2-carboxamide | 9.36 | |
| 33 | N-{1-[3,5-bis(trifluoromethyl)phenyl]-3-hydroxypropyl}-7-(2-hydroxyethyl)-N-methyl-1-(2-methylphenyl)-6-oxo-octahydropyrrolo[1,2-a]piperazine-2-carboxamide | 9.8 | |
| 34 | N-{1-[3,5-bis(trifluoromethyl)phenyl]-3-hydroxypropyl}-7-(2-hydroxyethyl)-N-methyl-1-(2-methylphenyl)-6-oxo-octahydropyrrolo[1,2-a]piperazine-2-carboxamide | 7.81 | |

TABLE 1-continued

| Compound | Name | U251MG (FLIPR pIC$_{50}$) | Human in vitro Clint (mL/min/g liver) |
|---|---|---|---|
| 35 | N-{1-[3,5-bis(trifluoromethyl)phenyl]-3-hydroxypropyl}-7-(2-hydroxyethyl)-N-methyl-1-(2-methylphenyl)-6-oxo-octahydropyrrolo[1,2-a]piperazine-2-carboxamide | 9.7 | |
| 36 | N-{1-[3,5-bis(trifluoromethyl)phenyl]-3-hydroxypropyl}-7-(2-hydroxyethyl)-N-methyl-1-(2-methylphenyl)-octahydropyrrolo[1,2-a]piperazine-2-carboxamide | 9.14 | |
| 37 | 7-[(4-acetylpiperazin-1-yl)methyl]-N-{[3,5-bis(trifluoromethyl)phenyl]methyl}-N-methyl-1-(2-methylphenyl)-6-oxo-octahydropyrrolo[1,2-a]piperazine-2-carboxamide | 9.51 | |
| 38 | N-{[3,4-bis(trifluoromethyl)phenyl]methyl}-N-methyl-1-(2-methylphenyl)-7-(morpholin-4-ylmethyl)-6-oxa-octahydropyrrolo[1,2-a]piperazine-2-carboxamide as methansulfonic acid salt | 9.71 | 3.3 |
| 39 | N-{[3,4-bis(trifluoromethyl)phenyl]methyl}-N-methyl-1-(2-methylphenyl)-7-(morpholin-4-ylmethyl)-6-oxa-octahydropyrrolo[1,2-a]piperazine-2-carboxamide methansulfonic acid salt | 8.54 | |
| 40 | N-{[3,4-bis(trifluoromethyl)phenyl]methyl}-N-methyl-1-(2-methylphenyl)-7-(morpholin-4-ylmethyl)-6-oxa-octahydropyrrolo[1,2-a]piperazine-2-carboxamide methansulfonic acid salt | 8.11 | |
| 41 | N-{[3,4-bis(trifluoromethyl)phenyl]methyl}-N-methyl-1-(2-methylphenyl)-7-(morpholin-4-ylmethyl)-6-oxa-octahydropyrrolo[1,2-a]piperazine-2-carboxamide methansulfonic acid salt | 9.65 | 2.9 |
| 42 | N-{[3,5-bis(trifluoromethyl)phenyl]methyl}-7,7-bis(2-hydroxyethyl)-N-methyl-1-(2-methylphenyl)-6-oxo-octahydropyrrolo[1,2-a]piperazine-2-carboxamide | 10.02 | |
| 43 | N-{[3,5-bis(trifluoromethyl)phenyl]methyl}-7,7-bis(2-hydroxyethyl)-N-methyl-1-(2-methylphenyl)-6-oxo-octahydropyrrolo[1,2-a]piperazine-2-carboxamide | 9.28 | 3.7 |
| 44 | N-{[3,5-bis(trifluoromethyl)phenyl]methyl}-7,7-bis(2-hydroxyethyl)-N-methyl-1-(2-methylphenyl)-6-oxo-octahydropyrrolo[1,2-a]piperazine-2-carboxamide | 10.16 | 2.6 |
| 45 | (3'aS,4'S)-N-{[3,5-bis(trifluoromethyl) phenyl] methyl}-N,1-dimethyl-4'-(2-methylphenyl)-1'-oxo-hexahydro-1'H-spiro[piperidine-4,2'-pyrrolo[1,2-a]piperazine]-5'-carboxamide | 9.78 | 1.9 |
| 46 | N-{[3,5-bis(trifluoromethyl)phenyl]methyl}-N,1-dimethyl-4'-(2-methylphenyl)-1'-oxo-hexahydro-1'H-spiro[piperidine-4,2'-pyrrolo[1,2-a]piperazine]-5'-carboxamide | 8.34 | |
| 47 | N-{[3,5-bis(trifluoromethyl)phenyl]methyl}-N,1-dimethyl-4'-(2-methylphenyl)-1'-oxo-hexahydro-1'H-spiro[piperidine-4,2'-pyrrolo[1,2-a]piperazine]-5'-carboxamide | 10.03 | 0.4 |
| 48 | N-{[3,5-bis(trifluoromethyl)phenyl]methyl}-7-(hydroxymethyl)-N-methyl-1-(2-methylphenyl)-octahydropyrrolo[1,2-a]piperazine-2-carboxamide | 9.65 | |
| 49 | N-{[3,5-bis(trifluoromethyl)phenyl]methyl}-7-(hydroxymethyl)-N-methyl-1-(2-methylphenyl)-octahydropyrrolo[1,2-a]piperazine-2-carboxamide | 9.46 | 1.9 |
| 50 | N-{[3,4-bis(trifluoromethyl)phenyl]methyl}-N-methyl-1-(2-methylphenyl)-7-(morpholin-4-ylmethyl)-6-oxa-octahydropyrrolo[1,2-a]piperazine-2-carboxamide | 9.65 | 2.9 |
| 51 | N-{[3,4-bis(trifluoromethyl)phenyl]methyl}-N-methyl-1-(2-methylphenyl)-7-(morpholin-4-ylmethyl)-6-oxa-octahydropyrrolo[1,2-a]piperazine-2-carboxamide | 9.92 | |

TABLE 1-continued

| Compound | Name | U251MG (FLIPR pIC$_{50}$) | Human in vitro Clint (mL/min/g liver) |
|---|---|---|---|
| 52 | N-{[3,5-bis(trifluoromethyl)phenyl]methyl}-7-(hydroxymethyl)-N-methyl-1-(2-methylphenyl)-octahydropyrrolo[1,2-a]piperazine-2-carboxamide | 9.29 | 3.1 |
| 53 | N-[(1R)-1-[3,5-bis(trifluoromethyl)phenyl]ethyl]-7,7-bis(2-hydroxyethyl)-N-methyl-1-(2-methylphenyl)-6-oxo-octahydropyrrolo[1,2-a]piperazine-2-carboxamide | 8.61 | |
| 54 | N-[(1R)-1-[3,5-bis(trifluoromethyl)phenyl]ethyl]-7,7-bis(2-hydroxyethyl)-N-methyl-1-(2-methylphenyl)-6-oxo-octahydropyrrolo[1,2-a]piperazine-2-carboxamide | 9.92 | 9.5 |
| 55 | N-[(1R)-1-[3,5-bis(trifluoromethyl)phenyl]ethyl]-7-(hydroxymethyl)-N-methyl-1-(2-methylphenyl)-6-oxo-octahydropyrrolo[1,2-a]piperazine-2-carboxamide | 9.82 | 2.4 |
| 56 | N-[(1R)-1-[3,5-bis(trifluoromethyl)phenyl]ethyl]-7-(hydroxymethyl)-N-methyl-1-(2-methylphenyl)-6-oxo-octahydropyrrolo[1,2-a]piperazine-2-carboxamide | 9.95 | 0.34 |
| 57 | N-[(1R)-1-[3,5-bis(trifluoromethyl)phenyl]ethyl]-7-(hydroxymethyl)-N-methyl-1-(2-methylphenyl)-6-oxo-octahydropyrrolo[1,2-a]piperazine-2-carboxamide | 8.82 | |
| 58 | N-[(1R)-1-[3,5-bis(trifluoromethyl)phenyl]ethyl]-7-(hydroxymethyl)-N-methyl-1-(2-methylphenyl)-6-oxo-octahydropyrrolo[1,2-a]piperazine-2-carboxamide | 7.94 | |
| 59 | N-[(1R)-1-[3,5-bis(trifluoromethyl)phenyl]ethyl]-7,7-bis(2-hydroxyethyl)-N-methyl-1-(2-methylphenyl)-octahydropyrrolo[1,2-a]piperazine-2-carboxamide | 7.22 | |
| 60 | N-[(1R)-1-[3,5-bis(trifluoromethyl)phenyl]ethyl]-7,7-bis(2-hydroxyethyl)-N-methyl-1-(2-methylphenyl)-octahydropyrrolo[1,2-a]piperazine-2-carboxamide | 9.47 | 6.1 |
| 61 | N-{[3,5-bis(trifluoromethyl)phenyl]methyl}-N-methyl-1-(2-methylphenyl)-octahydropyrrolo[1,2-a]piperazine-2-carboxamide | <7 | |
| 62 | N-{[3,5-bis(trifluoromethyl)phenyl]methyl}-N-methyl-1-(2-methylphenyl)-octahydropyrrolo[1,2-a]piperazine-2-carboxamide | 9.02 | |
| 63 | N-[(1R)-1-[3,5-bis(trifluoromethyl)phenyl]ethyl]-N-methyl-1-(2-methylphenyl)-octahydropyrrolo[1,2-a]piperazine-2-carboxamide | 9.49 | 11 |
| 64 | N-[(1R)-1-[3,5-bis(trifluoromethyl)phenyl]ethyl]-N-methyl-1-(2-methylphenyl)-octahydropyrrolo[1,2-a]piperazine-2-carboxamide | 7.37 | |
| 65 | N-{[3,5-bis(trifluoromethyl)phenyl]methyl}-7,7-bis(2-hydroxyethyl)-N-methyl-1-(2-methylphenyl)-octahydropyrrolo[1,2-a]piperazine-2-carboxamide | 7.52 | |
| 66 | N-{[3,5-bis(trifluoromethyl)phenyl]methyl}-7,7-bis(2-hydroxyethyl)-N-methyl-1-(2-methylphenyl)-octahydropyrrolo[1,2-a]piperazine-2-carboxamide | 10.1 | 4.2 |
| 67 | N-[(1R)-1-[3,5-bis(trifluoromethyl)phenyl]ethyl]-7-(hydroxymethyl)-N-methyl-1-(2-methylphenyl)-octahydropyrrolo[1,2-a]piperazine-2-carboxamide | 9.69 | |

TABLE 1-continued

| Compound | Name | U251MG (FLIPR pIC$_{50}$) | Human in vitro Clint (mL/min/g liver) |
|---|---|---|---|
| 68 | N-[(1R)-1-[3,5-bis(trifluoromethyl)phenyl]ethyl]-7-(hydroxymethyl)-N-methyl-1-(2-methylphenyl)-octahydropyrrolo[1,2-a]piperazine-2-carboxamide | 8.35 | |
| 69 | N-[(1R)-1-[3,5-bis(trifluoromethyl)phenyl]ethyl]-7-(hydroxymethyl)-N-methyl-1-(2-methylphenyl)-octahydropyrrolo[1,2-a]piperazine-2-carboxamide | 9.67 | |
| 70 | N-[(1R)-1-[3,5-bis(trifluoromethyl)phenyl]ethyl]-7-(hydroxymethyl)-N-methyl-1-(2-methylphenyl)-octahydropyrrolo[1,2-a]piperazine-2-carboxamide | 7.18 | |
| 71 | N-[(1R)-1-[3,5-bis(trifluoromethyl)phenyl]ethyl]-N-methyl-1-(2-methylphenyl)-7-(morpholin-4-ylmethyl)-6-oxo-octahydropyrrolo[1,2-a]piperazine-2-carboxamide | 7.55 | |
| 72 | N-[(1R)-1-[3,5-bis(trifluoromethyl)phenyl]ethyl]-N-methyl-1-(2-methylphenyl)-7-(morpholin-4-ylmethyl)-6-oxo-octahydropyrrolo[1,2-a]piperazine-2-carboxamide | 8.09 | |
| 73 | N-[(1R)-1-[3,5-bis(trifluoromethyl)phenyl]ethyl]-N-methyl-1-(2-methylphenyl)-7-(morpholin-4-ylmethyl)-6-oxo-octahydropyrrolo[1,2-a]piperazine-2-carboxamide | 9.97 | |
| 74 | N-[(1R)-1-[3,5-is(trifluoromethyl)phenyl]ethyl]-N-methyl-1-(2-methylphenyl)-7-(morpholin-4-ylmethyl)-6-oxo-octahydropyrrolo[1,2-a]piperazine-2-carboxamide | 10.05 | |
| 75 | N-[(1R)-1-[3,5-is(trifluoromethyl)phenyl]ethyl]-N-methyl-1-(2-methylphenyl)-6-oxo-octahydropyrrolo[1,2-a] piperazine 2 carboxamide | 10.5 | 32 |
| 76 | (1S,8aS)-N-(3-fluoro-5-(trifluoromethyl)benzyl)-7,7-bis(2-hydroxyethyl)-N-methyl-6-oxo-1-o-tolylhexahydropyrrolo[1,2-a]pyrazine-2(1H)-carboxamide | 9.83 | 12 |
| 77 | (1S,8aS)-7,7-bis(2-hydroxyethyl)-N-methyl-N-(3-methyl-5-(trifluoromethyl)benzyl)-6-oxo-1-o-tolylhexahydropyrrolo[1,2-a]pyrazine-2(1H)-carboxamide | 10.2 | 15 |
| 78 | (1S,8aS)-7,7-bis(2-hydroxyethyl)-N-(3-methoxy-5-(trifluoromethyl)benzyl)-N-methyl-6-oxo-1-o-tolylhexahydropyrrolo[1,2-a]pyrazine-2(1H)-carboxamide | 9.95 | 4.6 |
| 79 | (1S,8aS)-N-(3-chloro-5-(trifluoromethyl)benzyl)-7,7-bis(2-hydroxyethyl)-N-methyl-6-oxo-1-o-tolylhexahydropyrrolo[1,2-a]pyrazine-2(1H)-carboxamide | 9.98 | 14 |
| 80 | (1S,8aS)-7,7-bis(2-hydroxyethyl)-N-methyl-6-oxo-1-o-tolyl-N-(3-(trifluoromethyl)benzyl)hexahydropyrrolo[1,2-a]pyrazine-2(1H)-carboxamide | 9.33 | |
| 81 | (1S,8aS)-N-(1-(3,5-bis(trifluoromethyl)phenyl)-3-hydroxypropyl)-7,7-bis(2-hydroxyethyl)-N-methyl-6-oxo-1-o-tolylhexahydropyrrolo[1,2-a]pyrazine-2(1H)-carboxamide | 9.92 | |
| 82 | (1S,8aS)-N-(1-(3,5-bis(trifluoromethyl)phenyl)-3-hydroxypropyl)-7,7-bis(2-hydroxyethyl)-N-methyl-6-oxo-1-o-tolylhexahydropyrrolo[1,2-a]pyrazine-2(1H)-carboxamide | 9.95 | |

TABLE 1-continued

| Compound | Name | U251MG (FLIPR pIC$_{50}$) | Human in vitro Clint (mL/min/g liver) |
|---|---|---|---|
| 83 | (1S,8aS)-N-(1-(3,5-bis(trifluoromethyl)phenyl)propyl)-7,7-bis(2-hydroxyethyl)-N-methyl-6-oxo-1-o-tolylhexahydropyrrolo[1,2-a]pyrazine-2(1H)-carboxamide | 9.88 | 7.8 |
| 84 | (1S,8aS)-7,7-bis(2-hydroxyethyl)-N-methyl-N-((S)-1-(3-methyl-5-(trifluoromethyl)phenyl)ethyl)-6-oxo-1-o-tolylhexahydropyrrolo[1,2-a]pyrazine-2(1H)-carboxamide | 10.2 | 8.5 |
| 85 | (1S,8aS)-7,7-bis(2-hydroxyethyl)-N-methyl-N-((R)-1-(3-methyl-5-(trifluoromethyl)phenyl)ethyl)-6-oxo-1-o-tolylhexahydropyrrolo[1,2-a]pyrazine-2(1H)-carboxamide | 10.1 | 17 |
| 86 | (1S,8aS)-N-((S)-1-(3,5-bis(trifluoromethyl)phenyl)-2-hydroxyethyl)-7,7-bis(2-hydroxyethyl)-N-methyl-6-oxo-1-o-tolylhexahydropyrrolo[1,2-a]pyrazine-2(1H)-carboxamide | 9.89 | 2.8 |
| 87 | (1S,8aS)-N-((R)-1-(3,5-bis(trifluoromethyl)phenyl)-2-hydroxyethyl)-7,7-bis(2-hydroxyethyl)-N-methyl-6-oxo-1-o-tolylhexahydropyrrolo[1,2-a]pyrazine-2(1H)-carboxamide | 9.69 | |
| 88 | (1S,8aS)-7,7-bis(2-hydroxyethyl)-N-methyl-6-oxo-1-o-tolyl-N-((R)-1-(3-(trifluoromethyl)phenyl)ethyl)hexahydro-pyrrolo[1,2-a]pyrazine-2(1H)-carboxamide | 10.2 | 13 |
| 89 | (1S,8aS)-N-((R)-1-(3-chloro-5-(trifluoromethyl)phenyl)ethyl)-7,7-bis(2-hydroxyethyl)-N-methyl-6-oxo-1-o-tolylhexahydropyrrolo[1,2-a]pyrazine-2(1H)-carboxamide | 9.90 | 15 |
| 90 | (1S,8aS)-N-((S)-1-(3-chloro-5-(trifluoromethyl)phenyl)ethyl)-7,7-bis(2-hydroxyethyl)-N-methyl-6-oxo-1-o-tolylhexahydropyrrolo[1,2-a]pyrazine-2(1H)-carboxamide | 10.4 | 7.6 |
| 91 | (1S,8aS)-7,7-bis(2-hydroxyethyl)-N-((R)-1-(3-methoxy-5-(trifluoromethyl)phenyl)ethyl)-N-methyl-6-oxo-1-o-tolylhexahydropyrrolo[1,2-a]pyrazine-2(1H)-carboxamide | 10.2 | 8.5 |
| 92 | (1S,8aS)-N-((S)-1-(3-fluoro-5-(trifluoromethyl)phenyl)ethyl)-7,7-bis(2-hydroxyethyl)-N-methyl-6-oxo-1-o-tolylhexahydropyrrolo[1,2-a]pyrazine-2(1H)-carboxamide | 10.8 | 11 |
| 93 | (1S,8aS)-N-((R)-1-(3-fluoro-5-(trifluoromethyl)phenyl)ethyl)-7,7-bis(2-hydroxyethyl)-N-methyl-6-oxo-1-o-tolylhexahydropyrrolo[1,2-a]pyrazine-2(1H)-carboxamide | 10.1 | 10 |
| 94 | (1S,8aS)-N-((S)-1-(3-fluoro-5-(trifluoromethyl)phenyl)-2-hydroxyethyl)-7,7-bis(2-hydroxyethyl)-N-methyl-6-oxo-1-o-tolylhexahydropyrrolo[1,2-a]pyrazine-2(1H)-carboxamide | 10.3 | 3.4 |
| 95 | (1S,8aS)-N((S)-2-hydroxy-1-(3-methoxy-5-(trifluoromethyl)phenyl)ethyl)-7,7-bis(2-hydroxyethyl)-N-methyl-6-oxo-1-o-tolylhexahydropyrrolo[1,2-a]pyrazine-2(1H)-carboxamide | 9.81 | 2.1 |
| 96 | (1S,8aS)-N-((S)-2-hydroxy-1-(3-(trifluoromethyl)phenyl)ethyl)-7,7-bis(2-hydroxyethyl)-N-methyl-6-oxo-1-o-tolylhexahydropyrrolo[1,2-a]pyrazine-2(1H)-carboxamide | 10.1 | 4.8 |
| 97 | (1S,8aS)-N-((R)-1-(3-(difluoromethyl)-5-(trifluoromethyl)phenyl)ethyl)-7,7-bis(2-hydroxyethyl)-N-methyl-6-oxo-1-o-tolylhexahydropyrrolo[1,2-a]pyrazine-2(1H)-carboxamide | 10.3 | 14 |

TABLE 1-continued

| Compound | Name | U251MG (FLIPR pIC$_{50}$) | Human in vitro Clint (mL/min/g liver) |
|---|---|---|---|
| 98 | (1S,8aS)-N-((R)-1-(3-(difluoromethyl)-5-(trifluoromethyl)phenyl)ethyl)-7,7-bis(2-hydroxyethyl)-N-methyl-6-oxo-1-o-tolylhexahydropyrrolo[1,2-a]pyrazine-2(1H)-carboxamide | 9.93 | 4.0 |
| 99 | (1S,8aS)-N-((S)-1-(3,5-bis(trifluoromethyl)phenyl)ethyl)-7,7-bis(2-hydroxyethyl)-N-methyl-6-oxo-1-o-tolylhexahydropyrrolo[1,2-a]pyrazine-2(1H)-carboxamid | 9.78 | 5.4 |
| 100 | (1'S,8a'S)-N-((R)-1-(3,5-bis(trifluoromethyl)phenyl)ethyl)-N-methyl-6'-oxo-1'-o-tolyloctahydro-1'H-spiro[pyran-4,7'-pyrrolo[1,2-a]pyrazine]-2'(6'H)-carboxamide | 9.90 | 3.0 |
| 101 | (1'S,8a'S)-N-((R)-1-(3,5-bis(trifluoromethyl)phenyl)ethyl)-N-methyl-6'-oxo-1'-o-tolyloctahydro-1'H-spiro[pyran-4,7'-pyrrolo[1,2-a]pyrazine]-2'(6'H)-carboxamide | 10.6 | 6.9 |
| 102 | (1S,8aS)-7-(hydroxymethyl)-N-methyl-N-((R)-1-(3-methyl-5-(trifluoromethyl)phenyl)ethyl)-6-oxo-1-o-tolylhexahydropyrrolo[1,2-a]pyrazine-2(1H)-carboxamide | 9.67 | 5.6 |
| 103 | (1S,8aS)-7,7-bis(hydroxymethyl)-N-methyl-N-((R)-1-(3-methyl-5-(trifluoromethyl)phenyl)ethyl)-6-oxo-1-o-tolylhexahydropyrrolo[1,2-a]pyrazine-2(1H)-carboxamide | 10.1 | 4.8 |
| 104 | (1S,8aS)-N-((R)-1-(3,5-bis(trifluoromethyl)phenyl)ethyl)-7,7-bis(hydroxymethyl)-N-methyl-6-oxo-1-o-tolylhexahydropyrrolo[1,2-a]pyrazine-2(1H)-carboxamide | 10.0 | 3.1 |
| 105 | (1'S,8a'S)-N-((R)-1-(3,5-bis(trifluoromethyl)phenyl)ethyl)-N,1-dimethyl-6'-oxo-1'-o-tolyltetrahydro-1'H-spiro[piperidine-4,7'-pyrrolo[1,2-a]pyrazine]-2'(6'H)-carboxamide, formic acid salt | 9.62 | 1.2 |
| 106 | (1'S,8a'S)-N-((R)-1-(3,5-bis(trifluoromethyl)phenyl)ethyl)-N-methyl-6'-oxo-1'-o-tolyltetrahydro-1'H-spiro[piperidine-4,7'-pyrrolo[1,2-a]pyrazine]-2'(6'H)-carboxamide, formic acid salt | 9.94 | 0.19 |
| 107 | (1S,8aS)-N-methyl-N-((R)-1-(3-methyl-5-(trifluoromethyl)phenyl)ethyl)-6-oxo-1-o-tolylhexahydropyrrolo[1,2-a]pyrazine-2(1H)-carboxamide | 9.97 | 9.2 |
| 108 | (1S,8aS)-N-((R)-1-(3-chloro-5-(trifluoromethyl)phenyl)ethyl)-7,7-bis(hydroxymethyl)-N-methyl-6-oxo-1-o-tolylhexahydropyrrolo[1,2-a]pyrazine-2(1H)-carboxamide | 10.5 | 4.3 |
| 109 | (1S,8aS)-N-((R)-1-(3-ethyl-5-(trifluoromethyl)phenyl)ethyl)-N-methyl-6-oxo-1-o-tolylhexahydropyrrolo[1,2-a]pyrazine-2(1H)-carboxamide | 10.0 | 13 |
| 110 | (1S,8aS)-N-((R)-1-(3-ethyl-5-(trifluoromethyl)phenyl)ethyl)-7,7-bis(2-hydroxyethyl)-N-methyl-6-oxo-1-o-tolylhexahydropyrrolo[1,2-a]pyrazine-2(1H)-carboxamide | 10.2 | 13 |
| 111 | (1S,8aS)-N-((S)-2-hydroxy-1-(3-methyl-5-(trifluoromethyl)phenyl)ethyl)-7,7-bis(2-hydroxyethyl)-N-methyl-6-oxo-1-o-tolylhexahydropyrrolo[1,2-a]pyrazine-2(1H)-carboxamide | 10.21 | 3.7 |
| 112 | (1S,8aS)-N-((R)-1-(3-isopropyl-5-(trifluoromethyl)phenyl)ethyl)-N-methyl-6-oxo-1-o-tolylhexahydropyrrolo[1,2-a]pyrazine-2(1H)-carboxamide | 10.5 | 51 |

TABLE 1-continued

| Compound | Name | U251MG (FLIPR pIC$_{50}$) | Human in vitro Clint (mL/min/g liver) |
|---|---|---|---|
| 113 | (1S,8aS)-7,7-bis(2-hydroxyethyl)-N-((R)-1-(3-isopropyl-5-(trifluoromethyl)phenyl)ethyl)-N-methyl-6-oxo-1-o-tolylhexahydropyrrolo[1,2-a]pyrazine-2(1H)-carboxamide | 10.5 | 56 |

Example 122

Gerbil Scratching Model

Some compounds of the present invention were tested in the gerbil scratching model to evaluate the effect of the compounds in the scratching behavior induced in gerbil by administration of GR73632 (5-Aminopentanoyl-L-phenylalanyl-L-phenylalanyl-L-prolyl-L-(N-methyl)leucyl-L-methioninamide), a selective NK-1 receptor agonist. The gerbil was selected for this study as this species shares higher homology to the human in terms of NK-1 receptor pharmacology compared to other laboratory rodents.

Experimental Procedure

The day before the testing, animals (male Mongolian gerbils) were shaved on the rostral part of the back (approximately at the intrascapular level) to expose the skin around the area of GR73632 injection.

Each test compound was tested on 11 or 12 animals. On the day of the test, the gerbils (four animals simultaneously) were put into a Plexiglas cage (42×42×35 cm) composed of four cells (20.5×20.5×35 cm) for 10 minutes of habituation. After this period, the test compound (1% w/v in acetone and transcutol 9:1) was topically applied on the shaven area in a volume of 20 μL. Topical application was performed using a Hamilton syringe (25 μL) and a square stencil of impermeable paper (1.5×1.5 cm) to allow application over a defined skin area (2.25 cm2). After 20 minutes the animals received an intradermal (i.d.) injection of GR73632 (100 nmol/100 μL in NaCl 0.9%) in the centre of the pretreated area and were housed individually to prevent the animals from chafing each other's skin. I.d. injection was made with a Hamilton syringe (250 μL) connected to a 27 gauge needle. Immediately after injection, animals were placed back into the same cell of the Plexiglas cage they were previously habituated in and their behaviour was recorded on video remotely for 30 minutes. The experimenter remained out of the observation room in order to minimize disturbance to the animals. The video was subsequently analysed to assess scratching behaviour. Scratching of the injection site by the hind paws was counted while scratching of other sites such as ears and snout were disregarded. Scratching episodes were measured over 10-minutes time intervals, for a total of 30 minutes.

Results were expressed as mean value±SEM. Statistical analysis was performed by a one-way ANOVA followed by LSD post hoc test with the exception of time-course analysis for a repeated-measure ANOVA followed by LSD post hoc test was performed.
Results FIG. 1 and FIG. 1a shows that topical application of Compound 9 and Compound 44 were able to attenuate the scratching induced in gerbils by the NK-1 selective agonist (GR73632).

The time course of scratching behaviours over 30 minutes after the intradermal injection of GR73632 (100 nmol/100 μL) is shown in FIG. 1. The repeated-measure ANOVA showed that GR73632 induced an increase in the number of scratches [treat: $F(1,3)=15.36$, $p<0.001$; time: $F(1,2)=57.79$, $p<0.001$; time×treat: $F(1,6)=10.30$, $p<0.001$]. In particular, LSD's post hoc analysis revealed a peaked effect of GR73632 within the first 10 minutes and this effect was maintained for the second 10-minute interval.

The effect of Compound 9 and Compound 44 during the first 10 minutes of the scratching model is shown in FIG. 1a. One-way ANOVA analysis revealed a significant differences between treatment groups [$F(1,3)=13.33$, $p<0.001$]. The post hoc test revealed a statistically significant effect for compound 9 ($p<0.05$) and compound 44 ($p<0.001$).

FIG. 2 and FIG. 2a show that topical application of Compound 54 and Compound 60 was able to attenuate the scratching induced in gerbils by the NK-1 selective agonist (GR73632).

The time course of scratching behaviours over 30 minutes after the intradermal injection of GR73632 (100 nmol/100 μL) is shown in FIG. 2. The repeated-measure ANOVA statistical analysis showed that GR73632 induced an increase of scratching [treat: $F(1,4)=12.54$, $p<0.001$; time: $F(1,2)=80.77$, $p<0.001$; time×treat: $F(1,8)=5.58$, $p<0.001$]. In particular, LSD post hoc analysis revealed a peak effect of GR73632 within the first 10 minutes which was maintained during the second 10-minute interval The effect of Compound 54 and Compound 60 in during the first 10 minutes of the scratching model is shown in FIG. 2a. One-way ANOVA analysis showed significant differences between treatment groups [$F(1,4)=7.57$, $p<0.001$]. The post hoc test revealed a statistically significant effect for compound 60 ($p<0.01$), compound 54 ($p<0.01$) and for the reference compound, Aprepitant ($p<0.01$).

FIG. 3 and FIG. 3a shows that topical application of Compound 38 and Compound 55 was not able to attenuate the scratching induced in gerbils by the NK-1 selective agonist (GR73632)

The time course of scratching behaviour over 30 minutes after the intradermal injection of GR73632 (100 nmol/100 μL) is shown in FIG. 3. The repeated-measure ANOVA statistical analysis showed that GR73632 induced an increase of scratching [treat: $F(1,3)=7.47$, $p<0.001$; time: $F(1,2)=79.22$, $p<0.001$; time×treat: $F(1,6)=6.47$, $p<0.001$]. In particular, LSD post hoc analysis revealed a maximum effect of GR73632 within the first 10 minutes.

The effect of Compound 38 and Compound 55 in the first 10 minutes of the scratching model is shown in FIG. 3a. One-way ANOVA statistical analysis revealed significant differences between treatment groups [$F(1,3)=7.43$, $p<0.001$]. The post hoc test showed only a significant effect for induction of scratching behavior by GR73632 ($p<0.001$) compared to vehicle. However, neither Compound 38 nor Compound 55 showed any statistically significant effect on reducing scratching behavior induced by GR73632.

The invention claimed is:

1. A compound of formula A wherein n is 1 or 2;

R1 and R2 are independently hydrogen, $C_{1-4}$ alkyl, $C_{1-4}$ haloalkyl, $C_{1-4}$ alkoxy, $CD_3$ or halogen;

R3 is hydrogen, C(=O)OR7 or $C_{1-4}$ alkyl optionally substituted with hydroxy or NR8R9;

R4 is hydrogen or oxo;

R5 and R6 are independently hydrogen, hydroxy, NR8R9, C(=O)R7, C(=O)OR7, C(=O)NR8R9, $C_{1-4}$ alkyl, wherein said $C_{1-4}$ alkyl is optionally substituted with hydroxy, NR8R9 or a 5- or 6-membered heterocyclic ring, wherein said 5- or 6-membered heterocyclic ring is optionally substituted with $C_1$-$C_4$ alkyl or C(=O)R7; or R5 and R6, together with the carbon atom to which they are attached, form =$CH_2$ or a 5- or 6-membered heterocycloalkyl, wherein said heterocycloalkyl is optionally substituted with $C_{1-4}$ alkyl;

R7 is hydrogen or $C_{1-4}$ alkyl; and

R8 and R9 are independently hydrogen or $C_{1-4}$ alkyl, or R8 and R9, together with the nitrogen atom to which they are attached, form a 5- or 6-membered heterocyclic ring, or a pharmaceutically acceptable salt thereof.

2. The compound according to claim 1 of formula A(i)

or a pharmaceutically acceptable salt thereof.

3. The compound according to claim 1 of formula A(ii)

or a pharmaceutically acceptable salt thereof.

4. The compound according to claim 1 of formula A(iii)

or a pharmaceutically acceptable salt thereof.

5. The compound according to claim 4, wherein R1 is hydrogen, $CH_3$, fluoro or trifluoromethyl.

6. The compound according to claims 4, wherein R2 is hydrogen, chloro, $CH_3$, $CH_2CH_3$, isopropyl, $OCH_3$, difluoromethyl or trifluoromethyl.

7. The compound according to claim 4, wherein R1 and R2 are both trifluoromethyl.

8. The compound according to claim 4, wherein R1 is trifluoromethyl and R2 is methyl, ethyl or isopropyl.

9. The compound according to claim 1, wherein n is 1.

10. The compound according to claim 1, wherein R4 is oxo.

11. The compound according to claim 1, wherein R4 is hydrogen.

12. The compound according to claim 1, wherein R3 is hydrogen, $CH_3$, $CH_2CH_3$, $CH_2OH$, $CH_2CH_2OH$, $COOCH_3$ or $CH_2N(CH_3)_2$.

13. The compound according to claim 1, wherein R5 and R6 are both hydrogen.

14. The compound according to claim 1, wherein R5 is hydrogen, $CH_3$, $CH_2OH$ or $CH_2CH_2OH$, and R6 is COOH, $COOCH_3$, $CH_2OH$, $CH_2CH_2OH$, $CON(CH_3)_2$ or $CH_2$-morpholine, $CH_2$-pyrrolidine, $CH_2$-piperazine optionally N-substituted with acetyl, or $CH_2$-piperidine.

15. The compound according to claim 1, wherein R5 and R6, together with the carbon atom to which they are attached form =$CH_2$, a piperidine ring optionally substituted with $C_{1-4}$ alkyl, or a tetrahydropyran ring.

16. The compound according to claim 1 selected from the group consisting of

N-[(3,5-dimethylphenyl)methyl]-N-methyl-1-(2-methylphenyl)-6-oxo-octahydropyrrolo[1,2-a]piperazine-2-carboxamide, N-[(3,5-dimethylphenyl)methyl]-N-methyl-1-(2-methylphenyl)-6-oxo-octahydropyrrolo[1,2-a]piperazine-2-carboxamide, N-{[3-fluoro-5-(trifluoromethyl)phenyl]methyl}-N-methyl-1-(2-methylphenyl)-6-oxo-octahydropyrrolo[1,2-a]piperazine-2-carboxamide, N-{[3-fluoro-5-(trifluoromethyl)phenyl]methyl}-N-methyl-1-(2-methylphenyl)-6-oxo-octahydropyrrolo[1,2-a]piperazine-2-carboxamide, N-methyl-1-(2-methylphenyl)-6-oxo-N-{[3-(trifluoromethyl)phenyl]methyl}-octahydropyrrolo[1,2-a]piperazine-2-carboxamide, N-methyl-1-(2-methylphenyl)-6-oxo-N-{[3-(trifluoromethyl)phenyl]methyl}-octahydropyrrolo[1,2-a]piperazine-2-carboxamide, N-{[3,5-bis(trifluoromethyl)phenyl]methyl}-N-methyl-1-(2-methylphenyl)-7-oxo-octahydro-1H-pyrrolo[1,2-a][1,4]diazepine-2-carboxamide, 2-({[3,5-bis(trifluoromethyl)phenyl]methyl}(methyl)carbamoyl)-7-methyl-1-(2-methylphenyl)-6-oxo-octahydropyrrolo[1,2-a]piperazine-7-carboxylic acid, N-[(1R)-1-[3,5-bis(trifluoromethyl)phenyl]ethyl]-N-methyl-1-(2-methylphenyl)-6-oxo-octahydropyrrolo[1,2-a]piperazine 2 carboxamide, N-[(1R)-1-[3,5-bis(trifluoromethyl)phenyl]ethyl]-N-methyl-1-(2-methylphenyl)-6-oxo-octahydropyrrolo[1,2-a]piperazine 2 carboxamide, (1S,8aS)-N-[(1R)-1-[3,5-bis(trifluoromethyl)phenyl]ethyl]-N-methyl-1-(2-methylphenyl)-6-oxo-octahydropyrrolo[1,2-a]piperazine-2-carboxamide, (1R,8aR)-N-[(1R)-1-[3,5-bis(trifluoromethyl)phenyl]ethyl]-N-methyl-1-(2-methylphenyl)-6-oxo-octahydropyrrolo[1,2-a]piperazine-2-carboxamide, Methyl 2-({[3,5-bis(trifluoromethyl)phenyl]methyl}(methyl)carbamoyl)-7-methyl-1-(2-methylphenyl)-6-oxo-octahydropyrrolo{1,2-a}piperazine-7-carboxylate, Methyl 2-({[3,5-bis(trifluoromethyl)phenyl]methyl}(methyl)carbamoyl)-7-methyl-1-(2-methylphenyl)-6-oxo-octahydropyrrolo {1,2-a}piperazine-7-carboxylate, Methyl 2-({[3,5-bis(trifluoromethyl)phenyl]methyl}(methyl)carbamoyl)-7-methyl-1-(2-methylphenyl)-6-oxo-octahydropyrrolo {1,2-a}piperazine-7-carboxylate, Methyl 2-({[3,5-bis(trifluoromethyl)phenyl]methyl}(methyl)carbamoyl)-7-methyl-1-(2-methylphenyl)-6-oxo-octahydropyrrolo[1,2-a]piperazine-7-carboxylate, Methyl 2-({[3,5-bis(trifluoromethyl)phenyl]methyl}(methyl)carbamoyl)-7-methyl-1-(2-methylphenyl)-6-oxo-octahydropyrrolo {1,2-a}piperazine-7-carboxylate, N-{[3,5-bis(trifluoromethyl)phenyl]methyl}-N-methyl-1-(2-methylphenyl)-6-oxo-octahydropyrrolo[1,2-a]piperazine-2-carboxamide, N-{[3,5-bis(trifluoromethyl)phenyl]methyl}-N-methyl-1-(2-methylphenyl)-6-oxo-octahydropyrrolo[1,2-a]piperazine-2-carboxamide, N-{[3,5-bis(trifluoromethyl)phenyl]methyl}-N-methyl-1-(2-methylphenyl)-6-oxo-octahydropyrrolo[1,2-a]piperazine-2-carboxamide, N-{[3,5-bis(trifluoromethyl)phenyl]methyl}-7-(hydroxymethyl)-N-methyl-1-(2-methylphenyl)-6-oxo-octahydropyrrolo[1,2-a]piperazine-2-carboxamide, N-{[3,5-bis(trifluoromethyl)phenyl]methyl}-7-(hydroxymethyl)-N-methyl-1-(2-methylphenyl)-6-oxo-octahydropyrrolo[1,2-a]piperazine-2-carboxamide, N-{[3,5-bis(trifluoromethyl)phenyl]methyl}-7-(hydroxymethyl)-N-methyl-1-(2-methylphenyl)-6-oxo-octahydropyrrolo[1,2-a]piperazine-2-carboxamide, N-{[3,5-bis(trifluoromethyl)phenyl]methyl}-7-(hydroxymethyl)-N-methyl-1-(2-methylphenyl)-6-oxo-octahydropyrrolo[1,2-a]piperazine-2-carboxamide, N-{[3,5-bis(trifluoromethyl)phenyl]methyl}-7-(hydroxymethyl)-N-methyl-1-(2-methylphenyl)-6-oxo-octahydropyrrolo[1,2-a]piperazine-2-carboxamide, N-{[3,5-bis(trifluoromethyl)phenyl]methyl}-N-methyl-1-(2-methylphenyl)-octahydropyrrolo[1,2-a]piperazine-2-carboxamide, 2-N-{[3,5-bis(trifluoromethyl)phenyl]methyl}-2-N,7-N,7-N,7-tetramethyl-1-(2-methylphenyl)-6-oxo-octahydropyrrolo[1,2-a]piperazine-2,7-dicarboxamide, 2-N-{[3,5-bis(trifluoromethyl)phenyl]methyl}-2-N,7-N,7-N,7-tetramethyl-1-(2-methylphenyl)-6-oxo-octahydropyrrolo[1,2-a]piperazine-2,7-dicarboxamide, N-{[3,5-bis(trifluoromethyl)phenyl]methyl}-7-(hydroxymethyl)-N-methyl-1-(2-methylphenyl)-octahydropyrrolo[1,2-a]piperazine-2-carboxamide methanesulfonic acid salt, N-{[3,5-bis(trifluoromethyl)phenyl]methyl}-7-(hydroxymethyl)-N-methyl-1-(2-methylphenyl)-octahydropyrrolo[1,2-a]piperazine-2-carboxamide methanesulfonic acid salt, N-{[3,5-bis(trifluoromethyl)phenyl]methyl}-N-methyl-1-(2-methylphenyl)-7-(morpholin-4-ylmethyl)-6-oxo-octahydropyrrolo[1,2-a]piperazine-2-carboxamide, N-{[3,5-bis(trifluoromethyl)phenyl]methyl}-N-methyl-1-(2-methylphenyl)-6-oxo-7-(pyrrolidin-1-ylmethyl)-octahydropyrrolo[1,2-a]piperazine-2-carboxamide, N-{[3,5-bis(trifluoromethyl)phenyl]methyl}-N-ethyl-1-(2-methylphenyl)-6-oxo-7-(pyrrolidin-1-ylmethyl)-octahydropyrrolo[1,2-a]piperazine-2-carboxamide, N-{[3,5-bis(trifluoromethyl)phenyl]methyl}-N-methyl-7-methylidene-1-(2-methylphenyl)-6-oxo-octahydropyrrolo[1,2-a]piperazine-2-carboxamide, N-{1-[3,5-bis(trifluoromethyl)phenyl]-3-hydroxypropyl}-7-(2-hydroxyethyl)-N-methyl-1-(2-methylphenyl)-6-oxo-octahydropyrrolo[1,2-a]piperazine-2-carboxamide, N-{1-[3,5-bis(trifluoromethyl)phenyl]-3-hydroxypropyl}-7-(2-hydroxyethyl)-N-methyl-1-(2-methylphenyl)-6-oxo-octahydropyrrolo[1,2-a]piperazine-2-carboxamide, N-{1-[3,5-bis(trifluoromethyl)phenyl]-3-hydroxypropyl}-7-(2-hydroxyethyl)-N-methyl-1-(2-methylphenyl)-6-oxo-octahydropyrrolo[1,2-a]piperazine-2-carboxamide, N-{1-[3,5-bis(trifluoromethyl)phenyl]-3-hydroxypropyl}-7-(2-hydroxyethyl)-N-methyl-1-(2-methylphenyl)-octahydropyrrolo[1,2-a]piperazine-2-carboxamide, 7-[(4-acetylpiperazin-1-yl)methyl]-N-{[3,5-bis(trifluoromethyl)phenyl]methyl}-N-methyl-1-(2-methylphenyl)-6-oxo-octahydropyrrolo[1,2-a]piperazine-2-carboxamide, N-{[3,4-bis(trifluoromethyl)phenyl]methyl}-N-methyl-1-(2-methylphenyl)-7-(morpholin-4-ylmethyl)-6-oxa-octahydropyrrolo[1,2-a]piperazine-2-carboxamide as methansulfonic acid salt, N-{[3,4-bis(trifluoromethyl)phenyl]methyl}-N-methyl-1-(2-methylphenyl)-7-(morpholin-4-ylmethyl)-6-oxa-octahydropyrrolo[1,2-a]piperazine-2-carboxamide methansulfonic acid salt, N-{[3,4-bis(trifluoromethyl)phenyl]methyl}-N-methyl-1-(2-methylphenyl)-7-(morpholin-4-ylmethyl)-6-oxa-octahydropyrrolo[1,2-a]piperazine-2-carboxamide methansulfonic acid salt, N-{[3,4-bis(trifluoromethyl)phenyl]methyl}-N-methyl-1-(2-methylphenyl)-7-(morpholin-4-ylmethyl)-6-oxa-octahydropyrrolo[1,2-a]piperazine-2-carboxamide methansulfonic acid salt, N-{[3,5-bis(trifluoromethyl)phenyl]methyl}-7,7-bis(2-hydroxyethyl)-N-methyl-1-(2-methylphenyl)-6-oxo-octahydropyrrolo[1,2-a]piperazine-2-carboxamide, N-{[3,5-bis(trifluoromethyl)phenyl]methyl}-7,7-bis(2-hydroxyethyl)-N-methyl-1-(2-methylphenyl)-6-oxo-octahydropyrrolo[1,2-a]piperazine-2-carboxamide, (3'aS,4'S)-N-{[3,5-bis(trifluoromethyl)phenyl]methyl}-N,1-dimethyl-4'-(2-methylphenyl)-1'-oxo-hexahydro-1'H-spiro[piperidine-4,2'-pyrrolo[1,2-a]piperazine]-5'-carboxamide, N-{[3,5-bis(trifluoromethyl)phenyl]methyl}-N, 1-dimethyl-4'-(2-methylphenyl)-1'-oxo-hexahydro-1'H-spiro[piperidine-4,2'-pyrrolo[1,2-a]piperazine]-5'-carboxamide, N-{[3,5-bis(trifluoromethyl)phenyl]methyl}-N, 1-dimethyl-4'-(2-methylphenyl)-1'-oxo-hexahydro-1'H-spiro[piperidine-4,2'-pyrrolo[1,2-a]piperazine]-5'-carboxamide, N-{[3,5-bis(trifluoromethyl)phenyl]methyl}-7-(hydroxymethyl)-N-methyl-1-(2-methylphenyl)-octahydropyrrolo[1,2-a]piperazine-2-carboxamide, N-{[3,5-bis(trifluoromethyl)phenyl]methyl}-7-(hydroxymethyl)-N-methyl-1-(2-methylphenyl)-octahydropyrrolo[1,2-a]piperazine-2-carboxamide, N-[(1R)-1-[3,5-bis(trifluoromethyl)phenyl]ethyl]-7,7-bis(2-hydroxyethyl)-N-methyl-1-(2-methylphenyl)-6-oxo-octahydropyrrolo[1,2-a]piperazine-2-carboxamide, N-[(1R)-1-[3,5-bis(trifluoromethyl)phenyl]ethyl]-7,7-bis(2-hydroxyethyl)-N-methyl-1-2-methylphenyl)-6-oxo-octahydropyrrolo[1,2-a]piperazine-2-carboxamide, N-[(1R)-1-[3,5-bis(trifluoromethyl)phenyl]ethyl]-7-(hydroxymethyl)-N-methyl-1-(2-methylphenyl)-6-oxo-octahydropyrrolo[1,2-a]piperazine-2-carboxamide, N-[(1R)-1-[3,5-bis(trifluoromethyl)phenyl]ethyl]-7-(hydroxymethyl)-N-methyl-1-(2-methylphenyl)-6-oxo-octahydropyrrolo[1,2-a]piperazine-2-carboxamide, N-[(1R)-1-[3,5-bis(trifluoromethyl)phenyl]ethyl]-7-(hydroxymethyl)-N-methyl-1-(2-methylphenyl)-6-oxo-octahydropyrrolo[1,2-a]piperazine-2-carboxamide, N-[(1R)-1-[3,5-bis(trifluoromethyl)phenyl]ethyl]-7-(hydroxymethyl)-N-methyl-1-(2-methylphenyl)-6-oxo-octahydropyrrolo[1,2-a]piperazine-2-carboxamide, N-[(1R)-1-[3,5-bis(trifluoromethyl)phenyl]ethyl]-7,7-bis(2-hydroxyethyl)-N-methyl-1-(2-methylphenyl)-octahydropyrrolo[1,2-a]piperazine-2-carboxamide, N-[(1R)-1-[3,5-bis(trifluoromethyl)phenyl]ethyl]-7,7-bis(2-hydroxyethyl)-N-methyl-1-(2-methylphenyl)-octahydropyrrolo[1,2-a]piperazine-2-carboxamide, N-{[3,5-bis(trifluoromethyl)phenyl]methyl}-N-methyl-1-(2-methylphenyl)-octahydropyrrolo[1,2-a]piperazine-2-carboxamide, N-{[3,5-bis(trifluoromethyl)phenyl]methyl}-N-methyl-1-(2-methylphenyl)-octahydropyrrolo[1,2-a]piperazine-2-carboxamide, N-[(1R)-1-[3,5-bis(trifluoromethyl)phenyl]ethyl]-N-methyl-1-(2-methylphenyl)-octahydropyrrolo[1,2-a]piperazine-2-carboxamide, N-[(1R)-1-[3,5-bis(trifluoromethyl)phenyl]ethyl]-N-methyl-1-(2-methylphenyl)-octahydropyrrolo[1,2-a]piperazine-2-carboxamide, N-{[3,5-bis(trifluoromethyl)phenyl]methyl}-7,7-bis(2-hydroxyethyl)-N-methyl-1-(2-methylphenyl)-octahydropyrrolo[1,2-a]piperazine-2-carboxamide, N-{[3,5-bis(trifluoromethyl)phenyl]methyl}-7,7-bis(2-hydroxyethyl)-N-methyl-1-(2-methylphenyl)-octahydropyrrolo[1,2-a]piperazine-2-carboxamide, N-[(1R)-1-[3,5-bis(trifluoromethyl)phenyl]ethyl]-7-(hydroxymethyl)-N-methyl-1-(2-methylphenyl)-octahydropyrrolo[1,2-a]piperazine-2-carboxamide, N-[(1R)-1-[3,5-bis(trifluoromethyl)phenyl]ethyl]-7-(hydroxymethyl)-N-methyl-1-(2-methylphenyl)-octahydropyrrolo[1,2-a]piperazine-2-carboxamide, N-[(1R)-1-[3,5-bis(trifluoromethyl)phenyl]ethyl]-7-(hydroxymethyl)-N-methyl-1-(2-methylphenyl)-octahydropyrrolo[1,2-a]piperazine-2-carboxamide, N-[(1R)-1-[3,5-bis(trifluoromethyl)phenyl]ethyl]-7-(hydroxymethyl)-N-methyl-1-(2-methylphenyl)-octahydropyrrolo[1,2-a]piperazine-2-carboxamide, N-[(1R)-1-[3,5-bis(trifluoromethyl)phenyl]ethyl]-N-methyl-1-(2-methylphenyl)-7-(morpholin-4-ylmethyl)-6-oxo-octahydropyrrolo[1,2-a]piperazine-2-carboxamide, N-[(1R)-1-[3,5-bis(trifluoromethyl)phenyl]ethyl]-N-methyl-1-(2-methylphenyl)-7-(morpholin-4-ylmethyl)-6-oxo-octahydropyrrolo[1,2-a]piperazine-2-carboxamide, N-[(1R)-1-[3,5-bis(trifluoromethyl)phenyl]ethyl]-N-methyl-1-(2-methylphenyl)-7-(morpholin-4-ylmethyl)-6-oxo-octahydropyrrolo[1,2-a]piperazine-2-carboxamide, N-[(1R)-1-[3,5-bis(trifluoromethyl)phenyl]ethyl]-N-methyl-1-(2-methylphenyl)-7-(morpholin-4-ylmethyl)-6-oxo-octahydropyrrolo[1,2-a]piperazine-2-carboxamide, N-[(1R)-1-[3,5-bis(trifluoromethyl)phenyl]ethyl]-N-methyl-1-(2-methylphenyl)-6-oxo-octahydropyrrolo[1,2-a]piperazine 2 carboxamide, (1S,8aS)-N-(3-fluoro-5-(trifluoromethyl)benzyl)-7,7-bis(2-hydroxyethyl)-N-methyl-6-oxo-1-o-tolylhexahydropyrrolo[1,2-a]pyrazine-2(1H)-carboxamide, (1S,8aS)-7,7-bis(2-hydroxyethyl)-N-methyl-N-(3-methyl-5-(trifluoromethyl)benzyl)-6-oxo-1-o-tolyl-hexahydropyrrolo[1,2-a]pyrazine-2(1H)-carboxamide, (1S,8aS)-7,7-bis(2-hydroxyethyl)-N-(3-methoxy-5-(trifluoromethyl)benzyl)-N-methyl-6-oxo-1-o-tolyl-hexahydropyrrolo[1,2-a]pyrazine-2(1H)-carboxamide, (1S,8aS)-N-(3-chloro-5-(trifluoromethyl)benzyl)-7,7-bis(2-hydroxyethyl)-N-methyl-6-oxo-1-o-tolylhexahydropyrrolo[1,2-a]pyrazine-2(1H)-carboxamide, (1S,8aS)-7,7-bis(2-hydroxyethyl)-N-methyl-6-oxo-1-o-tolyl-N-(3-(trifluoromethyl)benzyl)hexahydropyrrolo pyrazine-2(1H)-carboxamide, (1S,8aS)-N-(1-(3,5-bis(trifluoromethyl)phenyl)-3-hydroxypropyl)-7,7-bis(2-hydroxyethyl)-N-methyl-6-oxo-1-o-tolylhexahydropyrrolo[1,2-a]pyrazine-2(1H)-carboxamide, (1S,8aS)-N-(1-(3,5-bis(trifluoromethyl)phenyl)propyl)-7,7-bis(2-hydroxyethyl)-N-methyl-6-oxo-1-o-tolyl-hexahydropyrrolo[1,2-a]pyrazine-2(1H)-carboxamide, (1S,8aS)-7,7-bis(2-hydroxyethyl)-N-methyl-N-((S)-1-(3-methyl-5-(trifluoromethyl)phenyl)ethyl)-6-oxo-1-o-tolylhexahydropyrrolo[1,2-a]pyrazine-2(1H)-carboxamide, (1S,8aS)-7,7-bis(2-hydroxyethyl)-N-methyl-N-((R)-1-(3-methyl-5-(trifluoromethyl)phenyl)ethyl)-6-oxo-1-o-tolylhexahydropyrrolo[1,2-a]pyrazine-2(1H)-carboxamide, (1S,8aS)-N-((S)-1-(3,5-bis(trifluoromethyl)phenyl)-2-hydroxyethyl)-7,7-bis(2-hydroxyethyl)-N-methyl-6-oxo-1-o-tolylhexahydropyrrolo[1,2-a]pyrazine-2(1H)-carboxamide, (1S,8aS)-N-((R)-1-(3,5-bis(trifluoromethyl)phenyl)-2-hydroxyethyl)-7,7-bis(2-hydroxyethyl)-N-methyl-6-oxo-1-o-tolylhexahydropyrrolo[1,2-a]pyrazine-2(1H)-carboxamide, (1S,8aS)-7,7-bis(2-hydroxyethyl)-N-methyl-6-oxo-1-o-tolyl-N-((R)-1-(3-(trifluoromethyl)phenyl)ethyl)hexahydropyrrolo[1,2-a]pyrazine-2(1H)-carboxamide, (1S,8aS)-N-((R)-1-(3-chloro-5-(trifluoromethyl)phenyl)ethyl)-7,7-bis(2-hydroxyethyl)-N-methyl-6-oxo-1-o-tolylhexahydropyrrolo[1,2-a]pyrazine-2(1H)-carboxamide, (1S,8aS)-N-((S)-1-(3-chloro-5-(trifluoromethyl)phenyl)ethyl)-7,7-bis(2-hydroxyethyl)-N-methyl-6-oxo-1-o-tolylhexahydropyrrolo[1,2-a]pyrazine-2(1H)-carboxamide, (1S,8aS)-7,7-bis(2-hydroxyethyl)-N-((R)-1-(3-methoxy-5-(trifluoromethyl)phenyl)ethyl)-N-methyl-6-oxo-1-o-tolylhexahydropyrrolo[1,2-a]pyrazine-2(1H)-carboxamide, (1S,8aS)-N-((S)-1-(3-fluoro-5-(trifluoromethyl)phenyl)ethyl)-7,7-bis(2-hydroxyethyl)-N-methyl-6-oxo-1-o-tolylhexahydropyrrolo[1,2-a]pyrazine-2(1H)-carboxamide, (1S,8aS)-N-((R)-1-(3-fluoro-5-(trifluoromethyl)phenyl)ethyl)-7,7-bis(2-hydroxyethyl)-N-methyl-6-oxo-1-o-tolylhexahydropyrrolo[1,2-a]pyrazine-2(1H)-carboxamide, (1S,8 aS)-N-((S)-1-(3-fluoro-5-(trifluoromethyl)phenyl)-2-hydroxyethyl)-7,7-bis(2-hydroxyethyl)-N-methyl-6-oxo-1-o-tolylhexahydropyrrolo[1,2-a]pyrazine-2(1H)-carboxamide, (1S,8aS)-N-((S)-2-hydroxy-1-(3-methoxy-5-(trifluoromethyl)phenyl)ethyl)-7,7-bis(2-hydroxyethyl)-N-methyl-6-oxo-1-o-tolylhexahydropyrrolo[1,2-a]pyrazine-2(1H)-carboxamide, (1S,8aS)-N-((S)-2-hydroxy-1-(3-(trifluoromethyl)phenyl)ethyl)-7,7-bis(2-hydroxyethyl)-N-methyl-6-oxo-1-o-tolylhexahydropyrrolo[1,2-a]pyrazine-2(1H)-carboxamide, (1S,8aS)-N-((S)-2-hydroxy-1-(3-methyl-5-(trifluoromethyl)phenyl)ethyl)-7,7-bis(2-hydroxyethyl)-N-methyl-6-oxo-1-o-tolylhexahydropyrrolo[1,2-a]pyrazine-2(1H)-carboxamide, (1S,8aS)-N-((R)-1-(3-(difluoromethyl)-5-(trifluoromethyl)phenyl)ethyl)-7,7-bis(2-hydroxyethyl)-N-methyl-6-oxo-1-o-tolylhexahydropyrrolo[1,2-a]pyrazine-2(1H)-carboxamide, (1S,8aS)-N-((R)-1-(3-(difluoromethyl)-5-(trifluoromethyl)phenyl)ethyl)-7,7-bis(2-hydroxyethyl)-N-methyl-6-oxo-1-o-tolylhexahydropyrrolo[1,2-a]pyrazine-2 (1H)-carboxamide, (1S,8aS)-N-((S)-1-(3,5-bis(trifluoromethyl)phenyl)ethyl)-7,7-bis(2-hydroxyethyl)-N-methyl-6-oxo-1-o-tolylhexahydropyrrolo[1,2-a]pyrazine-2(1H)-carboxamide, (1'S,8a'S)-N-((R)-1-(3,5-bis(trifluoromethyl)phenyl)ethyl)-N-methyl-6'-oxo-1'-o-tolyloctahydro-1'H-spiro[pyran-4,7'-pyrrolo[1,2-a]pyrazine]-2'(6'H)-carboxamide, (1'S,8a'S)-N-((R)-1-(3,5-bis(trifluoromethyl)phenyl)ethyl)-N-methyl-6'-oxo-1'-o-tolyltetrahydro-1'H-spiro[pyran-4,7'-pyrrolo[1,2-a]pyrazine]-2'(6'H)-carboxamide, (1S,8aS)-7-(hydroxymethyl)-N-methyl-N-((R)-1-(3-methyl-5-(trifluoromethyl)phenyl)ethyl)-6-oxo-1-o-tolylhexahydropyrrolo[1,2-a]pyrazine-2(1H)-carboxamide, (1S,8 aS)-7,7-bis(hydroxymethyl)-N-methyl-N-((R)-1-(3-methyl-5-(trifluoromethyl)phenyl)ethyl)-6-oxo-1-o-tolylhexahydropyrrolo[1,2-a]pyrazine-2(1H)-carboxamide, (1S,8 aS)-N-((R)-1-(3,5-bis(trifluoromethyl)phenyl)ethyl)-7,7-bis(hydroxymethyl)-N-methyl-6-oxo-1-o-tolylhexahydropyrrolo[1,2-a]pyrazine-2(1H)-carboxamide, (1'S,8a'S)-N-((R)-1-(3,5-bis(trifluoromethyl)phenyl)ethyl)-N,1-dimethyl-6'-oxo-1'-o-tolyltetrahydro-1'H-spiro[piperidine-4,7'-pyrrolo[1,2-a]pyrazine]-2'(6'H)-carboxamide, formic acid salt, (1'S,8a'S)-N-((R)-1-(3,5-bis(trifluoromethyl)phenyl)ethyl)-N-methyl-6'-oxo-1'-o-tolyltetrahydro-1'H-spiro[piperidine-4,7'-pyrrolo[1,2-a]pyrazine]-2'(6'H)-carboxamide, formic acid salt, (1S,8aS)-N-methyl-N-((R)-1-(3-methyl-5-(trifluoromethyl)phenyl)ethyl)-6-oxo-1-o-tolylhexahydropyrrolo[1,2-a]pyrazine-2(1H)-carboxamide, (1S,8aS)-N-((R)-1-(3-chloro-5-(trifluoromethyl)phenyl)ethyl)-7,7-bis(hydroxymethyl)-N-methyl-6-oxo-1-o-tolylhexahydropyrrolo[1,2-a]pyrazine-2(1H)-carboxamide, (1S,8aS)-N-((R)-1-(3-ethyl-5-(trifluoromethyl)phenyl)ethyl)-N-methyl-6-oxo-1-o-tolylhexahydropyrrolo[1,2-a]pyrazine-2(1H)-carboxamide, (1S,8aS)-N-((R)-1-(3-ethyl-5-(trifluoromethyl)phenyl)ethyl)-7,7-bis(2-hydroxyethyl)-N-methyl-6-oxo-1-o-tolylhexahydropyrrolo[1,2-a]pyrazine-2(1H)-carboxamide, (1S,8aS)-N-((R)-1-(3-isopropyl-5-(trifluoromethyl)phenyl)ethyl)-N-methyl-6-oxo-1-o-tolylhexahydropyrrolo[1,2-a]pyrazine-2(1H)-carboxamide, (1S,8aS)-7,7-bis(2-hydroxyethyl)-N-((R)-1-(3-isopropyl-5-(trifluoromethyl)phenyl)ethyl)-N-methyl-6-oxo-1-o-tolylhexahydropyrrolo[1,2-a]pyrazine-2(1H)-carboxamide or a pharmaceutically acceptable salt thereof.

17. A pharmaceutical composition comprising, as a therapeutically active ingredient, a compound according to claim 1 and a pharmaceutically acceptable carrier or vehicle.

18. A pharmaceutical composition according to claim 17, wherein the pharmaceutically acceptable carrier or vehicle is suitable for topical administration.

19. A method of modulating neurokinin 1 receptor activity in a patient suffering from a condition, the method comprising administering to said patient a therapeutically effective amount of a compound according to claim 1, optionally together with a pharmaceutically acceptable carrier or one or more excipients.

20. The method according to claim 19, wherein the condition is selected from the group consisting of acute pruritus in any condition; chronic pruritus on inflammatory diseased skin, infectious diseased skin, or autoimmune cutaneous diseased skin; pruritic diseases on non-diseased skin of systemic, neurological or psychosomatic/psychiatric origin; mastocytosis; pruritus of unknown cause; and pruritus with chronic secondary scratch lesions.

21. The method according to claim 19, wherein the condition is selected from the group consisting of chronic pruritus on diseased skin caused by genodermatoses, drug reactions, dermatoses of pregnancy and skin lymphomas, prurigo, lichen planus, atopic dermatitis, eczema, contact dermatitis, allergic dermatitis, nummular dermatitis, lichen simplex, psoriasis, Sézary syndrome, cutaneous lymphomas, bullous pemphigoid, alopecia areata, scabies, vitiligo, urticaria and drug-induced pruritus; pruritic diseases on non-diseased skin resulting from endocrine and metabolic disorders, infections, haematological and lymphoproliferative diseases, solid neoplasms and drug-induced pruritus; and all types of prurigo.

22. The method according to claim 19, wherein the condition is selected from prurigo, lichen planus, atopic dermatitis, eczema, contact dermatitis, allergic dermatitis, nummular dermatitis, lichen simplex, psoriasis, Sézary syndrome, cutaneous lymphomas, urticaria, mastocytosis and pruritus with chronic secondary scratch lesions.

23. A compound according to formula B

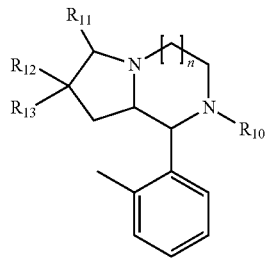

B wherein
R10 is selected from the group consisting of hydrogen and —C(O)OR14;
R11 is selected from the group consisting of hydrogen and oxo;
R12 and R13 are independently selected from the group consisting of hydrogen, $C_1$-$C_4$ alkyl, allyl and —C(O)O($C_1$-$C_4$ alkyl);
R14 is selected from the group consisting of $C_1$-$C_4$ alkyl; and
n is 1 or 2;
or a pharmaceutically acceptable salt thereof.

24. The compound according to claim 23 selected from the group consisting of:
1-(2-methylphenyl)-octahydro-1H-pyrrolo[1,2-a][1,4]diazepin-7-one;
1-(2-methylphenyl)-octahydropyrrolo[1,2-a]piperazin-6-one benzyl N-(2-{2-[(2-methylphenyl)carbonyl]-5-oxopyrrolidin-1-yl}ethyl)carbamate;
tert-butyl 1-(2-methylphenyl)-6-oxo-octahydropyrrolo[1,2-a]piperazine-2-carboxylate;
2-tert-butyl 7-methyl-1-(2-methylphenyl)-6-oxo-octahydropyrrolo[1,2-a]piperazine-2,7dicarboxylate;
(tert-butyl 1-(2-methylphenyl)-6-oxohexahydropyrrolo[1,2-a]pyrazine-2(1H)-carboxylate);
methyl 7-methyl-1-(2-methylphenyl)-6-oxo-octahydropyrrolo[1,2-a]piperazine-7-carboxylate;
methyl 1-(2-methylphenyl)-6-oxo-octahydropyrrolo[1,2-a]piperazine-7-carboxylate;
tert-butyl 1-(2-methylphenyl)-octahydropyrrolo[1,2-a]piperazine-2-carboxylate;
1-(2-methylphenyl)-octahydropyrrolo[1,2-a]piperazine;
1-(2-methylphenyl)-octahydropyrrolo[1,2-a]piperazin-6-one hydrochloride salt;
2-tert-butyl 7,7-dimethyl 1-(2-methylphenyl)-6-oxo-octahydropyrrolo[1,2-a]piperazine-2,7,7-tricarboxylate;
7,7-dimethyl 1-(2-methylphenyl)-6-oxo-octahydropyrrolo[1,2-a]piperazine-7,7-dicarboxylate;
tert-butyl 1-(2-methylphenyl)-6-oxo-7,7-bis(prop-2-en-1-yl)-octahydropyrrolo[1,2-a]piperazine-2-carboxylate and
1-(2-methylphenyl)-7,7-bis(prop-2-en-1-yl)-octahydropyrrolo[1,2-a]piperazin-6-one;
or a pharmaceutically acceptable salt thereof.

25. A compound which is (1S,8aS)-N-[(1R)-1-[3,5-bis(trifluoromethyl)phenyl]ethyl]-N-methyl-1-(2-methylphenyl)-6-oxo-octahydropyrrolo[1,2-a] piperazine-2-carboxamide.

* * * * *

UNITED STATES PATENT AND TRADEMARK OFFICE
CERTIFICATE OF CORRECTION

PATENT NO.         : 9,181,259 B2
APPLICATION NO.    : 14/380078
DATED              : November 10, 2015
INVENTOR(S)        : Morten Dahl Sørensen et al.

Page 1 of 1

It is certified that error appears in the above-identified patent and that said Letters Patent is hereby corrected as shown below:

ON THE TITLE PAGE AND IN THE SPECIFICATION:

At item (54) on the Title Page and at Column 1, lines 1-4, change the title from:

"SUBSTITUTED PYRROLO[1,2-A]PIPERAZINES AND PYRROLO[1,2-A][1,4]DIAZEPINES AS NEUROKININ RECEPTOR ANTAGONISTS"

to:

--SUBSTITUTED PYRROLO[1,2-a]PIPERAZINES AND PYRROLO[1,2-a][1,4]DIAZEPINES AS NEUROKININ RECEPTOR ANTAGONISTS--.

Signed and Sealed this
Nineteenth Day of April, 2016

Michelle K. Lee
*Director of the United States Patent and Trademark Office*